(12) United States Patent
Joung et al.

(10) Patent No.: US 12,319,938 B2
(45) Date of Patent: Jun. 3, 2025

(54) ENHANCED VIRUS-LIKE PARTICLES AND METHODS OF USE THEREOF FOR DELIVERY TO CELLS

(71) Applicants: The General Hospital Corporation; President and Fellows of Harvard College, Cambridge, MA (US)

(72) Inventors: J. Keith Joung, Winchester, MA (US); Peter Cabeceiras, Boston, MA (US)

(73) Assignees: The General Hospital Corporation, Boston, MA (US); President and Fellows of Harvard College, Cambridge, MA (US)

(*) Notice: Subject to any disclaimer, the term of this patent is extended or adjusted under 35 U.S.C. 154(b) by 0 days.

(21) Appl. No.: 18/158,173

(22) Filed: Jan. 23, 2023

(65) Prior Publication Data

US 2023/0227793 A1    Jul. 20, 2023

Related U.S. Application Data

(63) Continuation of application No. PCT/US2021/043151, filed on Jul. 26, 2021.

(60) Provisional application No. 63/056,125, filed on Jul. 24, 2020.

(51) Int. Cl.
*C12N 7/00* (2006.01)
*C12N 9/22* (2006.01)
*C12N 15/11* (2006.01)

(52) U.S. Cl.
CPC ............... *C12N 7/00* (2013.01); *C12N 9/22* (2013.01); *C12N 15/11* (2013.01); *C12N 2310/20* (2017.05); *C12N 2760/20223* (2013.01); *C12N 2760/20252* (2013.01); *C12N 2800/80* (2013.01)

(58) Field of Classification Search
None
See application file for complete search history.

(56) References Cited

U.S. PATENT DOCUMENTS

| | | |
|---|---|---|
| 4,880,635 A | 11/1989 | Janoff et al. |
| 4,906,477 A | 3/1990 | Kurono et al. |
| 4,911,928 A | 3/1990 | Wallach |
| 4,917,951 A | 4/1990 | Wallach |
| 4,920,016 A | 4/1990 | Allen et al. |
| 4,921,757 A | 5/1990 | Wheatley et al. |
| 5,244,797 A | 9/1993 | Kotewicz et al. |
| 5,892,020 A | 4/1999 | Mezes et al. |
| 6,054,297 A | 4/2000 | Carter et al. |
| 6,099,857 A | 8/2000 | Gross |
| 6,416,997 B1 | 7/2002 | Mir-Shekari et al. |
| 6,453,242 B1 | 9/2002 | Eisenberg et al. |
| 6,479,626 B1 | 11/2002 | Kim et al. |
| 6,534,261 B1 | 3/2003 | Cox, III et al. |
| 6,607,882 B1 | 8/2003 | Cox, III et al. |
| 6,746,838 B1 | 6/2004 | Choo et al. |
| 6,785,613 B2 | 8/2004 | Eisenberg et al. |
| 6,794,136 B1 | 9/2004 | Eisenberg et al. |
| 6,824,978 B1 | 11/2004 | Cox, III et al. |
| 6,866,997 B1 | 3/2005 | Choo et al. |
| 6,903,185 B2 | 6/2005 | Kim et al. |
| 6,933,113 B2 | 8/2005 | Case et al. |
| 6,979,539 B2 | 12/2005 | Cox, III et al. |
| 7,011,966 B2 | 3/2006 | Samuelson et al. |
| 7,013,219 B2 | 3/2006 | Case et al. |
| 7,030,215 B2 | 4/2006 | Liu et al. |
| 7,220,719 B2 | 5/2007 | Case et al. |
| 7,241,573 B2 | 7/2007 | Choo et al. |
| 7,241,574 B2 | 7/2007 | Choo et al. |
| 7,329,807 B2 | 2/2008 | Vadrucci |
| 7,510,706 B2 | 3/2009 | Yonemitsu et al. |
| 7,556,940 B2 | 7/2009 | Galarza et al. |
| 7,585,849 B2 | 9/2009 | Liu et al. |
| 7,595,376 B2 | 9/2009 | Kim et al. |
| 7,842,489 B2 | 11/2010 | Arnould et al. |
| 7,897,372 B2 | 3/2011 | Duchateau et al. |
| 7,998,733 B2 | 8/2011 | Yao et al. |
| 8,021,867 B2 | 9/2011 | Smith et al. |
| 8,119,361 B2 | 2/2012 | Smith et al. |
| 8,119,381 B2 | 2/2012 | Smith et al. |
| 8,124,369 B2 | 2/2012 | Smith et al. |
| 8,129,134 B2 | 3/2012 | Smith et al. |
| 8,133,697 B2 | 3/2012 | Smith et al. |
| 8,163,514 B2 | 4/2012 | Smith et al. |
| 8,420,104 B2 | 4/2013 | Charneau et al. |
| 8,440,431 B2 | 5/2013 | Voytas et al. |

(Continued)

FOREIGN PATENT DOCUMENTS

| | | |
|---|---|---|
| CA | 3079215 A1 | 5/2019 |
| EP | 2134841 | 12/2009 |

(Continued)

OTHER PUBLICATIONS

Campbell, L. et al., Mol. Ther., Jan. 2019: vol. 27: pp. 151-163.*
Castellano, F. et al., Cur. Biol., 1999, vol. 9: pp. 351-S1.*
Morell, M. et al., Clontech Labs poster, 2015, 1 page.*
IDimerize manual, Takara Bio USA, 2017, 16 pages.*
Aoki, T et al., Gene Therapy, 2011, vol. 18: pp. 936-941.*
Zhen, S. et al., Cancer Gene Ther., 2019, vol. 27: pp. 515-527.*
Hsu, P. et al., Nat. Biotech., 2013, vol. 31: pp. 827-834.*
Abounit and Zurzolo, "Wiring through tunneling nanotubes—from electrical signals to organelle transfer," Journal of Cell Science, Mar. 2012, 125(Pt 5):1089-1098.
Akishiba et al., "Cytosolic antibody delivery by lipid-sensitive endosomolytic peptide," Nature Chemistry, Aug. 2017, 9(8):751-761, 11 pages.

(Continued)

*Primary Examiner* — Michael D Burkhart
(74) *Attorney, Agent, or Firm* — Fish & Richardson P.C.

(57) ABSTRACT

Enhanced virus-like particles (eVLPs), comprising a membrane comprising a phospholipid bilayer with one or more virally-derived glycoproteins on the external side; and a cargo disposed in the core of the eVLP on the inside of the membrane, wherein the eVLP does not comprise an exogenous gag/pol protein, and methods of use thereof for delivery of the cargo to cells.

37 Claims, 24 Drawing Sheets

Specification includes a Sequence Listing.

(56) References Cited

U.S. PATENT DOCUMENTS

| | | |
|---|---|---|
| 8,440,432 B2 | 5/2013 | Voytas et al. |
| 8,450,471 B2 | 5/2013 | Voytas et al. |
| 8,530,441 B2 | 9/2013 | Hall et al. |
| 8,557,971 B2 | 10/2013 | Pedersen et al. |
| 8,586,363 B2 | 11/2013 | Voytas et al. |
| 8,652,460 B2 | 2/2014 | Kasahara et al. |
| 8,663,989 B2 | 3/2014 | Stitz |
| 8,673,612 B2 | 3/2014 | Klatzmann et al. |
| 8,697,359 B1 | 4/2014 | Zhang |
| 8,697,439 B2 | 4/2014 | Mangeot et al. |
| 8,697,853 B2 | 4/2014 | Voytas et al. |
| 8,729,038 B2 | 5/2014 | Gruber et al. |
| 8,741,279 B2 | 6/2014 | Kasahara et al. |
| 9,181,535 B2 | 11/2015 | Liu et al. |
| 9,249,426 B2 | 2/2016 | Girard-Gagnepain et al. |
| 9,296,790 B2 | 3/2016 | Chatterjee et al. |
| 9,347,065 B2 | 5/2016 | Parks et al. |
| 9,393,257 B2 | 7/2016 | Osborn et al. |
| 9,458,484 B2 | 10/2016 | Ma et al. |
| 9,534,201 B2 | 1/2017 | Pitaru |
| 9,580,698 B1 | 2/2017 | Xu et al. |
| 9,593,356 B2 | 3/2017 | Haugwitz et al. |
| 9,695,446 B2 | 7/2017 | Mangeot et al. |
| 9,737,480 B2 | 8/2017 | Lu et al. |
| 9,765,304 B2 | 9/2017 | Klatzmann et al. |
| 9,777,043 B2 | 10/2017 | Anderson et al. |
| 9,783,791 B2 | 10/2017 | Hogrefe et al. |
| 9,791,435 B2 | 10/2017 | Sitbon et al. |
| 9,816,080 B2 | 11/2017 | Lu et al. |
| 9,829,483 B2 | 11/2017 | Balaj et al. |
| 9,840,699 B2 | 12/2017 | Liu et al. |
| 9,932,567 B1 | 4/2018 | Xu et al. |
| 10,010,607 B2 | 7/2018 | Manel et al. |
| 10,040,830 B2 | 8/2018 | Chatterjee et al. |
| 10,047,355 B2 | 8/2018 | Yin et al. |
| 10,072,273 B2 | 9/2018 | Anastasov et al. |
| 10,077,453 B2 | 9/2018 | Liu et al. |
| 10,113,163 B2 | 10/2018 | Liu et al. |
| 10,137,206 B2 | 11/2018 | Angel et al. |
| 10,150,955 B2 | 12/2018 | Lambowitz et al. |
| 10,167,457 B2 | 1/2019 | Liu et al. |
| 10,189,831 B2 | 1/2019 | Arrington et al. |
| 10,202,658 B2 | 2/2019 | Parkin et al. |
| 10,233,445 B2 | 3/2019 | Seow et al. |
| 10,260,055 B2 | 4/2019 | Lu et al. |
| 10,314,906 B2 | 6/2019 | Ogembo et al. |
| 10,316,295 B2 | 6/2019 | Schmitt et al. |
| 10,407,695 B2 | 9/2019 | Charneau et al. |
| 10,442,863 B2 | 10/2019 | Arndt et al. |
| 10,538,570 B2 | 1/2020 | Leonard et al. |
| 10,538,743 B2 | 1/2020 | Kaczmarczyk et al. |
| 10,577,397 B2 | 3/2020 | Chatterjee et al. |
| 10,577,630 B2 | 3/2020 | Zhang et al. |
| 10,583,104 B2 | 3/2020 | Kline et al. |
| 10,584,321 B2 | 3/2020 | Gao et al. |
| 10,624,849 B2 | 4/2020 | Leonard et al. |
| 10,675,244 B2 | 6/2020 | Gho et al. |
| 10,793,828 B2 | 10/2020 | Haugwitz et al. |
| 10,870,865 B2 | 12/2020 | Bouille et al. |
| 10,906,943 B2 | 2/2021 | Carrillo Molina et al. |
| 10,941,395 B2 | 3/2021 | Yin et al. |
| 10,945,954 B2 | 3/2021 | Lu et al. |
| 10,968,253 B2 | 4/2021 | Ohlmann et al. |
| 10,993,967 B2 | 5/2021 | Lu et al. |
| 11,001,817 B2 | 5/2021 | Lu et al. |
| 11,028,383 B2 | 6/2021 | King et al. |
| 11,034,750 B2 | 6/2021 | Puléet al. |
| 11,103,586 B2 | 8/2021 | Wood et al. |
| 11,124,775 B2 | 9/2021 | Bouille et al. |
| 11,129,892 B1 | 9/2021 | Gilbert et al. |
| 11,155,833 B2 | 10/2021 | Nakaishi et al. |
| 11,191,784 B2 | 12/2021 | Gill |
| 11,306,294 B2 | 4/2022 | Bellier et al. |
| 11,401,530 B2 | 8/2022 | Rao et al. |
| 11,447,527 B2 | 9/2022 | Malone et al. |
| 11,447,770 B1 | 9/2022 | Liu et al. |
| 11,479,767 B2 | 10/2022 | Smith et al. |
| 11,505,578 B2 | 11/2022 | Malone et al. |
| 11,572,556 B2 | 2/2023 | Abudayyeh et al. |
| 11,576,872 B2 | 2/2023 | von Maltzahn et al. |
| 11,576,982 B2 | 2/2023 | Lee et al. |
| 11,608,509 B2 | 3/2023 | Costa Fejoz et al. |
| 11,649,264 B2 | 5/2023 | Ohlmann et al. |
| 11,730,823 B2 | 8/2023 | Lu et al. |
| 11,827,881 B2 | 11/2023 | Abudayyeh et al. |
| 11,834,658 B2 | 12/2023 | Abudayyeh et al. |
| 2003/0232410 A1 | 12/2003 | Liljedahl et al. |
| 2004/0009604 A1 | 1/2004 | Zhang et al. |
| 2004/0028687 A1 | 2/2004 | Waelti |
| 2005/0026157 A1 | 2/2005 | Baltimore et al. |
| 2005/0064474 A1 | 3/2005 | Urnov et al. |
| 2005/0208489 A1 | 9/2005 | Carroll et al. |
| 2006/0063231 A1 | 3/2006 | Li et al. |
| 2006/0172377 A1 | 8/2006 | Padidam |
| 2006/0188987 A1 | 8/2006 | Guschin et al. |
| 2006/0216702 A1 | 9/2006 | Compans et al. |
| 2007/0224176 A1 | 9/2007 | Brink et al. |
| 2007/0298118 A1 | 12/2007 | Lotvall et al. |
| 2008/0171061 A1 | 7/2008 | Nixon et al. |
| 2009/0017543 A1 | 1/2009 | Wilkes et al. |
| 2009/0061010 A1 | 3/2009 | Zale et al. |
| 2009/0202622 A1 | 8/2009 | Fleury et al. |
| 2009/0203140 A1 | 8/2009 | Amacher et al. |
| 2009/0263783 A1 | 10/2009 | Alliel et al. |
| 2009/0305419 A1 | 12/2009 | Miller |
| 2010/0120092 A1 | 5/2010 | Grgacic et al. |
| 2010/0167377 A1 | 7/2010 | Whitt et al. |
| 2011/0059502 A1 | 3/2011 | Chalasani |
| 2011/0206740 A1 | 8/2011 | Karp et al. |
| 2011/0311587 A1 | 12/2011 | Walpita |
| 2011/0311616 A1 | 12/2011 | Smith et al. |
| 2012/0021403 A1 | 1/2012 | Laderoute et al. |
| 2012/0135034 A1 | 5/2012 | Dropulic |
| 2012/0177574 A1 | 7/2012 | Gho et al. |
| 2012/0315335 A1 | 12/2012 | de los Rios et al. |
| 2013/0017210 A1 | 1/2013 | Peabody et al. |
| 2013/0053426 A1 | 2/2013 | Seow et al. |
| 2013/0065296 A1 | 3/2013 | McCray et al. |
| 2013/0202559 A1 | 8/2013 | Skog et al. |
| 2013/0266611 A1 | 10/2013 | Rabinovich et al. |
| 2014/0010885 A1 | 1/2014 | de Los Rios et al. |
| 2014/0162329 A1 | 6/2014 | Coppersmith et al. |
| 2014/0255467 A1 | 9/2014 | Bancel et al. |
| 2014/0256046 A1 | 9/2014 | Zhang et al. |
| 2014/0303232 A1 | 10/2014 | Baryza et al. |
| 2014/0304847 A1 | 10/2014 | Kühn et al. |
| 2014/0348754 A1 | 11/2014 | Wiley et al. |
| 2015/0025127 A1 | 1/2015 | McGarrity |
| 2015/0045417 A1 | 2/2015 | Demina et al. |
| 2015/0166980 A1 | 6/2015 | Liu et al. |
| 2015/0166982 A1 | 6/2015 | Liu et al. |
| 2015/0216998 A1 | 8/2015 | Feinstein et al. |
| 2015/0359879 A1 | 12/2015 | Wellnitz et al. |
| 2016/0051697 A1 | 2/2016 | Pope et al. |
| 2016/0106842 A1 | 4/2016 | Baryza et al. |
| 2016/0137716 A1 | 5/2016 | El Andaloussi et al. |
| 2016/0208221 A1 | 7/2016 | Arhancet et al. |
| 2016/0222409 A1 | 8/2016 | Baltimore et al. |
| 2016/0311759 A1 | 10/2016 | Brito et al. |
| 2017/0065588 A1 | 3/2017 | Lin et al. |
| 2017/0087087 A1 | 3/2017 | Leonard et al. |
| 2017/0112773 A1 | 4/2017 | Stachowiak et al. |
| 2017/0121693 A1 | 5/2017 | Liu et al. |
| 2017/0145492 A1 | 5/2017 | Pham et al. |
| 2017/0173113 A1 | 6/2017 | Besner et al. |
| 2017/0175086 A1 | 6/2017 | Schmitt et al. |
| 2017/0189362 A1 | 7/2017 | Kline et al. |
| 2018/0073012 A1 | 3/2018 | Liu et al. |
| 2018/0085842 A1 | 3/2018 | Lattner et al. |
| 2018/0155789 A1 | 6/2018 | Maeder et al. |
| 2018/0170984 A1 | 6/2018 | Harris et al. |
| 2018/0177727 A1 | 6/2018 | Kalluri et al. |
| 2018/0187185 A1 | 7/2018 | Ostertag et al. |
| 2018/0208976 A1 | 7/2018 | Doudna et al. |

(56) References Cited

U.S. PATENT DOCUMENTS

| | | |
|---|---|---|
| 2018/0230494 A1 | 8/2018 | Joung et al. |
| 2018/0245065 A1 | 8/2018 | Ihry et al. |
| 2018/0290965 A1 | 10/2018 | Brito et al. |
| 2018/0298359 A1 | 10/2018 | Lee et al. |
| 2018/0312825 A1 | 11/2018 | Liu et al. |
| 2018/0312828 A1 | 11/2018 | Liu et al. |
| 2018/0339166 A1 | 11/2018 | Kraft et al. |
| 2019/0135869 A1 | 5/2019 | Chatterjee et al. |
| 2019/0136231 A1 | 5/2019 | Morrissey et al. |
| 2019/0167810 A1 | 6/2019 | Hean et al. |
| 2019/0203228 A1 | 7/2019 | Bouille et al. |
| 2019/0211361 A1 | 7/2019 | Kahvejian et al. |
| 2019/0224331 A1 | 7/2019 | Wiklander |
| 2019/0225963 A1 | 7/2019 | Khalili et al. |
| 2019/0300902 A1 | 10/2019 | Galy |
| 2019/0345490 A1 | 11/2019 | Cotta-Ramusino et al. |
| 2019/0388347 A1 | 12/2019 | Wiklander et al. |
| 2020/0010835 A1 | 1/2020 | Maianti et al. |
| 2020/0023012 A1 | 1/2020 | Joseph et al. |
| 2020/0060980 A1 | 2/2020 | Von Maltzahn et al. |
| 2020/0062813 A1 | 2/2020 | Nordin et al. |
| 2020/0080112 A1 | 3/2020 | Zhang et al. |
| 2020/0102353 A1 | 4/2020 | Heidmann et al. |
| 2020/0109183 A1 | 4/2020 | Wiklander et al. |
| 2020/0109398 A1 | 4/2020 | Rubens et al. |
| 2020/0157570 A1 | 5/2020 | Loiler |
| 2020/0172886 A1 | 6/2020 | Doudna et al. |
| 2020/0172931 A1 | 6/2020 | Liu et al. |
| 2020/0206360 A1 | 7/2020 | Choi et al. |
| 2020/0248156 A1 | 8/2020 | Joung et al. |
| 2020/0283743 A1 | 9/2020 | Zhang et al. |
| 2020/0291072 A1 | 9/2020 | Wang et al. |
| 2020/0330586 A1 | 10/2020 | Holst et al. |
| 2020/0339980 A1 | 10/2020 | Dellinger et al. |
| 2020/0347100 A1 | 11/2020 | Zhang |
| 2020/0392473 A1 | 12/2020 | Zhang et al. |
| 2020/0399626 A1 | 12/2020 | Liu et al. |
| 2020/0405639 A1 | 12/2020 | Zhang et al. |
| 2020/0407418 A1 | 12/2020 | Nordin |
| 2021/0030850 A1 | 2/2021 | Leonard et al. |
| 2021/0040158 A1 | 2/2021 | Parks et al. |
| 2021/0047375 A1 | 2/2021 | Lu et al. |
| 2021/0069254 A1 | 3/2021 | Görgens et al. |
| 2021/0078936 A1 | 3/2021 | Brito et al. |
| 2021/0079389 A1 | 3/2021 | Ryan et al. |
| 2021/0137839 A1 | 5/2021 | Von Maltzahn et al. |
| 2021/0163933 A1 | 6/2021 | Budnik et al. |
| 2021/0187018 A1 | 6/2021 | von Maltzahn et al. |
| 2021/0188903 A1 | 6/2021 | Wiklander et al. |
| 2021/0189432 A1 | 6/2021 | Shepherd et al. |
| 2021/0198330 A1 | 7/2021 | Liu et al. |
| 2021/0198636 A1 | 7/2021 | Galy et al. |
| 2021/0198698 A1 | 7/2021 | von Maltzahn et al. |
| 2021/0214697 A1 | 7/2021 | Doudna et al. |
| 2021/0228627 A1 | 7/2021 | Von Maltzahn et al. |
| 2021/0230577 A1 | 7/2021 | Liu et al. |
| 2021/0261930 A1 | 8/2021 | Lu et al. |
| 2021/0261957 A1 | 8/2021 | Petris et al. |
| 2021/0269790 A1 | 9/2021 | Hotta et al. |
| 2021/0277379 A1 | 9/2021 | Gaudelli et al. |
| 2021/0284697 A1 | 9/2021 | Ohlmann et al. |
| 2021/0292769 A1 | 9/2021 | Halperin |
| 2021/0301265 A1 | 9/2021 | Bouille et al. |
| 2021/0301274 A1 | 9/2021 | Bryson |
| 2021/0315814 A1 | 10/2021 | Lu et al. |
| 2021/0324370 A1 | 10/2021 | Yin et al. |
| 2021/0332386 A1 | 10/2021 | Gallego-Perez et al. |
| 2021/0346504 A1 | 11/2021 | Wood et al. |
| 2021/0347829 A1 | 11/2021 | Malone et al. |
| 2021/0353543 A1 | 11/2021 | Trudeau et al. |
| 2021/0371858 A1 | 12/2021 | Evans et al. |
| 2021/0380955 A1 | 12/2021 | Bryson et al. |
| 2021/0403907 A1 | 12/2021 | Malone et al. |
| 2022/0002358 A1 | 1/2022 | Malone et al. |
| 2022/0002718 A1 | 1/2022 | Joung et al. |
| 2022/0008557 A1 | 1/2022 | von Maltzahn et al. |
| 2022/0016032 A1 | 1/2022 | Malone et al. |
| 2022/0025397 A1 | 1/2022 | Morizono |
| 2022/0088224 A1 | 3/2022 | Malone et al. |
| 2022/0090139 A1 | 3/2022 | Rao et al. |
| 2022/0127622 A1 | 4/2022 | Evans et al. |
| 2022/0184225 A1 | 6/2022 | Tilton et al. |
| 2022/0241328 A1 | 8/2022 | Bandoro et al. |
| 2022/0249373 A1 | 8/2022 | Dooley et al. |
| 2022/0249566 A1 | 8/2022 | Culshaw et al. |
| 2022/0259617 A1 | 8/2022 | Joung et al. |
| 2022/0287968 A1 | 9/2022 | Suo et al. |
| 2022/0313799 A1 | 10/2022 | Gehrke et al. |
| 2022/0333132 A1 | 10/2022 | Emmanuel et al. |
| 2022/0333134 A1 | 10/2022 | Cruite et al. |
| 2022/0340889 A1 | 10/2022 | Doudna et al. |
| 2022/0356469 A1 | 11/2022 | Liu et al. |
| 2022/0380740 A1 | 12/2022 | Liu et al. |
| 2022/0389062 A1 | 12/2022 | Zhang et al. |
| 2022/0389451 A1 | 12/2022 | Zhang et al. |
| 2022/0403003 A1 | 12/2022 | Lu et al. |
| 2022/0403379 A1 | 12/2022 | Doudna et al. |
| 2022/0409739 A1 | 12/2022 | Dar et al. |
| 2023/0025039 A1 | 1/2023 | Zhang et al. |
| 2023/0040216 A1 | 2/2023 | Zhang et al. |
| 2023/0043255 A1 | 2/2023 | von Maltzahn et al. |
| 2023/0048166 A1 | 2/2023 | von Maltzahn et al. |
| 2023/0055682 A1 | 2/2023 | Cafferty et al. |
| 2023/0057793 A1 | 2/2023 | Malone et al. |
| 2023/0068547 A1 | 3/2023 | von Maltzahn et al. |
| 2023/0078265 A1 | 3/2023 | Liu et al. |
| 2023/0081117 A1 | 3/2023 | Oakes et al. |
| 2023/0086199 A1 | 3/2023 | Liu et al. |
| 2023/0090221 A1 | 3/2023 | Liu et al. |
| 2023/0140670 A1 | 5/2023 | Wood et al. |
| 2023/0159913 A1 | 5/2023 | Liu et al. |
| 2023/0173094 A1 | 6/2023 | Stice et al. |
| 2023/0174598 A1 | 6/2023 | Smith et al. |
| 2023/0183691 A1 | 6/2023 | Fernandes et al. |
| 2023/0193255 A1 | 6/2023 | Doudna et al. |
| 2023/0201337 A1 | 6/2023 | Gilbert et al. |
| 2023/0220374 A1 | 7/2023 | Liu et al. |
| 2023/0227793 A1 | 7/2023 | Joung et al. |
| 2023/0227852 A1 | 7/2023 | Lu et al. |
| 2023/0270674 A1 | 8/2023 | Verma et al. |
| 2023/0279373 A1 | 9/2023 | Zetsche et al. |
| 2023/0312657 A1 | 10/2023 | Malone et al. |
| 2023/0357766 A1 | 11/2023 | Liu et al. |
| 2023/0365989 A1 | 11/2023 | Zhang et al. |
| 2023/0383282 A1 | 11/2023 | Zhang et al. |
| 2023/0407276 A1 | 12/2023 | Doudna et al. |
| 2024/0011049 A1 | 1/2024 | Joung et al. |
| 2024/0011050 A1 | 1/2024 | Joung et al. |
| 2024/0018544 A1 | 1/2024 | Joung et al. |
| 2024/0052331 A1 | 2/2024 | Liu et al. |
| 2024/0082303 A1 | 3/2024 | Hung et al. |
| 2024/0102052 A1 | 3/2024 | Malone et al. |
| 2024/0132547 A1 | 4/2024 | Ohlmann et al. |
| 2024/0189247 A1 | 6/2024 | Joung et al. |
| 2024/0191208 A1 | 6/2024 | Joung et al. |
| 2024/0191256 A1 | 6/2024 | Joung et al. |
| 2024/0209359 A1 | 6/2024 | Zhang et al. |
| 2024/0216523 A1 | 7/2024 | Parhiz et al. |

FOREIGN PATENT DOCUMENTS

| | | |
|---|---|---|
| EP | 2134841 B1 | 2/2012 |
| EP | 2450032 | 5/2012 |
| EP | 2350295 | 5/2013 |
| EP | 1974043 B1 | 11/2013 |
| EP | 2371376 | 4/2014 |
| EP | 2877490 A2 | 6/2015 |
| EP | 2583974 | 4/2017 |
| EP | 2788019 B1 | 4/2017 |
| EP | 3155116 A2 | 4/2017 |
| EP | 2761010 B1 | 7/2017 |
| EP | 3192526 A2 | 7/2017 |
| EP | 3235828 A1 | 10/2017 |
| EP | 2498823 B1 | 8/2018 |

(56) References Cited

FOREIGN PATENT DOCUMENTS

| | | |
|---|---|---|
| EP | 3365437 A1 | 8/2018 |
| EP | 3430024 A1 | 1/2019 |
| EP | 3445862 A1 | 2/2019 |
| EP | 3454889 A2 | 3/2019 |
| EP | 3008192 B1 | 7/2019 |
| EP | 3518981 | 8/2019 |
| EP | 3079725 | 10/2019 |
| EP | 3563866 A1 | 11/2019 |
| EP | 3622079 A1 | 3/2020 |
| EP | 3635103 A1 | 4/2020 |
| EP | 3715453 A1 | 9/2020 |
| EP | 3723732 | 10/2020 |
| EP | 3727351 A1 | 10/2020 |
| EP | 3727469 A1 | 10/2020 |
| EP | 3389700 | 11/2020 |
| EP | 3294756 | 12/2020 |
| EP | 3752623 A1 | 12/2020 |
| EP | 2776567 B1 | 1/2021 |
| EP | 3788155 A1 | 3/2021 |
| EP | 3793570 A2 | 3/2021 |
| EP | 3455239 | 4/2021 |
| EP | 3820995 A1 | 5/2021 |
| EP | 3844272 A1 | 7/2021 |
| EP | 3852813 A2 | 7/2021 |
| EP | 3880717 A1 | 9/2021 |
| EP | 3880831 | 9/2021 |
| EP | 3921432 A1 | 12/2021 |
| EP | 3971286 A2 | 3/2022 |
| EP | 4031561 A1 | 7/2022 |
| EP | 4034088 | 8/2022 |
| EP | 4061941 | 9/2022 |
| EP | 4117627 A1 | 1/2023 |
| EP | 4153245 | 3/2023 |
| EP | 4164694 | 4/2023 |
| EP | 4175622 A1 | 5/2023 |
| EP | 4189096 | 6/2023 |
| EP | 4228669 | 8/2023 |
| EP | 4256045 A1 | 10/2023 |
| EP | 4284813 A1 | 12/2023 |
| JP | 2003-061694 A | 3/2003 |
| JP | 2008-521430 A | 6/2008 |
| JP | 2018-531023 A | 10/2018 |
| WO | WO 1989/001041 | 2/1989 |
| WO | WO 1990/012099 | 10/1990 |
| WO | WO 1994/020621 | 9/1994 |
| WO | WO 1995/022614 | 8/1995 |
| WO | WO 1998/050538 | 11/1998 |
| WO | WO 2001/011042 A1 | 2/2001 |
| WO | WO 2001/038547 A2 | 5/2001 |
| WO | WO 2002/102709 A1 | 12/2002 |
| WO | WO 2004/087748 A1 | 10/2004 |
| WO | WO 2006/027202 | 3/2006 |
| WO | WO 2007/014275 | 2/2007 |
| WO | WO 2007/020965 | 2/2007 |
| WO | WO 2008/110914 | 9/2008 |
| WO | WO 2010/040023 A2 | 4/2010 |
| WO | WO 2013/003555 A1 | 1/2013 |
| WO | WO 2013/045632 A1 | 4/2013 |
| WO | WO 2013/074999 A1 | 5/2013 |
| WO | WO 2014/005219 | 1/2014 |
| WO | WO 2014/055782 A1 | 4/2014 |
| WO | WO 2014/093661 | 6/2014 |
| WO | WO 2014/134412 | 9/2014 |
| WO | WO 2014/136086 | 9/2014 |
| WO | WO 2014/168548 A2 | 10/2014 |
| WO | WO 2015/027134 A1 | 2/2015 |
| WO | WO 2015/089406 | 6/2015 |
| WO | WO 2015/095340 | 6/2015 |
| WO | WO 2015/104376 | 7/2015 |
| WO | WO 2015/138878 A1 | 9/2015 |
| WO | WO 2015/167710 | 11/2015 |
| WO | WO 2015/171543 A1 | 11/2015 |
| WO | WO 2015/191911 A2 | 12/2015 |
| WO | WO 2016/069774 A1 | 5/2016 |
| WO | WO 2016/149426 | 9/2016 |
| WO | WO 2017/059241 | 4/2017 |
| WO | WO 2017/068077 | 4/2017 |
| WO | WO 2017/070632 | 4/2017 |
| WO | WO 2017/070633 A2 | 4/2017 |
| WO | WO 2017/173054 | 10/2017 |
| WO | WO 2017/182607 | 10/2017 |
| WO | WO 2017/184786 | 10/2017 |
| WO | WO 2017/184786 A8 | 12/2017 |
| WO | WO 2017/212264 | 12/2017 |
| WO | WO 2018/027078 | 2/2018 |
| WO | WO 2018/085842 | 5/2018 |
| WO | WO 2018/165629 | 9/2018 |
| WO | WO 2018/176009 A1 | 9/2018 |
| WO | WO 2018/218166 | 11/2018 |
| WO | WO 2018/218188 | 11/2018 |
| WO | WO 2018/027078 A8 | 12/2018 |
| WO | WO 2019/023680 A1 | 1/2019 |
| WO | WO 2019/043127 | 3/2019 |
| WO | WO 2019/067992 | 4/2019 |
| WO | WO 2019/077150 | 4/2019 |
| WO | WO 2019/118497 | 6/2019 |
| WO | WO 2019/175428 A1 | 9/2019 |
| WO | WO 2019/213257 | 11/2019 |
| WO | WO 2019/217941 A1 | 11/2019 |
| WO | WO 2019/226953 A1 | 11/2019 |
| WO | WO 2020/027982 A1 | 2/2020 |
| WO | WO 2020/041751 A1 | 2/2020 |
| WO | WO 2020/051360 A1 | 3/2020 |
| WO | WO 2020/051562 A2 | 3/2020 |
| WO | WO 2020/086627 | 4/2020 |
| WO | WO 2020/086908 | 4/2020 |
| WO | WO 2020/092453 A1 | 5/2020 |
| WO | WO 2020/102578 A1 | 5/2020 |
| WO | WO 2020/102659 A1 | 5/2020 |
| WO | WO 2020/102709 A1 | 5/2020 |
| WO | WO 2020/160418 | 8/2020 |
| WO | WO 2020/160481 A1 | 8/2020 |
| WO | WO 2020/180975 A1 | 9/2020 |
| WO | WO 2020/191234 A1 | 9/2020 |
| WO | WO 2020/191239 A1 | 9/2020 |
| WO | WO 2020/191241 A1 | 9/2020 |
| WO | WO 2020/191242 A1 | 9/2020 |
| WO | WO 2020/191248 A1 | 9/2020 |
| WO | WO 2020/193696 | 10/2020 |
| WO | WO 2020/205681 A1 | 10/2020 |
| WO | WO 2020/210751 A1 | 10/2020 |
| WO | WO 2020/214842 A1 | 10/2020 |
| WO | WO 2020/219713 A1 | 10/2020 |
| WO | WO 2020/225287 | 11/2020 |
| WO | WO 2020/252455 | 12/2020 |
| WO | WO 2021/041885 A2 | 3/2021 |
| WO | WO 2021/046143 | 3/2021 |
| WO | WO 2021/050512 A1 | 3/2021 |
| WO | WO 2021/050601 A1 | 3/2021 |
| WO | WO 2021/055855 A1 | 3/2021 |
| WO | WO 2021/055874 A1 | 3/2021 |
| WO | WO 2021/072328 A1 | 4/2021 |
| WO | WO 2021/091974 A1 | 5/2021 |
| WO | WO 2021/102042 A1 | 5/2021 |
| WO | WO 2021/113494 A1 | 6/2021 |
| WO | WO 2021/113772 | 6/2021 |
| WO | WO 2021/183761 | 9/2021 |
| WO | WO 2021/183961 | 9/2021 |
| WO | WO 2021/188996 | 9/2021 |
| WO | WO 2021/226077 A2 | 11/2021 |
| WO | WO 2021/226558 A1 | 11/2021 |
| WO | WO 2021/252924 A1 | 12/2021 |
| WO | WO 2021/262788 | 12/2021 |
| WO | WO 2022/010889 A1 | 1/2022 |
| WO | WO 2022/020800 | 1/2022 |
| WO | WO 2022/067130 A2 | 3/2022 |
| WO | WO 2022/067446 A1 | 4/2022 |
| WO | WO 2022/081954 | 4/2022 |
| WO | WO 2022/081957 | 4/2022 |
| WO | WO 2022/081987 | 4/2022 |
| WO | WO 2022/109275 | 5/2022 |
| WO | WO 2022/164942 | 8/2022 |
| WO | WO 2022/165262 | 8/2022 |
| WO | WO 2022/173830 | 8/2022 |

(56) References Cited

FOREIGN PATENT DOCUMENTS

| WO | WO 2022/232514 A1 | 11/2022 |
|---|---|---|
| WO | WO 2022/251712 A1 | 12/2022 |
| WO | WO 2022/261148 | 12/2022 |
| WO | WO 2022/261149 | 12/2022 |
| WO | WO 2022/261150 | 12/2022 |
| WO | WO 2023/015217 A1 | 2/2023 |
| WO | WO 2023/023055 A1 | 2/2023 |
| WO | WO 2023/076898 A1 | 5/2023 |
| WO | WO 2023/077107 A1 | 5/2023 |
| WO | WO 2023/077148 A1 | 5/2023 |
| WO | WO 2023/102537 A2 | 6/2023 |
| WO | WO 2023/102538 A1 | 6/2023 |
| WO | WO 2023/102550 A2 | 6/2023 |
| WO | WO 2023/108089 | 6/2023 |
| WO | WO 2023/114949 A1 | 6/2023 |
| WO | WO 2023/115039 A2 | 6/2023 |
| WO | WO 2023/115041 A1 | 6/2023 |
| WO | WO 2023/117378 A1 | 6/2023 |
| WO | WO 2023/122764 A1 | 6/2023 |
| WO | WO 2023/102537 A3 | 7/2023 |
| WO | WO 2023/115039 A3 | 7/2023 |
| WO | WO 2023/129993 | 7/2023 |
| WO | WO 2023/133422 | 7/2023 |
| WO | WO 2023/133425 | 7/2023 |
| WO | WO 2023/102550 A3 | 8/2023 |
| WO | WO 2023/173028 A2 | 9/2023 |
| WO | WO 2023/173140 | 9/2023 |
| WO | WO 2023/205708 A1 | 10/2023 |
| WO | WO 2023/205710 A1 | 10/2023 |
| WO | WO 2023/205744 A1 | 10/2023 |
| WO | WO 2023/215831 A1 | 11/2023 |
| WO | WO 2023/225572 A2 | 11/2023 |
| WO | WO 2023/225670 A2 | 11/2023 |
| WO | WO 2023/230498 A1 | 11/2023 |
| WO | WO 2023/230601 A1 | 11/2023 |
| WO | WO 2023/240027 A1 | 12/2023 |
| WO | WO 2023/240124 A1 | 12/2023 |
| WO | WO 2023/245134 A2 | 12/2023 |
| WO | WO 2024/006988 A2 | 1/2024 |
| WO | WO 2024/018003 A1 | 1/2024 |
| WO | WO 2024/023504 A1 | 2/2024 |
| WO | WO 2024/026295 A1 | 2/2024 |
| WO | WO 2024/044655 A1 | 2/2024 |
| WO | WO 2024/050007 A1 | 3/2024 |
| WO | WO 2024/081820 A1 | 4/2024 |
| WO | WO 2024/107959 | 5/2024 |
| WO | WO 2024/107983 | 5/2024 |
| WO | WO 2024/108001 | 5/2024 |
| WO | WO 2024/138033 A2 | 6/2024 |
| WO | WO 2024/108001 A3 | 7/2024 |
| WO | WO 2024/138033 A3 | 9/2024 |

OTHER PUBLICATIONS

Anzalone et al., "Search-and-replace genome editing without double-strand breaks or donor DNA," Nature, Dec. 2019, 576(7785):149-157, 30 pages.

Asati et al., "RGD Peptide as a Targeting Moiety for Theranostic Purpose: An Update Study," International Journal of Peptide Research and Therapeutics, 2019, 25:49-65, 17 pages.

Azuma et al., "Controlling leucine-zipper partner recognition in cells through modification of a-g interactions," Chemical Communications, 2014, 50(48):6364-6367.

Babaei et al., "Production of a recombinant anti-human CD4 single-chain variable-fragment antibody using phage display technology and its expression in *Escherichia coli*," J Microbiol Biotechnol., May 2011, 21(5):529-35.

Balla and Várnai, "Visualizing Cellular Phosphoinositide Pools with GFP-Fused Protein-Modules," Sci STKE, Mar. 2002, 2002(125):p. 13, 16 pages.

Bannas et al., "Nanobodies and Nanobody-Based Human Heavy Chain Antibodies as Antitumor Therapeutics," Front. Immunol., Nov. 2017, 8:1603, 13 pages.

Banskota et al., "Engineered virus-like particles for efficient in vivo delivery of therapeutic proteins," Cell, Jan. 2022, 185(2):250-265, 33 pages.

Baranov et al., "SWAP70 Organizes the Actin Cytoskeleton and Is Essential for Phagocytosis," Cell Reports, Nov. 2016, 17(6):1518-1531.

Bastida-Ruiz et al., "The Dark Side of Cell Fusion," Int J Mol Sci., Apr. 2016, 17(5):638, 20 pages.

Bendix Johnsen et al., "Evaluation of electroporation-induced adverse effects on adipose-derived stem cell exosomes," Cytotechnology, Oct. 2016, 68(5):2125-2138.

Benedict et al., "Determination of the binding affinity of an anti-CD34 single-chain antibody using a novel, flow cytometry based assay," J Immunol Methods, Feb. 1997, 201(2):223-31.

Beskow, "Lessons from HeLa Cells: The Ethics and Policy of Biospecimens," Annu Rev Genomics Hum Genet., Aug. 2016, 17:395-417, 25 pages.

Blanco-Melo et al., "Co-option of an endogenous retrovirus envelope for host defense in hominid ancestors," eLife, Apr. 2017, 6:e22519, 19 pages.

Cai et al., "Targeted genome editing by lentiviral protein transduction of zinc finger and TAL-effector nucleases," eLife, Apr. 2014, 3:e01911, 19 pages.

Carpten et al., "A transforming mutation in the pleckstrin homology domain of AKT1 in cancer," Nature, Jul. 2007, 448(7152):439-445.

Caussinus et al., "Fluorescent fusion protein knockout mediated by anti-GFP nanobody," Nature Structural & Molecular Biology, Dec. 2011, 19(1):117-121.

Chadwick et al., "Reduced Blood Lipid Levels With in Vivo CRISPR-Cas9 Base Editing of ANGPTL3," Circulation, 2018, 137(9):975-977.

Chang et al., "Functional Characterization of the Placental Fusogenic Membrane Protein Syncytin," Biol Reprod., Dec. 2004, 71(6):1956-62.

Charlesworth et al., "Identification of preexisting adaptive immunity to Cas9 proteins in humans," Nature Medicine, Feb. 2019, 25(2):249-254, 18 pages.

Chavez et al., "Comparison of Cas9 Activators in Multiple Species," Nature Methods, Jul. 2016, 13(7):563-567, 7 pages.

Chen et al., "ACE2-targeting monoclonal antibody as potent and broad-spectrum coronavirus blocker," Signal Transduct Target Ther., Aug. 2021, 6(1):315, 9 pages.

Cheynet et al., "Identification of the hASCT2-binding domain of the Env ERVWE1/syncytin-1 fusogenic glycoprotein," Retrovirology, Jul. 2006, 3(41): 7 pages.

Choi et al., "Lentivirus pre-packed with Cas9 protein for safer gene editing," Gene Therapy, 2016, 23(7):627-633.

Chu et al., "Akt Kinase Activation Mechanisms Revealed Using Protein Semisynthesis," Cell, Aug. 2018, 174(4):897-907.e14, 25 pages.

Chu et al., "Rationally Designed Base Editors for Precise Editing of the Sickle Cell Disease Mutation," Crispr J., Apr. 2021, 4(2):169-177.

Ci et al., "Vesicular stomatitis virus G protein transmembrane region is crucial for the hemi-fusion to full fusion transition," Sci Rep., Jul. 2018, 8(1):10669, 11 pages.

Cleverley and Lenard, "The transmembrane domain in viral fusion: Essential role for a conserved glycine residue in vesicular stomatitis virus G protein," Proc Natl Acad Sci U S A, Mar. 1998, 95:3425-3430.

Clift et al., "A Method for the Acute and Rapid Degradation of Endogenous Proteins," Cell, Dec. 2017, 171(7):1692-1706.e18, 34 pages.

Colella et al., "Emerging Issues in AAV-Mediated in Vivo Gene Therapy," Molecular Therapy: Methods & Clinical Development, Dec. 2017, 8:87-104.

Cong et al., "Multiplex Genome Engineering Using CRISPR/Cas Systems," Science, Feb. 2013, 339(6121):819-823.

Contreras-Galindo et al., "Human Endogenous Retrovirus Type K (HER V-K) Particles Package and Transmit HER V-K-Related Sequences," J. Virol., Apr. 2015, 89(14):7187-7201.

(56) References Cited

OTHER PUBLICATIONS

Coquin et al., "Syncytins enable novel possibilities to transduce human or mouse primary B cells and to achieve well-tolerated in vivo gene transfer," bioRxiv, Oct. 2019, 34 pages.

Dalton and Rose, "Vesicular Stomatitis Virus Glycoprotein Containing the Entire Green Fluorescent Protein on Its Cytoplasmic Domain Is Incorporated Efficiently into Virus Particles," Virology, Jan. 2001, 279(2):414-21.

Davis et al., "Membrane nanotubes: dynamic long-distance connections between animal cells," Nature Reviews: Molecular Cell Biology, 2008, 9:431-436.

de Parseval et al., "Survey of human genes of retroviral origin: identification and transcriptome of the genes with coding capacity for complete envelope proteins," Journal of Virology, Oct. 2003, 77(19):10414-10422.

Dehbashi et al., "A Novel CAR Expressing NK Cell Targeting CD25 With the Prospect of Overcoming Immune Escape Mechanism in Cancers," Front Oncol., May 2021, 11:649710, 17 pages.

Del'Guidice et al., "Membrane permeabilizing amphiphilic peptide delivers recombinant transcription factor and CRISPR-Cas9/Cpf1 ribonucleoproteins in hard-to-modify cells," PLoS ONE, Apr. 2018, 13(4):e0195558, 26 pages.

Devanabanda et al., "Immunotoxic effects of gold and silver nanoparticles: Inhibition of mitogen-induced proliferative responses and viability of human and murine lymphocytes in vitro," Journal of Immunotoxicology, 2016, 13(6): 897-902.

Dobson et al., "Antigen identification and high-throughput interaction mapping by reprogramming viral entry," Nature Methods, Apr. 2022, 19(4):449-460, 25 pages.

Draber et al., "LST1/A is a myeloid leukocyte-specific transmembrane adaptor protein recruiting protein tyrosine phosphatases SHP-1 and SHP-2 to the plasma membrane," Journal of Biological Chemistry, Jun. 2012, 287(27):22812-22821.

Drewlo et al., "C-Terminal truncations of syncytin-1 (ERVWE1 envelope) that increase its fusogenicity," Biol. Chem., Aug. 2006, 387:1113-1120.

Dupont et al., "Tunneling nanotubes: intimate Communication between Myeloid Cells," Frontiers of Immunology, Jan. 2018, 9(43):1-6.

Ebner et al., "PI(3,4,5)P3 Engagement Restricts Akt Activity to Cellular Membranes," Mol Cell, 2017, 65(3):416-431, 23 pages.

Esnault et al., "A placenta-specific receptor for the fusogenic, endogenous retrovirus-derived, human syncytin-2," Proc Natl Acad Sci U S A, Nov. 2008, 105(45):17532-7.

Fan et al., "Secretory expression of human ScFv against keratin in Pichia pastoris and its effects on cultured keratinocytes," Arch Dermatol Res., Jun. 2009, 301(5):367-372.

Feng et al., "Improved split fluorescent proteins for endogenous protein labeling," Nature Communications, 2017, 8:1-11.

Ferdosi et al., "Multifunctional CRISPR-Cas9 with engineered immunosilenced human T cell epitopes," Nature Communications, 2019, 10:1842, 10 pages.

Finn et al., "A single administration of CRISPR/Cas9 lipid nanoparticles achieves robust and persistent in vivo genome editing," Cell Reports, 2018, 22(9):2227-2235.

Frejd et al., "Affibody molecules as engineered protein drugs," Experimental & Molecular Medicine, 2017, 49:1-8.

Fuchs et al., "First-in-Human Evaluation of the Safety and Immunogenicity of a Recombinant Vesicular Stomatitis Virus Human Immunodeficiency Virus-1 gag Vaccine (HVTN 090)," Open Forum Infectious Diseases, 2015, 2(3):1-9.

Fujimoto et al., "Selective EGLN Inhibition Enables Ablative Radiotherapy and Improves Survival in Unresectable Pancreatic Cancer," Cancer Research, 2019, 79(9):2327-2338.

Gao et al., "Treatment of autosomal dominant hearing loss by in vivo delivery of genome editing agents," Nature, 2018, 553(7687):217-221, 21 pages.

Gaudelli et al., "Programmable base editing of A•T to G•C in genomic DNA without DNA cleavage," Nature, 2017, 551:464-471.

Gerdes et al., "Tunneling nanotubes: A new route for the exchange of components between animal cells," FEBS Letters, 2007, 581:2194-2201.

Giesecke et al., "Synthetic protein-protein interaction domains created by shuffling Cys2His2 zinc-fingers," Molecular Systems Biology, 2006, 2:1-15.

Grandi and Tramontano, "HER V Envelope Proteins: Physiological Role and Pathogenic Potential in Cancer and Autoimmunity," Front Microbiol., Mar. 2018, 9:462, 26 pages.

Guo et al., "Structural insights into a high fidelity variant of SpCas9," Cell Res., Mar. 2019, 29(3):183-192.

Haimovich et al., "Intercellular mRNA trafficking via membrane nanotube-like extensions in mammalian cells," Proceedings of the National Academy of Sciences, 2017, 114:E9873-E9882.

Hamann et al., "Improved targeting of human $CD4^+T$ cells by nanobody-modified AAV2 gene therapy vectors," PLoS One, Dec. 2021, 16(12):e0261269, 21 pages.

Han et al., "The critical role of AMPK in driving Akt activation under stress, tumorigenesis and drug resistance," Nat Commun, Nov. 2018, 9(1):4728, 16 pages.

Händel et al., "Versatile and efficient genome editing in human cells by combining zinc-finger nucleases with adeno-associated viral vectors," Human Gene Therapy, 2012, 23(3):321-329.

Hanke et al., "Reconstitution of the Ancestral Glycoprotein of Human Endogenous Retrovirus K and Modulation of Its Functional Activity by Truncation of the Cytoplasmic Domain," J Virol., Dec. 2009, 83(24):12790-800.

Hao et al., "A novel therapeutic drug for colon cancer EpCAM scFv-truncated protamine (tp)-siRNA," Cell Biol Int., Aug. 2013, 37(8):860-4.

Harrasser et al., "Inducible localized delivery of an anti-PD-1 scFv enhances anti-tumor activity of ROR1 CAR-T cells in TNBC," Breast Cancer Res., Jun. 2022, 24(1):39, 10 pages.

Hase et al., "M-Sec promotes membrane nanotube formation by interacting with Ral and the exocyst complex," Nature Cell Biology, Dec. 2009, 11(12):1427-1432, 18 pages.

Hashimoto et al., "Potential Role of the Formation of Tunneling Nanotubes in HIV-1 Spread in Macrophages," J Immunol., Feb. 2016, 196(4):1832-41, 15 pages.

Heidmann et al., "HEMO, an ancestral endogenous retroviral envelope protein shed in the blood of pregnant women and expressed in pluripotent stem cells and tumors," Proc Natl Acad Sci U S A, Jul. 2017, 114(32):E6642-E6651.

Heim and Tsien, "Engineering green fluorescent protein for improved brightness, longer wavelengths and fluorescence resonance energy transfer," Current Biology, 1996, 6(2):178-182.

Hosseinzadeh et al., "Production and Evaluation of Specific Single-Chain Antibodies against CTLA-4 for Cancer-Targeted Therapy," Rep Biochem Mol Biol., Oct. 2017, 6(1):8-14.

Inobe and Nukina, "Rapamycin-induced oligomer formation system of FRB-FKBP fusion proteins," Journal of Bioscience and Bioengineering, 2016, 122(1):40-46.

International Preliminary Report on Patentability in International Appln. No. PCT/US2020/037740, mailed Dec. 23, 2021, 10 pages.

International Preliminary Report on Patentability in International Appln. No. PCT/US2021/043151, mailed Feb. 2, 2023, 8 pages.

International Search Report and Written Opinion in International Appln. No. PCT/US2020/037740, mailed Nov. 6, 2020, 15 pages.

International Search Report and Written Opinion in International Appln. No. PCT/US2021/038588, mailed Dec. 21, 2021, 14 pages.

International Search Report and Written Opinion in International Appln. No. PCT/US2021/043151, mailed Feb. 8, 2022, 12 pages.

Invitation to Pay Additional Fees and, Where Applicable, Protest Fee in International Appln. No. PCT/US2021/038588, mailed Sep. 28, 2021, 2 pages.

Invitation to Pay Additional Fees and, Where Applicable, Protest Fee in International Appln. No. PCT/US2021/043151, mailed Dec. 8, 2021, 3 pages.

Iordanova et al., "Design and characterization of a chimeric ferritin with enhanced iron loading and transverse NMR relaxation rate," J. Biol. Inorg. Chem., 2010, 15:957-965.

(56) References Cited

OTHER PUBLICATIONS

Jeetendra et al., "The Membrane-Proximal Domain of Vesicular Stomatitis Virus G Protein Functions as a Membrane Fusion Potentiator and Can Induce Hemifusion," Journal of Virology, Dec. 2002, 76(23):12300-12311.

Jeetendra et al., "The Membrane-Proximal Region of Vesicular Stomatitis Virus Glycoprotein G Ectodomain Is Critical for Fusion and Virus Infectivity," Journal of Virology, Dec. 2003, 77(23):12807-12818.

Jiang et al., "Internally inlaid SaCas9 base editors enable window specific base editing," Theranostics, Jun. 2022, 12(10):4767-4778.

Jo et al., "Small molecule-induced cytosolic activation of protein kinase Akt rescues ischemia-elicited neuronal death," Proc Natl Acad Sci U S A., Jun. 2012, 109(26):10581-10586.

Kaczmarczyk et al., "Protein delivery using engineered virus-like particles," Proc Natl Acad Sci U S A, 2011, 108(41):16998-17003.

Kennedy et al., "Rapid blue-light-mediated induction of protein interactions in living cells," Nature Methods, 2010, 7(12):973-975.

Kim and Pabo, "Getting a handhold on DNA: Design of poly-zinc finger proteins with femtomolar dissociation constants," PNAS, 1998, 95(6):2812-2817.

Kim et al., "CRISPR RNAs trigger innate immune responses in human cells," Genome Research, 2018, 28:367-373.

Kimizuka et al., "Production and characterization of functional domains of human fibronectin expressed in *Escherichia coli*," J Biochem., Aug. 1991, 110(2):284-91.

Kimura et al., Distinct Roles for the N- and C-terminal Regions of M-Sec in Plasma Membrane Deformation during Tunneling Nanotube Formation, Scientific Reports, 2016, 6:33548, 12 pages.

Kober et al., "Optimized signal peptides for the development of high expressing CHO cell lines," Biotechnol. Bioeng., Apr. 2013, 110(4):1164-1173.

Koide et al., "Chapter six—Target-Binding Proteins Based on the 10th Human Fibronectin Type III Domain ($^{10}$Fn3)," Methods in Enzymology, 2012, 503:135-156.

Komor et al., "Programmable editing of a target base in genomic DNA without double-stranded DNA cleavage," Nature, 2016, 533(7603):420-424, 17 pages.

Kramer et al., "Combinatorial Control of Drosophila Circular RNA Expression by Intronic Repeats, hnRNPs, and SR Proteins," Genes Dev., 2015, 29(20):2168-2182.

Kreiss et al., "Plasmid DNA size does not affect the physicochemical properties of lipoplexes but modulates gene transfer efficiency," Nucleic Acids Research, 1999, 27(19):3792-3798.

Kubala et al., "Structural and Thermodynamic Analysis of the GFP:GFP-nanobody complex," Protein Sci., Dec. 2010, 19(12): 2389-2401.

Lainšček et al., "Delivery of an Artificial Transcription Regulator dCas9-VPR by Extracellular Vesicles for Therapeutic Gene Activation," ACS Synthetic Biology, 2018, 7(12):2715-2725.

Leach et al., "Anti-DLL4 VNAR targeted nanoparticles for targeting of both tumour and tumour associated vasculature," Nanoscale, Jul. 2020, 12(27):14751-14763.

Leddon et al., "The CD28 Transmembrane Domain Contains an Essential Dimerization Motif," Front Immunol., Jul. 2020, 11:1519, 15 pages.

Lee and Bieniasz, "Reconstitution of an infectious human endogenous retrovirus," PLoS Pathog., Jan. 2007, 3(1):e10, 12 pages.

Lee et al., "Nanoparticle delivery of Cas9 ribonucleoprotein and donor DNA in vivo induces homology-directed DNA repair," Nature Biomedical Engineering, 2017, 1:889-901, 15 pages.

Li et al., "A rationally designed semiconducting polymer brush for NIR-II imaging guided light-triggered remote control of CRISPR/Cas9 genome editing," Advanced Materials, 2019, 31(21):1901187, 9 pages.

Li et al., "Autophosphorylation of Akt at Threonine 72 and Serine 246: A potential mechanism of regulation of Akt kinase activity," Journal of Biological Chemistry, May 2006, 281(19):13837-13843.

Liao et al., "Peptidyl-prolyl cis/trans isomerase Pin1 is critical for the regulation of PKB/Akt stability and activation phosphorylation," Oncogene, Jul. 2009, 28(26):2436-45.

Liu et al., "Engineering Genetically-Encoded Mineralization and Magnetism via Directed Evolution," Scientific Reports, 2016, 6:38019, 11 pages.

Lu et al., "Delivering SaCas9 mRNA by lentivirus-like bionanoparticles for transient expression and efficient genome editing," Nucleic Acids Research, 2019, 47(8):e44, 13 pages.

Lü et al., "Discovery of an Heparin-Binding Epidermal Growth Factor Domain Antibody from a Phage Library and Analysis of Its Inhibitory Effects in SKOV3 Cells," Cancer Biother Radiopharm, Sep. 2021, 8 pages.

Luan et al., "Engineering exosomes as refined biological nanoplatforms for drug delivery," Acta Pharmacologica Sinica, 2017, 38:754-763, 10 pages.

Lučić et al., "Conformational sampling of membranes by Akt controls its activation and inactivation," Proc Natl Acad Sci U S A, Apr. 2018, 115(17):E3940-E3949.

Lukacs et al., "Size-dependent DNA Mobility in Cytoplasm and Nucleus," Journal of Biological Chemistry, 1999, 275(3):1625-1629.

Malecha and Miettinen, "Expression of keratin 13 in human epithelial neoplasms," Virchows Arch A Pathol Anat Histopathol., 1991, 418(3):249-54.

Mangeot et al., "Genome editing in primary cells and in vivo using viral-derived Nanoblades loaded with Cas9-sgRNA ribonucleoproteins," Nature Communications, 2019, 10:45, 15 pages.

Mangeot et al., "Protein transfer into human cells by VSV-G-induced nanovesicles," Molecular Therapy, 2011, 19(9):1656-1666.

Martín-Otal et al., "Targeting the extra domain A of fibronectin for cancer therapy with CAR-T cells," J Immunother Cancer, Aug. 2022, 10(8):e004479, 20 pages.

Meyer et al., "Pseudotyping exosomes for enhanced protein delivery in mammalian cells," International Journal of Nanomedicine, 2017, 12:3153-3170.

Moazen et al., "Selection and Evaluation of Specific Single Chain Antibodies against CD90, a Marker for Mesenchymal and Cancer Stem Cells," Rep Biochem Mol Biol., Oct. 2018, 7(1):45-51.

Moll et al., "Expression of keratin 5 as a distinctive feature of epithelial and biphasic mesotheliomas. An immunohistochemical study using monoclonal antibody AE14," Virchows Arch B Cell Pathol Incl Mol Pathol., 1989, 58(2):129-45.

Momen-Heravi et al., "Exosome-mediated delivery of functionally active miRNA-155 inhibitor to macrophages," Nanomedicine: Nanotechnology, Biology, and Medicine, 2014, 10(7):1517-1527, 12 pages.

Morsut et al., "Engineering Customized Cell Sensing and Response Behaviors Using Synthetic Notch Receptors," Cell, Feb. 2016, 164(4):780-91.

Mout et al., "Direct cytosolic delivery of CRISPR/Cas9-ribonucleoprotein for efficient gene editing," ACS Nano, Mar. 2017, 11(3):2452-2458.

Münch et al., "Displaying High-affinity Ligands on Adeno-associated Viral Vectors Enables Tumor Cell-specific and Safe Gene Transfer," Molecular Therapy, Jan. 2013, 21(1):109-118.

Nafissi et al., "DNA Ministrings: Highly Safe and Effective Gene Delivery Vectors," Molecular Therapy-Nucleic Acids, May 2014, 3(6):e165, 12 pages.

Naso et al., "Adeno-Associated Virus (AAV) as a Vector for Gene Therapy," BioDrugs, 2017, 31(4):317-334.

Nguyen Tran et al., "Engineering domain-inlaid SaCas9 adenine base editors with reduced RNA off-targets and increased on-target DNA editing," Nat Commun., Sep. 2020, 11(1):4871, 10 pages.

Nikolic et al., "Structural basis for the recognition of LDL-receptor family members by VSV glycoprotein," Nat Commun., Mar. 2018, 9(1):1029, 13 pages.

Oesch-Bartlomowicz et al., "Aryl hydrocarbon receptor activation by cAMP vs. dioxin divergent signaling pathways," Proc Natl Acad Sci U S A, Jun. 2005, 102(26):9218-23.

(56) References Cited

OTHER PUBLICATIONS

Okimoto et al., "VSV-G envelope glycoprotein forms complexes with plasmid DNA and MLV retrovirus-like particles in cell-free conditions and enhances DNA transfection," Molecular Therapy, 2001, 4(3):232-238.
Omsland et al., "Inhibition of Tunneling Nanotube (TNT) Formation and Human T-cell Leukemia Virus Type 1 (HTL V-1) Transmission by Cytarabine," Scientific Reports, 2018, 8(11118):1-17.
Osman et al., "M-CSF inhibits anti-HIV-1 activity of IL-32, but they enhance M2-like phenotypes of macrophages," J Immunol., Jun. 2014, 192(11):5083-9.
Parikh et al., "Disruption of PH-kinase domain interactions leads to oncogenic activation of AKT in human cancers," PNAS, Nov. 2012, 109(47):19368-19373.
Parrish et al., "A Transmembrane Domain GGxxG Motif in CD4 Contributes to Its Lck-Independent Function but Does Not Mediate CD4 Dimerization," PLoS One, Jul. 2015, 10(7):e0132333, 14 pages.
Pastuzyn et al., "The Neuronal Gene Arc Encodes a Repurposed Retrotransposon Gag Protein that Mediates Intercellular RNA Transfer," Cell, 2018, 172:275-288, 33 pages.
Peralta et al., "Mechanism of Membranous Tunnelling Nanotube Formation in Viral Genome delivery," PLoS Biology, 2013, 11(9):e1001667, 15 pages.
Qiao et al., "Cytosolic delivery of CRISPR/Cas9 ribonucleoproteins for genome editing using chitosan-coated red fluorescent protein," Chemical Communications, 2019, 55(32):4707-4710.
Rafiq et al., "Targeted delivery of a PD-1-blocking scFv by CAR-T cells enhances anti-tumor efficacy in vivo," Nat Biotechnol., Oct. 2018, 36(9):847-856, 28 pages.
Ran et al., "In vivo genome editing using *Staphylococcus aureus* Cas9," Nature, Apr. 2015, 520(7546):186-191, 18 pages.
Rechavi et al., "Intercellular exchange of proteins: The immune cell habit of sharing," FEBS Letters, 2009, 583(11):1792-1799.
Renteln, "A synthetic mitochondrial-based vector for therapeutic purposes," Medical Hypotheses, Aug. 2018, 117:28-30.
Rittner et al., "New Basic Membrane-Destabilizing Peptides for Plasmid-Based Gene Delivery in Vitro and in Vivo," Molecular Therapy, Mar. 2002, 5(2):104-114.
Robinson-McCarthy et al., "Reconstruction of the cell entry pathway of an extinct virus," PLoS Pathog., Aug. 2018, 14(8):e1007123, 23 pages.
Rose et al., "Vesicular stomatitis virus glycoprotein is anchored in the viral membrane by a hydrophobic domain near the COOH terminus," Proc Natl Acad Sci U S A, Jul. 1980, 77(7):3884-3888.
Roselli et al., "4-1BB and optimized CD28 co-stimulation enhances function of human mono-specific and bi-specific third-generation CAR T cells," J Immunother Cancer, Oct. 2021, 9(10):e003354, 15 pages.
Sartori-Rupp et al., "Correlative cryo-electron microscopy reveals the structure of TNTs in neuronal cells," Nature Communications, 2019, 10:1-16.
Sato et al., "Nonspecific binding of common anti-CFTR antibodies in ciliated cells of human airway epithelium," Sci Rep., Dec. 2021, 11(1):23256, 15 pages.
Schenkwein et al., "Production of HIV-1 Integrase Fusion Protein-Carrying Lentiviral Vectors for Gene Therapy and Protein Transduction," Human Gene Therapy, 2010, 21(5):589-602.
Schiller et al., "LST1 promotes the assembly of a molecular machinery responsible for tunneling nanotube formation," Journal of Cell Science, Feb. 2013, 126(3):767-777.
Sebollela et al., "A human scFv antibody that targets and neutralizes high molecular weight pathogenic amyloid-β oligomers," J Neurochem., Sep. 2017, 142(6):934-947.
Selgrade et al., "Protein Scaffold-Activated Protein Trans-Splicing in Mammalian Cells," J. Am. Chem. Soc., 2013, 135(20):7713-7719.
Shin et al., "Biomedical applications of nisin," J. Applied Microbial., 2015, 120(6):1449-1465, 17 pages.
Slomovic and Collins, "DNA sense-and-respond protein modules for mammalian cells," Nature Methods, 2015, 12:1085-1089, 8 pages.
Staahl et al., "Efficient genome editing in the mouse brain by local delivery of engineered Cas9 ribonucleoprotein complexes," Nature Biotechnology, May 2017, 35(5):431-433, 7 pages.
Stausbøl-Grøn et al., "De novo identification of cell-type specific antibody-antigen pairs by phage display subtraction. Isolation of a human single chain antibody fragment against human keratin 14," Eur J Biochem., May 2001, 268(10):3099-107.
Stepanek et al., "Palmitoylated transmembrane adaptor proteins in leukocyte signaling," Cellular Signaling, 2014, 26(5):895-902.
Stevens et al., "A promiscuous split intein with expanded protein engineering applications," PNAS, 2017, 114(32):8538-8543.
Tai et al., "Differential Expression of Metallothionein 1 and 2 Isoforms in Breast Cancer Lines with Different Invasive Potential: Identification of a Novel Nonsilent Metallothionein-1H Mutant Variant," American Journal of Pathology, 2003, 163(5):2009-2019.
Tillotson et al., "Engineering an Anti-Transferrin Receptor ScFv for pH-Sensitive Binding Leads to Increased Intracellular Accumulation," PLoS One, Dec. 2015, 10(12):e0145820, 21 pages.
Tiwari et al., "Control of fibrotic changes through the synergistic effects of anti-fibronectin antibody and an RGDS-tagged form of the same antibody," Sci Rep., Aug. 2016, 6:30872, 13 pages.
Toffalini and Demoulin, "The Transmembrane Domain of PDGFR-β Plays an Important Role in ETV6-PDGFR-β Activation," Blood, Nov. 2008, 112(11):5320, 2 pages.
Trahtenherts and Benhar, "An internalizing antibody specific for the human asialoglycoprotein receptor," Hybridoma (Larchmt.), Aug. 2009, 28(4):225-33.
Tsuchiya et al., "Gene design of signal sequence for effective secretion of protein," Nucleic Acids Research, 2003, Supplement No. 3: 261-262.
Urano et al., "Substitution of the myristoylation signal of human immunodeficiency virus type 1 Pr55Gag with the phospholipase C-delta 1 pleckstrin homology domain results in infectious pseudovirion production," J. Gen Virology, 2008, 89:3144-3149.
Várnai et al., "Selective cellular effects of overexpressed pleckstrin-homology domains that recognize PtdIns(3,4,5)P3 suggest their interaction with protein binding partners," Journal of Cell Science, Oct. 2005, 118(Pt 20):4879-4888.
Verweij et al., "Quantifying exosome secretion from single cells reveals a modulatory role for GPCR signaling," J Cell Biol., Mar. 2018, 217(3):1129-1142.
Voelkel et al., "Protein transduction from retroviral Gag precursors," Proc Natl Acad Sci USA, 2010, 107(17):7805-7810.
von Heijne, "Signal sequences. The limits of variation," J Mol Biol., Jul. 1985, 184(1):99-105.
Wagner et al., "High prevalence of *Streptococcus pyogenes* Cas9-reactive T cells within the adult human population," Nature Medicine, 2019, 25:242-248, 12 pages.
Wang et al., "Adenovirus-mediated somatic genome editing of Pten by CRISPR/Cas9 in mouse liver in spite of Cas9-specific immune responses," Human Gene Therapy, 2015, 26(7):432-442.
Wang et al., "Antibody fragments directed against different portions of the human neural cell adhesion molecule L1 act as inhibitors or activators of L1 function," PLoS One, Dec. 2012, 7(12):e52404, 13 pages.
Wang et al., "Anti-HER2 scFv-Directed Extracellular Vesicle-Mediated mRNA-Based Gene Delivery Inhibits Growth of HER2-Positive Human Breast Tumor Xenografts by Prodrug Activation," Mol Cancer Ther., May 2018, 17(5):1133-1142.
Wang et al., "ARMMs as a versatile platform for intracellular delivery of macromolecules," Nature Communications, 2018, 9:960, 7 pages.
Wang et al., "Nonviral gene editing via CRISPR/Cas9 delivery by membrane-disruptive and endosomolytic helical polypeptide," PNAS, 2018, 115:4903-4908.
Wang et al., "Transfer of mitochondria via tunneling nanotubes rescues apoptotic PC12 cells," Cell Death and Differentiation, 2015, 22:1181-1191.

(56) References Cited

OTHER PUBLICATIONS

Warrington et al., "Adeno-Associated Virus Type 2 VP2 Capsid Protein Is Nonessential and Can Tolerate Large Peptide Insertions at Its N Terminus," J. Virol., 2004, 78(12):6595-6609.
Watkins et al., "Functional Connectivity between Immune Cells Mediated by Tunneling Nanotubules," Immunity, 2005, 23(3):309-318.
Weidle et al., "LST1: A multifunctional gene encoded in the MHC class III region," Immunobiology, 2018, 223(11):699-708.
Wildschutte and Coffin, "Pushing the envelope," eLife, Apr. 2017, 6:e26397, 3 pages.
Wroblewska et al., "Mammalian synthetic circuits with RNA binding proteins for RNA-only Delivery," Nature Biotechnology, 2015, 33:839-841, 5 pages.
Yin et al., "Structure-guided chemical modification of guide RNA enables potent non-viral in vivo genome editing," Nature Biotechnology, 2017, 35(12):1179-1187, 22 pages.
Zetsche et al., "Cpf1 Is a Single RNA-Guided Endonuclease of a Class 2 CRISPR-Cas System," Cell, 2015, 163(3):759-771.
Zhang et al., "Suppression of p75 neurotrophin receptor surface expression with intrabodies influences Bcl-xL mRNA expression and neurite outgrowth in PC12 cells," PLoS One, 2012, 7(1):e30684, 13 pages.
Zhao et al., "Quantitatively Predictable Control of Cellular Protein Levels through Proteasomal Degradation," ACS Synthetic Biology, 2018, 7(2):540-552.
Zhao et al., "SpyCLIP: an easy-to-use and high-throughput compatible CLIP platform for the characterization of protein-RNA interactions with high accuracy," Nucleic Acids Research, 2019, 47(6):e33, 12 pages.
Zhuo et al., "Engineered virus-like particles: paving the way for effective somatic genome editing," Signal Transduction and Targeted Therapy, Aug. 2022, 7:279, 3 pages.
Zuris et al., "Cationic lipid-mediated delivery of proteins enables efficient protein-based genome editing in vitro and in vivo," Nature Biotechnology, 2015, 33:73-80, 10 pages.
McCarthy et al., "Structure of the Receptor Binding Domain of EnvP(b)1, an Endogenous Retroviral Envelope Protein Expressed in Human Tissues," MBio®, Nov. 2020, 11(6):e02772-20, 13 pages.
International Search Report and Written Opinion in International Appln. No. PCT/US2023/080020, mailed May 7, 2024, 11 pages.
International Search Report and Written Opinion in International Appln. No. PCT/US2023/080061, mailed May 8, 2024, 11 pages.
International Search Report and Written Opinion in International Appln. No. PCT/US2023/080086, mailed May 30, 2024, 16 pages.
Abed et al., "The Gag protein PEG10 binds to RNA and regulates trophoblast stem cell lineage specification," PLoS One, 2019, 14(4):e0214110, 18 pages.
Accola et al., "Efficient particle production by minimal Gag constructs which retain the carboxy-terminal domain of human immunodeficiency virus type 1 capsid-p2 and a late assembly domain," J Virol, Jun. 2000, 74(12):5395-402.
Ashley et al., "Retrovirus-like Gag protein Arc1 binds RNA and traffics across synaptic boutons," Cell, Jan. 2018, 172(1-2):262-274.
Bender et al., "Receptor-Targeted Nipah Virus Glycoproteins Improve Cell-Type Selective Gene Delivery and Reveal a Preference for Membrane-Proximal Cell Attachment," Journals PLoS Pathogens, Jun. 2016, 12(6):e1005641, 19 pages.
Cai et al., "Targeted genome editing by lentiviral protein transduction of zinc-finger and TAL-effector nucleases," eLife, Apr. 2014, 3:e01911, 47 pages.
Cai, "Abstract OR021: Targeted genome editing by lentiviral protein transduction of ZFN and Cas9 proteins," Abstract, Presented at Proceedings of the ESGCT and NVGCT Collaborative Congress: The Hague, Oct. 23-26, 2014; Human gene therapy, Nov. 2014, 15 pages.
Cai, "Protein Transduction Using Lentiviral Vectors for Transposition and Site-directed Gene Editing," Thesis for the degree of Doctor of Philosophy, Aarhus University, Department of Biomedicine, 2014, 74 pages.
Campillos et al., "Computational characterization of multiple Gag-like human proteins," Trends Genet, 2006, 22(11):585-9.
Chandler et al., "Recombinant Adeno-Associated Viral Integration and Genotoxicity: Insights from Animal Models," Hum Gene Ther, 2017, 28:314-322.
Chavez and Calos, "Therapeutic applications of the ΦC31 integrase system," Curr Gene Ther, Oct. 2011, 11(5):375-381.
Chudak et al., "Identification of late assembly domains of the human endogenous retrovirus-K (HML-2)," Retrovirology, 2013, 10:140, 14 pages.
Cronin et al., "Altering the tropism of lentiviral vectors through pseudotyping," Curr Gene Ther., 2005, 5:387-398.
Croyle et al., "PEGylation of a Vesicular Stomatitis Virus G Pseudotyped Lentivirus Vector Prevents Inactivation in Serum," J Virol, 2004, 78(2):912-21.
Dahlman et al., "Barcoded nanoparticles for high throughput in vivo discovery of targeted therapeutics," PNAS, 2017, 114(8):2060-2065.
Dai et al., "Advances and challenges in enveloped virus-like particle (VLP)-based vaccines," Journal of Immunological Sciences, Apr. 2018, 2(2):36-41.
David et al., "Viral Vectors: The Road to Reducing Genotoxicity," Toxicol Sci., 2017, 155:315-325.
De Baar et al., "Subtype-Specific Sequence Variation of the HIV Type 1 Long Terminal Repeat and Primer-Binding Site," AIDS Research and Human Retroviruses, Mar. 2000, 16(5):499-504.
Derakhshankhah and Jafari, "Cell penetrating peptides: A concise review with emphasis on biomedical applications," Biomedicine and Pharmacotherapy, Dec. 2018, 108:1090-1096.
Deverman et al., "Cre-dependent selection yields AAV variants for widespread gene transfer to the adult brain," Nat Biotechnol., 2016, 34:204-209.
Doudna, "The promise and challenge of therapeutic genome editing," Nature, 2020, 578:229-236.
Enkirch et al., "Targeted lentiviral vectors pseudotyped with the Tupaia paramyxovirus glycoproteins," Gene Therapy, Jan. 2013, 20(1):16-23.
ESGCT and FSGT Collaborative Congress Abstracts, Helsinki, Finland, Sep. 17-20, 2015; Hum Gene Ther., Oct. 2015, 26(10):A1-108, 108 pages.
ESGCT and NVGCT Collaborative Congress: The Hague Abstracts, Oct. 23-26, 2014; Human gene therapy, Nov. 2014, 25(11):A1-A121, 121 pages.
Extended European Search Report in European Appln. No. 20822926.0, dated Jun. 20, 2023, 10 pages.
Falkenburger et al., "Phosphoinositides: lipid regulators of membrane proteins," J Physiol., Sep. 2010, 588(Pt 17):3179-85.
Feher et al., "Characterization of the murine leukemia virus protease and its comparison with the human immunodeficiency virus type 1 protease," J Gen Virol, 2006, 87:1321-1330.
Frank et al., "Surface-Engineered Lentiviral Vectors for Selective Gene Transfer into Subtypes of Lymphocytes," Molecular Therapy Methods & Clinical Development, Mar. 2019, 12:19-31.
Freed, "Viral late domains," J Virol., 2002, 76(10):4679-4687.
Gee et al., "Extracellular nanovesicles for packaging of CRISPR-Cas9 protein and sgRNA to induce therapeutic exon skipping," Nat Commun, 2020, 11:1334.
Gifford et al., "Nomenclature for endogenous retrovirus (ERV) loci," Retrovirology, 2018, 15:59, 11 pages.
Girard-Gagnepain et al., "Baboon envelope pseudotyped L Vs outperform VSV-G-L Vs for gene transfer into early-cytokine-stimulated and resting HSCs," Blood, Aug. 2014, 124(8):1221-31.
Griffiths, "Endogenous retroviruses in the human genome sequence," Genome Biol., 2001, 2(6):REVIEWS1017, 5 pages.
Guimaraes et al., "Ionizable lipid nanoparticles encapsulating barcoded mRNA for accelerated in vivo delivery screening," J Control Release, 2019, 316:404-417.
Gutierrez-Guerrero et al., "Baboon Envelope Pseudotyped 'Nanoblades' Carrying Cas9/gRNA Complexes Allow Efficient Genome Editing in Human T, B, and CD34+Cells and Knock-in of AAV6-Encoded Donor DNA in CD34+Cells," Front Genome Ed., Feb. 2021, 3:6043.
Haglund et al., "Expression of human immunodeficiency virus type 1 Gag protein precursor and envelope proteins from a vesicular

(56) References Cited

OTHER PUBLICATIONS stomatitis virus recombinant: high-level production of virus-like particles containing HIV envelope," Virology, Mar. 2000, 268:112-121.
Hamilton JR et al., "Targeted delivery of CRISPR-Cas9 and transgenes enables complex immune cell engineering," Cell Rep., Jun. 2021, 35(9):109207, 17 pages.
Humbel et al., "Maximizing lentiviral vector gene transfer in the CNS," Gene Ther, 2021, 28:75-88.
Indikova et al., "Highly efficient 'hit-and-run' genome editing with unconcentrated lentivectors carrying VprProtCas9 protein produced from RRE-containing transcripts," Nucleic Acids Res, 2020, 48:8178-8187.
Irie et al., "L-domain flanking sequences are important for host interactions and efficient budding of vesicular stomatitis virus recombinants," J Virol., Oct. 2005, 79(20):12617-22.
Jalaguier et al., "Efficient Production of HIV-1 Virus-Like Particles from a Mammalian Expression Vector Requires the N-Terminal Capsid Domain," PLoS ONE, 20111, 6(11):e28314, 13 pages.
Johnson et al., "Mass spectrometry analysis reveals differences in the host cell protein species found in pseudotyped lentiviral vectors," Biologicals, 2018, 52:59-66.
Johnson et al., "Nucleic acid-independent retrovirus assembly can be driven by dimerization," J Virol., Nov. 2002, 76(22):11177-85.
Kato et al., "The entire nucleotide sequence of baboon endogenous virus DNA: a chimeric genome structure of murine type C and simian type D retroviruses," The Japanese Journal of Genetics, 1987, 62(2):127-37.
Katoh et al., "Exploitation of the interaction of measles virus fusogenic envelope proteins with the surface receptor CD46 on human cells for microcell-mediated chromosome transfer," BMC Biotechnology, 2010, 10:37, 11 pages.
Klingler et al., "How HIV-1 Gag Manipulates Its Host Cell Proteins: A Focus on Interactors of the Nucleocapsid Domain," Viruses, Aug. 2020, 12(8):888, 42 pages.
Kneissl et al., "Measles Virus Glycoprotein-Based Lentiviral Targeting Vectors That Avoid Neutralizing Antibodies," PLoS One, 2012, 7(10):e46667, 8 pages.
Kozlov et al., "Membrane tension and membrane fusion," Curr Op Struc Bio, Aug. 2015, 33:61-67.
Krebs et al., "Lentiviral LTR-directed expression sequence variation, disease pathogenesis," HIV Sequence Compendium, 2001, 2001:29-70.
Landgraf et al., "Molecular mechanism of an oncogenic mutation that alters membrane targeting: Glu17Lys modifies the PIP lipid specificity of the AKT1 Ph domain," Biochemistry, Nov. 2008, 47(47):12260-12269, 20 pages.
Lech et al., "Antibody neutralization of retargeted measles viruses," Virology, 2014, 454-455:237-46.
Lyu et al., Adenine Base Editor Ribonucleoproteins Delivered by Lentivirus-Like Particles Show High On-Target Base Editing and Undetectable RNA Off-Target Activities, CRISPR J, Feb. 2021, 4(1):69-81.
Lyu et al., "Delivering Cas9/sgRNA ribonucleoprotein (RNP) by lentiviral capsid-based bionanoparticles for efficient 'hit-and-run' genome editing," Nucleic Acids Res, 2019, 47(17):e99, 13 pages.
Martin et al., "Envelope-Targeted Retrovirus Vectors Transduce Melanoma Xenografts but Not Spleen or Liver," Molecular Therapy, Mar. 2002, 5(3):269-274.
McCarthy et al., "Structure of the Receptor Binding Domain of EnvP(b)1, an Endogenous Retroviral Envelope Protein Expressed in Human Tissues," MBioR®, Nov. 2020, 11(6):e02772-20, 13 pages.
Mikkelsen, "Repurposing lentiviral vectors for delivery of genome editing tool kits," Cell Gene Therapy Insights, 2016, 2(5):599-614.
Milone et al., "Clinical use of lentiviral vectors," Leukemia, 2018, 32:1529-1541.
Monde et al., "A Human endogenous retrovirus K Gag coassembles with HIV-1 Gag and reduces the release efficiency and infectivity of HIV-1," J Virol., 2012, 86(20):11194-11208.
Montagna et al., "VSV-G-Enveloped Vesicles for Traceless Delivery of CRISPR-Cas9," Mol Ther Nucleic Acids, 2018, 12:453-462.
Motsa and Stahelin, "Lipid-protein interactions in virus assembly and budding from the host cell plasma membrane," Biochemical Society Transactions, Aug. 2021, 49(4):1633-1641.
Nooraei et al., "Virus-like particles: preparation, immunogenicity and their roles as nanovaccines and drug nanocarriers," Journal of Nanobiotechnology, 2021, 19(59):1-27.
Ostertag et al., "Biology of Mammalian L1 Retrotransposons," Annual Review of Genetics, 2001, 35:501-538.
Pan et al., "Biodistribution and toxicity studies of VSVG-pseudotyped lentiviral vector after intravenous administration in mice with the observation of in vivo transduction of bone marrow," Mol Ther., 2002, 6:19-29.
Parr-Brownlie et al., "Lentiviral vectors as tools to understand central nervous system biology in mammalian model organisms," Front Mol Neurosci., May 2015, 8:14, 12 pages.
Peifang et al., "Enhanced activation of human T cell clones specific for virus-like particles expressing the HIV V3 loop in the presence of HIV V3 loop-specific polyclonal antibodies," Clin Exp Immunol., Sep. 1994, 97(3):361-6.
Perach and Hizi, "A Catalytic Features of the Recombinant Reverse Transcriptase of Bovine Leukemia Virus Expressed in Bacteria," Virology, Jun. 1999, 259(1):176-189.
Peruzzi et al., "Barcoding biological reactions with DNA-functionalized vesicles," Angewandte Chemie, Oct. 2019, 58(51):18683-18690.
Podbilewicz, "Virus and Cell Fusion," Mechanisms Annual Review of Cell and Developmental Biology, 2014, 30:111-139.
Prel et al., "Highly efficient in vitro and in vivo delivery of functional RNAs using new versatile MS2-chimeric retrovirus-like particles," Mol Ther Methods Clin Dev, Oct. 2015, 2:15039, 15 pages.
Presse. Inserm.fr [online], "Press Releases: Nanoblades: shuttles for genome surgery," Mar. 27, 2019, retrieved on Jan. 10, 2023, retrieved from URL<https://presseinsermfr/en/nanoblades-shuttles-for-genome-surgery/34250/>, 10 pages.
Puppo et al., "Retinal transduction profiles by high-capacity viral vectors," Gene Ther., 2014, 21:855-865.
Renner et al., "Intact Viral Particle Counts Measured by Flow Virometry Provide Insight into the Infectivity and Genome Packaging Efficiency of Moloney Murine Leukemia Virus," J Virol., Jan. 2020, 94(2):e01600-19.
Richard et al., "Intracellular curvature-generating proteins in cell-to-cell fusion," Biochem J., Dec. 2011, 440(Pt 2):185-193.
Rohovie et al., "Virus-like particles: Next-generation nanoparticles for targeted therapeutic delivery," Bioengineering & Translational Medicine, 2017, 2:43-57.
Shaw et al., "Design and Potential of Non-Integrating Lentiviral Vectors," Biomedicines, Jan. 2014, 2(1):14-35.
Shiller et al., "Enhanced Production of Exosome-Associated AAV by Overexpression of the Tetraspanin CD9," Mol Ther Methods Clin Dev., Mar. 2018, 9:278-287.
Singh et al., "Redefining the specificity of phosphoinositide-binding by human PH domain-containing proteins," Nat Commun., Jul. 2021, 12(1):4339, 13 pages.
Skipper and Mikkelsen, "Delivering the Goods for Genome Engineering and Editing," Hum Gene Ther, Aug. 2015, 26(8):486-97.
Stahelin et al., "Cellular and molecular interactions of phosphoinositides and peripheral proteins," Chem Phys Lipids, Sep. 2014, 182:3-18, 37 pages.
Stahelin, "Lipid binding domains: more than simple lipid effectors," Journal of Lipid Research, Apr. 2009, 50 Suppl(Suppl):S299-304.
Throm et al., "Efficient construction of producer cell lines for a SIN lentiviral vector for SCID-X1 gene therapy by concatemeric array transfection," Blood, May 2009, 113(21):5104-5110.
Van Beveren et al., "Structure of Moloney murine leukemia viral DNA: Nucleotide sequence of the 5' long terminal repeat and adjacent cellular sequences," Proc Natl Acad Sci USA, Jun. 1980, 77(6):3307-3311.
Wang et al., "CRISPR-Based Therapeutic Genome Editing: Strategies and in Vivo Delivery by AAV Vectors," Cell, Apr. 2020, 181(1):136-150.

(56) References Cited

OTHER PUBLICATIONS

Wang et al., "Efficient transduction of LEDGF/p75 mutant cells by complementary gain-of-function HIV-1 integrase mutant viruses," Molecular Therapy-Methods & Clinical Development, Jan. 2014, 1:2, 9 pages.

Wanisch et al., "Integration-deficient lentiviral vectors: a slow coming of age," Mol Ther, Aug. 2009, 17(8):1316-1332.

Wei et al., "Systemic nanoparticle delivery of CRISPR-Cas9 ribonucleoproteins for effective tissue specific genome editing," Nat Commun, 2020, 11:3232, 12 pages.

Wheeler et al., "Proteomics analysis of cellular components in lentiviral vector production using Gel-LC-MS/MS," Proteomics Clin Appl., Feb. 2007, 1(2):224-230.

White et al., "Structures and mechanisms of viral membrane fusion proteins: multiple variations on a common theme," Crit Rev Biochem Mol Biol., May-Jun. 2008, 43(3):189-219, 50 pages.

Wu et al., "MLV based viral-like-particles for delivery of toxic proteins and nuclear transcription factors," Biomaterials, 2014, 35:8416-8426.

Yao et al., "Engineered extracellular vesicles as versatile ribonucleoprotein delivery vehicles for efficient and safe CRISPR genome editing," J Extracell Vesicles, 2021, 10:e12076, 14 pages.

Zhadina et al., "Functional interchangeability of late domains, late domain cofactors and ubiquitin in viral budding," PLoS Pathog., Oct. 2010, 6(10):e1001153, 18 pages.

Zhang et al., "Morphology and ultrastructure of retrovirus particles," AIMS Biophys, 2015, 2(3):343-369.

Abe et al., "Enhanced Gene Transfer With Fusogenic Liposomes Containing Vesicular Stomatitis Virus G Glycoprotein," Journal of Virology, Jul. 1998, 72(7):6159-6163.

Abe et al., "In Vitro Cell-free Conversion of Noninfectious Moloney Retrovirus Particles to an Infectious Form by the Addition of the Vesicular Stomatitis Virus Surrogate Envelope G Protein," Journal of Virology, Aug. 1998, 72(8):6356-6361.

Abifadel et al., "Mutations in PCSK9 Cause Autosomal Dominant Hypercholesterolemia," Nature Genetics, Jun. 2003, 34(2):154-156.

Abudayyeh et al., "C2c2 is a single-component programmable RNA-guided RNA-targeting CRISPR effector," Science, 2016, 353(6299):1-17.

Abudu et al., "Murine Retrovirus Escapes From Murine APOBEC3 via Two Distinct Novel Mechanisms," Current Biology, Aug. 2006, 16(15):1565-1570.

Adamson et al., "Approaches to Maximize sgRNA-barcode Coupling in Perturb-seq Screens," bioRxiv, posted Apr. 11, 2018, 14 pages.

Ahn et al., "Structural and Quantitative Expression Analyses of HER V Gene Family in Human Tissues," Molecular Cells, Aug. 2009, 28(2):99-103.

Aihara et al., "A Conformational Switch Controls the DNA Cleavage Activity of A Integrase," Molecular Cell, Jul. 2003, 12(1):187-198.

Akcakaya et al., "In vivo CRISPR Editing with no Detectable Genome-wide Off-target Mutations," Nature, 2018, 561(7723):416-419, 27 pages.

Akopian et al., "Chimeric Recombinases with Designed DNA sequence Recognition," Proceedings of the National Academy of Sciences of the United States of America, Jul. 2003, 100(15):8688-8691.

Alanis-Lobato et al., "Frequent Loss of Heterozygosity in CRISPR-Cas9-edited Early Human Embryos," Proceedings of the National Academy of Sciences of the United States of America, Jun. 2021, 118(22):e2004832117, 9 pages.

Altschul et al., "Basic Local Alignment Search Tool," Journal of Molecular Biology, Oct. 1990, 215(3):403-410.

Altschul et al., "Gapped Blast and PSI-Blast: A New Generation of Protein Database Search Programs," Nucleic Acids Research, Sep. 1997, 25(17):3389-3402.

Álvarez et al., "The Eukaryotic Translation Initiation Factor 4GI is Cleaved by Different Retroviral Proteases," Journal of Virology, Dec. 2003, 77(23):12392-12400.

Amendola et al., "Recent Progress in Genome Editing for Gene Therapy Applications: The French Perspective," Hum Gene Ther., Oct. 2021, 32(19-20):1059-1075.

Amirache et al., "Mystery Solved: VSV-G-L Vs Do Not Allow Efficient Gene Transfer into Unstimulated T Cells, B Cells, and HSCs Because They Lack the LDL Receptor," Blood, Feb. 2014, 123(9):1422-1424.

Andersson et al., "Developmental Expression of HER V-R (ER V3) and HER V-K in Human Tissue," Virology, Jun. 2002, 297(2):220-225.

Andrake et al., "Retroviral Integrase: Then and Now," Annual Review of Virology, Nov. 2015, 2(1):241-264.

Annoni et al., "Modulation of Immune Responses in Lentiviral Vector-mediated Gene Transfer," Cellular Immunology, published online Apr. 27, 2018, 342:103802, 8 pages.

Anzalone et al., "Genome editing with CRISPR-Cas nucleases, base editors, transposases and prime editors," Nature Biotechnology, Jul. 2020, 38(7):824-844.

Aquino-Jarquin, "CRISPR-Cas14 is now part of the Artillery for Gene Editing and Molecular Diagnostic," Nanomedicine, Jun. 2019, 18:428-431, 15 pages.

Araki et al., "Activation of the thrombopoietin receptor by mutant calreticulin in CALR-mutant myeloproliferative neoplasms," Blood, Mar. 2016, 127(10):1307-1316.

Arezi et al., "Novel mutations in Moloney Murine Leukemia Virus reverse transcriptase increase thermostability through tighter binding to template-primer," Nucleic Acids Research, 2009, 37(2):473-481.

Arnold et al., "Mutants of Tn3 Resolvase which do not Require Accessory Binding sites for Recombination Activity," EMBO Journal, Mar. 1999, 18(5):1407-1414.

Autieri et al., "IRT-1, a Novel Interferon-γ-responsive Transcript Encoding a Growth-suppressing Basic Leucine Zipper Protein," Journal of Biological Chemistry, Jun. 1998, 273(24):14731-14737.

Avidan et al., "The processivity and fidelity of DNA synthesis exhibited by the reverse transcriptase of bovine leukemia virus," European Journal of Biochemistry, Feb. 2002, 269(3):859-867.

Bacquin et al., "A Cell Fusion-Based Screening Method Identifies Glycosylphosphatidylinositol-Anchored Protein Ly6e as the Receptor for Mouse Endogenous Retroviral Envelope Syncytin-A," Journal of Virology, Aug. 2017, 91(18):e00832-17.

Bae et al., "Design and Testing of Vector-Producing HEK293T Cells Bearing a Genomic Deletion of the SV40 T Antigen Coding Region," Molecular Therapy Methods and Clinical Development, Jul. 2020, 18:631-638.

Bandeira et al., "Downstream Processing of Lentiviral Vectors: Releasing Bottlenecks," Human Gene Therapy Methods, Aug. 2012, 23(4):255-263.

Banerjee et al., "Viral glycoproteins: biological role and application in diagnosis," VirusDisease, Mar. 2016, 27(1):1-11.

Bannert et al., "Retroelements and the Human Genome: New Perspectives on an Old Relation," Proceedings of the National Academy of Sciences of the United States of America, Oct. 2004, 101(Suppl 2):14572-14579.

Baranauskas et al., "Generation and characterization of new highly thermostable and processive M-MuL V reverse transcriptase variants," Protein engineering, design & selection, Oct. 2012, 25(10):657-668.

Barash et al., "Human Secretory Signal Peptide Description by Hidden Markov Model and Generation of a Strong Artificial Signal Peptide for Secreted Protein Expression," Biochemical and Biophysical Research Communications, Jun. 2002, 294(4):835-842.

Barrangou et al., "CRISPR Provides Acquired Resistance Against Viruses in Prokaryotes," Science, Mar. 2007, 315(5819):1709-1712.

Bartel et al., "Directed evolution of novel adeno-associated viruses for therapeutic gene delivery," Gene Therapy, Jun. 2012, 19(6):694-700.

Basel et al., "Designing a Cleavable Cell Surface Protein for Cytotherapy and Drug Delivery Applications," Applied Sciences, 2021, 11(6):2792, 11 pages.

Basyuk et al., "The Packaging Signal of ML V is an Integrated Module That Mediates Intracellular Transport of Genomic RNAs," Journal of molecular biology, Nov. 2005, 354(2):330-339.

(56) References Cited

OTHER PUBLICATIONS

Bauler et al., "Production of Lentiviral Vectors Using Suspension Cells Grown in Serum-free Media. Molecular therapy," Methods and Clinical Development, 2020, 17:58-68.
Beal et al., "Model-Driven Engineering of Gene Expression From RNA Replicons," ACS Synthetic Biology, Jan. 2015, 4(1):48-56.
Becer et al., "Click chemistry beyond metal-catalyzed cycloaddition," Angew Chem Int Ed Engl., 2009, 48(27):4900-4908.
Beerli et al., "Toward controlling gene expression at will: specific regulation of the erbB-2/HER-2 promoter by using polydactyl zinc finger proteins constructed from modular building blocks," Proceedings of the National Academy of Sciences, Dec. 1998, 95(25):14628-14633.
Beilstein et al., "Conditional Control of Mammalian Gene Expression by Tetracycline-dependent Hammerhead Ribozymes," ACS Synthetic Biology, May 2015, 4(5):526-534.
Beilstein et al., "Identification of a pH-Sensitive Switch in VSV-G and a Crystal Structure of the G Pre-fusion State Highlight the VSV-G Structural Transition Pathway," Cell Reports, Aug. 2020, 32(7):108042, 15 pages.
Berens et al., "A Tetracycline-binding RNA Aptamer," Bioorganic & Medicinal Chemistry, Oct. 2001, 9(10):2549-2456.
Berger et al., "Reverse Transcriptase and Its Associated Ribonuclease H: Interplay of Two Enzyme Activities Controls the Yield of Single-Stranded Complementary Deoxyribonucleic Acid," Biochemistry, May 1983, 22(10):2365-2372.
Berkhout et al., "Identification of an Active Reverse Transcriptase Enzyme Encoded by a Human Endogenous HER V-K Retrovirus," Journal of Virology, Mar. 1999, 73(3):2365-2375.
Beurdeley et al., "Compact Designer TALENs for Efficient Genome Engineering," Nature Communications, 2013, 4(1762):1-8.
Bianchi et al., "Mammalian fertilization: Does sperm IZUMO1 mediate fusion as well as adhesion?," Journal of Cell Biology, Feb. 2023, 222(2):e202301035, 2 pages.
Biswas et al., "A structural basis for allosteric control of DNA recombination by lambda integrase," Nature, Jun. 2005, 435(7045):1059-1066, 16 pages.
Blain et al., "Nuclease Activities of Moloney Murine Leukemia Virus Reverse Transcriptase," The Journal of Biological Chemistry, Nov. 1993, 268(31):23585-23592.
Bleker et al., "Mutational Analysis of Narrow Pores at the Fivefold Symmetry Axes of Adeno-associated Virus Type 2 Capsids Reveals a Dual Role in Genome Packaging and Activation of Phospholipase A2 Activity," Journal of Virology, Feb. 2005, 79(4):2528-2540.
Blond et al., "Molecular Characterization and Placental Expression of HER V-W, a New Human Endogenous Retrovirus Family," Journal of Virology, Feb. 1999, 73(2):1175-1185.
Boch et al., "Breaking the Code of DNA Binding Specificity of TAL-Type III Effectors," Science, Dec. 2009, 3126(5959):1509-1512.
Bogdanove et al., "TAL Effectors: Customizable Proteins for DNA Targeting," Science, Sep. 2011, 333(6051): 1843-1846.
Bojar et al., "Caffeine-inducible Gene Switches Controlling Experimental Diabetes," Nature Communications, Jun. 2018, 9(1):2318, 10 pages.
Böker et al., "The Impact of the CD9 Tetraspanin on Lentivirus Infectivity and Exosome Secretion," Molecular Therapy: the journal of the American Society of Gene Therapy, 2018, 26(2):634-647.
Bokhoven et al., "Insertional Gene Activation by Lentiviral and Gammaretroviral Vectors," Journal of Virology, Jan. 2009, 83(1):283-294.
Boller et al., "Human Endogenous Retrovirus HER V-K113 is Capable of Producing Intact Viral Particles," The Journal of General Virology, Mar. 2008, 89(Pt 2):567-572.
Bonnaud et al., "Evidence of Selection on the Domesticated ERVWE1 env Retroviral Element Involved in Placentation," Molecular Biology and Evolution, Oct. 2004, 21(10):1895-1901.
Brown et al., "Serine Recombinases as Tools for Genome Engineering," Methods, Apr. 2011, 53(4):372-379.
Brown et al., "Structure-based Mutagenesis of the Human Immunodeficiency Virus Type 1 DNA Attachment Site: Effects on Integration and cDNA Synthesis," Journal of Virology, Nov. 1999, 73(11):9011-9020.
Buchwald et al., "Long-term, continuous intravenous heparin administration by an implantable infusion pump in ambulatory patients with recurrent venous thrombosis," Surgery, Oct. 1980, 88(4):507-516.
Burdick et al., "HIV-1 Uncoats in the Nucleus Near Sites of Integration," Proceedings of the National Academy of Sciences of the United States of America, Mar. 2020, 117(10):5486-5493.
Burke et al., "Activating Mutations of Tn3 Resolvase Marking Interfaces Important in Recombination Catalysis and its Regulation," Molecular Microbiology, 2004, 51:937-948.
Burstein et al., "New CRISPR-Cas systems from uncultivated microbes," Nature, Feb. 2017, 542(7640):237-241, 28 pages.
Byrne et al., "In Vivo-directed Evolution of Adeno-associated Virus in the Primate Retina," JCI Insight, May 2020, 5(10):e135112, 12 pages.
Cabeceiras et al., "Novel Humanized Particles for Efficient Delivery of CRISPR and Other Gene Editors," Poster, Presented at Proceedings of the American Society of Gene and Cell Therapy (ASGCT) 27th Annual Meeting, Nvelop Therapeutics, Baltimore, MD, May 9, 2024, 1 page.
Cabeceiras, Novel Extracellular Vesicle Modalities for Delivery of Genome Editor Ribonucleoprotein Complexes, Thesis for the degree of Doctor of Philosophy, Harvard University Graduate School of Arts and Sciences, Apr. 29, 2022, retrieved on Jun. 6, 2024, retrieved from URL<https://nrs.harvard.edu/URN-3:HUL.INSTREPOS:37372269>, 138 pages.
Cade et al., "Highly efficient generation of heritable zebrafish gene mutations using homo-and heterodimeric TALENs," Nucleic acids research, Sep. 2012, 40(16):8001-8010.
Callahan et al., "Link Between Genome Packaging and Rate of Budding for Rous Sarcoma Virus," Journal of Virology, Sep. 2003, 77(17):9388-9398.
Carr et al., "Genome engineering," Nat Biotechnol., Dec. 2009, 27(12):1151-62.
Carroll, "Genome Engineering With Zinc-Finger Nucleases," Genet., Aug. 2011, 188(4):773-782.
Cermak et al., "Efficient Design and Assembly of Custom TALEN and Other TAL Effector-based Constructs for DNA Targeting," Nucleic Acids Research, 2011, 39(12):e82, 11 pages.
Cervera et al., "Generation of HIV-1 Gag VLPs by transient transfection of HEK 293 suspension cell cultures using an optimized animal-derived component free medium," Journal of biotechnology, Jul. 2013, 166(4):152-165.
Cervera-Carrascon et al., "Adenovirus armed with TNFa and IL2 added to aPD-1 regimen mediates antitumor efficacy in tumors refractory to aPD-1," Front. Immunol., 2021, 12:706517, 12 pages.
Chadwick et al., "In Vivo Base Editing of PCSK9 (Proprotein Convertase Subtilisin/Kexin Type 9) as a Therapeutic Alternative to Genome Editing," Arteriosclerosis, Thrombosis, and Vascular Biology, Sep. 2017, 37(9):1741-1747.
Chaikind et al., "A programmable Cas9-serine recombinase fusion protein that operates on DNA sequences in mammalian cells," Nucleic Acids Research, Nov. 2016, 44(20):9758-9770.
Chan et al., "Catalytic domain of restriction endonuclease BmrI as a cleavage module for engineering endonucleases with novel substrate specificities," Nucleic acids research, 2007, 35(18):6238-6248.
Chan et al., "Engineered AA Vs for efficient noninvasive gene delivery to the central and peripheral nervous systems," Nature Neuroscience, 2017, 20(8):1172-1179, 27 pages.
Chen et al., "Decorating Chromatin for Enhanced Genome Editing using CRISPR-Cas9," Proceedings of the National Academy of Sciences of the United States of America, 2022, 119(49):1-9.
Chen et al., "Dynamic Imaging of Genomic Loci in Living Human Cells by an Optimized CRISPR/Cas System," Cell, Dec. 2013, 155(7):1479-1491.
Chen et al., "Enhanced Prime Editing Systems by Manipulating Cellular Determinants of Editing Outcomes," Cell, 2021, 184(22):5635-5652.el-e29.

(56) References Cited

OTHER PUBLICATIONS

Chen et al., "Enhanced proofreading governs CRISPR-Cas9 targeting accuracy," Nature, 2017, 550(7676):407-410, 25 pages.
Chen et al., "Fastp: an Ultra-Fast All-in-One FASTQ Preprocessor," Bioinformatics, 2018, 34(17):1884-1890.
Cheng et al., "New paradigms on hematopoietic stem cell differentiation," Protein Cell, 2020, 11(1):34-44.
Chua et al., "A novel platform for virus-like particle-display of flaviviral envelope domain III: induction of Dengue and West Nile virus neutralizing antibodies," Virology Journal, Apr. 2013, 10:129, 18 pages.
Chuang et al., "Points of View on the Tools for Genome/Gene Editing," International Journal of Molecular Sciences, 2021, 22(18):9872, 17 pages.
Chylinski et al., "The tracrRNA and Cas9 families of type II CRISPR-Cas immunity systems," RNA Biology, May 2013, 10(5):726-737.
Cideciyan, "Leber Congenital Amaurosis Due to RPE65 Mutations and Its Treatment with Gene Therapy," Progress in Retinal and Eye Research, Sep. 2010, 29(5):398-427.
Clement et al., "CRISPResso2 Provides Accurate and Rapid Genome Editing Sequence Analysis," Nature Biotechnology, Mar. 2019, 37(3):224-226.
ClinicalTrials.gov [online], "Identifier: NCT03872479. Single Ascending Dose Study in Participants With LCA10," record created Mar. 11, 2019, retrieved on Aug. 8, 2024, retrieved from URL<https://clinicaltrials.gov/study/NCT03872479?cond=NCT03872479&rank=1>, 13 pages.
Cocucci et al., "Ectosomes and Exosomes: Shedding the Confusion Between Extracellular Vesicles," Trends in Cell Biology, Jun. 2015, 25(6):364-372.
Cohen et al., "Low LDL Cholesterol in Individuals of African Descent Resulting from Frequent Nonsense Mutations in PCSK9," Nature Genetics, Feb. 2005, 37(2):161-165.
Cohen et al., "Sequence Variations in PCSK9, Low LDL, and Protection Against Coronary Heart Disease," The New England Journal of Medicine, Mar. 2006, 354:1264-1272.
Cooper et al., "Safety-Modified Episomal Vectors for Human Gene Therapy," Proceedings of the National Academy of Sciences of the United States of America, Jun. 1997, 94(12):6450-6455.
Cosset et al., "Retroviral retargeting by envelopes expressing an N-terminal binding domain," Journal of Virology, 1995, 69(10):6314-6322.
Costa et al., "Optimal Design, Anti-tumour Efficacy and Tolerability of Anti-CXCR4 Antibody Drug Conjugates," Scientific Reports, 2019, 9(1):2443, 19 pages.
Craigie, "The Molecular Biology of HIV Integrase," Future Virology, 2012, 7(7):679-686.
Curley et al., "Sequential Deletion of CD63 Identifies Topologically Distinct Scaffolds for Surface Engineering of Exosomes in Living Human Cells," Nanoscale, Jun. 2020, 12(22):12014-12026.
Czechowicz et al., "Selective hematopoietic stem cell ablation using CD117-antibody-drug-conjugates enables safe and effective transplantation with immunity preservation," Nature Communications, 2019, 10(1):617, 12 pages.
Dabrowski et al., "The Human Herpes-Virus Proteases. In: Proteases as Targets for Therapy," Handbook of Experimental Pharmacology, 2000, 140:95-115.
Dalkara et al., "In Vivo-Directed Evolution of a New Adeno-Associated Virus for Therapeutic Outer Retinal Gene Delivery from the Vitreous," Science Translational Medicine, 2013, 5(189): 12 pages.
Das et al., "The Crystal Structure of the Monomeric Reverse Transcriptase from Moloney Murine Leukemia Virus," Structure, May 2004, 12(5):819-29.
Davis et al., "Efficient in Vivo Base Editing via Single Adeno-associated Viruses With Size-optimized Genomes Encoding Compact Adenine Base Editors," Nature biomedical engineering, 2022, 6(11):1272-1283.
Davis et al., "Efficient prime editing in mouse brain, liver and heart with dual AAVs," Nature biotechnology, 2024, 42(2):253-264.
Davis et al., "Small Molecule-triggered Cas9 Protein with Improved Genome-editing Specificity," Nature Chemical Biology, 2015, 11:316-318, 9 pages.
De León Vázquez et al., "A Short Sequence Immediately Upstream of the Internal Repeat Elements Is Critical for KSHV LANA Mediated DNA Replication and Impacts Episome Persistence," Virology, Jan. 2014, 448:344-355.
Delebecque et al., "Organization of intracellular reactions with rationally designed RNA assemblies," Science, 2011, 333(6041):470-474.
Delenda et al., "Real-time Quantitative PCR for the Design of Lentiviral Vector Analytical Assays," Gene Therapy, 2005, 12(Suppl 1):S36-S50.
Deltcheva et al., CRISPR RNA maturation by trans-encoded small RNA and host factor RNase III, Nature, Mar. 2011, 471(7340):602-607, 19 pages.
den Hollander et al., "Leber Congenital Amaurosis: Genes, Proteins and Disease Mechanisms," Progress in Retinal and Eye Research, 2008, 27(4):391-419.
DePolo et al., "VSV-G Pseudotyped Lentiviral Vector Particles Produced in Human Cells are Inactivated by Human Serum," Molecular Therapy: the Journal of the American Society of Gene Therapy, 2000, 2(3):218-222.
Desjarlais et al., "Use of a zinc-finger consensus sequence framework and specificity rules to design specific DNA binding proteins," PNAS, Mar. 1993, 90:2256-2260.
Dewannieux et al., "Identification of a Functional Envelope Protein From the HER V-K Family of Human Endogenous Retroviruses," Journal of Virology, Dec. 2005, 79(24):15573-15577.
Dilley et al., "An LYSPL Late Domain in the Gag Protein Contributes to the Efficient Release and Replication of Rous Sarcoma Virus," Journal of Virology, 2010, 84(13):6276-6287.
Dingwall et al., "Nuclear targeting sequences—a consensus?," Trends in biochemical sciences, Dec. 1991, 16(12):478-481.
Doman et al., "Evaluation and Minimization of Cas9-independent off-target DNA Editing by Cytosine base Editors," Nature Biotechnology, 2020, 38:620-628.
Donaldson et al., "ARF family G proteins and their regulators: roles in membrane transport, development and disease," Nat Rev Mol Cell Biol., Jun. 2011, 12(6): 362-75; Erratum in: Nat Rev Mol Cell Biol., 2011, 12(8):533.
Doudna, "Hammering Out the Shape of a Ribozyme," Structure, 1994, 2(12):1271-1272.
Dreja et al., "The Effects of N-terminal Insertion into VSV-G of an scFv Peptide," Virology Journal, 2006, 3:69, 8 pages.
D'Souza et al., "Structural Basis for Packaging the Dimeric Genome of Moloney Murine Leukaemia Virus," Nature, 2004, 431(7008):586-590.
DuBridge et al., "Analysis of Mutation in Human Cells by Using an Epstein-Barr Virus Shuttle System," Molecular and Cellular Biology, 1987, 7(1):379-387.
Duchon et al., "Plasma Membrane Anchoring and Gag:Gag Multimerization on Viral RNA are Critical Properties of HIV-1 Gag Required to Mediate Efficient Genome Packaging," mBio, 2021, 12(6):e0325421, 17 pages.
Dudek et al., "GPR108 Is a Highly Conserved AAV Entry Factor," Molecular therapy: the journal of the American Society of Gene Therapy, 2020, 28(2):367-381.
Durai et al., "Zinc finger nucleases: custom-designed molecular scissors for genome engineering of plant and mammalian cells," Nucleic Acids Research, 2005, 33(18):5978-5990.
During et al., "Controlled release of dopamine from a polymeric brain implant: In vivo characterization," Ann. Neurol., 1989, 25:351-356.
East-Seletsky et al., "Two distinct Rnase activities of CRISPR-C2c2 enable guide-RNA processing and RNA detection," Nature, Oct. 2016, 538(7624):270-273, 26 pages.
Ecker et al., "High-Yield Expression and Purification of Recombinant Influenza Virus Proteins from Stably-Transfected Mammalian Cell Lines," Vaccines, 2020, 8(3):462, 20 pages.

(56) References Cited

OTHER PUBLICATIONS

Eidelman et al., "pH-dependent Fusion Induced by Vesicular Stomatitis Virus Glycoprotein Reconstituted Into Phospholipid Vesicles," The Journal of Biological Chemistry, 1984, 259(7):4622-4628.

Evans et al., "Protein trans-Splicing and Cyclization by a Naturally Split Intein from the dnaE Gene of Synechocystis Species PCC6803," Journal of Biological Chemistry, 2000, 275(13):9091-9094.

Evans et al., "Restriction digest screening facilitates efficient detection of site-directed mutations introduced by CRISPR in C. albicans UME6," PeerJ, Jun. 2018, 6:e4920, 13 pages.

Evans, "The Rise of Azide-Alkyne 1,3-Dipolar 'Click' Cycloaddition and its Application to Polymer Science and Surface Modification," Australian Journal of Chemistry, 2007, 60(6):384-395.

Extended European Search Reporting in European Appln. No. 21847293.4, mailed on Nov. 5, 2024, 17 pages.

Farsani et al., "Identification of a novel human rhinovirus C type by antibody capture VIDISCA-454," Viruses, 2015, 7(1):239-251.

Feldman et al., "Lentiviral Co-packaging Mitigates the Effects of Intermolecular Recombination and Multiple Integrations in Pooled Genetic Screens," bioRxiv, posted Feb. 8, 2018, 6 pages.

Feng et al., "Human L 1 Retrotransposon Encodes a Conserved Endonuclease Required for Retrotransposition," Cell, 1996, 87(5):905-916.

Ferré-D'Amaré et al., "Crystal Structure of a Hepatitis Delta Virus Ribozyme," Nature, 1998, 395(6702):567-574.

Ferretti et al., "Complete genome sequence of an M1 strain of Streptococcus pyogenes," Proc. Natl. Acad. Sci. USA, 2001, 98(8):4658-4663.

Fielding et al., "Inverse Targeting of Retroviral Vectors: Selective Gene Transfer in a Mixed Population of Hematopoietic and Nonhematopoietic Cells," Blood, 1998, 91(5):1802-1809.

Fitzgerald et al., "Effect of an RNA Interference Drug on the Synthesis of Proprotein Convertase Subtilisin/kexin Type 9 (PCSK9) and the Concentration of Serum LDL Cholesterol in Healthy Volunteers: A Randomised, Single-blind, Placebo-Controlled, Phase 1 Trial," Lancet, 2014, 383:60-68.

Fitzgerald et al., "Exploiting Highly Ordered Subnanoliter Volume Microcapillaries as Microtools for the Analysis of Antibody Producing Cells," Anal Chem., 2014, 87:997-1003.

Flajolet et al., "Woodchuck Hepatitis Virus Enhancer I and Enhancer II are Both Involved in N-myc2 Activation in Woodchuck Liver Tumors," Journal of Virology, 1998, 72(7):6175-80.

Flockerzi et al., "Expression Patterns of Transcribed Human Endogenous Retrovirus HER V-K(HML-2) Loci in Human Tissues and the Need for a HER V Transcriptome Project," BMC Genomics, 2008, 9:354, 17 pages.

Fontana et al., "Rabies Virus-like Particles Expressed in HEK293 Cells," Vaccine, 2014, 32(24):2799-2804.

Frappier, "The Epstein-Barr Virus EBNA1 Protein," Scientifica, 2012, 2012:438204, 15 pages.

Frietze et al., "Engineering Virus-like Particles as Vaccine Platforms," Current opinion in virology, 2016, 18:44-46.

Fujiwara et al., "Hinge and Transmembrane Domains of Chimeric Antigen Receptor Regulate Receptor Expression and Signaling Threshold," Cells, May 2020, 9(5):1182, 17 pages.

Fung et al., "Structural determinants of nuclear export signal orientation in binding to exportin CRM1," eLife, Sep. 2015, 4:e10034, 19 pages.

Gadok et al., "Connectosomes for Direct Molecular Delivery to the Cellular Cytoplasm," Journal of the American Chemical Society, 2016, 138(39):12833-12840.

Gaj et al., "Structure-guided Reprogramming of Serine Recombinase DNA sequence specificity," Proceedings of the National Academy of Sciences of the United States of America, 2011, 108(2):498-503.

Gaj et al., "Targeted Gene Knockout By Direct Delivery of Zinc-finger Nuclease Proteins," Nature Methods, 2012, 9(8):805-7, 10 pages.

Gaj et al., "ZFN, TALEN, and CRISPR/CAS-based methods for genome engineering," Trends in Biotechnology, 2013, 31:397-405.

Gallardo et al., "Recombinant Retroviruses Pseudotyped With the Vesicular Stomatitis Virus G Glycoprotein Mediate Both Stable Gene Transfer and Pseudotransduction in Human Peripheral Blood Lymphocytes," Blood, 1997, 90(3):952-957.

Gao et al., "A truncated reverse transcriptase enhances prime editing by split AAV vectors," Molecular Therapy, 2022, 30(9):2942-2951.

Gao et al., "DNA-guided genome editing using the Natronobacterium gregoryi Argonaute," Nature Biotechnology, 2016, 34(7):768-773, 27 pages.

Garneau et al., "The CRISPR/Cas bacterial immune system cleaves bacteriophage and plasmid DNA," Nature, 2010, 468(7320):67-71.

Gasiunas et al., "Cas9-crRNA Ribonucleoprotein complex Mediates specific DNA cleavage for Adaptive Immunity in Bacteria," Proceedings of the National Academy of Sciences of the United States of America, 2012, 109(39):E2579-E2586.

Gaudelli et al., "Directed Evolution of Adenine Base Editors with Increased Activity and Therapeutic Application," Nature Biotechnology, 2020, 38(7):892-900.

Gehrke et al., "An APOBEC3A-Cas9 base Editor with Minimized Bystander and off-target Activities," Nature Biotechnology, 2018, 36(10):977-982.

Gentili et al., "Transmission of Innate Immune Signaling by Packaging of cGAMP in Viral Particles," Science, 2015, 349(6253):1232-1236.

Gerard et al., "Influence on stability in Escherichia coli of the carboxy-terminal structure of cloned Moloney murine leukemia virus reverse transcriptase," DNA, 1986, 5(4):271-279.

Gerard, "The role of template-primer in protection of reverse transcriptase from thermal inactivation," Nucleic acids research, 2002, 30(14):3118-3129.

Gerbaud et al., "Review: an Overview of Molecular Events Occurring in Human Trophoblast Fusion," Placenta, 2015, 36(Suppl 1):S35-S42.

Giannoukos et al., "UDiTaS, A Genome Editing Detection Method for Indels and Genome Rearrangements," BMC Genomics, 2018, 19:212, 10 pages.

Gill et al., "Optimized Transgene Delivery Using Third-Generation Lentiviruses," Current Protocols in Molecular Biology, 2020, 133(1):e125, 21 pages.

GitHub.com [online], "CRISPResso2," retrieved on Aug. 9, 2024, retrieved from URL<github.com/pinellolab/CRISPResso2>, 4 pages.

Golczak et al., "Importance of Membrane Structural Integrity for RPE65 Retinoid Isomerization Activity," Journal of Biological Chemistry, 2010, 285(13):9667-9682.

González-Domínguez et al., "A Four-Step Purification Process for Gag VLPs: From Culture Supernatant to High-Purity Lyophilized Particles," Vaccines, 2021, 9(10):1154, 19 pages.

Gordley et al., "Evolution of Programmable Zinc Finger-Recombinases with activity in Human Cells," Journal of Molecular Biology, 2007, 367:802-813.

Gordley et al., "Synthesis of Programmable Integrases," Proceedings of the National Academy of Sciences of the United States of America, 2009, 106:5053-5058.

Gorelick et al., "Characterization of the Block in Replication of Nucleocapsid Protein Zinc Finger Mutants From Moloney Murine Leukemia Virus," Journal of virology, 1999, 73(10):8185-8195.

Graham et al., "Characteristics of a Human Cell line Transformed by DNA from Human Adenovirus type 5," Journal of General Virology, 1977, 36(1):59-72.

Gray et al., "HIV-1 Rev Interacts with HER V-K RcREs Present in the Human Genome and Promotes Export of Unspliced HER V-K Proviral RNA," Retrovirology, 2019, 16(1):40, 17 pages.

Greig et al., "Integrated Vector Genomes May Contribute to Long-term Expression in Primate Liver After AAV Administration," Nature biotechnology, 2023, 11 pages.

Grieger et al., "Surface-exposed Adeno-associated Virus Vp1-NLS Capsid Fusion Protein Rescues Infectivity of Noninfectious Wild-type Vp2/Vp3 and Vp3-only Capsids but not that of Fivefold Pore Mutant Virions," Journal of Virology, 2007, 81(15):7833-7843.

Grindley et al., "Mechanism of site-specific Recombination," Annual Review of Biochemistry, 2006, 75:567-605.

(56) References Cited

OTHER PUBLICATIONS

Gröger et al., "Formation of HER V-K and HER V-Fc1 Envelope Family Members is Suppressed on Transcriptional and Translational Level," International Journal of Molecular Sciences, 2020, 21(21):7855, 23 pages.
Groot et al., "The role of Adams in Notch signaling," Adv Exp Med Biol., 2012, 727:15-36, 25 pages.
Groth et al., "Phage Integrases: Biology and Applications," Journal of Molecular Biology, 2004, 335(3):667-678.
Gruber et al., "The Vienna RNA Websuite," Nucleic Acids Research, 2008, 36(Web Server issue): W70-W74.
Grünewald et al., "A Dual-deaminase CRISPR Base Editor Enables Concurrent Adenine and Cytosine Editing," Nature Biotechnology, 2020, 38(7):861-864, 22 pages.
Grünewald et al., "Transcriptome-wide off-target RNA Editing Induced by CRISPR-guided DNA Base Editors," Nature, 2019, 569(7756):433-437.
Guerrerio et al., "Design of single-stranded nucleic acid binding peptides based on nucleocapsid CCHC-box zinc-binding domains," Journal of the American Chemical Society, 2010, 132(28):9638-9643.
Guha et al., "Programmable genome editing tools and their regulation for efficient genome engineering," Computational and Structural Biotechnology Journal, Jan. 2017, 15:146-160.
Guibinga et al., "Cell Surface Heparan Sulfate is a Receptor for Attachment of Envelope Protein-free Retrovirus-like Particles and VSV-G Pseudotyped Mlv-derived Retrovirus Vectors to Target Cells," Molecular Therapy, 2002, 5(5):538-546.
Guilinger et al., "Fusion of catalytically inactive Cas9 to FokI nuclease improves the specificity of genome modification," Nature biotechnology, 2014, 32(6):577-582, 17 pages.
Gulen, "Inside Job: Viruses Transfer cGAMP between Cells," Cell Host Microbe, 2015, 18(3):263-265.
Guo et al., "CXCL12/CXCR4: a symbiotic bridge linking cancer cells and their stromal neighbors in oncogenic communication networks," Oncogene, 2016, 35(7):816-826.
Guo et al., "Structure of Cre Recombinase Complexed with DNA in a Site-specific Recombination Synapse," Nature, 1997, 389(6646):40-46.
Gutierrez-Guerrero et al., "Lentiviral vector pseudotypes: precious tools to improve gene modification of hematopoietic cells for research and gene therapy," Viruses, 2020, 12(9):1016, 20 pages.
Gutkin et al., "RNA Delivery with a Human Virus-like Particle," Nature Biotechnology, 2021, 39(12):1514-1515.
Haldrup et al., "Engineered Lentivirus-derived Nanoparticles (L VNPs) for Delivery of CRISPR/Cas Ribonucleoprotein Complexes Supporting Base Editing, Prime Editing and in Vivo Gene Modification," Nucleic acids research, 2023, 51(18):10059-10074.
Halvas et al., "Role of Murine Leukemia Virus Reverse Transcriptase Deoxyribonucleoside Triphosphate-binding Site in Retroviral Replication and in Vivo Fidelity," Journal of Virology, 2000, 74(22):10349-10358.
Hamilton et al., "Cell Type-programmable Genome Editing With Enveloped Delivery Vehicles," bioRxiv, posted Aug. 24, 2022, 22 pages.
Hamilton et al., "Programmable enveloped delivery vehicles for human genome engineering in vivo," bioRxiv, posted Apr. 2, 2023, 21 pages.
Hanlon et al., "High Levels of AAV Vector Integration into CRISPR-induced DNA Breaks," Nature communications, 2019, 10(1):4439, 11 pages.
Harrington et al., "Programmed DNA Destruction by Miniature CRISPR-Cas14 Enzymes," Science, 2018, 362(6416):839-842, 12 pages.
Hartung et al., "Cre Mutants with altered DNA Binding Properties," Journal of Biological Chemistry, 1998, 273:22884-22891.
Havecker et al., "The Diversity of LTR Retrotransposons," Genome Biology, 2004, 5:225, 6 pages.
Henderson et al., "Gag proteins of the highly replicative MN strain of human immunodeficiency virus type 1: posttranslational modifications, proteolytic processings, and complete amino acid sequences," Journal of virology, 1992, 66(4):1856-1865.
Heng et al., "Chromatin Loops are Selectively Anchored using Scaffold/matrix-attachment Regions," Journal of Cell Science, 2004, 117(Pt 7):999-1008.
Herbst-Kralovetz et al., "Norwalk Virus-like Particles as Vaccines," Expert review of vaccines, 2010, 9(3):299-307.
Herschhorn et al., "Retroviral reverse transcriptases," Cellular and molecular life sciences, 2010, 67(16):2717-2747.
Herzig et al., "A Novel Leu92 Mutant of HIV-1 Reverse Transcriptase with a Selective Deficiency in Strand Transfer Causes a Loss of Viral Replication," Journal of virology, 2015, 89(16):8119-8129.
Hindi et al., Enveloped viruses pseudotyped with mammalian myogenic cell fusogens target skeletal muscle for gene delivery, Cell, 2023, 186(10):2062-2077.
Hirano et al., "Highly Efficient Retrograde Gene Transfer Into Motor Neurons by a Lentiviral Vector Pseudotyped With Fusion Glycoprotein," PloS One, 2013, 8(9):e75896, 8 pages.
Hirano et al., "Site-specific Recombinases as Tools for Heterologous Gene Integration," Applied Microbiology and Biotechnology, 2011, 92(2):227-239.
HLA-Ligand-Atlas.org [online], "HLA Ligand Atlas—University of Tübingen. Interface Release 0.9.16," Apr. 23, 2021, retrieved on Mar. 12, 2024, retrieved from URL<https://hla-ligand-atlas.org/welcome>, 2 pages.
Ho et al., "Decoupling the Functional Pleiotropy of Stem Cell Factor by Tuning c-Kit Signaling," Cell, 2017, 168(6):1041-1052. e18.
Hohn et al., "CMV-promoter Driven Codon-optimized Expression Alters the Assembly Type and Morphology of a Reconstituted HER V-k(HML-2)," Viruses, 2014, 6(11):4332-4345.
Hong et al., "Novel Recombinant Hepatitis B Virus Vectors Efficiently Deliver Protein and RNA Encoding Genes Into Primary Hepatocytes," Journal of virology, 2013, 87(12):6615-6624.
Hooper et al., The C679X mutation in PCSK9 is Present and Lowers Blood Cholesterol in a Southern African Population, Atherosclerosis, 2007, 193:445-448.
Hou et al., Lipid nanoparticles for mRNA delivery, Nature Reviews Materials, 2021, 6:1078-1094.
Howard et al., "Intracerebral Drug Delivery in Rats With Lesion-induced Memory Deficits," Journal of Neurosurgery, 1989, 71(1):105-112.
Howe et al., "Insertional Mutagenesis Combined with Acquired Somatic Mutations Causes Leukemogenesis Following Gene Therapy of SCID-X1 Patients," Journal of Clinical Investigation, 2008, 118(9):3143-3150.
Hsu et al., "PrimeDesign Software for Rapid and Simplified Design of Prime Editing Guide RNAs," Nature Communications, 2021, 12:1034, 6 pages.
Hu et al., HIV-1 Reverse Transcription. Cold Spring Harbor Perspectives in Medicine, 2012, 2(10):a006882, 23 pages.
Huang et al., "Circularly Permuted and PAM-modified Cas9 Variants Broaden the Targeting Scope of Base Editors," Nature Biotechnology, 2019, 37(6):626-631.
Huang et al., "Precision genome editing using cytosine and adenine base editors in mammalian cells," Nature Protocols, 2021, 16(2):1089-1128.
Hug et al., "Fusogenic Virosomes Prepared by Partitioning of Vesicular Stomatitis Virus G Protein Into Preformed Vesicles," The Journal of Biological Chemistry, 1994, 269(6):4050-4056.
Humbert et al., "Development of Third-generation Cocal Envelope Producer Cell Lines for Robust Lentiviral Gene Transfer Into Hematopoietic Stem Cells and T-cells," Molecular therapy: the Journal of the American Society of Gene Therapy, 2016, 24(7):1237-1246.
Hwang et al., "Engineering a Serum-resistant and Thermostable Vesicular Stomatitis Virus G Glycoprotein for Pseudotyping Retroviral and Lentiviral Vectors," Gene Therapy, 2013, 20(8):807-815.
Hwang et al., "Lineage tracing using a Cas9-deaminase barcoding system targeting endogenous L 1 elements," Nature Communication, 2019, 10:1234, 9 pages.
ICTV.Global [online], "International Committee on Taxonomy of Viruses (ICTV). Genus: Vesiculovirus," accessed Jun. 2023, retrieved

(56) References Cited

OTHER PUBLICATIONS from URL<https://ictv.global/report/chapter/rhabdoviridae/rhabdoviridae/vesiculovirus>, 10 pages.
International Preliminary Report on Patentability in International Appln. No. PCT/US2022/080834, mailed Jun. 13, 2024, 13 pages.
International Preliminary Report on Patentability in International Appln. No. PCT/US2022/080836, mailed Jun. 13, 2024, 13 pages.
International Preliminary Report on Patentability in International Appln. No. PCT/US2022/080856, mailed Jun. 13, 2024, 18 pages.
International Search Report and Written Opinion in International Appln. No. PCT/US2023/085507, mailed Aug. 9, 2024, 31 pages.
International Search Report and Written Opinion in International Appln. No. PCT/US2020/016229, mailed Jun. 19, 2020, 18 pages.
International Search Report and Written Opinion in International Appln. No. PCT/US2022/080834, mailed Apr. 3, 2023, 19 pages.
International Search Report and Written Opinion in International Appln. No. PCT/US2022/080836, mailed Mar. 29, 2023, 19 pages.
International Search Report and Written Opinion in International Appln. No. PCT/US2022/080856, mailed Jul. 24, 2023, 26 pages.
International Search Report and Written Opinion in International Appln. No. PCT/US2023/067140, mailed Feb. 7, 2024, 21 pages.
International Search Report and Written Opinion in International Appln. No. PCT/US2024/033139, mailed Sep. 3, 2024, 12 pages.
Invitation to Pay Additional Fees and, Where Applicable, Protest Fee in International Appln. No. PCT/US2024/033111, mailed Aug. 19, 2024, 4 pages.
Invitation to Pay Additional Fees in International Appln. No. PCT/US2023/067140, mailed Nov. 2, 2023, 2 pages.
Invitation to Pay Additional Fees in International Appln. No. PCT/US2023/085507, mailed Jun. 10, 2024, 4 pages.
Ioannidi et al., "Drag-and-drop genome insertion without DNA cleavage with CRISPR-directed integrases," bioRxiv, posted on Nov. 1, 2021, retrieved from URL<https://www.biorxiv.org/content/10.1101/2021.11.01.466786v1>, 61 pages.
Irion et al., "Identification and targeting of the ROSA26 locus in human embryonic stem cells," Nature Biotechnology, 2007, 25:1477-1482.
Iwai et al., "Highly Efficient Protein Trans-splicing by a Naturally Split DnaE Intein From Nostoc Punctiforme," FEBS letters, 2006, 580(7):1853-1858.
Jacobs, "Determination of the base recognition positions of zinc fingers from sequence analysis," EMBO Journal, 1992, 11(12):4507-4517.
Jang et al., "High-purity Production and Precise Editing of DNA base Editing Ribonucleoproteins," Science Advances, 2021, 7(35):eabg2661, 11 pages.
Jenke et al., "Nuclear Scaffold/matrix Attached Region Modules Linked to a Transcription Unit are Sufficient for Replication and Maintenance of a Mammalian Episome," Proc Natl Acad Sci USA, 2004, 101(31):11322-11327.
Jensen et al., "Proteases of human rhinovirus: role in infection," Methods in Molecular Biology, 2015, 1221:129-141.
Jern et al., "Use of Endogenous Retroviral Sequences (ERVs) and Structural Markers for Retroviral Phylogenetic Inference and Taxonomy," Retrovirology, 2005, 2:50, 12 pages.
Jha et al., "Human Endogenous Retrovirus K106 (HERV-K106) Was Infectious After the Emergence of Anatomically Modern Humans," PLoS One, 2011, 6(5):e20234, 8 pages.
Jiang et al., "An Optimized Method for High-titer Lentivirus Preparations Without Ultracentrifugation," Scientific Reports, 2015, 5:13875, 9 pages.
Jiang et al., "RNA-guided Editing of Bacterial Genomes using CRISPR-Cas Systems," Nature Biotechnology, 2013, 31:233-239.
Jin et al., "Safe Engineering of CAR T Cells for Adoptive Cell Therapy of Cancer Using Long-term Episomal Gene Transfer," EMBO Molecular Medicine, 2016, 8(7):702-711.
Jinek et al., "A Programmable dual-RNA-guided DNA Endonuclease in adaptive Bacterial Immunity," Science, 2012, 337(6096):816-821.
Jo et al., "Deactivation of Akt by a Small Molecule Inhibitor Targeting Pleckstrin Homology Domain and Facilitating Akt Ubiquitination," Proceedings of the National Academy of Sciences of the United States of America, 2011, 108(16):6486-6491.
Jo et al., "Therapeutic Adenine base Editing Corrects Nonsense Mutation and Improves Visual Function in a Mouse Model of Leber Congenital Amaurosis," bioRxiv, posted on Jan. 8, 2021, 19 pages.
Johansson et al., "RNA Recognition by the MS2 Phage Coat Protein," Seminars in Virology, 1997, 8(3):176-185.
Johnson, "Origins and Evolutionary Consequences of Ancient Endogenous Retroviruses," Nature Reviews Microbiology, 2019, 17(6):355-370.
Jorgenson et al., "Foreign Glycoproteins Can Be Actively Recruited to Virus Assembly Sites During Pseudotyping," Journal of Virology, 2009, 83(9):4060-4067.
Joung et al., "TALENs: A Widely Applicable Technology for Targeted Genome Editing," Nature Reviews Molecular Cell Biology, 2013, 14(1):49-55.
June et al., "CAR T Cell Immunotherapy for Human Cancer," Science, 2018, 359(6382):1361-1365.
Kaczorowska et al., "Human Anelloviruses: Diverse, Omnipresent and Commensal Members of the Virome," FEMS Microbiology Reviews, 2020, 44(3):305-313.
Kanai et al., "FAST Proteins: Development and Use of Reverse Genetics Systems for Reoviridae Viruses," Annual Reviews, The Annual Review of Virology, 2021, 8:515-536.
Kang et al., "Chimeric Rabies Virus-like Particles Containing Membrane-anchored GM-CSF Enhances the Immune Response Against Rabies Virus," Viruses, 2015, 7(3):1134-1152.
Kang et al., "Increased Intracellular $Ca^{2+}$ Concentrations Prevent Membrane Localization of Ph Domains Through the Formation of $Ca^{2+}$-phosphoinositides," Proceedings of the National Academy of Sciences of the United States of America, 2017, 114(45):11926-11931.
Kannan et al., "Compact RNA Editors with Small Cas13 Proteins," Nature Biotechnology, 2021,40(2):194-197.
Karikó et al., "Incorporation of Pseudouridine into mRNA Yields Superior Nonimmunogenic Vector with Increased Translational Capacity and Biological Stability," Molecular therapy, 2008, 16(11):1833-1840.
Karimova et al., "CRISPR/Cas9 nickase-mediated disruption of hepatitis B virus open reading frame S and X," Sci Rep., Sep. 2015, 5:13734, 16 pages.
Karpenshif et al., "From yeast to mammals: Recent Advances in Genetic control of Homologous Recombination," DNA Repair (Amst), 2012, 11(10):781-788, 16 pages.
Kato et al., "A lentiviral strategy for highly efficient retrograde gene transfer by pseudotyping with fusion envelope glycoprotein," Human gene therapy, 2011, 22(2):197-206.
Kato et al., "Enhancement of the Transduction Efficiency of a Lentiviral Vector for Neuron-specific Retrograde Gene Delivery Through the Point Mutation of Fusion Glycoprotein Type E," Journal of Neuroscience Methods, 2019, 311:147-155.
Kato et al., "Selective Neural Pathway Targeting Reveals Key Roles of Thalamostriatal Projection in the Control of Visual Discrimination," The Journal of Neuroscience, 2011, 31:17169-17179.
Katz et al., "Membrane Assembly in Vitro: Synthesis, Glycosylation, and Asymmetric Insertion of a Transmembrane Protein," Proceedings of the National Academy of Sciences of the United States of America, 1977, 74(8):3278-3282.
Keijzers et al., "Human Exonuclease 1 (EXO1) Activity Characterization and Its Function on Flap Structures," Bioscience reports, 2015, 35(3):e00206, 13 pages.
Kilbride et al., "Determinants of product topology in a hybrid Cre-Tn3 resolvase site-specific recombination system," J Mol Bio, 2006, 355:185-195.
Kim et al., "Enhancement of Protein Expression By Alphavirus Replicons By Designing Self-replicating Subgenomic RNAs," Proceedings of the National Academy of Sciences of the United States of America, 2014, 111(29):10708-10713.
Kim et al., "Increasing the Genome-targeting Scope and Precision of Base Editing With Engineered Cas9-cytidine Deaminase Fusions," Nature Biotechnology, 2017, 35(4):371-376, 15 pages.

(56) References Cited

OTHER PUBLICATIONS

Kim et al., "Mutational Analysis of Oncogenic Akt E17K Mutation in Common Solid Cancers and Acute Leukaemias," British Journal of Cancer, 2008, 98(9):1533-1535.
Kim et al., "Precision genome engineering with programmable DNA-nicking enzymes," Genome Res., 2012, 22(7):1327-33.
Kisielow et al., "Deciphering CD4+T cell specificity using novel MHC-TCR chimeric receptors," Nature Immunology, 2019, 20:652-662.
Kitamura et al., "Human Endogenous Retrovirus K10 Encodes a Functional Integrase," Journal of Virology, 1996, 70(5):3302-3306.
Klehr et al., "Scaffold-attached Regions from the Human Interferon Beta Domain can be used to Enhance the Stable Expression of Genes Under the Control of Various Promoters," Biochemistry, 1991, 30(5):1264-1270.
Kleinstiver et al., "Engineered CRISPR-Cas12a Variants With Increased Activities and Improved Targeting Ranges for Gene, Epigenetic and Base Editing," Nature Biotechnology, 2019, 37(3):276-282.
Kleinstiver et al., "High-fidelity CRISPR-Cas9 Nucleases With No Detectable Genome-wide Off-target Effects," Nature, 2016, 529(7587):490-495.
Klippel et al., "Isolation and Characterization of Unusual Gin Mutants," The EMBO journal, 1988, 7(12):3983-3989.
Koblan et al., "Improving Cytidine and Adenine Base Editors by Expression Optimization and Ancestral Reconstruction," Nature Biotechnology, 2018, 36(9):843-846, 4 pages.
Koblan et al., "In vivo Base Editing Rescues Hutchinson-Gilford Progeria Syndrome in Mice," Nature, 2021, 589:608-614.
Kohn et al., "Akt, A Pleckstrin Homology Domain Containing Kinase, is Activated Primarily by Phosphorylation," Journal of Biological Chemistry, 1996, 271(36):21920-21926.
Kolb et al., "Click Chemistry: Diverse Chemical Function from a Few Good Reactions," Angewandte Chemie, 2001, 40(11):2004-2021.
Kolykhalov et al., "Specificity of the hepatitis C virus NS3 serine protease: effects of substitutions at the 3/4A, 4A/4B, 4B/5A, and 5A/5B cleavage sites on polyprotein processing," Journal of Virology, 1994, 68(11):7525-7233.
Komor et al., "Improved Base Excision Repair Inhibition and Bacteriophage Mu Gam Protein Yields C:g-to-t:a Base Editors With Higher Efficiency and Product Purity," Science Advances, 2017, 3(8):eaao4774, 9 pages.
Kosicki et al., "Repair of Double-strand Breaks Induced by CRISPR-Cas9 Leads to Large Deletions and Complex Rearrangements," Nature Biotechnology, 2018, 36(8):765-771, 16 pages.
Kosugi et al., "Nuclear Export Signal Consensus Sequences Defined Using a Localization-based Yeast Selection System," Traffic, 2008, 9(12):2053-2062.
Kotewicz et al., "Cloning and Overexpression of Moloney Murine Leukemia Virus Reverse Transcriptase in *Escherichia coli*," Gene, 1985, 35(3):249-258.
Kotewicz et al., "Isolation of Cloned Moloney Murine Leukemia Virus Reverse Transcriptase Lacking Ribonuclease H Activity," Nucleic acids research, 1988, 16(1):265-277.
Kronenberg et al., "A Conformational Change in the Adeno-associated Virus Type 2 Capsid Leads to the Exposure of Hidden VP1 N Termini," Journal of Virology, 2005, 79(9):5296-5303.
Kung et al., "The Role of RNA Editing in Cancer Development and Metabolic Disorders," Frontiers in Endocrinology, 2018, 9(762): 21 pages.
Kushnir et al., "Virus-like Particles as a Highly Efficient Vaccine Platform: Diversity of Targets and Production Systems and Advances in Clinical Development," Vaccine, 2012, 31(1):58-83.
Kuzikov et al., "Identification of Inhibitors of SARS-CoV-2 3CL-Pro Enzymatic Activity Using a Small Molecule in Vitro Repurposing Screen," ACS Pharmacology and Translational Science, 2021, 4(3):1096-1110.
la Cour et al., "NESbase Version 1.0: a Database of Nuclear Export Signals," Nucleic Acids Res, 2003, 31(1):393-396.
Lander et al., "Initial Sequencing and Analysis of the Human Genome," Nature, 2001, 409(6822):860-921.
Langer et al., "Chemical and physical structure of polymers as carriers for controlled release of bioactive agents: a review," Journal of Macromolecular Science-Reviews in Macromolecular Chemistry and Physics, 1983, 23(1):61-126.
Langer, "New methods of drug delivery," Science, 1990, 249(4976):1527-1533.
Lapinaite et al., "DNA capture by a CRISPR-Cas9-guided adenine base editor," Science, 2020, 369(6503):566-571, 14 pages.
Latham et al., "Formation of Wild-type and Chimeric Influenza Virus-like Particles Following Simultaneous Expression of Only Four Structural Proteins," Journal of virology, 2001, 75(13):6154-6165.
Lazzarotto et al.: Change-seq Reveals Genetic and Epigenetic Effects on CRISPR-Cas9 Genome-wide Activity, Nature Biotechnology, 2020, 38:1317-1327, 33 pages.
Lee et al., "Receptor Mediated Uptake of Peptides That Bind the Human Transferrin Receptor," European journal of biochemistry, 2001, 268(7):2004-2012.
Leibowitz et al., "Chromothripsis as an on-target Consequence of CRISPR-Cas9 genome editing," Nat Genet., 2021, 53:895-905, 26 pages.
LeibundGut-Landmann et al., "Mini-review: Specificity and expression of CIITA, the master regulator of MHC class II genes," Eur. J. Immunol., 2004, 34(6):1513-1525.
Lemmon, "Pleckstrin Homology (PH) Domains and Phosphoinositides," Biochemical Soceity Symposium, 2007, 74:81-93.
Levis et al., "Deletion Mapping of Sindbis Virus DI RNAs Derived From cDNAs Defines the Sequences Essential for Replication and Packaging," Cell, 1986, 44(1):137-145.
Levy et al., "Inhibition of Calcification of Bioprosthetic Heart Valves by Local Controlled-release Diphosphonate," Science, 1985, 228(4696):190-192.
Lew et al., "Protein Splicing in Vitro With a Semisynthetic Two-component Minimal Intein," The Journal of biological chemistry, 1998, 273(26):15887-15890.
Li et al., "Directed Evolution of Gold Nanoparticle Delivery to Cells," Chemical communications, 2010, 46(3):392-394.
Li et al., "Expression and Self-Assembly of Empty Virus-Like Particles of Hepatitis E Virus," Journal of Virology, 1997, 71(10):7207-7213.
Li et al., "Safe and Efficient in Vivo Hematopoietic Stem Cell Transduction in Nonhuman Primates Using HDAd5/35++ Vectors. Molecular therapy," Methods & clinical development, 2022, 24:127-141.
Li et al., "Structure and Dynamics of Zika Virus Protease and Its Insights into Inhibitor Design," Biomedicines, 2021, 9(8):1044, 16 pages.
Li et al., "The Importance of Glycans of Viral and Host Proteins in Enveloped Virus Infection," Frontiers in immunology, 2021, 12:638573, 12 pages.
Liao et al., "Physiological Regulation of Akt Activity and Stability," American Journal of Translational Research, 2010, 2(1):19-42.
Lim et al., "Crystal structure of the moloney murine leukemia virus RNase H domain," Journal of virology, 2006, 80(17):8379-8389.
Limberis et al., "AAV6.2: An Efficient and Safe Gene Therapy Clinical Candidate for the Treatment of Cystic Fibrosis Airway Disease," Molecular Therapy, 2007, 15(Suppl 1):S160.
Lin et al., "A Drug-controllable Tag for Visualizing Newly Synthesized Proteins in Cells and Whole Animals," Proceedings of the National Academy of Sciences of the United States of America, 2008, 105(22):7744-7749.
Ling et al., "Lentiviral Delivery of Co-packaged Cas9 mRNA and a Vegfa-targeting Guide RNA Prevents Wet Age-related Macular Degeneration in Mice," Nature Biomedical Engineering, 2021, 5(2):144-156.
Litke et al., "Highly Efficient Expression of Circular RNA Aptamers in Cells Using Autocatalytic Transcripts," Nature Biotechnology, 2019, 37(6):667-675.
Liu et al., "A Split Prime Editor With Untethered Reverse Transcriptase and Circular RNA Template," Nature Biotechnology, 2022, 40(9):1388-1393.

(56) References Cited

OTHER PUBLICATIONS

Liu et al., "Advanced Genetic Tools for Plant Biotechnology," Nature Reviews Genetics, 2013, 14(11):781-793.
Liu et al., "C2c1-sgRNA Complex Structure Reveals RNA-Guided DNA Cleavage Mechanism," Mol Cell., 2017, 65(2):310-322.
Liu et al., "CasX Enzymes Comprise a Distinct Family of Rna-guided Genome Editors," Nature, 2019, 566(7743):218-223.
Liu et al., "Reverse Transcriptase-Mediated Tropism Switching in Bordetella Bacteriophage," Science, 2002, 295(5562):2091-2094.
Lokossou et al., "Implication of Human Endogenous Retrovirus Envelope Proteins in Placental Functions," Viruses, 2014, 6(11):4609-4627.
Loughrey et al., "Non-liver mRNA Delivery," Accounts of chemical research, 2022, 55(1):13-23.
Louis et al., "Cloning and Sequencing of the Cellular-viral Junctions From the Human Adenovirus Type 5 Transformed 293 Cell Line," Virology, 1997, 233(2):423-429.
Lower et al., "The Viruses in All of US: Characteristics and Biological Significance of Human Endogenous Retrovirus Sequences," Proceedings of the National Academy of Sciences of the United States of America, 1996, 93(11):5177-5184.
Lu et al., "Lentiviral Capsid-Mediated *Streptococcus pyogenes* Cas9 Ribonucleoprotein Delivery for Efficient and Safe Multiplex Genome Editing," The CRISPR journal, 2021, 4(6):914-928.
Lu et al., "Prime Editing: An All-Rounder for Genome Editing," International Journal of Molecular Sciences, 2022, 23(17):9862, 15 pages.
Lu et al., "Types of Nuclear Localization Signals and Mechanisms of Protein Import into the Nucleus," Cell Communication Signal, 2021, 19(1):60, 10 pages.
Luan et al., "Reverse Transcription of R2Bm RNA Is Primed by a Nick at the Chromosomal Target Site: A Mechanism for Non-LTR Retrotransposition," Cell, 1993, 72(4):595-605.
Ludwig et al., "Virus-like Particles-universal Molecular Toolboxes," Current opinion in biotechnology, 2007, 18(6):537-545.
Lufino et al., "Advances in High-capacity Extrachromosomal Vector Technology: Episomal Maintenance, Vector Delivery, and Transgene Expression," Molecular Therapy, 2008, 16(9):1525-1538.
Lundin et al., "Endonuclease specificity and sequence dependence of type IIS restriction enzymes," PLoS One, Jan. 2015, 10(1):e0117059, 14 pages.
Lyu et al., "New Advances in Using Virus-like Particles and Related Technologies for Eukaryotic Genome Editing Delivery," International Journal of Molecular Sciences, 2022, 23(15):8750, 17 pages.
Maeder et al., "Development of a Gene-editing Approach to Restore Vision Loss in Leber Congenital Amaurosis Type 10," Nature Medicine, 2019, 25(2):229-233.
Maetzig et al., "Retroviral Protein Transfer: Falling Apart to Make an Impact," Current gene therapy, 2012, 12(5):389-409.
Magin et al., "Corf, the Rev/Rex homologue of HTDV/HER V-K, encodes an arginine-rich nuclear localization signal that exerts a trans-dominant phenotype when mutated," Virology, 2000, 74(1):11-16.
Maguire et al., "Microvesicle-associated AAV Vector as a Novel Gene Delivery System," Molecular Therapy, 2012, 20(5):960-971.
Maheshri et al., "Directed evolution of adeno-associated virus yields enhanced gene delivery vectors", Nature Biotechnology, 2006, 24(2):198-204.
Makarova et al., "An updated evolutionary classification of CRISPR-Cas systems," Nature Reviews Microbiology, 2015, 13:722-736, 31 pages.
Makarova et al., "Evolution and classification of the CRISPR-Cas systems," Nat Rev Microbiol., 2011, 9(6):467-477.
Mali et al., "CAS9 transcriptional activators for target specificity screening and paired nickases for cooperative genome engineering," Nat Biotech., 2013, 31(9):833-838, 17 pages.
Mangeot et al., "A Universal Transgene Silencing Method Based on RNA Interference," Nucleic Acids Research, 2004, 32(12):e102, 6 pages.
Mangeot et al., "Development of Minimal Lentivirus Vectors Derived from Simian Immunodeficiency Virus (SIVmac251) and Their Use for Gene Transfer into Human Dendritic Cells," J. Virol., 2000, 74(18):8307-8315.
Marcu et al., "HLA Ligand Atlas: a benign reference of HLA-presented peptides to improve T-cell-based cancer immunotherapy," J Immunother Cancer, 2021, 9(4):e002071, 18 pages.
Martinez-Escobar et al., "CRISPR-dCas9-Based Artificial Transcription Factors to Improve Efficacy of Cancer Treatment With Drug Repurposing: Proposal for Future Research," Frontiers in Oncology, 2021, 10:604948, 7 pages.
Martins et al., "Improved Integration Time Estimation of Endogenous Retroviruses With Phylogenetic Data," PLoS One, 2011, 6(3):e14745, 6 pages.
Masuda et al., "Specific and Independent Recognition of U3 and U5 att Sites by Human Immunodeficiency Virus Type 1 Integrase in vivo," Journal of Virology, 1998, 72(10):8396-8402.
Mayer et al., "An Almost-intact Human Endogenous Retrovirus K on Human Chromosome 7," Nature Genetics, 1999, 21(3):257-258.
McDonnell et al., "Solution Structure and Dynamics of the Bioactive Retroviral M Domain From Rous Sarcoma Virus," Journal of Molecular Biology, 1998, 279(4):921-928.
Mehta et al., "Immunogenicity of Cas9 Protein," Journal of Pharmaceutical Sciences, 2020, 109(1):62-67.
Meldolesi, "Exosomes and Ectosomes in Intercellular Communication," Current Biology, 2018, 28(8):R435-R444.
Meng et al., "Targeted gene inactivation in zebrafish using engineered zinc finger nucleases," Nat. Biotechnol., Jun. 2008, 26(6):695-701, 17 pages.
Mercuri et al., "Nusinersen versus Sham Control in Later-Onset Spinal Muscular Atrophy," N Engl J Med., 2018, 378:625-635.
Merten et al., "Editorial (Thematic Issue: Proceedings from the EMBO Workshop: "Modern DNA Concepts and Tools for Safe Gene Transfer and Modification")," Curr Gene Ther., 2016, 16(3):153-5.
Merten et al., "Fusoselect: Cell-cell Fusion Activity Engineered by Directed Evolution of a Retroviral Glycoprotein," Nucleic Acids Research, 2006, 34(5):e41, 9 pages.
Metsikkö et al., "Reconstitution of the Fusogenic Activity of Vesicular Stomatitis Virus," The EMBO Journal, 1986, 5(13):3429-3435.
Meunier et al., "Drug-Induced Liver Injury: Biomarkers, Requirements, Candidates, and Validation," Front Pharmacol., 2019, 10:1482, 8 pages.
Mi et al., "Syncytin is a Captive Retroviral Envelope Protein Involved in Human Placental Morphogenesis," Nature, 2000, 403(6771):785-789.
Milanesi et al., "BK Virus-Plasmid Expression Vector That Persists Episomally in Human Cells and Shuttles Into *Escherichia coli*," Molecular and Cellular Biology, 1984, 4(8):1551-1560.
Mills et al., "Protein splicing in trans by purified N- and C-terminal fragments of the Mycobacterium tuberculosis RecA intein," Proceedings of the National Academy of Sciences of the United States of America, 1998, 95(7):3543-3548.
Mingozzi, "AAV Immunogenicity: A Matter of Sensitivity," Molecular Therapy, 2018, 26(10):2335-2336.
Miyado et al., The fusing ability of sperm is bestowed by CD9-containing vesicles released from eggs in mice, Proceedings of the National Academy of Sciences, 2008, 105(35):12921-12926.
Miyanohara, "Preparation of Vesicular Stomatitis Virus-G (VSV-G) Conjugate and Its Use in Gene Transfer," Cold Spring Harbor Protocols, 2012, 2012(4):453-456.
Mock et al., "Novel Lentiviral Vectors With Mutated Reverse Transcriptase for mRNA Delivery of TALE Nucleases," Scientific Reports, 2014, 4:6409, 8 pages.
Moede et al., "Identification of a nuclear localization signal, RRMKWKK, in the homeodomain transcription factor PDX-1," FEBS Lett, 1999, 461(3):229-234.
Mohr et al., "A reverse transcriptase-Cas1 fusion protein contains a Cas6 domain required for both CRISPR RNA biogenesis and RNA spacer acquisition," Molecular cell, 2018, 72(4):700-714.

(56) References Cited

OTHER PUBLICATIONS

Mohr et al., Thermostable group II intron reverse transcriptase fusion proteins and their use in cDNA synthesis and next-generation RNA sequencing, RNA, Jul. 2013, 19(7):958-70.
Monde et al., "Molecular Mechanisms by Which HER V-K Gag Interferes With HIV-1 Gag Assembly and Particle Infectivity," Retrovirology, 2017, 14(1):27, 16 pages.
Monot et al., "The Specificity and Flexibility of L 1 Reverse Transcription Priming at Imperfect T-Tracts," PLOS Genetics, 2013, 9(5):e1003499, 18 pages.
Mselli-Lakhal et al., "Gene Transfer System Derived from the Caprine Arthritis-encephalitis Lentivirus," Journal of Virological Methods, 2006, 136(1-2):177-184.
Murawski et al., "Newcastle Disease Virus-like Particles Containing Respiratory Syncytial Virus G Protein Induced Protection in BALB/c Mice, with no Evidence of Immunopathology," Journal of Virology, 2010, 84(2):1110-1123.
Murphy, "Phage Recombinases and Their Applications," Advances in Virus Research, 2012, 83:367-414.
Musunuru et al., "In vivo CRISPR Base Editing of PCSK9 Durably Lowers Cholesterol in Primates," Nature, 2021, 593(7859):429-434.
Myers et al., "Optimal alignments in linear space," Comput Appl Biosci., 1988, 4(1):11-7.
Naik et al., "Cellular barcoding: a technical appraisal," Experimental Hematology, 2014, 42(8):598-608.
Narwade et al., "Mapping of Scaffold/matrix Attachment Regions in Human Genome: a Data Mining Exercise," Nucleic Acids Research, 2019, 47(14):7247-7261.
Naskalska et al., "Virus Like Particles as Immunogens and Universal Nanocarriers," Polish Journal of Microbiology, 2015, 64 (1):3-13.
Nawaz et al., "Extracellular Vesicles, Tunneling Nanotubes, and Cellular Interplay: Synergies and Missing Links," Front Mol Biosci., Jul. 2017, 4:50, 12 pages.
NCBI.NLM.NIH.gov [online], "Engineered virus-like particles for efficient in vivo delivery of therapeutic proteins," registered Oct. 4, 2021, retrieved on Aug. 15, 2024, retrieved from URL<https://www.ncbi.nlm.nih.gov/bioproject/?term=PRJNA768458>, 1 page.
Needleman et al., "A General Method Applicable to the Search for Similarities in the Amino Acid Sequence of Two Proteins," Journal of Molecular Biology, 1970, 48(3):443-453.
Nègre et al., "Characterization of Novel Safe Lentiviral Vectors Derived from Simian Immunodeficiency Virus (SIVmac251) that Efficiently Transduce Mature Human Dendritic Cells," Gene Ther., 2000, 7(19):1613-1623.
Nelson et al., "Engineered pegRNAs Improve Prime Editing Efficiency," Nature Biotechnology, 2022, 40(3):402-410.
Newby et al., "Base Editing of Haematopoietic Stem Cells Rescues Sickle Cell Disease in Mice," Nature, 2021, 595(7866):295-302.
Newby et al., "In vivo somatic cell base editing and prime editing," Molecular therapy, 2021, 29(11):3107-3124.
Newman et al., "Comprehensive Identification of Human bZIP Interactions with Coiled-coil Arrays," Science, 2003, 300(5628):2097-2101.
Nishida et al., "Targeted Nucelotide Editing Using Hybrid Prokaryotic and Vertebrate Adaptive Immune Systems," Science, 2016, 353(6305):aaf8729, 10 pages.
Norris et al., "A Method for Multiprotein Assembly in Cells Reveals Independent Action of Kinesins in Complex," Journal of Cell Biology, 2014, 207(3):393-406.
Nottingham et al., "RNA-seq of human reference RNA samples using a thermostable group II intron reverse transcriptase," RNA, Apr. 2016, 22(4):597-613.
Noureddine et al., "Engineering of Monosized Lipid-coated Mesoporous Silica Nanoparticles for CRISPR Delivery," Acta Biomaterialia, 2020, 114:358-368.
NovoProLabs.com [online], "Commonly used leader peptide sequences for mammalian cells expression. NovoPro," Apr. 21, 2018, retrieved on Aug. 5, 2024, retrieved from URL<https://www.novoprolabs.com/support/articles/commonly-used-leader-peptide-sequences-for-efficient-secretion-of-a-recombinant-protein-expressed-in-mammalian-cells-201804211337.html>, 3 pages.
Nowak et al., "Structural analysis of monomeric retroviral reverse transcriptase in complex with an RNA/DNA hybrid," Nucleic Acids Res., 2013, 41(6):3874-3887.
Numrych et al., "A comparison of the effects of single-base and triple-base changes in the integrase arm-type binding sites on the site-specific recombination of bacteriophage," Nucleic Acids Res, 1990, 18(13):3953-3959.
O'Carroll et al., "Structural Mimicry Drives HIV-1 Rev-Mediated HER V-K Expression," Journal of Molecular Biology, 2020, 432(24):166711, 43 pages.
Odell et al., "Influence of Membrane Anchoring and Cytoplasmic Domains on the Fusogenic Activity of Vesicular Stomatitis Virus Glycoprotein G," Journal of Virology, 1997, 71(10):7996-8000.
Office Action in Chinese Appln. No. 202080057410.3, dated Jul. 30, 2024, 11 pages (with English translation).
Office Action in Japanese Appln. No. 2021-573607, dated May 28, 2024, 13 pages (with English translation).
Office Action in U.S. Appl. No. 18/158,173, dated Jan. 19, 2024, 7 pages.
Office Action in U.S. Appl. No. 18/158,173, dated Jul. 5, 2024, 9 pages.
Office Action in U.S. Appl. No. 18/158,173, dated Oct. 6, 2023, 11 pages.
Office Action in U.S. Appl. No. 18/351,674, dated Mar. 18, 2024, 15 pages.
Office Action in U.S. Appl. No. 18/351,674, dated Nov. 21, 2023, 17 pages.
Office Action in U.S. Appl. No. 18/351,674, dated Nov. 29, 2023, 18 pages.
Office Action in U.S. Appl. No. 18/351,674, dated Nov. 9, 2023, 14 pages.
Office Action in U.S. Appl. No. 18/351,689, dated Mar. 7, 2024, 9 pages.
Office Action in U.S. Appl. No. 18/351,689, dated Nov. 24, 2023, 12 pages.
Office Action in U.S. Appl. No. 18/351,800, dated Mar. 7, 2024, 11 pages.
Office Action in U.S. Appl. No. 18/351,800, dated Nov. 21, 2023, 14 pages.
Ogasawara et al., "Recombinant Viral-like Particles of Parvovirus B19 as Antigen Carriers of Anthrax Protective Antigen," In Vivo, 2006, 20(3):319-324.
Ogata et al., "Integrase of Human Endogenous Retrovirus K-10 Supports the Replication of Replication-incompetent Int- Human Immunodeficiency Virus Type 1 Mutant," Japanese Journal of Infectious Diseases, 1999, 52(6):251-252.
Ogden et al., "Comprehensive AAV Capsid Fitness Landscape Reveals a Viral Gene and Enables Machine-guided Design," Science, 2019, 366(6469):1139-1143.
Olorunniji et al., "Synapsis and Catalysis by Activated Tn3 Resolvase Mutants," Nucleic acids research, 2008, 36:7181-7191.
Olsen, "Gene Transfer Vectors Derived from Equine Infectious Anemia Virus," Gene Therapy, 1998, 5(11):1481-1487.
Oroszlan et al., "Primary structure and processing of gag and env gene products of human T-cell leukemia viruses HTL V-$I_{CR}$ and HTL V-$I_{ATK}$." Current topics in microbiology and immunology, 1985, 115: 221-33.
Osborn et al., "Base Editor Correction of COL7A1 in Recessive Dystrophic Epidermolysis Bullosa Patient-Derived Fibroblasts and iPSCs," J Invest Dermatol., 2020, 140:338-347.e335, 52 pages.
Oshaben et al., "The native GCN4 leucine-zipper domain does not uniquely specify a dimeric oligomerization state," Biochemistry, Nov. 2012, 51(47):9581-91, 27 pages.
Otomo et al., "Improved Segmental Isotope Labeling of Proteins and Application to a Larger Protein," Journal of Biomolecular NMR, 1999, 4(2):105-114.
Otomo et al., "NMR Observation of Selected Segments in a Larger Protein: Central-segment Isotope Labeling Through Intein-mediated Ligation," Biochemistry, 1999, 38(49):16040-16044.

(56) References Cited

OTHER PUBLICATIONS

Ou et al., "Quantification of Virus-envelope-mediated Cell Fusion Using a Tetracycline Transcriptional Transactivator: Fusion Does Not Correlate With Syncytium Formation," Virology, 2004, 324(2):263-272.
Paces et al., "HER Vd: Database of Human Endogenous Retroviruses," Nucleic Acids Research, 2002, 30(1):205-206.
Packer et al., Methods for the directed evolution of proteins, Nat Rev Genet., 2015, 16(7):379-394.
Pan et al., "Placement of leucine zipper motifs at the carboxyl terminus of HIV-1 protease significantly reduces virion production," PLoS One, 2012, 7(3):e32845, 11 pages.
Pandelakis et al., CRISPR-Based Synthetic Transcription Factors In Vivo: The Future of Therapeutic Cellular Programming, Cell Systems, 2020, 10(1): 14 pages.
Pang et al., "A community-based fitness and mobility exercise program for older adults with chronic stroke: a randomized, controlled trial," J Am Geriatr Soc., 2005, 53(10)1667-1674.
Pang et al., "Retinal degeneration 12 (rd12): a New, Spontaneously Arising Mouse Model for Human Leber Congenital Amaurosis (LCA)," Mol Vis, 2005, 11:152-162, 17 pages.
Partial European Search Report in European Appln. No. 21847293.4, mailed on Aug. 13, 2024, 17 pages.
Passos et al., "Retroviral Integrase: Structure, Mechanism, and Inhibition," Enzymes, 2021, 50:249-300, 47 pages.
Patel et al., "Flap endonucleases pass 5'-flaps through a flexible arch using a disorder-thread-order mechanism to confer specificity for free 5'-ends," Nucleic Acids Res., 2012, 40(10):4507-4519.
Paunovska et al., "Drug delivery systems for RNA therapeutics," Nat. Rev. Genet., 2022, 23:(5):265-280.
Pausch et al., "CRISPR-CasΦ from huge phages is a hypercompact genome editor," Science, 2020, 369(6501): 333-337.
Pausch et al., "DNA interference states of the hypercompact CRISPR-CasΦ effector," Nature Structural & Molecular Biology, 2021, 28(8): 652-661.
Pavlicev et al., "Detecting Endogenous Retrovirus-driven Tissue-specific Gene Transcription," Genome Biology and Evolution, 2015, 7(4):1082-1097.
Petri et al., "Reconstitution Into Liposomes of the Glycoprotein of Vesicular Stomatitis Virus by Detergent Dialysis," Journal of Biological Chemistry, 1979, 254(11):4313-4316.
Petrillo et al., "Cyclosporine H Overcomes Innate Immune Restrictions to Improve Lentiviral Transduction and Gene Editing in Human Hematopoietic Stem Cells," Cell Stem Cell, 2018, 23(6):820-832.
Piccioni et al., "Pooled Lentiviral-Delivery Genetic Screens," Current Protocols in Molecular Biology, 2018, 121:32.1.1-32.1.21.
Pinello et al., "Analyzing CRISPR Genome-editing Experiments With CRISPResso," Nature Biotechnology, 2016, 34(7):695-697.
Pisani et al., "CXCL12-PLGA/Pluronic Nanoparticle Internalization Abrogates CXCR4-Mediated Cell Migration," Nanomaterials (Basel, Switzerland), 2020, 10(11):2304, 19 pages.
Poletti et al., "Designing Lentiviral Vectors for Gene Therapy of Genetic Diseases," Viruses, 2021, 13(8):1526, 14 pages.
Popov et al., "HIV-1 Gag Recruits PACSIN2 to Promote Virus Spreading," Proceedings of the National Academy of Sciences of the United States of America, 2018, 115(27):7093-7098.
ProData.SWMed.edu [online], "NESdb ©. [Website] UT Southwestern Medical Center," updated May 2021, retrieved on Mar. 12, 2024, retrieved from URL<http://prodata.swmed.edu/LRNes/index.php>, 1 page.
Proudfoot et al., "Zinc finger Recombinases with Adaptable DNA Sequence Specificity," PLoS One, 2011, 6(4):e19537, 9 pages.
Przybylowski et al., "Production Scale-up and Validation of Packaging Cell Clearance of Clinical-grade Retroviral Vector Stocks Produced in Cell Factories," Gene Therapy, 2006, 13(1):95-100.
Pushko et al., "Development of Virus-like Particle Technology From Small Highly Symmetric to Large Complex Virus-like Particle Structures," Intervirology, 2013, 56(3):141-165.
Pushko et al., "Replicon-Helper Systems From Attenuated Venezuelan Equine Encephalitis Virus: Expression of Heterologous Genes in Vitro and Immunization Against Heterologous Pathogens in Vivo," Virology, 1997, 239(2):389-401.
Qi et al., "Repurposing CRISPR as an RNA-Guided platform for sequence-specific control of gene expression," Cell, 2013, 152(5):1173-1183, 22 pages.
Qu et al., "Structure and Architecture of Immature and Mature Murine Leukemia Virus Capsids," Proceedings of the National Academy of Sciences of the United States of America, 2018, 115(50):E11751-E11760.
Quan et al., "Influenza M1 VLPs Containing Neuraminidase Induce Heterosubtypic Cross-protection," Virology, 2012, 430(2):127-135.
Raguram et al., "Therapeutic in Vivo Delivery of Gene Editing Agents," Cell, 2022, 185(15):2806-2827.
Ramadan, "Identification and Analysis of the Heparan Sulfate-Binding Domain and Cellular Factors Involved in the Entry of Human Endogenous Retrovirus K HER V-K (HML-2)," Inaugural-Dissertation for the degree of Doctor rerum naturalium, Freie University Berlin, Department of Biology, Chemistry, Pharmacy, Oct. 5, 2022, 156 pages.
Ramirez et al., "Engineered Zinc Finger Nickases Induce Homology-directed Repair With Reduced Mutagenic Effects," Nucleic Acids Research, 2012, 40(12):5560-5568.
Ran et al., "Genome engineering using the CRISPR-Cas9 system," Nature Protocols, 2013, 8(11):2281-2308.
Rao et al., "Large-Scale Phenome-Wide Association Study of PCSK9 Variants Demonstrates Protection Against Ischemic Stroke," Circ Genom Precis Med., 2018, 11:e002162, 8 pages.
Rasmussen et al., "Characterization of Virus-like Particles Produced by a Recombinant Baculovirus Containing the Gag Gene of the Bovine Immunodeficiency-like Virus," Virology, 1990, 178(2):435-451.
Rees et al., "Base editing: precision chemistry on the genome and transcriptome of living cells," Nat Rev Genet., 2018, 19(12):770-788, 41 pages.
Rees et al., "Improving the DNA Specificity and Applicability of Base Editing Through Protein Engineering and Protein Delivery," Nature Communications, 2017, 8:15790, 10 pages.
Renner et al., "A fully automated high-throughput workflow for 3D-based chemical screening in human midbrain organoids," eLife, 2020, 9:e52904, 39 pages.
Resh, "A Myristoyl Switch Regulates Membrane Binding of HIV-1 Gag," Proceedings of the National Academy of Sciences of the United States of America, 2004, 101(2):417-418.
Retroviruses, 1st ed., Coffin et al. (eds)., 1997, Chapter 7, 74 pages.
Reul et al., "Ligand Coupling to the AAV Capsid for Cell-Specific Gene Transfer," Methods in Molecular Biology, 2019, 1950:35-50.
Reynolds et al., "The SARS-CoV-2 Sshhps Recognized by the Papain-like Protease," ACS Infectious Diseases, 2021, 7(6):1483-1502.
Richter et al., "Phage-assisted Evolution of an Adenine Base Editor with Improved Cas Domain Compatibility and Activity," Nature Biotechnology, 2020, 38(7):883-891.
Robinson et al., "Infectious Entry Pathway Mediated by the Human Endogenous Retrovirus K Envelope Protein," Journal of Virology, 2016, 90(7):3640-3649.
Robison et al., "The Membrane-proximal Stem Region of Vesicular Stomatitis Virus G Protein Confers Efficient Virus Assembly," Journal of Virology, 2000, 74(5):2239-2246.
Rodriguez et al., "Minimal 'Self' Peptides That Inhibit Phagocytic Clearance and Enhance Delivery of Nanoparticles," Science, 2013, 339(6122):971-975.
Rohland et al., "Cost-effective, High-throughput DNA Sequencing Libraries for Multiplexed Target Capture," Genome Research, 2012, 22(5):939-946.
Rongrong et al., "Effect of deletion mutation on the recombination activity of Cre recombinase," Acta Biochimica Polonica, 2005, 52(2):541-544.
Rothgangl et al., "In Vivo Adenine Base Editing of Pcsk9 in Macaques Reduces Ld1 Cholesterol Levels," Nat Biotechnol., 2021, 39:949-957.

(56) References Cited

OTHER PUBLICATIONS

Rouet et al., "Receptor-Mediated Delivery of CRISPR-Cas9 Endonuclease for Cell-Type-Specific Gene Editing," Journal of the American Chemical Society, 2018, 140(21):6596-6603.

Rousseau, "Engineering Virus-Like Particles for the Delivery of Genome Editing Enzymes," Thesis for the degree of Doctor of Philosophy, University of Michigan, Biological Chemistry, 2022, 172 pages.

Rowland et al., "Regulatory Mutations in Sin Recombinase support a structure-based model of the Synaptosome," Molecular Microbiology, 2009, 74:282-298.

Rust et al., "Envelope-Specific Adaptive Immunity following Transplantation of Hematopoietic Stem Cells Modified with VSV-G Lentivirus," Molecular Therapy Methods & Clinical Development, 2020, 19:438-446.

Sack et al., "Sources of Error in Mammalian Genetic Screens," G3, 2016, 6(9):2781-2790.

Saenz et al., "Feline immunodeficiency virus-based lentiviral vectors," Cold Spring Harbor protocols, 2012, 2012(1):71-76.

Saenz et al., "Production and harvest of feline immunodeficiency virus-based lentiviral vector from cells grown in T75 tissue-culture flasks," Cold Spring Harbor Protocols, 2012, 1:124-125.

Saenz et al., "Production, harvest, and concentration of feline immunodeficiency virus-based lentiviral vector from cells grown in CF10 or CF2 devices," Cold Spring Harbor Protocols, 2011, 1:118-123.

Sago et al., "High-throughput in Vivo Screen of Functional mRNA Delivery Identifies Nanoparticles for Endothelial Cell Gene Editing," Proceedings of the National Academy of Sciences of the United States of America, 2018, 115(42):E9944-E9952.

Sakuma et al., "MMEJ-assisted Gene Knock-in Using TALENs and CRISPR-Cas9 With the PITCh Systems," Nature Protocols, 2016, 11(1):118-133.

Sander et al., "CRISPR-Cas Systems for Editing, Regulating and Targeting Genomes," Nature Biotechnology, 2014, 32(4):347-355.

Sang et al., "A unique uracil-DNA binding protein of the uracil DNA glycosylase superfamily," Nucleic Acids Res., 2015, 43(17):8452-8463.

Sanjana et al., "Improved vectors and genome-wide libraries for CRISPR screening," Nat. Methods, 2014, 11(8):783-784.

Sansbury et al., "Understanding the Diversity of Genetic Outcomes From CRISPR-Cas Generated Homology-directed Repair," Communications Biology, 2019, 2:458, 10 pages.

Sapir et al., Viral and Developmental Cell Fusion Mechanisms: Conservation and Divergence, Developmental Cell, 2008, 14(1): 11-21.

Sapranauskas et al., The *Streptococcus* thermophilus CRISPR/Cas system provides immunity in *Escherichia coli*, Nucleic Acids Res, 2011, 39: 9275-9282.

Sastry et al., "Evaluation of Plasmid DNA Removal From Lentiviral Vectors by Benzonase Treatment," Human Gene Therapy, 2004, 15(2):221-226.

Saudek et al., "A preliminary trial of the programmable implantable medication system for insulin delivery," The New England Journal of Medicine, 1989, 321(9):574-579.

Schäfer et al., "A Novel Siglec-4 Derived Spacer Improves the Functionality of CAR T Cells Against Membrane-proximal Epitopes," Frontiers in Immunology, 2020, 11:1704, 18 pages.

Scharenberg et al., Genome engineering with TAL-effector nucleases and alternative modular nuclease technologies, Current Gene Therapy, 2013, 13(4):291-303.

Schauber-Plewa et al., "Complement Regulatory Proteins are Incorporated Into Lentiviral Vectors and Protect Particles Against Complement Inactivation," Gene Therapy, 2005, 12(3):238-245.

Schellenberger et al., "A recombinant polypeptide extends the in vivo half-life of peptides and proteins in a tunable manner," Nat Biotech., 2009, 27:1186-1190.

Schiller et al., "Tunneling nanotubes enable intercellular transfer of MHC class I molecules," Human Immunology, Apr. 2013, 74(4):412-416.

Scholefield et al., Prime Editing—An Update on the Field, Gene Therapy, 2021, 28(7-8):396-401.

Scott et al., "Production of Cyclic Peptides and Proteins in Vivo," Proceedings of the National Academy of Sciences of the United States of America, 1999, 96(24):13638-13643.

Sefton, "Implantable Pumps," Critical Reviews in Biomedical Engineering, 1987, 14(3):201-240, 41 pages.

Segel et al., "Mammalian Retrovirus-like Protein PEG10 Packages Its Own mRNA and Can Be Pseudotyped for mRNA Delivery," Science, 2021, 373(6557):882-889.

Selyutina et al., "Nuclear Import of the HIV-1 Core Precedes Reverse Transcription and Uncoating," Cell Reports, 2020, 32(13):108201, 17 pages.

Sera, "Zinc-Finger-based Artificial Transcription Factors and Their Applications," Advanced Drug Delivery Reviews, 2009, 61(7-8):513-26.

Serreze et al., "Major histocompatibility complex class I-deficient NOD-B2m$^{null}$ mice are diabetes and insulitis resistant," Diabetes, 1994, 43:505-509.

Services.HealthTech.dtu.dk [online], "NESbase 1.0," retrieved on Mar. 12, 2024, retrieved from URL<https://services.healthtech.dtu.dk/datasets/NESbase-1.0/>, 3 pages.

Shah et al., "Protospacer Recognition Motifs: Mixed Identities and Functional Diversity," RNA Biology, 2013, 10(5):891-899.

Shaikh et al., "Chimeras of the Flp and Cre Recombinases: Tests of the mode of cleavage by Flp and Cre," Journal of Molecular Biology, 2000, 302:27-48.

Sharma et al., "Noninfectious Virus-like Particles Produced by Moloney Murine Leukemia Virus-based Retrovirus Packaging Cells Deficient in Viral Envelope Become Infectious in the Presence of Lipofection Reagents," Proceedings of the National Academy of Sciences of the United States of America, 1997, 94(20):10803-10808.

Shechner et al., "Multiplexable, locus-specific targeting of long RNAs with CRISPR-Display," Nature methods, 2015, 12(7):664-670.

Shen et al., "SeqKit: A Cross-Platform and Ultrafast Toolkit for FASTA/Q File Manipulation," PLoS one, 2016, 11(10):e0163962, 10 pages.

Sheridan et al., "Generation of Retroviral Packaging and Producer Cell Lines for Large-scale Vector Production and Clinical Application: Improved Safety and High Titer," Molecular Therapy, 2000, 2(3):262-275.

Shin et al., "Human-specific HER V-K Insertion Causes Genomic Variations in the Human Genome," PLoS One, 2013, 8(4):e60605, 10 pages.

Shingledecker et al., "Molecular dissection of the Mycobacterium tuberculosis RecA intein: design of a minimal intein and of a trans-splicing system involving two intein Fragments," Gene, 1998, 207(2):187-195.

Shirley et al., "Immune Responses to Viral Gene Therapy Vectors," Molecular therapy, 2020, 28(3):709-722.

Shmakov et al., "Discovery and Functional Characterization of Diverse Class 2 CRISPR-Cas Systems," Molecular Cell, 2015, 60:385-397.

Shtyrya et al., "Influenza virus neuraminidase: structure and function," Acta naturae, 2009, 1(2):26-32.

SigmaAldrich.com [online], "SimpliconTM Expression System: Designing, Cloning and RNA Synthesis for Expression of Self-Replicative RNA—Catalog No. SCR724, SCR725, SCR726, SCR727, SCR728, SCR729," May 2018, retrieved on Aug. 23, 2024, retrieved from URL<https://www.sigmaaldrich.com/deepweb/assets/sigmaaldrich/product/documents/252/611/scr726-manual.pdf>, 48 pages.

Silva et al., Meganucleases and Other Tools for Targeted Genome Engineering: Perspectives and Challenges for Gene Therapy, Curr Gene Ther., 2011, 11(1):11-27.

Smith et al., "Diversity in the Serine Recombinases," Molecular Microbiology, 2002, 44(2):299-307.

Sockolosky et al., "Fusion of a Short Peptide That Binds Immunoglobulin G to a Recombinant Protein Substantially Increases Its Plasma Half-life in Mice," PLoS One, 2014, 9(7):e102566, 10 pages.

(56) References Cited

OTHER PUBLICATIONS

Sodi et al., RPE65-Associated Inherited Retinal Diseases: Consensus Recommendations for Eligibility to Gene Therapy, Orphanet J Rare Dis., 2021, 16:257, 11 pages.
Soldi et al., "Laboratory-Scale Lentiviral Vector Production and Purification for Enhanced Ex Vivo and in Vivo Genetic Engineering," Molecular Therapy Methods & Clinical Development, 2020, 19:411-425.
Song et al., Large-Fragment Deletions Induced by Cas9 Cleavage while Not in the BEs System, Mol Ther Nucleic Acids, 2020, 21:523-526.
Soo et al., "Nanoparticle Tracking Analysis Monitors Microvesicle and Exosome Secretion From Immune Cells," Immunology, 2012, 136(2):192-197.
Southworth et al., "Control of Protein Splicing by Intein Fragment Reassembly," EMBO Journal, 1998, 17(4):918-926.
Spisák et al., "Causel: an epigenome- and genome-editing pipeline for establishing function of noncoding GWAS variants," Nat Med, Nov. 2015, 21(11): 1357-63, 25 pages.
Stadtmauer et al., "CRISPR-engineered T cells in patients with refractory cancer," Science, 2020, 367(6481):eaba7365, 20 pages.
Stahnke et al., "Intrinsic Phospholipase A2 Activity of Adeno-associated Virus is Involved in Endosomal Escape of Incoming Particles," Virology, 2011, 409(1):77-83.
Stamos et al., "Structure of a thermostable group II intron reverse transcriptase with template-primer and its functional and evolutionary implications," Molecular cell, 2017, 68(5): 926-939.
Stavrou et al., "Episomal vectors based on S/MAR and the β-globin Replicator, encoding a synthetic transcriptional activator, mediate efficient γ-globin activation in haematopoietic cells," Scientific Reports, 2019, 9:19765, 16 pages.
Steele-Ogus et al., "Disc and Actin Associated Protein 1 influences attachment in the intestinal parasite Giardia lamblia," PLoS Pathogens, 2022, 18(3):e1010433, 22 pages.
Stein et al., "Human endogenous retroviruses: our genomic fossils and companions," Physiol Genomics, 2023, 55:249-258.
Sternberg et al., "DNA Interrogation by the CRISPR RNA-Guided Endonuclease Cas9," Nature, 2014, 507(7490):62-67, 16 pages.
Strobel et al., "A Small-Molecule-Responsive Riboswitch Enables Conditional Induction of Viral Vector-Mediated Gene Expression in Mice," ACS Synthetic Biology, 2020, 9(6):1292-1305.
Subramanian et al., "Identification, Characterization, and Comparative Genomic Distribution of the HER V-K (HML-2) Group of Human Endogenous Retroviruses," Retrovirology, 2011, 8:90, 22 pages.
Sugita et al., "Screening of peptide ligands that bind to the Fc region of IgG using peptide array and its application to affinity purification of antibody," Biochemical Engineering Journal, 2013, 79:33-40.
Suh et al., Restoration of Visual Function in Adult Mice With an Inherited Retinal Disease via Adenine Base Editing, Nat Biomed Eng, 2021, 5(2):169-178.
Sun et al., "Reconstructed glycosylase base editors GBE2.0 with enhanced C-to-G base editing efficiency and purity," Mol Ther., 2022, 30(7):2452-2463.
Suresh et al., "Bispecific Monoclonal Antibodies From Hybrid Hybridomas," Methods in Enzymology, 1986, 121:210-228.
Swiech et al., "In vivo interrogation of gene function in the mammalian brain using CRISPR-Cas9," Nature biotechnology, 2015, 33(1): 102-106, 22 pages.
Tabebordbar et al., "Directed Evolution of a Family of AAV Capsid Variants Enabling Potent Muscle-directed Gene Delivery Across Species," Cell, 2021, 184(19):4919-4938.
Tague et al., "Chemogenetic Control of Gene Expression and Cell Signaling With Antiviral Drugs," Nature Methods, 2018, 15(7):519-522.
Taha et al., "Real E. Upstream of N-Ras (Unr/CSDE1) Interacts with NCp7 and Gag, Modulating HIV-1 IRES-Mediated Translation Initiation," Viruses, 2022, 14(8):1798, 21 pages.

Takahashi et al., "Induction of Pluripotent Stem Cells From Mouse Embryonic and Adult Fibroblast Cultures by Defined Factors," Cell, 2006, 126(4):663-676.
TakaraBio.com [online], "Guide-it™ CRISPR/Cas9 Gesicle Production System User Manual. Cat. Nos. 632612, 632613, 632616 (May 30, 2017)," 2017, retrieved on Mar. 13, 2024, retrieved from URL<https://www.takarabio.com/documents/User%20Manual/Guide/Guide-it%20CRISPR-Cas9%20Gesicle%20Production%20System%20User%20Manual_053017.pdf>, 23 pages.
Takematsu et al., "Transmembrane Stem Cell Factor Protein Therapeutics Enhance Revascularization in Ischemia Without Mast Cell Activation," Nature communications, 2022, 13(1):2497, 13 pages.
Takeuchi et al., "Redesign of extensive protein-DNA interfaces of meganucleases using iterative cycles of in vitro compartmentalization," PNAS, Mar. 2014, 111(11):4061-4066.
Taube et al., "Reverse Transcriptase of Mouse Mammary Tumour Virus: Expression in Bacteria, Purification and Biochemical Characterization," The Biochemical Journal, 1998, 329(3):579-587.
Taylor, "Ocular immune privilege," Eye (Lond)., 2009, 23:1885-1889.
Telesnitsky et al., "RNase H domain mutations affect the interaction between Moloney murine leukemia virus reverse transcriptase and its primer-template," PNAS USA, 1993, 90(4):1276-1280.
Termini et al., Tetraspanins Function as Regulators of Cellular Signaling. Frontiers in Cell and Developmental Biology, 2017, 5:34, 14 pages.
Thomas et al., "CD90-Targeted Cocal-Pseudotyped Lentivirus as a Robust Platform for Human HSC Gene Therapy," Blood, 2023, 142:2254, 2 pages.
Thompson et al., "Long Terminal Repeats: From Parasitic Elements to Building Blocks of the Transcriptional Regulatory Repertoire," Molecular Cell Review, 2016, 62(5):766-776.
Thompson et al., "SYNZIP Protein Interaction Toolbox: in Vitro and in Vivo Specifications of Heterospecific Coiled-coil Interaction Domains," ACS Synthetic Biology, 2012, 1(4):118-129.
Thorne et al., in Vivo Diffusion Analysis With Quantum Dots and Dextrans Predicts the Width of Brain Extracellular Space, Proc Natl Acad Sci USA, 2006, 103:5567-5572.
Tinland et al., "The T-DNA-linked VirD2 Protein Contains Two Distinct Functional Nuclear Localization Signals," Proceedings of the National Academy of Sciences, 1992, 89(16):7442-7446.
Tirumalai et al., "The recognition of core-type DNA sites by lambda integrase," J Mol Biol., 1998, 279:513-527.
Tomé-Amat et al., "Secreted Production of Assembled Norovirus Virus-like Particles from Pichia Pastoris," Microbial Cell Factories, 2014, 13:134, 9 pages.
Toonen et al., "Intracerebroventricular Administration of a 2'-O-Methyl Phosphorothioate Antisense Oligonucleotide Results in Activation of the Innate Immune System in Mouse Brain," Nucleic Acid Therapeutics, 2018, 28(2):63-73.
Trobridge et al., "Cocal-pseudotyped Lentiviral Vectors Resist Inactivation by Human Serum and Efficiently Transduce Primate Hematopoietic Repopulating Cells," Molecular Therapy, 2010, 18(4):725-733.
Truebestein et al., "Coiled-coils: the Long and Short of It," BioEssays, 2016, 38(9):903-916.
Truong et al., "Development of an Intein-mediated Split-Cas9 System for Gene Therapy," Nucleic Acids Research, 2015, 43(13):6450-6458.
Tsai et al., "Amplification-free, CRISPR-Cas9 Targeted Enrichment and SMRT Sequencing of Repeat-Expansion Disease Causative Genomic Regions," bioRxiv, posted Oct. 16, 2017, 26 pages.
Tsai et al., "CIRCLE-seq: a Highly Sensitive in Vitro Screen for Genome-wide CRISPR-Cas9 nuclease off-targets," Nat Methods, 2017, 14:607-614, 10 pages.
Tsuchida et al., Chimeric CRISPR-CasX enzymes and guide RNAs for improved genome editing activity, Molecular Cell, 2022, 82(6):1199-1209, 28 pages.
Tsutakawa et al., "Human flap endonuclease structures, DNA double-base flipping, and a unified understanding of the FENI superfamily," Cell, 2011, 145(2):198-211.

(56) References Cited

OTHER PUBLICATIONS

Turan et al., "Site-specific Recombinases: From Tag-and-target- to Tag-and-exchange-based Genomic Modifications," FASEB journal, 2011, 25(12):4088-4107.
Turchiano et al., "Quantitative evaluation of chromosomal rearrangements in gene-edited human stem cells by CAST-Seq," Cell Stem Cell, 2021, 28:1136-1147.e5.
Tycko et al., "High-Throughput Discovery and Characterization of Human Transcriptional Effectors," Cell, 2020, 183(7):2020-2035.
Urnov et al., "Genome editing with engineered zinc finger nucleases," Nature Reviews Genetics, 2010, 11:636-646.
Van Dongen et al., "Extracellular Vesicles Exploit Viral Entry Routes for Cargo Delivery," Microbiology and Molecular Biology Reviews: MMBR, 2016, 80(2):369-386.
Van Duyne, "Teaching Cre to follow directions," Proc Natl Acad Sci USA, 2009, 106(1):4-5.
van Haasteren et al., "The Delivery Challenge: Fulfilling the Promise of Therapeutic Genome Editing," Nature biotechnology, 2020, 38(7):845-855.
Vandenberghe et al., "Heparin Binding Directs Activation of T Cells Against Adeno-associated Virus Serotype 2 Capsid," Nature Medicine, 2006, 12(8):967-971.
Várnai et al., "Visualization of Phosphoinositides That Bind Pleckstrin Homology Domains: Calcium- and Agonist-induced Dynamic Changes and Relationship to Myo-[$^3$H]inositol-labeled Phosphoinositide Pools," J Cell Biol., 1998, 143(2):501-510.
Veletanlic et al., "Multiple rotavirus species encode fusion-associated small transmembrane (FAST) proteins with cell type-specific activity," bioRxiv, posted Apr. 8, 2023, 46 pages.
Venken et al., "Genome-wide manipulations of Drosophila melanogaster with transposons, Flp recombinase, and ΦC31 integrase," Methods in Molecular Biology, 2012, 859:203-228.
Verhoeyen et al., "Novel Lentiviral Vectors Displaying "Early-acting Cytokines" Selectively Promote Survival and Transduction of NOD/SCID Repopulating Human Hematopoietic Stem Cells," Blood, 2005, 106(10):3386-3395.
Verma, "The reverse transcriptase," Biochim Biophys Acta., 1977, 473:1-38.
Voigtlander et al., "A Novel Adenoviral Hybrid-vector System Carrying a Plasmid Replicon for Safe and Efficient Cell and Gene Therapeutic Applications," Molecular Therapy-Nucleic Acids, 2013, 2(4):e83, 14 pages.
Voisset et al., "Phylogeny of a Novel Family of Human Endogenous Retrovirus Sequences, HER V-W, in Humans and Other Primates," Aids Research and Human Retroviruses, 1999, 15(17):1529-1533.
von Heijne, "A new method for predicting signal sequence cleavage sites," Nucleic Acids Research, 1986, 14(11):4683-4690.
Vonkova et al., "Lipid Cooperativity as a General Membrane-Recruitment Principle for PH Domains," Cell Reports, 2015, 12(9):1519-1530.
Vu et al., "Engineering of a Stable Retroviral Gene Delivery Vector by Directed Evolution," Molecular therapy, 2008, 16(2):308-314.
Wahlfors et al., "Evaluation of Recombinant Alphaviruses as Vectors in Gene Therapy," Gene Therapy, 2000, 7(6):472-480.
Walpita et al., "Mammalian Cell-derived Respiratory Syncytial Virus-like Particles Protect the Lower as well as the Upper Respiratory Tract," PLoS One, 2015, 10(7):E0130755, 18 pages.
Wang et al., "Anchoring of Actin to the Plasma Membrane Enables Tension Production in the Fission Yeast Cytokinetic Ring," Molecular Biology of the Cell, 2019, 30(16):2053-2064.
Wang et al., "Characterization of an Mps I-h Knock-in Mouse That Carries a Nonsense Mutation Analogous to the Human Idua-w402x Mutation," Mol Genet Metab., 2010, 99:62-71.
Wang et al., "Directed Evolution: Methodologies and Applications," Chemical reviews, 2021, 121(20):12384-12444, 61 pages.
Wang et al., "Shortened nuclear matrix attachment regions are sufficient for replication and maintenance of episomes in mammalian cells," Molecular Biology of the Cell, 2019, 30(22): 2737-2857.
Wang et al., "Tangential Flow Microfiltration for Viral Separation and Concentration," Micromachines, 2019, 10(5):320, 13 pages.

Wang et al., "Virus-like Particles for the Prevention of Human Papillomavirus-associated Malignancies," Expert Review of Vaccines, 2013, 12(2): 129-141.
Warren et al., "A chimeric cre recombinase with regulated directionality," Proc Natl Acad Sci USA, 2008, 105(47):18278-18283.
Warren et al., "Mutations in the amino-terminal domain of lambda-integrase have differential effects on integrative and excisive recombination," Molecular Microbiology, 2005, 55(4):1104-1112.
Webber et al., "Highly efficient multiplex human T cell engineering without double-strand breaks using Cas9 base editors," Nat Commun., 2019, 10:5222, 10 pages.
Wei et al., "Delivery of Tissue-Targeted Scalpels: Opportunities and Challenges for In Vivo CRISPR/Cas-Based Genome Editing," ACS nano, 2020, 14(8):9243-9262.
Wei et al., "Systemic Nanoparticle Delivery of CRISPR-Cas9 Ribonucleoproteins for Effective Tissue Specific Genome Editing," Nature communications, 2020, 11(1):3232, 12 pages.
Weldon et al., "Characterization of a Small (25-kilodalton) Derivative of the Rous Sarcoma Virus Gag Protein Competent for Particle Release," Journal of Virology, 1993, 67(9):5550-5561.
Welsh et al., "FCMPASS Software Aids Extracellular Vesicle Light Scatter Standardization," Cytometry Part A, 2020, 97(6):569-581.
Wickramasinghe et al., "Tangential Flow Microfiltration and Ultrafiltration for Human Influenza a Virus Concentration and Purification," Biotechnology and Bioengineering, 2005, 92(2):199-208.
Wildschutte et al., "Discovery of Unfixed Endogenous Retrovirus Insertions in Diverse Human Populations," Proceedings of the National Academy of Sciences of the United States of America, 2016, 113(16):E2326-E2334.
Wolff et al., "Delivering Genes With Human Immunodeficiency Virus-Derived Vehicles: Still State-of-the-Art After 25 Years," Journal of Biomedical Science, 2022, 29:79, 22 pages.
Wong et al., "Genetic Modification of Dividing Cells Using Episomally Maintained S/MAR DNA Vectors," Molecular Therapy-Nucleic Acids, 2013, 2(8):e115, 12 pages.
Wu et al., "Effect of genome size on AAV vector packaging," Mol Ther., 2010, 18:80-86.
Wu et al., "Protein trans-splicing and functional mini-inteins of a cyanobacterial dnaB intein," Biochim Biophys Acta, 1998, 1387(1-2):422-32.
Xiong et al., "Origin and Evolution of Retroelements Based Upon their Reverse Transcriptase Sequences," The EMBO Journal, 1990, 9(10):3353-3362.
Xu et al., "NESdb: A Database of NES-containing CRM1 Cargoes," Molecular Biology of the Cell, 2012, 23(18):3673-3676.
Xu et al., "piggyBac mediates efficient in vivo CRISPR library screening for tumorigenesis in mice," Proceedings of the National Academy of Sciences, 2017, 114(4):722-727.
Xu et al., "Sequence and Structural Analyses of Nuclear Export Signals in the NESdb Database," Molecular Biology of the Cell, 2012, 23(18):3677-3693.
Yamano et al., "Crystal structure of Cpf1 in complex with guide RNA and target DNA," Cell, 2016, 165(4): 949-962.
Yamazaki et al., "Segmental Isotope Labeling for Protein NMR Using Peptide Splicing," Journal of the American Chemical Society, 1998, 120(22):5591-5592.
Yang et al., "HIV-1 Virus-like Particles Produced by Stably Transfected Drosophila S2 Cells: a Desirable Vaccine Component," Journal of virology, 2012, 86(14):7662-7676.
Yang et al., "PAM-Dependent Target DNA Recognition and Cleavage by C2cl CRISPR-Cas Endonuclease," Cell, 2016, 167(7):1814-1828.e12.
Yarnall et al., "Drag-and-drop genome insertion of large sequences without double-strand DNA cleavage using CRISPR-directed integrases," Nature Biotechnology, 2023, 41:500-512.
Yee et al., "A General Method for the Generation of High-titer, Pantropic Retroviral Vectors: Highly Efficient Infection of Primary Hepatocytes," Proceedings of the National Academy of Sciences, 1994, 91(20):9564-9568.
Yeh et al., "In vivo base editing of post-mitotic sensory cells," Nat Commun., 2018, 9(1):2184, 10 pages.

(56) References Cited

OTHER PUBLICATIONS

Yeh et al., "In Vivo Base Editing Restores Sensory Transduction and Transiently Improves Auditory Function in a Mouse Model of Recessive Deafness," Sci Transl Med., 2020, 12(546):eaay9101, 13 pages.
Yi et al., "Expression and Phylogenetic Analyses of Human Endogenous Retrovirus HC2 Belonging to the HER V-T Family in Human Tissues and Cancer Cells," Journal of Human Genetics, 2007, 52(4):285-296.
Yim et al., "Exosome Engineering for Efficient Intracellular Delivery of Soluble Proteins Using Optically Reversible Protein-protein Interaction Module," Nature Communications, 2016, 7:12277, 9 pages.
Yin et al., "Hepatitis A Virus Picornain 3C," Handbook of Proteolytic Enzymes, 2013, Chapter 542:2417-2423.
Yu et al., "Cytosine Base Editors With Minimized Unguided DNA and RNA Off-target Events and High on-target Activity," Nat Commun., 2020, 11:2052, 10 pages.
Yu et al., "Engineered cell entry links receptor biology with single-cell genomics," Cell, 2022, 185:4904-4920.
Yu et al., "The zinc finger of nucleocapsid protein of Friend murine leukemia virus is critical for proviral DNA synthesis in vivo," Journal of virology, 1996, 70(9):5791-5798.
Zábranský et al., "Identification of a Minimal HIV-1 Gag Domain Sufficient for Self-Association," Virology, 2002, 294(1):141-150.
Zalatan et al., "Engineering complex synthetic transcriptional programs with CRISPR RNA scaffolds," Cell, 2015, 160(1-2):339-350.
Zaslavskiy et al., "Efficient Design of Meganucleases Using a Machine Learning Approach," BMC Bioinformatics, 2014, 15 (191): 11 pages.
Závada, "The Pseudotypic Paradox," Journal of General Virology, 1982, 63(Pt 1):15-24.
Zeltins, "Construction and Characterization of Virus-Like Particles: A Review," Mol Biotechnol., 2013, 53:92-107.
Zeng et al., Therapeutic base editing of Human Hematopoietic Stem Cells, Nat Med., 2020, 26:535-541.
Zhang et al., "Conditional Gene Manipulation: Cre-ating a new Biological Era," Journal of Zhejiang University Science B, 2012, 13(7):511-524.
Zhang et al., "Optogenetic Control with a Photocleavable Protein, PhoCl," Nature Methods, 2017, 14(4):391-394.
Zhang et al., "Stabilized plasmid-lipid particles for regional gene therapy: formulation and transfection properties," Gene Therapy, 1999, 6:1438-1447.
Zhang et al., "Transduction of Bone-marrow-derived Mesenchymal Stem Cells by Using Lentivirus Vectors Pseudotyped With Modified Rd114 Envelope Glycoproteins," Journal of Virology, 2004, 78(3):1219-1229.
Zhao et al., "An ultraprocessive, accurate reverse transcriptase encoded by a metazoan group II intron,," RNA, 2018, 24(2):183-195.
Zhao et al., "Crystal structures of a group II intron maturase reveal a missing link in spliceosome evolution," Nature structural & molecular biology, 2016, 23(6):558-565.
Zheng et al., "Development of a flexible split prime editor using truncated reverse transcriptase," bioRxiv, posted Aug. 29, 2021, 16 pages.
Zhong et al., "Seven Novel Variants Expand the Spectrum of Rpe65-related Leber Congenital Amaurosis in the Chinese Population," Mol Vis., 2019, 25:204-214.
Zhu et al., "An engineered leucine zipper a position mutant with an unusual three-state unfolding pathway," Protein Sci., Jan. 2001, 10(1):24-33.
Zhu et al., "Guide RNAs with embedded barcodes boost CRISPR-pooled screens," Genome Biology, 2019, 20:20, 12 pages.
Zimmerberg et al., How proteins produce cellular membrane curvature, Nature Reviews Molecular Cell Biology, 2006, 7(1):9-19.
Zimmerly et al., "An Unexplored Diversity of Reverse Transcriptases in Bacteria," Microbiology spectrum, 2015, 3(2):MDNA3-0058-2014, 16 pages.
Zimmerly et al., "Group II Intron Mobility Occurs by Target DNA-primed Reverse Transcription," Cell, 1995, 82(4):545-554.
Zincarelli et al., "Analysis of AAV Serotypes 1-9 Mediated Gene Expression and Tropism in Mice After Systemic Injection," Molecular Therapy, 2008, 16(6):1073-1080.
Zufferey et al.: Woodchuck hepatitis virus posttranscriptional regulatory element enhances expression of transgenes delivered by retroviral vectors, Journal of Virology, 1999, 73(4):2886-2892.
Zuker et al., "Optimal computer folding of large RNA sequences using thermodynamics and auxiliary information," Nucleic Acids Res., 1981, 9:133-148.
Akinc et al., "Targeted Delivery of RNAi Therapeutics with Endogenous and Exogenous Ligand-Based Mechanisms," Molecular Therapy, Jul. 2010, 18(7):1357-1364.
Apolonia et al., "Stable Gene Transfer to Muscle Using Non-integrating Lentiviral Vectors," Molecular Therapy, 2007, 15(11):1947-1954.
Argaw et al., "In Vivo Targeting of Lentiviral Vectors Pseudotyped With the Tupaia Paramyxovirus H Glycoprotein Bearing a Cell-specific Ligand," Molecular Therapy Methods & Clinical Development, 2021, 24:21:670-680.
Ausubel et al., "Production of CGMP-Grade Lentiviral Vectors," BioProcess International, 2012, 10(2):32-48.
Breakefield et al., "Gesicles: Microvesicle "Cookies" for Transient Information Transfer Between Cells," Molecular Therapy, 2011, 19(9):1574-1576.
Cai et al., "Lentiviral Delivery of Proteins for Genome Engineering," Current Gene Therapy, 2016, 16:194-206.
Ciechonska et al., "Reovirus Fast proteins: virus-encoded cellular fusogens," Trends in Microbiology, 2014, 22(12):715-724.
Cocucci et al., "Shedding microvesicles: artifacts No. more," Trends Cell Biol., 2009, 19(2):43-51.
Coquin, "Characterization of lentiviral vectors pseudotyped with murine syncytins and their cellular targets in vitro and in vivo," Thesis for the degree of Doctor of Philosophy, University of Évry Val d'Essonne, Defense on Dec. 10, 2019, 238 pages (with English abstract).
Cornelis et al., "Retro-viral envelope gene captures and syncytin exaptation for placentation in marsupials," PNAS USA, 2015, 112:E487-E496.
Duncan, "Fusogenic Reoviruses and Their Fusion-Associated Small Transmembrane (FAST) Proteins," Annual Review of Virology, 2019, 6(1):341-363.
Fenard et al., "Vectofusin-1, a New Viral Entry Enhancer, Strongly Promotes Lentiviral Transduction of Human Hematopoietic Stem Cells," Molecular Therapy Nucleic Acids, 2013, 2(5):e90, 10 pages.
György et al., "Extracellular vesicles: nature's nanoparticles for improving gene transfer with adeno-associated virus vectors," Wires Nanomedicine and Nanobiotechnology, 2018, 10(3):e1488, 13 pages.
Hamilton et al., "Knocking Out Barriers to Engineered Cell Activity," Science, 2020, 367(6481):976-977.
Hare et al., "A novel co-crystal structure affords the design of gain-of-function lentiviral integrase mutants in the presence of modified PSIP1/LEDGF/p75," PLoS Pathog., Jan. 2009, 5(1):e1000259, 12 pages.
Hellmund et al., "Coordination of Genomic RNA Packaging With Viral Assembly in HIV-1," Viruses, 2016, 8(7):192, 13 pages.
Katane et al., "Factors Affecting the Direct Targeting of Murine Leukemia Virus Vectors Containing Peptide Ligands in the Envelope Protein," European Molecular Biology Organization Reports, 2002, 3(9):899-904.
Kim et al., "Mechanism of Membrane Fusion Induced By Vesicular Stomatitis Virus G Protein," Proceedings of the National Academy of Sciences of the United States of America, 2017, 114(1):E28-E36.
Lavillette et al., "The envelope glycoprotein of human endogenous retrovirus type W uses a divergent family of amino acid transporters/cell surface receptors," J. Virol., 2002, 76(13):6442-6452.
Lee et al., "Adenovirus-Mediated Gene Delivery: Potential Applications for Gene and Cell-Based Therapies in the New Era of Personalized Medicine," Genes Dis., 2017, 4(2):42-63.
Lin et al., "Enhanced homology-directed human genome engineering by controlled timing of CRISPR/Cas9 delivery," eLife, 2014, 3:e04766, 13 pages.

(56) References Cited

OTHER PUBLICATIONS

Lyu et al., "Virus-Like Particle Mediated CRISPR/Cas9 Delivery for Efficient and Safe Genome Editing," Life, Dec. 2020, 10(12):366, 16 pages.
McCullough et al., "Structures, Functions, and Dynamics of ESCRT-III/Vps4 Membrane Remodeling and Fission Complexes," Annual Review of Cell and Developmental Biology, 2018, 34:85-109.
Montagna et al., "VSV-G-Enveloped Vesicles for Traceless Delivery of CRISPR-Cas9," Molecular Therapy Nucleic Acids, 2018, 12:453-462, 26 pages (with Supplementary Information).
Naldini et al., "In vivo gene delivery and stable transduction of nondividing cells by a lentiviral vector," Science, 1996, 272:263-7.
Nesbitt, "Targeted Intracellular Therapeutic Delivery Using Liposomes Formulated with Multifunctional FAST proteins," Thesis for the Degree of Master of Science, The University of Western Ontario, 2012; Electronic Thesis and Dissertation Repository, 388, 126 pages.
Nightingale et al., "Transient Gene Expression by Nonintegrating Lentiviral Vectors," Molecular Therapy, 2006, 13(6):1121-1132.
Ortinski et al., "Integrase-deficient Lentiviral Vector as an All-in-one Platform for Highly Efficient CRISPR/Cas9-mediated Gene Editing," Molecular Therapy Methods & Clinical Development, 2017, 5:153-164, 17 pages (with Supplementary Information).
Park et al., "Sendai Virus, An RNA Virus With No Risk of Genomic Integration, Delivers CRISPR/Cas9 for Efficient Gene Editing," Molecular Therapy Methods & Clinical Development, 2016, 24(3): 9 pages.
Robert et al., "Virus-Like Particles Derived from HIV-1 for Delivery of Nuclear Proteins: Improvement of Production and Activity by Protein Engineering," Molecular Biotechnology, 2017, 59(1):9-23.
Sabnis et al., "A Novel Amino Lipid Series for mRNA Delivery: Improved Endosomal Escape and Sustained Pharmacology and Safety in Non-human Primates," Molecular Therapy, 2018, 26:1509-1519.
Scholz et al., "Analysis of human immunodeficiency virus matrix domain replacements," Virology, 2008, 371:322-335.
Sette et al., "The ESCRT-associated protein Alix recruits the ubiquitin ligase Nedd4-1 to facilitate HIV-1 release through the LYPXnL L domain motif," J Virol., Aug. 2010, 84(16):8181-92.
Top et al., "Liposome Reconstitution of a Minimal Protein-mediated Membrane Fusion Machine," The EMBO Journal, 2005, 24(17):2980-2988.
Vance et al., Virus and eukaryote fusogen superfamilies, Current Biology Magazine, Jul. 2020, 30:R750-R754.
Verghese et al., "S/MAR sequence confers long-term mitotic stability on non-integrating lentiviral vector episomes without selection," Nucleic Acids Res., 2014, 42(7):e53, 13 pages.
Vijayraghavan and Kantor, "A Protocol for the Production of Integrase-deficient Lentiviral Vectors for CRISPR/Cas9-mediated Gene Knockout in Dividing Cells," J Vis Exp., Dec. 2017, 12(130):56915, 8 pages.
Zuris et al., "Cationic Lipid-mediated Delivery of Proteins Enables Efficient Protein-based Genome Editing in Vitro and in Vivo," Nature Biotechnology, 2015, 33(1):73-80, 59 pages (with Supplementary Information).
Abudayyeh et al., "A cytosine deaminase for programmable single-base RNA editing," Science, Jul. 2019, 365(6451):382-386, 9 pages.
Akhoundi et al., "CAR T cell therapy as a promising approach in cancer immunotherapy: challenges and opportunities," Cell Oncol (Dordr)., 2021, 44(3):495-523, 29 pages.
Baeumler et al., "Engineering Synthetic Signaling Pathways with Programmable dCas9-Based Chimeric Receptors," Cell Rep., Sep. 2017, 20(11):2639-2653.
Barnea et al., "The genetic design of signaling cascades to record receptor activation," Proc. Natl. Acad. Sci., 2008, 105(1):64-69.
Benmebarek et al., "Killing Mechanisms of Chimeric Antigen Receptor (CAR) T Cells," Int J Mol Sci., Mar. 2019, 20(6):1283, 21 pages.

Bluestone et al., "Type 1 diabetes immunotherapy using polyclonal regulatory T cells," Sci. Transl. Med., Nov. 2015, 7(315):315ra189, 15 pages.
Borchardt et al., "Inducing circular RNA formation using the CRISPR endoribonuclease Csy4," RNA, May 2017, 23(5):619-627.
Brenner et al., "Synthetic biology: Sensing with modular receptors," Nature Chemical Biology, 2017, 13:131-132.
Chang and Chen, "CARs: Synthetic Immunoreceptors for Cancer Therapy and Beyond," Trends in Molecular Medicine, 2017, 23(5):430-450.
Cokol et al., "Finding nuclear localization signals.," EMBO Rep., Nov. 2000, 1(5):411-415.
Damo et al., "Inducible de novo expression of neoantigens in tumor cells and mice," Nat Biotechnol., Jul. 2020, 39(1):64-73, 26 pages.
Daringer et al., "Modular Extracellular sensor architecture for engineering mammalian cell-based devices," ACS Synth. Biol., 2014, 3(12):892-902.
Davenport et al., "Chimeric antigen receptor T cells form nonclassical and potent immune synapses driving rapid cytotoxicity," Proc Natl Acad Sci U S A, Feb. 2018, 115(9):E2068-E2076; Erratum in: Proc Natl Acad Sci U S A, May 2019, 116(22):11075-11076; 11 pages.
Dobbins et al., "Binding of the cytoplasmic domain of CD28 to the plasma membrane inhibits Lck recruitment and signaling," Sci. Signal., Jul. 2016, 9(438):ra75, 13 pages.
Freitas and Cunha, "Mechanisms and signals for the nuclear import of proteins," Curr Genomics, Dec. 2009, 10(8):550-557.
Gramespacher et al., "Intein 7ymogens: Conditional Assembly and Splicing of Split Inteins via Targeted Proteolysis," J Am Chem Soc., Jun. 2017, 139(24):8074-8077.
Gramespacher et al., "Proximity Induced Splicing Utilizing Caged Split Inteins," J Am Chem Soc., Sep. 2019, 141(35):13708-13712.
Gray et al., "Activation of specific apoptotic caspases with an engineered small-molecule-activated protease," Cell, Aug. 2010, 142(4):637-46.
Han et al., "Masked Chimeric Antigen Receptor for Tumor-Specific Activation," Mol. Ther., 2017, 25(1):274-284.
Harris and Kranz, "Adoptive T Cell Therapies: A Comparison of T Cell Receptors and Chimeric Antigen Receptors," Trends in Pharmacological Sciences, Mar. 2016, 37(3):220-230, 11 pages.
Joseph et al., "The calcium feedback loop and T cell activation: how cytoskeleton networks control intracellular calcium flux," Biochim Biophys Acta., Feb. 2014, 1838(2):557-68.
Levy et al., "Cytosine and adenine base editing of the brain, liver, retina, heart and skeletal muscle of mice via adeno-associated viruses," Nature Biomedical Engineering, 2020, 4:97-110.
Liang and Wilusz, "Short intronic repeat sequences facilitate circular RNA production," Genes Dev., Oct. 2014, 28(20):2233-47.
Lyubchenko et al., "Role of Calcium Influx in Cytotoxic T Lymphocyte Lytic Granule Exocytosis during Target Cell Killing," Immunity, Nov. 2001, 15(5):847-59.
Martínez-Lostao et al., "How Do Cytotoxic Lymphocytes Kill Cancer Cells?," Clin Cancer Res., Nov. 2015, 21(22):5047-56.
Maude et al., "Managing cytokine release syndrome associated with novel T cell-engaging therapies," Cancer Journal, 2014, 20(2):119-22.
Nissim et al., "Multiplexed and programmable regulation of gene networks with an integrated RNA and CRISPR/Cas toolkit in human cells," Mol Cell., May 2014, 54(4):698-710.
Office Action in Chinese Appln. No. 202080057410.3, mailed on Jan. 23, 2024, 9 pages (with English translation).
Office Action in Chinese Appln. No. 202080057410.3, mailed on Jun. 29, 2023, 13 pages (with English translation).
Orengo et al., "A bichromatic fluorescent reporter for cell-based screens of alternative splicing," Nucleic Acids Res., 2006, 34(22):e148, 10 pages.
Pinto et al., "An expanded library of orthogonal split inteins enables modular multi-peptide assemblies," Nat Comm., Mar. 2020, 11:1529, 16 pages.
Romano et al., "Treg therapy in transplantation: a general overview," Transplant International, 2017, 30(8):745-753.

(56) References Cited

OTHER PUBLICATIONS

Roybal et al., "Engineering T Cells with Customized Therapeutic Response Programs Using Synthetic Notch Receptors," Cell, 2016, 167(2):419-432, 31 pages.
Ryu et al., "Adenine base editing in mouse embryos and an adult mouse model of Duchenne muscular dystrophy," Nat Biotechnol., Jul. 2018, 36(6):536-539, 7 pages.
Salter et al., "Phosphoproteomic analysis of chimeric antigen receptor signaling reveals kinetic and quantitative differences that affect cell function," Sci. Signal., Aug. 2018, 11(544):eaat6753, 18 pages.
Sanchez and Ting, "Directed evolution improves the catalytic efficiency of TEV protease," Nat Methods, Feb. 2020, 17(2):167-174, 15 pages.
Sanchez et al., "Transcriptional readout of neuronal activity via an engineered $Ca^{2+}$-activated protease," Proc Natl Acad Sci U S A, Dec. 2020, 117(52):33186-96.
Schwarz et al., "Rewiring human cellular input-output using modular extracellular sensors," Nat. Chem. Biol., 2017, 13:202-209, 9 pages.
Stage et al., "Inhibition of the hammerhead ribozyme by neomycin," RNA, Mar. 1995, 1(1):95-101.
Stains et al., "A general approach for receptor and antibody-targeted detection of native proteins utilizing split-luciferase reassembly," ACS Chem. Biol., 2010, 5(10):943-952, 10 pages.
Stein and Alexandrov, "Protease-based synthetic sensing and signal amplification," PNAS, Nov. 2014, 111(45):15934-15939.
Tang et al., "Aptazyme-embedded guide RNAs enable ligand-responsive genome editing and transcriptional activation," Nat Commun., Jun. 2017, 8:15939, 8 pages.
Taylor et al., "A DNA-Based T Cell Receptor Reveals a Role for Receptor Clustering in Ligand Discrimination," Cell, 2017, 169(1):108-19.e20, 33 pages.
Wehr et al., "Analysis of transient phosphorylation-dependent protein-protein interactions in living mammalian cells using split-TEV," BMC Biotechnol., 2008, 8:55, 15 pages.
Wehr et al., "Monitoring regulated protein-protein interactions using split TEV," Nat Methods., Dec. 2006, 3(12):985-93.
Weissman et al., "Molecular cloning and chromosomal localization of the human T-cell receptor zeta chain: distinction from the molecular CD3 complex," Proc. Natl. Acad. Sci., 1988, 85(24):9709-13.
Wong et al., "Engineering a Dual Small Molecule Gated ZAP70 Switch in T Cells," ACS Synth Biol., 2018, 7(4):969-77.
Xu et al., "Regulation of T cell receptor activation by dynamic membrane binding of the CD3epsilon cytoplasmic tyrosine-based motif," Cell., Nov. 2008, 135(4):702-13.
Younis et al., "Rapid-response splicing reporter screens identify differential regulators of constitutive and alternative splicing," Mol Cell Biol., Apr. 2010, 30(7):1718-28.
Zetsche et al., "A Split-cas9 Architecture for Inducible Genome Editing and Transcription Modulation," Nature Biotechnology, 2015, 33(2):139-142.
Zhang et al., "Basic residues in the T-cell receptor ζ cytoplasmic domain mediate membrane association and modulate signaling," Proc Natl Acad Sci U S A, Nov. 2011, 108(48):19323-8.
Zhong et al., "Chimeric antigen receptors combining 4-1BB and CD28 signaling domains augment $PI_3$ kinase/AKT/Bcl-$X_L$ activation and $CD8^+$T cell-mediated tumor eradication," Mol. Ther., 2010, 18(2):413-420.
An et al., "442. The Human Endogenous Retrovirus HERV-W Envelope Glycoprotein Forms Pseudotypes with HIV-1 Vectors," Molecular Therapy, May 2002, 5(5): S144.
Office Action in Chinese Appln. No. 202080057410.3, mailed on Feb. 18, 2025, 13 pages (with English translation).
Office Action in Japanese Appln. No. 2021-573607, mailed on Mar. 4, 2025, 8 pages (with English translation).
Office Action in U.S. Appl. No. 17/617,490, mailed on Mar. 14, 2025, 15 pages.
Tönjes et al., "Characterization of human endogenous retrovirus type K virus-like particles generated from recombinant baculoviruses," Virology, Jul. 1997, 233(2):280-91.

\* cited by examiner

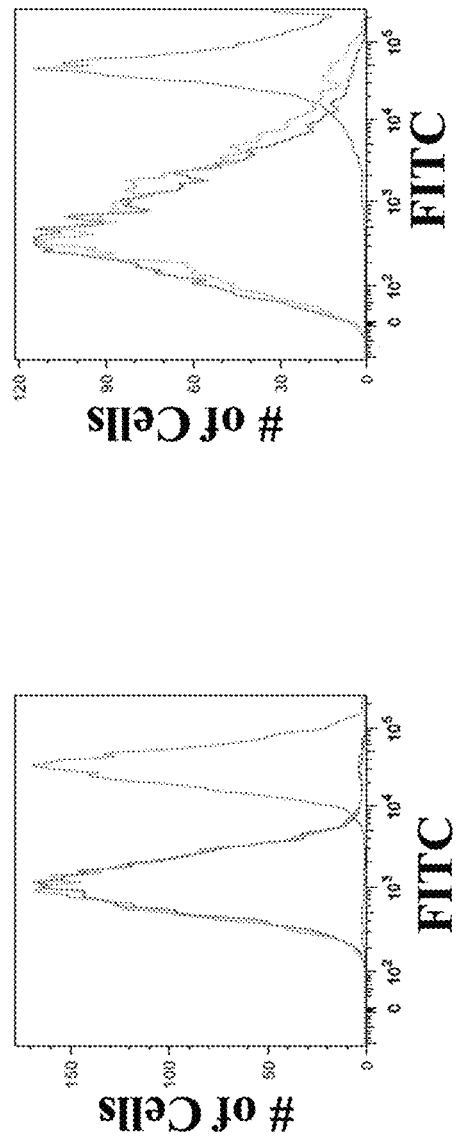
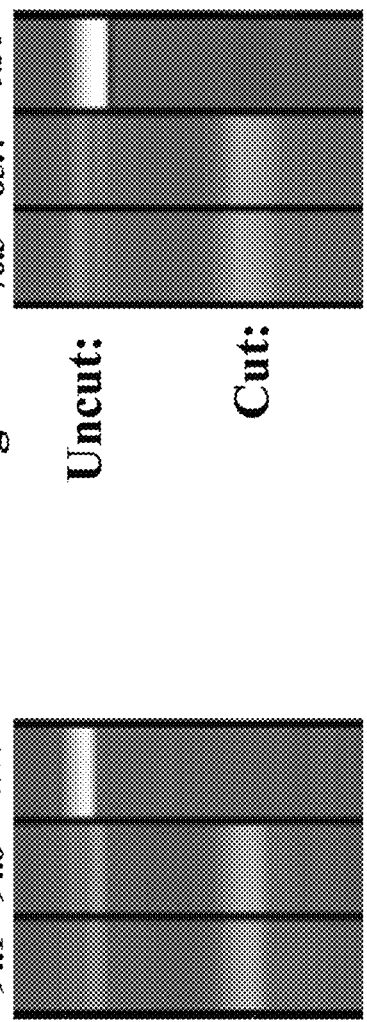
FIG. 5A
FIG. 5B

VEGF site #3

HEK site #3

ENHANCED VIRUS-LIKE PARTICLES AND METHODS OF USE THEREOF FOR DELIVERY TO CELLS

CLAIM OF PRIORITY

This application is a continuation of International Patent Application No. PCT/US2021/043151, filed on Jul. 26, 2021, which claims the benefit of U.S. Provisional Patent Application Ser. No. 63/056,125, filed on Jul. 24, 2020. The entire contents of the foregoing are hereby incorporated by reference.

FEDERALLY SPONSORED RESEARCH OR DEVELOPMENT

This invention was made with Government support under Grant No. GM118158 awarded by the National Institutes of Health. The Government has certain rights in the invention.

SEQUENCE LISTING

This application contains a Sequence Listing that has been submitted electronically as an XML file named "29539-0358001_SL_ST26.XML." The XML file, created on Jan. 18, 2023, is 268,384 bytes in size. The material in the XML file is hereby incorporated by reference in its entirety.

TECHNICAL FIELD

Described herein are enhanced virus-like particles (eVLPs), comprising a membrane comprising a phospholipid bilayer with one or more virally-derived glycoproteins on the external side; and a cargo disposed in the core of the eVLP on the inside of the membrane, wherein the eVLP does not comprise a protein from any human endogenous or exogenous viral gag or pol, and methods of use thereof for delivery of the cargo to cells.

BACKGROUND

Delivery of cargo such as proteins, nucleic acids, and/or chemicals into the cytosol of living cells has been a significant hurdle in the development of biological therapeutics.

SUMMARY

Described herein are enhanced virus-like particles (eVLPs) that are capable of packaging and delivering a wide variety of payloads, e.g., biomolecules including nucleic acids (DNA, RNA) or proteins, chemical compounds including small molecules, and/or other molecules, and any combination thereof, into eukaryotic cells. The non-viral eVLP systems described herein have the potential to be simpler, more efficient and safer than conventional, artificially-derived lipid/gold nanoparticles and viral particle-based delivery systems, at least because eVLPs have no virus-derived components except for ENV, eVLPs can utilize but do not require chemical-based dimerizers, and eVLPs have the ability to package and deliver specialty single and/or double-stranded DNA molecules (e.g., plasmid, mini circle, closed-ended linear DNA, AAV DNA, episomes, bacteriophage DNA, homology directed repair templates, etc.), single and/or double-stranded RNA molecules (e.g., single guide RNA, prime editing guide RNA, messenger RNA, transfer RNA, long non-coding RNA, circular RNA, RNA replicon, circular or linear splicing RNA, micro RNA, small interfering RNA, short hairpin RNA, piwi-interacting RNA, toehold switch RNA, RNAs that can be bound by RNA binding proteins, bacteriophage RNA, internal ribosomal entry site containing RNA, etc.), proteins, chemical compounds and/or molecules, and combinations of the above listed cargos (e.g. AAV particles). The eVLPs described herein are different from conventional retroviral particles, virus-like particles (VLPs), exosomes and other previously described extracellular vesicles that can be loaded with cargo because of the membrane configuration, vast diversity of possible cargos that are enabled by novel, innovative loading strategies, the lack of a limiting DNA/RNA length constraint, the lack of proteins derived from any viral gag or pol, and the mechanism of cellular entry.

Described herein are compositions and methods for cargo delivery that can be used with a diverse array of protein and nucleic acid molecules, including genome editing, epigenome modulation, transcriptome editing and proteome modulation reagents, that are applicable to many disease therapies.

Thus, provided herein are eVLPs that include a membrane comprising a phospholipid bilayer with one or more virally-derived glycoproteins (e.g., as shown in Table 1) on the external side; and optionally a cargo disposed in the core of the eVLP on the inside of the membrane, wherein the eVLP does not comprise any gag and/or pol protein.

Also provided herein are methods for delivering a cargo to a target cell, e.g., a cell in vivo or in vitro. The methods include contacting the cell with an eVLP as described herein comprising the biomolecule and/or chemical as cargo.

Additionally provided herein are methods for producing an eVLP, e.g., comprising a biomolecular cargo. The methods include providing a cell expressing one or more virally-derived glycoproteins (ENV) (e.g., as shown in Table 1), and a cargo biomolecule and/or chemical, wherein the cell does not express an exogenous gag and/or pol protein; and maintaining the cell under conditions such that the cells produce eVLPs.

In some embodiments, the methods include harvesting and optionally purifying and/or concentrating the produced eVLPs.

In some embodiments, the methods include using cells that have or have not been manipulated to express any exogenous proteins except for an ENV (e.g., as shown in Table 1), and, if desired, a plasma membrane recruitment domain (e.g., as shown in Table 6). In this embodiment, the "empty" particles that are produced can be loaded with cargo by utilizing nucleofection, lipid, polymer, or $CaCl_2$ transfection, sonication, freeze thaw, and/or heat shock of purified particles mixed with cargo. In all embodiments, producer cells do not express any viral gag protein. This type of loading allows for cargo to be unmodified by fusions to plasma membrane recruitment domains and represents a significant advancement from previous VLP technology.

Also provided herein are cells expressing one or more virally-derived glycoproteins (e.g., as shown in Table 1), and a cargo, wherein the cell does not express an exogenous gag protein. In some embodiments, the cells are primary or stable human cell lines, e.g., Human Embryonic Kidney (HEK) 293 cells or HEK293 T cells.

In some embodiments, the outer surface of the particle could contain scFvs, nanobodies, darpins, and/or other targeting peptides to enable cell-specific entry.

In some embodiments, the biomolecule cargo is a therapeutic or diagnostic protein or nucleic acid encoding a therapeutic or diagnostic protein.

In some embodiments, the cargo is a chemical compound or molecule.

In some embodiments, the chemical molecule is a trigger for protein-protein dimerization of multimerization, such as the A/C heterodimerizer or rapamycin.

In some embodiments, the chemical compound is a DNA PK inhibitor, such as M3814, NU7026, or NU7441 which potently enhance homology directed repair gene editing.

In some embodiments, the cargo is a gene editing reagent.

In some embodiments, the gene editing reagent comprises a zinc finger (ZF), transcription activator-like effector (TALE), and/or CRISPR-based genome editing or modulating protein; a nucleic acid encoding a zinc finger (ZF), transcription activator-like effector (TALE), and/or CRISPR-based genome editing or modulating protein; or a ribonucleoprotein complex (RNP) comprising a CRISPR-based genome editing or modulating protein.

In some embodiments, the gene editing reagent is selected from the proteins listed in Tables 2, 3, 4 & 5.

In some embodiments, the gene editing reagent comprises a CRISPR-based genome editing or modulating protein, and the eVLP further comprises one or more guide RNAs that bind to and direct the CRISPR-based genome editing or modulating protein to a target sequence.

In some embodiments, the cargo comprises a covalent or non-covalent connection to a plasma membrane recruitment domain, preferably as shown in Table 6. Covalent connections, for example, can include direct protein-protein fusions generated from a single reading frame, inteins that can form peptide bonds, other proteins that can form covalent connections at R-groups and/or RNA splicing. Non-covalent connections, for example, can include DNA/DNA, DNA/RNA, and/or RNA/RNA hybrids (nucleic acids base pairing to other nucleic acids via hydrogen-bonding interactions), protein domains that dimerize or multimerize with or without the need for a chemical compound/molecule to induce the protein-protein binding, single chain variable fragments, nanobodies, affibodies, proteins that bind to DNA and/or RNA, proteins with quaternary structural interactions, optogenetic protein domains that can dimerize or multimerize in the presence of certain light wavelengths, and/or naturally reconstituting split proteins.

In some embodiments, the cargo comprises a fusion to a dimerization domain or protein-protein binding domain that may or may not require a molecule to trigger dimerization or protein-protein binding.

In some embodiments, the producer cells are FDA-approved cells lines, allogenic cells, and/or autologous cells derived from a donor.

In some embodiments, the full or active peptide domains of human CD47 may be incorporated in the eVLP surface to reduce immunogenicity.

Examples of AAV proteins included here are AAV REP 52, REP 78, and VP1-3. The capsid site where proteins can be inserted is T138 starting from the VP1 amino acid counting. Dimerization domains could be inserted at this point in the capsid, for instance.

Examples of dimerization domains included here that may or may not need a small molecule inducer are dDZF1, dDZF2, DmrA, DmrB, DmrC, FKBP, FRB, GCN4 scFv, 10x/24x GCN4, GFP nanobody and GFP.

Examples of split inteins included here are Npu DnaE, Cfa, Vma, and Ssp DnaE.

Examples of other split proteins included here that make a covalent bond together are Spy Tag and Spy Catcher.

Examples of RNA binding proteins included here are MS2, Com, and PP7.

Examples of synthetic DNA-binding zinc fingers included here are ZF6/10, ZF8/7, ZF9, MK10, Zinc Finger 268, and Zinc Finger 268/NRE.

Examples of proteins that multimerize as a result of quaternary structure included here are *E. coli* ferritin, and the other chimeric forms of ferritin.

Examples of optogenetic "light-inducible proteins" included here are Cry2, CIBN, and Lov2-Ja.

Examples of peptides the enhance transduction included here are L17E, Vectofusin, KALA, and the various forms of nisin.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 5A-B: Exemplary T1eVLP-delivered spCas9 genome editing in vitro. A) U2OS eGFP and HEK293 eGFP cell lines transduced with VLPs containing Rous sarcoma virus gag fused to spCas9 and sgRNA, T1eVLPs containing PLC pleckstrin homology (PH) fused to spCas9 and sgRNA, or VLPs containing Rous sarcoma virus gag fused to the SV40 nuclear localization sequence (NLS) and sgRNA. The sgRNA targets GFP. Flow cytometry or T7E1 is performed 72 hours after transduction. The Rous sarcoma virus gag VLPs serve as controls. B) T7E1 analysis of a subpopulation of U2OS or 293 cells from the experiment in FIG. 5A. eVLPs and VLPs are pseudotyped with VSVG.

FIG. 8 discloses SEQ ID NO: 186.

FIG. 9 discloses SEQ ID NO: 183.

FIG. 10 discloses SEQ ID NOS 184, 184 and 184, respectively, in order of appearance.

FIG. 11 discloses SEQ ID NOS 185, 185 and 185, respectively, in order of appearance.

FIGS. 16-40: Schematic illustrations of various exemplary eVLP configurations and possible cargo.

DETAILED DESCRIPTION

Figure 1:
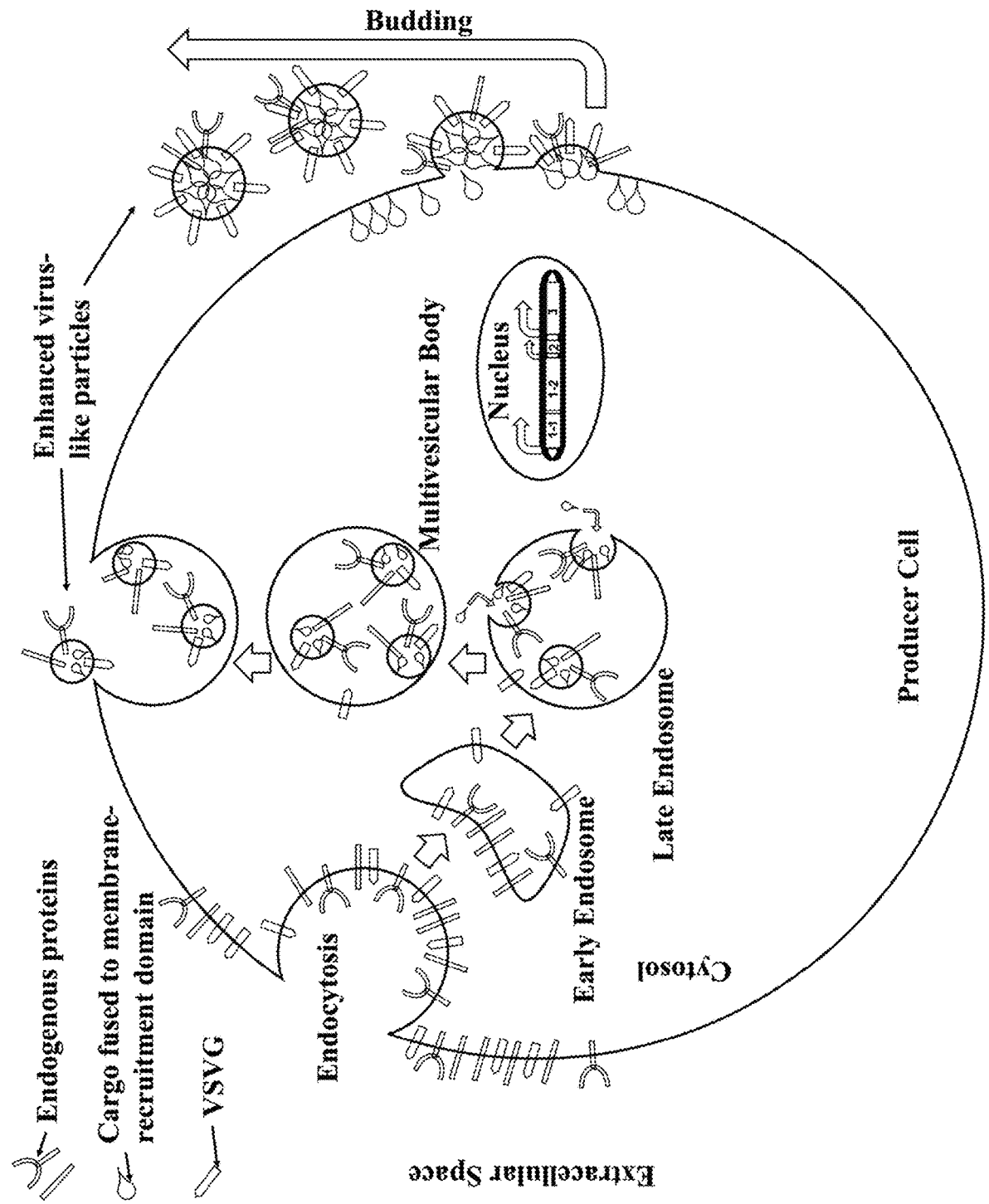
FIG. 1: Depiction of exemplary T2eVLP/T4eVLP production and transduction for RNP/protein delivery. All eVLP expression constructs are stably integrated in the genome of the producer cell. Construct 1-1 corresponds to the phospholipid bilayer recruitment domain. 1-2 corresponds to the cargo. 2 corresponds to an optional guide RNA. 1-1 and 1-2 is translated in the cytosol where it complexes with guide RNA before it is recruited to the phospholipid bilayer. 3 corresponds to a virally-derived glycoprotein (VSVG). The virally-derived glycoprotein is expressed as a transmembrane protein on the plasma membrane and helps to drive budding of cargo-containing eVLPs from the plasma membrane to extracellular space. These particles are purified and are able to fuse with target cells and deliver cargo by interacting with surface receptors at the target cell surface.

Therapeutic proteins and nucleic acids hold great promise, but for many of these large biomolecules delivery into cells is a hurdle to clinical development. Genome editing reagents such as zinc finger nucleases (ZFNs) or RNA-guided, enzymatically active/inactive DNA binding proteins such as Cas9 have undergone rapid advancements in terms of specificity and the types of edits that can be executed, but the hurdle of safe in vivo delivery still precludes efficacious gene editing therapies. Described herein are various embodiments of enhanced virus-like particles (eVLPs), as well as characteristics of various embodiments of eVLPs that provide a novel and optimal platform for the delivery of genome editing reagents, and contrasts eVLPs with canonical delivery modalities.

Retroviral particles, such as lentivirus, have been developed to deliver RNA that is reverse transcribed to DNA that may or may not be integrated into genomic DNA. VLPs have been developed that mimic virus particles in their ability to self-assemble, but are not infectious as they lack some of the core viral genes. Both lentiviral and VLP vectors are typically produced by transiently transfecting a producer cell line with plasmids that encode all components necessary to produce lentiviral particles or VLP. One major flaw that we have discovered regarding lentiviral particles and VSVG-based VLPs that are produced by this conventional transient transfection method is that, in addition to their conventional cargo, these particles package and deliver plasmid DNA that was used in the initial transient transfection. This unintended plasmid DNA delivery can be immunogenic and cause undesirable effects, such as plasmid DNA being integrated into genomic DNA. It is important to specify the type of biomolecules/chemicals that are to be delivered within particles, and eVLPs have been designed to possess this germane capability.

The eVLPs described herein can deliver a wide variety of cargo including DNA only, DNA+RNA+protein, or RNA+protein. Importantly, eVLPs are the first VSVG-based VLP delivery modality that can control the form of the cargo (DNA, protein, and/or RNA). Previously described VSVG-based vesicles and viral particles package and deliver unwanted plasmid DNA (or other types of DNA-based gene expression constructs) introduced into particle producer cells via transient transfection in addition to the intended protein and/or RNA cargo(s).

Another aspect of eVLPs is the ENV protein on the surface of the eVLP. Without wishing to be bound by theory, the ENV protein alone is responsible for eVLP particle generation and the ability of eVLPs to efficiently deliver cargo into cells. Lentivirus and VLPs commonly require GAG and ENV proteins to drive particle formation via budding off of the plasma membrane of producer cells into the cell culture medium. In addition, the majority of retroviral ENV proteins require post-translational modifications in the form of proteolytic cleavage of the intracellular domain (ICD) of the ENV protein in order to activate the fusogenicity of the ENV protein; this is essential for viral infectivity. The envelope proteins described in Table 1 are all derived from viruses. However, these eVLP ENV proteins do not require exogenous GAG for particle formation and they do not require ICD cleavage for fusogenicity.[1-3] The ENV is the only virally-derived component of eVLPs, and these ENV glycoproteins on the external surface of the eVLPs are used to facilitate fusion/entry of eVLPs into the target cell because they are known to be naturally fusogenic. In addition, eVLPs are different from previously described viral particles, VLPs, and extracellular vesicles because eVLPs are composed of a mixture of ectosomes and exosomes which can be separated by purification, if desired. Because of the above mentioned design simplifications and optimizations, eVLPs are particularly suited for delivery of cargo including DNA, RNA, protein, or combinations of biomolecules and/or chemicals, such as DNA-encoded or RNP-based genome editing reagents.

Large biomolecules including proteins and protein complexes such as genome editing reagents, especially CRISPR-CAS, zinc finger, and TAL-nuclease-based reagents, have the potential to become in vivo therapeutics for the treatment of a number of diseases including genetic diseases, but techniques for delivering these reagents into cells are severely limiting or unsafe for patients. Conventional therapeutic monoclonal antibody delivery is successful at utilizing direct injection for proteins. Unfortunately, strategies for direct injection of gene editing proteins, such as Cas9, are hampered by immunogenicity, degradation, ineffective cell specificity, and inability to cross the plasma membrane or escape endosomes/lysosomes.[4-10] More broad applications of protein therapy and gene editing could be achieved by delivering therapeutic protein cargo to the inside of cells. Cas9, for example, cannot efficiently cross the phospholipid bilayer to enter into cells, and has been shown to have innate and adaptive immunogenic potential.[4-8] Therefore, it is not practical or favorable to deliver Cas9 by direct injection or as an external/internal conjugate to lipid, protein or metal-based nanoparticles that have cytotoxic and immunogenic properties and often yield low levels of desired gene modifications.[9-20]

Nanoparticles that encapsulate cargo are another delivery strategy that can be used to deliver DNA, protein, RNA and RNPs into cells[9-18] Nanoparticles can be engineered for cell specificity and can trigger endocytosis and subsequent endosome lysis. However, nanoparticles can have varying levels of immunogenicity due to an artificially-derived vehicle shell.[9-20] Many nanoparticles rely on strong opposing charge distributions to maintain particle structural integrity, and the electrostatics can make it toxic and unfit for many in vivo therapeutic scenarios.[9] Nanoparticles that deliver RNA have had successes in recent clinical trials, but most have only been used to deliver siRNA or shRNA. Toxicity from such nanoparticles is still a major concern.[9] Nanoparticles that deliver mRNA coding for genome editing RNPs have also been a recent success, but these create a higher number of off-target effects compared to protein delivery and RNA stability is lower than that of protein.[17] Nanoparticles that deliver genome editing RNPs and DNA have been a significant breakthrough because they can leverage both homology directed repair (HDR) and non-homologous end joining (NHEJ), but exhibit prohibitively low gene modification frequencies in vitro and in vivo, and therefore currently have limited applications in vivo as a gene editing therapeutic.[15]

Currently, the clinical standard vehicles for delivering genome editing therapeutics are adeno-associated virus (AAV). Although AAV vectors are a promising delivery modality that can successfully deliver DNA into eukaryotic cells, AAV cannot efficiently package and deliver DNA constructs larger than 4.5 kb and this precludes delivery of many CRISPR-based gene editing reagents that require larger DNA expression constructs. CRISPR-based gene editing reagents can be split into multiple different AAV particles, but this strategy drastically reduces delivery and editing efficiency. Depending on the dose required, AAV and adenoviral vectors can have varying levels of immunogenicity. In addition, inverted-terminal repeats (ITRs) in the AAV DNA construct can promote the formation of spontaneous episomes leading to prolonged expression of genome editing reagents and increased off-target effects. ITRs can also promote the undesired integration of AAV DNA into genomic DNA.[21-24]

Recently, VLPs have been utilized to deliver mRNA and protein cargo into the cytosol of cells.[2,3,25-30] VLPs have emerged as a substitute delivery modality for retroviral particles. VLPs can be designed to lack the ability to integrate retroviral DNA, and to package and deliver protein/RNP/DNA. However, most VLPs, including recently conceived VLPs that deliver genome editing reagents known to date, utilize HIV or other virally-derived gag-pol protein fusions and viral proteases to generate retroviral-like particles.[25-27,29,30] Secondly, some VLPs containing RGNs also must package and express guide RNAs from a lentiviral DNA transcript.[27] Thirdly, some VLPs require a viral protease in order to form functional particles and release genome editing cargo.[25-27,29] Since this viral protease recognizes and cleaves at multiple amino acid motifs, it can cause damage to the protein cargo which could be hazardous for therapeutic applications. Fourthly, most published VLP modalities that deliver genome editing proteins to date exhibit low in vitro and in vivo gene modification efficiencies due to low packaging and transduction efficiency.[25-27] Fifthly, the complex viral genomes utilized for these VLP components possess multiple reading frames and employ RNA splicing that could result in spurious fusion protein products being delivered.[25-27,29,30] Sixthly, the presence of reverse transcriptase, integrase, capsid and a virally-derived envelope protein in these VLPs is not ideal for most therapeutic applications because of immunogenicity and off target editing concerns. Lastly, most retroviral particles, such as lentiviral particles, are pseudotyped with VSVG and nearly all described VLPs that deliver genome editing reagents hitherto possess and rely upon VSVG[2,3,25-30] We have discovered that VSVG-based particles that are formed by transiently transfecting producer cells package and deliver DNA that was transfected. The current versions of VSVG-based VLPs cannot prevent this inadvertent delivery of DNA and this impedes the use of VLPs in scenarios that necessitate minimal immunogenicity and off target effects.

Extracellular vesicles are another delivery modality that can package and deliver cargo within exosomes and ectosomes.[31,32] Similar to VLPs, extracellular vesicles are comprised of a phospholipid bilayer from a mammalian cell. Unlike VLPs, extracellular vesicles lack viral components and therefore have limited immunogenicity. Whereas VLPs have a great ability to enter cells due to external fusogenic glycoproteins (VSVG) extracellular vesicles mainly rely on cellular uptake via micropinocytosis and this limits the delivery efficiency of extracellular vesicles.

eVLPs are a safer and more effective alternative than previously described VLPs, extracellular vesicles, AAVs and nanoparticles-especially for delivery of genome editing reagents-because eVLPs are composed of all human components except for a virally-derived glycoprotein that has been demonstrated to be safe in humans in a clinical trial of a HIV-1 gag vaccine (VSVG),[33] eVLPs lack all other retroviral components besides a safe glycoprotein, eVLPs have the ability to deliver DNA+RNP, or RNP alone while other previously described VLPs cannot prevent transient transfection DNA from being unintentionally packaged and delivered, eVLPs can deliver specialty DNA molecules while previously described VLPs, nanoparticles and AAVs cannot or do not, and eVLPs can be produced with cells that have been derived from patients (autologous eVLPs) and other FDA-approved cell lines (allogenic eVLPs) to further reduce the risks of adverse immune reactions. Here, we describe methods and compositions for producing, purifying, and administering eVLPs for in vitro and in vivo applications, e.g., of genome editing, epigenome modulation, transcriptome editing and proteome modulation. The desired editing outcome depends on the therapeutic context and will require different gene editing reagents. *Streptococcus pyogenes* Cas9 (spCas9) and *acidaminococcus* sp. Cas12a (functionalize) are two of the most popular RNA-guided enzymes for editing that leverages NHEJ for introducing stop codons or deletions, or HDR for causing insertions.[34-36] Cas9-deaminase fusions, also known as base editors, are the current standard for precise editing of a single nucleotide without double stranded DNA cleavage.[37,38] Importantly, these methods address the phenomenon of inadvertent DNA delivery in VLPs and the first to control for the type of biomolecule to be delivered (DNA, RNA, and/or protein) thereby increasing the types of therapeutic in vivo genome modifications that are possible and minimizing deleterious off target effects.

Section 1: eVLP-Mediated Delivery of DNAs, Proteins and RNAs

Conventional VLPs that have been engineered to encapsulate and deliver protein-based cargo commonly fuse cargo to the INT or GAG polyprotein.[25-27,29,30,39,40] After transient transfection of production plasmid DNA constructs, these protein fusions are translated in the cytosol of conventional VLP production cell lines, the gag matrix is acetylated and recruited to the cell membrane, and the gag fusions are encapsulated (transient transfection DNA is also unintentionally encapsulated) within VLPs as VLPs bud off of the membrane into extracellular space.

Figure 2:
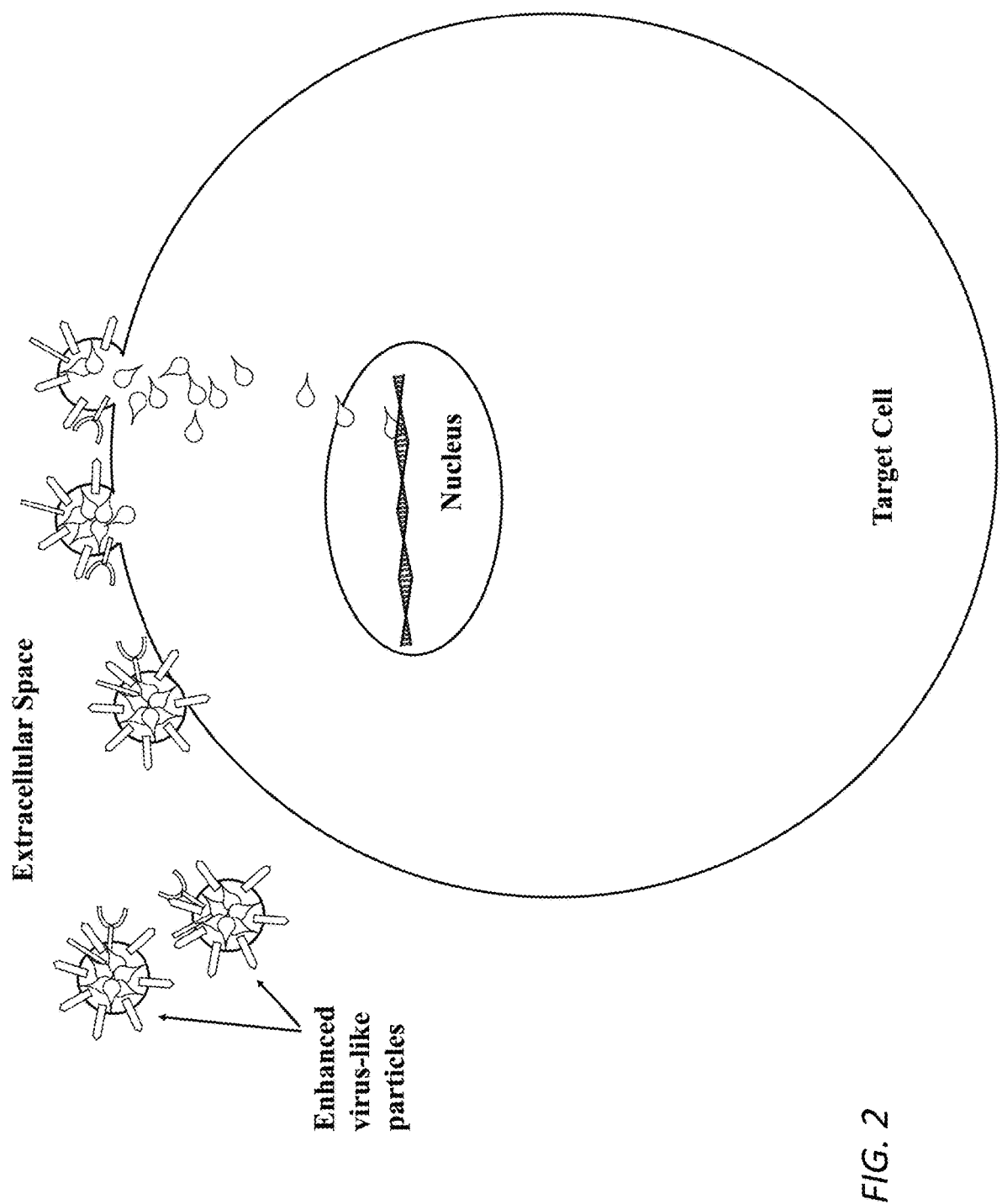
FIG. 2: Depiction of purified eVLPs entering a target cell and delivering cargo to the cytosol. Importantly, the phospholipid bilayer recruitment domain allows cargo to enter the target cell nucleus as long as cargo possesses a nuclear localization sequence.
Figure 3:
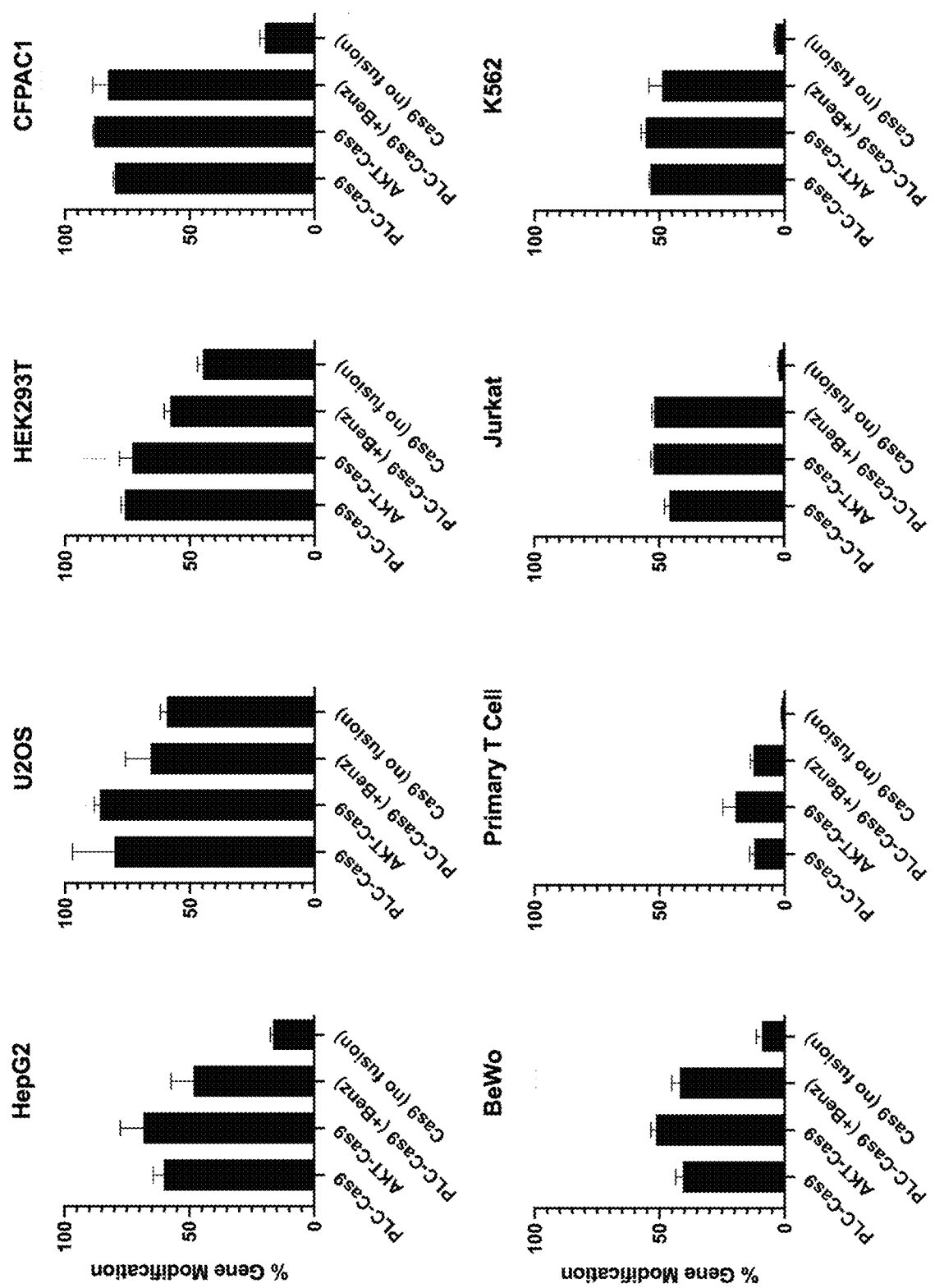
FIG. 3: Cas9 RNP was delivered in VSVG-pseudotyped T2eVLPs with or without a PH domain from hPLCδ1 or hAKT1. The PH domains were fused to the N-terminus of Cas9 via a 10 amino acid glycine/serine polypeptide linker. HepG2, U2OS, HEK293T, CFPAC1, BeWo, Jurkat, K562, and primary T cells were treated with purified and 100× concentrated T2eVLPs for 72 hours. Percent targeted gene modification of VEGF site #3 was determined by amplicon sequencing. The x-axis labels correspond to the contents of each T2eVLP preparation. Cas9 (no fusion) lacked a PH domain fusion. Benzonase (Benz) was used to degrade RNA and DNA outside of VLPs, and a Benzonase treated sample was included as a control.

In contrast, in some embodiments the eVLPs described herein can package protein-based cargo by integrating all production DNA into the genomic DNA of production cell lines. Once cell lines are created, protein delivery eVLPs can be produced in a constitutive or inducible fashion. Proteins are packaged into eVLP by fusing select human-derived phospholipid bilayer recruitment domains to protein-based cargo (e.g., as shown in Table 6). One such human-derived phospholipid bilayer recruitment domain used for this purpose is a human pleckstrin homology (PH) domain. PH domains interact with phosphatidylinositol lipids and proteins within biological membranes, such as PIP2, PIP3, βγ-subunits of GPCRs, and PKC.[41,42] Alternatively, the human Arc protein can be fused to protein-based cargo to recruit cargo to the cytosolic side of the phospholipid bilayer.[43] These human-derived phospholipid bilayer recruitment domains can be fused to the N-terminus or C-terminus of protein-based cargo via polypeptide linkers of variable length regardless of the location or locations of one or more nuclear localization sequence(s) (NLS) within the cargo. Preferably, the linker between protein-based cargo and the phospholipid bilayer recruitment domain is a polypeptide linker 5-20, e.g., 8-12, e.g., 10, amino acids in length primarily composed of glycines and serines. The human-derived phospholipid bilayer recruitment domain localizes the cargo to the phospholipid bilayer and this protein cargo is packaged within eVLPs that utilize a glycoprotein to trigger budding off of particles from the producer cell into extracellular space (FIG. 1). These human-derived domains and proteins can facilitate for localization of cargo to the cytosolic face of the plasma membrane within the eVLP production cells, and they also allow for cargo to localize to the nucleus of eVLP-transduced cells without the utilization of exogenous retroviral gag/pol or chemical and/or light-based dimerization systems (FIG. 2). The delivery of Cas9, for example, is significantly more efficient with a fusion to a plasma membrane recruitment domain compared to without a plasma membrane recruitment domain (FIG. 3).

Figure 4:
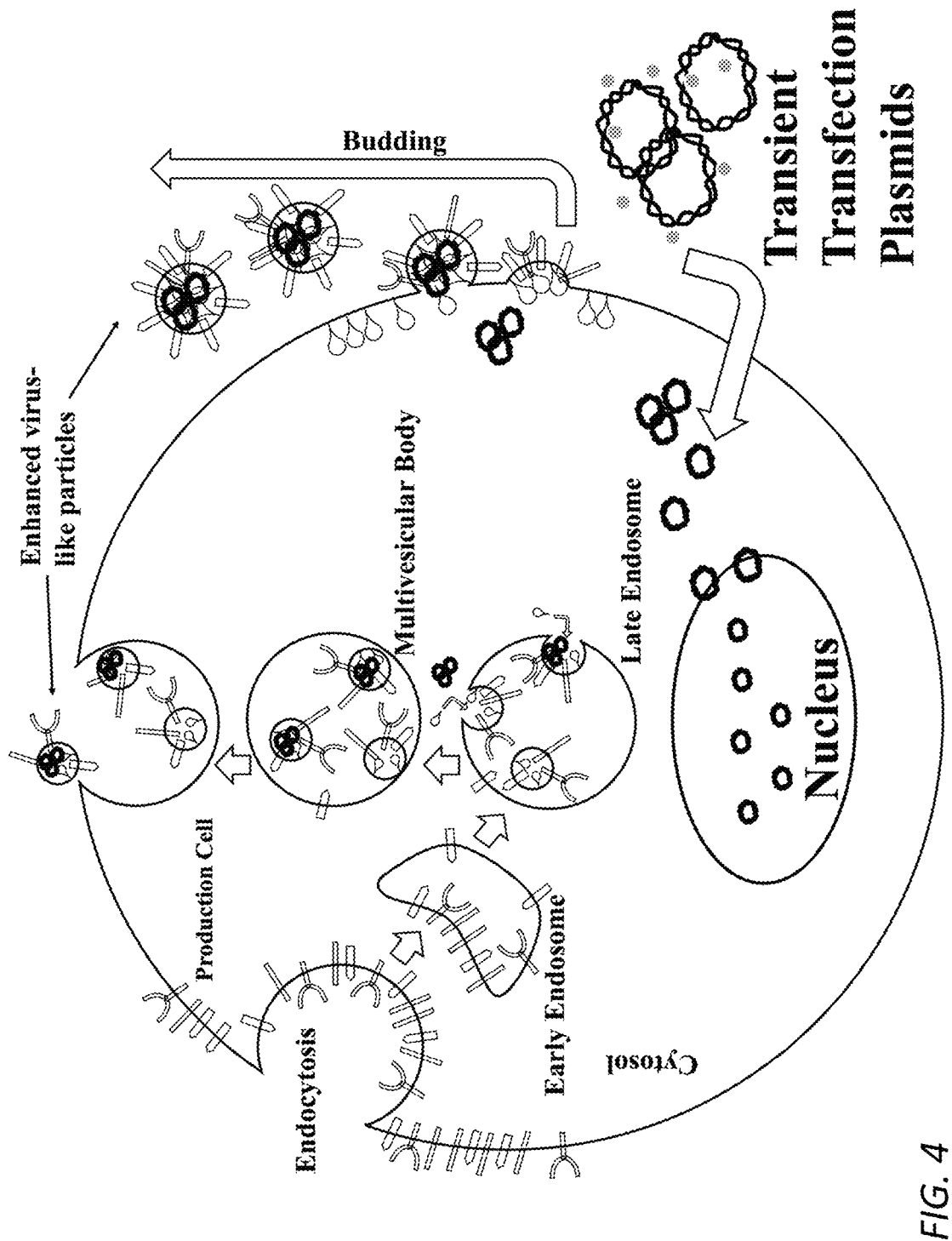
FIG. 4: Depiction of T1eVLP/T3eVLP production. Plasmid DNA constructs involved in the transfection encode cargo, an optional guide RNA and a virally-derived glycoprotein (VSVG). Plasmids, or other types of DNA molecules, will be distributed throughout the production cell, so constructs located in the nucleus will express eVLP components and cargo, and constructs located near the plasma membrane or endosomes will be encapsulated within budding eVLPs.

In some embodiments, eVLPs can also package and deliver a combination of DNA and RNA if eVLPs are produced via transient transfection of a production cell line. DNA that is transfected into cells will possess size-dependent mobility such that a fraction of the transfected DNA will remain in the cytosol while another fraction of the transfected DNA will localize to the nucleus.[44-46] One fraction of the transfected DNA in the nucleus will expressed components needed to create eVLPs and the other fraction in the cytosol/near the plasma membrane will be encapsulated and delivered in eVLPs (FIG. 4).

eVLP "Cargo" refers to a any payload that can be delivered, including chemicals, e.g., small molecule compounds, and biomolecules, including DNA, RNA, RNP, proteins, and combinations thereof, including combinations of DNA and RNP, RNP, combinations of DNA and proteins, or proteins, as well as viruses and portions thereof, e.g., for therapeutic or diagnostic use, or for the applications of genome editing, epigenome modulation, and/or transcriptome modulation. In order to simplify these distinctions, a combination of DNA and RNP will be referred to herein as type 1 cargo (T1eVLPs), RNP will be referred to herein to as type 2 cargo (T2eVLPs), a combination of DNA and proteins will be referred to herein to as type 3 cargo (T3eVLPs), and proteins will be referred to herein to as type 4 cargo (T4eVLPs). RNA in this context includes, for example, single guide RNA (sgRNA), Clustered Regularly Interspaced Palindromic Repeat (CRISPR) RNA (crRNA), and/or mRNA coding for cargo.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The cargo is limited by the diameter of the particles, e.g., which in some embodiments range from 30 nm to 500 nm.

Cargo developed for applications of genome editing also includes nucleases and base editors. Nucleases include FokI and AcuI ZFNs and Transcription activator-like effector nucleases (TALENs) and CRISPR based nucleases or a functional derivative thereof (e.g., as shown in Table 2) (ZFNs are described, for example, in United States Patent Publications 20030232410; 20050208489; 20050026157; 20050064474; 20060188987; 20060063231; and International Publication WO 07/014275) (TALENs are described, for example, in United States Patent Publication U.S. Pat. No. 9,393,257B2; and International Publication WO2014134412A1) (CRISPR based nucleases are described, for example, in United States Patent Publications U.S. Pat. No. 8,697,359B1; US20180208976A1; and International Publications WO2014093661A2; WO2017184786A8).[34-36] Base editors that are described by this work include any CRISPR based nuclease orthologs (wt, nickase, or catalytically inactive (CI)), e.g., as shown in Table 2, fused at the N-terminus to a deaminase or a functional derivative thereof (e.g., as shown in Table 3) with or without a fusion at the C-terminus to one or multiple uracil glycosylase inhibitors (UGIs) using polypeptide linkers of variable length (Base editors are described, for example, in United States Patent Publications US20150166982A1; US20180312825A1; U.S. Pat. No. 10,113,163B2; and International Publications WO2015089406A1; WO2018218188A2; WO2017070632A2; WO2018027078A8; WO2018165629A1).[37,38] In addition, prime editors are also compatible with eVLP delivery modalities (Prime editors are described, for example, in PMID: 31634902).

sgRNAs complex with genome editing reagents during the packaging process, and are co-delivered within eVLPs. To date, this concept has been validated in vitro by experiments that demonstrate the T1eVLP or T2eVLP delivery of RGN and CI RGN fused to deaminase and UGI (base editor) as protein for the purposes of site specific editing of exogenous and endogenous sites (FIGS. 3, 5, 6, 7, 8, 9, 10, 11 & 12). For example, T1eVLPs have been used to deliver Cas9 RNP to U2OS and HEK293 cells for the purposes of editing exogenous GFP, and endogenous HEK site #3 and VEGF site #2 & #3 (FIGS. 4, 5, 6 & 7). In addition, T1eVLPs have been used to deliver BE3 and BE4 RNP to HEK293T cells for the purpose of base editing endogenous VEGF site #2 & #3 and HEK site #3 (FIGS. 8, 9, 10 & 11). T1eVLPs have also been used to deliver Cas12a RNP to HEK293 cells for the purposes of editing endogenous FANCF site #1 (FIG. 12).

Cargo designed for the purposes of epigenome modulation includes the CI CRISPR based nucleases, zinc fingers (ZFs) and TALEs fused to an epigenome modulator or combination of epigenome modulators or a functional derivative thereof connected together by one or more variable length polypeptide linkers (Tables 2 & 4). T1-T4 cargo designed for the purposes of transcriptome editing includes CRISPR based nucleases or any functional derivatives thereof in Table 5 or CI CRISPR based nucleases or any functional derivatives thereof in Table 5 fused to deaminases in Table 3 by one or more variable length polypeptide linkers.

The cargo can also include any therapeutically or diagnostically useful protein, DNA, RNP, or combination of DNA, protein and/or RNP. See, e.g., WO2014005219; U.S. Pat. No. 10/137,206; US20180339166; U.S. Pat. No. 5,892,020A; EP2134841B1; WO2007020965A1. For example, cargo encoding or composed of nuclease or base editor proteins or RNPs or derivatives thereof can be delivered to retinal cells for the purposes of correcting a splice site defect responsible for Leber Congenital Amaurosis type 10. In the mammalian inner ear, eVLP delivery of base editing reagents or HDR promoting cargo to sensory cells such as cochlear supporting cells and hair cells for the purposes of editing β-catenin (β-catenin Ser 33 edited to Tyr, Pro, or Cys) in order to better stabilize β-catenin could help reverse hearing loss.

In another application, eVLP delivery of RNA editing reagents or proteome perturbing reagents could cause a transitory reduction in cellular levels of one or more specific proteins of interest (potentially at a systemic level, in a specific organ or a specific subset of cells, such as a tumor), and this could create a therapeutically actionable window when secondary drug(s) could be administered (this secondary drug is more effective in the absence of the protein of interest or in the presence of lower levels of the protein of interest). For example, eVLP delivery of RNA editing reagents or proteome perturbing reagents could trigger targeted degradation of MAPK and PI3K/AKT proteins and related mRNAs in vemurafenib/dabrafenib-resistant BRAF-driven tumor cells, and this could open a window for the administration of vemurafenib/dabrafenib because BRAF inhibitor resistance is temporarily abolished (resistance mechanisms based in the MAPK/PI3K/AKT pathways are temporarily downregulated by eVLP cargo). This example is especially pertinent when combined with eVLPs that are antigen inducible and therefore specific for tumor cells.

In some embodiments, eVLPs could be used deliver factors, e.g., including the Yamanaka factors Oct3/4, Sox2, Klf4, and c-Myc, to cells such as human or mouse fibroblasts, in order to generate induced pluripotent stem cells.

In some embodiments, eVLPs could deliver dominant-negative forms of proteins in order to elicit a therapeutic effect.

eVLPs that are antigen-specific (i.e., tumor-antigen specific) could be targeted to cancer cells in order to deliver proapoptotic proteins BIM, BID, PUMA, NOXA, BAD, BIK, BAX, BAK and/or HRK in order to trigger apoptosis of cancer cells. Tumor antigens are known in the art and include 90% of pancreatic cancer patients present with unresectable disease. Around 30% of patients with unresectable pancreatic tumors will die from local disease progression, so it is desirable to treat locally advanced pancreatic tumors with ablative radiation, but the intestinal tract cannot tolerate high doses of radiation needed to cause tumor ablation. Selective radioprotection of the intestinal tract enables ablative radiation therapy of pancreatic tumors while minimizing damage done to the surrounding gastrointestinal tract. To this end, eVLPs could be loaded with dCas9 fused to the transcriptional repressor KRAB and guide RNA targeting EGLN. EGLN inhibition has been shown to significantly reduce gastrointestinal toxicity from ablative radiation treatments because it causes selective radioprotection of the gastrointestinal tract but not the pancreatic tumor.[47] Such fusion proteins, eVLPs, and methods of making and using the same are provided herein.

Unbound steroid receptors reside in the cytosol. After binding to ligands, these receptors will translocate to the nucleus and initiate transcription of response genes. eVLPs could deliver single chain variable fragment (scFv) antibodies to the cytosol of cells that bind to and disrupt cytosolic steroid receptors. For example, the scFv could bind to the glucocorticoid receptor and prevent it from binding dexamethasone, and this would prevent transcription of response genes, such as metallothionein 1E which has been linked to tumorigenesis.[48]

eVLPs can be indicated for treatments that involve targeted disruption of proteins. For example, eVLPs can be utilized for targeting and disrupting proteins in the cytosol of cells by delivering antibodies/scFvs to the cytosol of cells. Classically, delivery of antibodies through the plasma membrane to the cytosol of cells has been notoriously difficult and inefficient. This mode of protein inhibition is similar to how a targeted small molecule binds to and disrupts proteins in the cytosol and could be useful for the treatment of a diverse array of diseases.[49-51] Such fusion proteins, eVLPs, and methods of making and using the same are In addition, the targeting of targeted small molecules is limited to proteins of a certain size that contain binding pockets which are relevant to catalytic function or protein-protein interactions. scFvs are not hampered by these limitations because scFvs can be generated that bind to many different moieties of a protein in order to disrupt catalysis and interactions with other proteins. For example, RAS oncoproteins are implicated across a multitude of cancer subtypes, and RAS is one of the most frequently observed oncogenes in cancer. For instance, the International Cancer Genome Consortium found KRAS to be mutated in 95% of their Pancreatic Adenocarcinoma samples. RAS isoforms are known to activate a variety of pathways that are dysregulated in human cancers, like the PI3K and MAPK pathways. Despite the aberrant roles RAS plays in cancer, no efficacious pharmacologic direct or indirect small molecule inhibitors of RAS have been developed and approved for clinical use. One strategy for targeting RAS could be eVLPs that can deliver specifically to cancer cells scFvs that bind to and disrupt the function of multiple RAS isoforms.[49-51]

Section 2: eVLP Composition, Production, Purification and Applications eVLPs can be produced from producer cell lines that are either transiently transfected with at least one plasmid or stably expressing constructs that have been integrated into the producer cell line genomic DNA. In some embodiments, for T1 and T3eVLPs, if a single plasmid is used in the transfection, it should comprise sequences encoding one or more virally-derived glycoproteins (e.g., as shown in Table 1), cargo (e.g., a therapeutic protein or a gene editing reagent such as a zinc finger, transcription activator-like effector (TALE), and/or CRISPR-based genome editing/modulating protein and/or RNP such as those found in Tables 2, 3, 4 & 5), with or without fusion to a plasma membrane recruitment domain (e.g., as shown in Table 6), and a guide RNA, if necessary. Preferably, two to three plasmids are used in the transfection. These two to three plasmids can include the following (any two or more can be combined in a single plasmid):

1. A plasmid comprising sequences encoding a therapeutic protein or a genome editing reagent, with or without a fusion to a plasma membrane recruitment domain.
2. A plasmid comprising one or more virally-derived glycoproteins (e.g., as listed in Table 1).
3. If the genome editing reagent from plasmid 1 requires one or more guide RNAs, a plasmid comprising one or more guide RNAs apposite for the genome editing reagent in plasmid 1.

If it is desired to deliver a type of DNA molecule other than plasmid(s), the above-mentioned transfection can be performed with double-stranded closed-end linear DNA, episome, mini circle, double-stranded oligonucleotide and/or other specialty DNA molecules. Alternatively, for T2 and T4eVLPs, the producer cell line can be made to stably express the constructs (1 through 3) described in the transfection above.

As stated earlier, in some embodiments, the methods include using cells that have or have not been manipulated to express any exogenous proteins except for a viral envelope (e.g., as shown in Table 1), and, if desired, a plasma membrane recruitment domain (e.g., as shown in Table 6). In this embodiment, the "empty" particles that are produced can be loaded with cargo by utilizing nucleofection, lipid, polymer, or $CaCl_2$ transfection, sonication, freeze thaw, and/or heat shock of purified particles mixed with cargo. In all embodiments, producer cells do not express any gag protein. This type of loading allows for cargo to be unmodified by fusions to plasma membrane recruitment domains and represents a significant advancement from previous VLP technology.

The plasmids, or other types of specialty DNA molecules known in the art or described above, can also preferably include other elements to drive expression or translation of the encoded sequences, e.g., a promoter sequence; an enhancer sequence, e.g., 5' untranslated region (UTR) or a 3' UTR; a polyadenylation site; an insulator sequence; or another sequence that increases or controls expression (e.g., an inducible promoter element).

Preferably, appropriate producer cell lines are primary or stable human cell lines refractory to the effects of transfection reagents and fusogenic effects due to virally-derived glycoproteins. Examples of appropriate cell lines include Human Embryonic Kidney (HEK) 293 cells, HEK293 T/17 SF cells kidney-derived Phoenix-AMPHO cells, and placenta-derived BeWo cells. For example, such cells could be selected for their ability to grow as adherent cells, or suspension cells. In some embodiments, the producer cells can be cultured in classical DMEM under serum conditions, serum-free conditions, or exosome-free serum conditions. eVLPs, e.g., T1 and T3eVLPs, can be produced from cells that have been derived from patients (autologous eVLPs) and other FDA-approved cell lines (allogenic eVLPs) as long as these cells can be transfected with DNA constructs that encode the aforementioned eVLP production components by various techniques known in the art.

In addition, if it is desirable, more than one genome editing reagent can be included in the transfection. The DNA constructs can be designed to overexpress proteins in the producer cell lines. The plasmid backbones, for example, used in the transfection can be familiar to those skilled in the art, such as the pCDNA3 backbone that employs the CMV promoter for RNA polymerase II transcripts or the U6 promoter for RNA polymerase III transcripts. Various techniques known in the art may be employed for introducing nucleic acid molecules into producer cells. Such techniques include chemical-facilitated transfection using compounds such as calcium phosphate, cationic lipids, cationic polymers, liposome-mediated transfection, such as cationic liposome like LIPOFECTAMINE (LIPOFECTAMINE 2000 or 3000 and TransIT-X2), polyethyleneimine, non-chemical methods such as electroporation, particle bombardment, or microinjection.

A human producer cell line that stably expresses the necessary eVLP components in a constitutive and/or inducible fashion can be used for production of T2 and T4eVLPs. T2 and T4eVLPs can be produced from cells that have been derived from patients (autologous eVLPs) and other FDA-approved cell lines (allogenic eVLPs) if these cells have been converted into stable cell lines that express the aforementioned eVLP components.

Also provided herein are the producer cells themselves.

Production of Cargo-Loaded eVLPs and Compositions

Preferably eVLPs are harvested from cell culture medium supernatant 36-48 hours post-transfection, or when eVLPs are at the maximum concentration in the medium of the producer cells (the producer cells are expelling particles into the media and at some point in time, the particle concentration in the media will be optimal for harvesting the particles). Supernatant can be purified by any known methods in the art, such as centrifugation, ultracentrifugation, precipitation, ultrafiltration, and/or chromatography. In some embodiments, the supernatant is first filtered, e.g., to remove particles larger than 1 µm, e.g., through 0.45 pore size polyvinylidene fluoride hydrophilic membrane (Millipore Millex-HV) or 0.8 µm pore size mixed cellulose esters hydrophilic membrane (Millipore Millex-AA). After filtration, the supernatant can be further purified and concentrated, e.g., using ultracentrifugation, e.g., at a speed of 80,000 to 100,000×g at a temperature between 1° C. and 5° C. for 1 to 2 hours, or at a speed of 8,000 to 15,000 g at a temperature between 1° C. and 5° C. for 10 to 16 hours. After this centrifugation step, the eVLPs are concentrated in the form of a centrifugate (pellet), which can be resuspended to a desired concentration, mixed with transduction-enhancing reagents, subjected to a buffer exchange, or used as is. In some embodiments, eVLP-containing supernatant can be filtered, precipitated, centrifuged and resuspended to a concentrated solution. For example, polyethylene glycol (PEG), e.g., PEG 8000, or antibody-bead conjugates that bind to eVLP surface proteins or membrane components can be used to precipitate particles. Purified particles are stable and can be stored at 4° C. for up to a week or −80° C. for years without losing appreciable activity.

Preferably, eVLPs are resuspended or undergo buffer exchange so that particles are suspended in an appropriate carrier. In some embodiments, buffer exchange can be performed by ultrafiltration (Sartorius Vivaspin 500 MWCO 100,000). An exemplary appropriate carrier for eVLPs to be used for in vitro applications would preferably be a cell culture medium that is suitable for the cells that are to be transduced by eVLPs. Transduction-enhancing reagents that can be mixed into the purified and concentrated eVLP solution for in vitro applications include reagents known by those familiar with the art (Miltenyi Biotec Vectofusin-1, Millipore Polybrene, Takara Retronectin, Sigma Protamine Sulfate, and the like). After eVLPs in an appropriate carrier are applied to the cells to be transduced, transduction efficiency can be further increased by centrifugation. Preferably, the plate containing eVLPs applied to cells can be centrifuged at a speed of 1,150 g at room temperature for 30 minutes. After centrifugation, cells are returned into the appropriate cell culture incubator (humidified incubator at 37° C. with 5% $CO_2$).

An appropriate carrier for eVLPs to be administered to a mammal, especially a human, would preferably be a pharmaceutically acceptable composition. A "pharmaceutically acceptable composition" refers to a non-toxic semisolid, liquid, or aerosolized filler, diluent, encapsulating material, colloidal suspension or formulation auxiliary of any type. Preferably, this composition is suitable for injection. These may be in particular isotonic, sterile, saline solutions (monosodium or disodium phosphate, sodium, potassium, calcium or magnesium chloride and similar solutions or mixtures of such salts), or dry, especially freeze-dried compositions which upon addition, depending on the case, of sterilized water or physiological saline, permit the constitution of injectable solutions. Another appropriate pharmaceutical form would be aerosolized particles for administration by intranasal inhalation or intratracheal intubation.

The pharmaceutical forms suitable for injectable use include sterile aqueous solutions or suspensions. The solution or suspension may comprise additives which are compatible with eVLPs and do not prevent eVLP entry into target cells. In all cases, the form must be sterile and must be fluid to the extent that the form can be administered with a syringe. It must be stable under the conditions of manufacture and storage and must be preserved against the contaminating action of microorganisms, such as bacteria and fungi. An example of an appropriate solution is a buffer, such as phosphate buffered saline.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

The compositions comprising cargo-loaded eVLPs can be included in a container, pack, or dispenser together with instructions for administration.

EXAMPLES

The invention is further described in the following examples, which do not limit the scope of the invention described in the claims.

Methods

The following methods were used in the Examples below. eVLP particles were produced by HEK293T cells using polyethylenimine (PEI) based transfection of plasmids. PEI is Polyethylenimine 25 kD linear (Polysciences #23966-2). To make a stock 'PEI MAX' solution, 1 g of PEI was added to 1 L endotoxin-free dH$_2$O that was previously heated to ~80° C. and cooled to room temperature. This mixture was neutralized to pH 7.1 by addition of 10N NaOH and filter sterilized with 0.22 μm polyethersulfone (PES). PEI MAX is stored at −20° C.

HEK293T cells were split to reach a confluency of 70%-90% at time of transfection and are cultured in 10% FBS DMEM media. Cargo vectors, such as one encoding a CMV promoter driving expression of a hPLCδ1 PH fusion to codon optimized Cas9 were co-transfected with a U6 promoter-sgRNA encoding plasmid and the VSV-G envelope plasmid pMD2.G (Addgene #12259). Transfection reactions were assembled in reduced serum media (Opti-MEM; GIBCO #31985-070). For eVLP particle production on 10 cm plates, 7.5 μg PH-Cas9 expressing plasmid, 7.5 μg sgRNA-expression plasmid and 5 μg pMD2.G were mixed in 1 mL Opti-MEM, followed by addition of 27.5 μl PEI MAX. After 20-30 min incubation at room temperature, the transfection reactions were dispersed dropwise over the HEK293T cells.

eVLPs were harvested at 48-72 hours post-transfection. eVLP supernatants were filtered using 0.45 μm cellulose acetate or 0.8 μm PES membrane filters and transferred to polypropylene Beckman ultracentrifuge tubes that are used with the SW28 rotor (Beckman Coulter #326823). Each ultracentrifuge tube is filled with eVLP-containing supernatant from 3 10 cm plates to reach an approximate final volume of 35-37.5 ml. eVLP supernatant underwent ultracentrifugation at approximately 100,000×g, or 25,000 rpm, at 4° C. for 2 hours. After ultracentrifugation, supernatants were decanted and eVLP pellets resuspended in DMEM 10% FBS media such that they are now approximately 1,000 times more concentrated than they were before ultracentrifugation. eVLPs were added dropwise to cells that were seeded in a 24-well plate 24 hours prior to transduction. Polybrene (5-10 μg/mL in cell culture medium; Sigma-Aldrich #TR-1003-G) was supplemented to enhance transduction efficiency, if necessary. Vectofusin-1 (10 μg/mL in cell culture medium, Miltenyi Biotec #130-111-163) was supplemented to enhance transduction efficiency, if necessary. Immediately following the addition of eVLPs, the 24-well plate was centrifuged at 1,150×g for 30 min at room temperature to enhance transduction efficiency, if necessary.

Example 1

Cas9 RNP was delivered in VSVG-pseudotyped VLPs with or without a fusion to a PH domain. T2eVLPs containing Cas9 with or without PH fusion and VEGF-targeting sgRNA were applied to HepG2, U2OS, HEK293T, CFPAC1, BeWo, Jurkat, K562, and primary T cells for 48 hours. Gene modification frequencies of the target site within VEGF were obtained by amplicon sequencing. FIG. 3 demonstrates that fusion to PH domains from hPLCδ1 or hAKT1 significantly enhanced delivery/editing efficiency of Cas9 in T2eVLPs.

Gag fusions to Cas9 or PH fusions to Cas9 with guide RNA targeting GFP were packaged in VLPs or T1eVLPs, respectively. U2OS or HEK293 cell line stably expressing a single copy of GFP were treated with these particles that were previously purified from HEK293T cell culture media (DMEM) 48 hours after transfection of VSVG, Cas9 fusions and guide RNA expressing plasmids. Particle purification and concentration was performed by PVDF filtration and ultracentrifugation at 100,000×g for 2 hours. Gene modification frequencies were determined by T7E1 and flow cytometry. The results are shown in FIGS. 5A-B.

Figure 6:
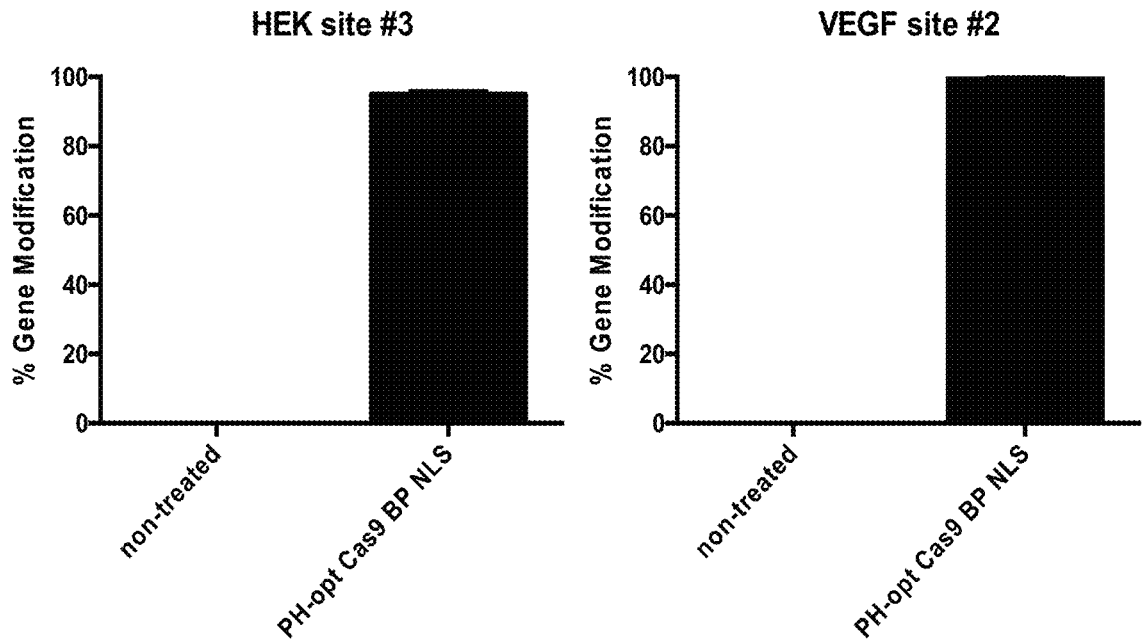
FIG. 6: Exemplary T1eVLP-delivered spCas9 genome editing in vitro. U2OS cells transduced with T1eVLPs containing PLC PH fused to spCas9 targeted to HEK site #3 or VEGF site #2. eVLPs are pseudotyped with VSVG Gene modification is measured by amplicon sequencing.

In FIG. 6, hPLCδ1 PH fusions to codon optimized Cas9 with guide RNA targeting HEK site #3 or VEGF site #2 were packaged in T1eVLPs. U2OS cells were treated with these particles that were previously purified from HEK293T cell culture media (DMEM, 10% FBS) 48 hours after transfection of VSVG, Cas9 fusions and guide RNA expressing plasmids. Particle purification and concentration was performed by filtration and ultracentrifugation at 100,000×g for 2 hours. Gene modification frequencies were determined by amplicon sequencing.

Figure 7:
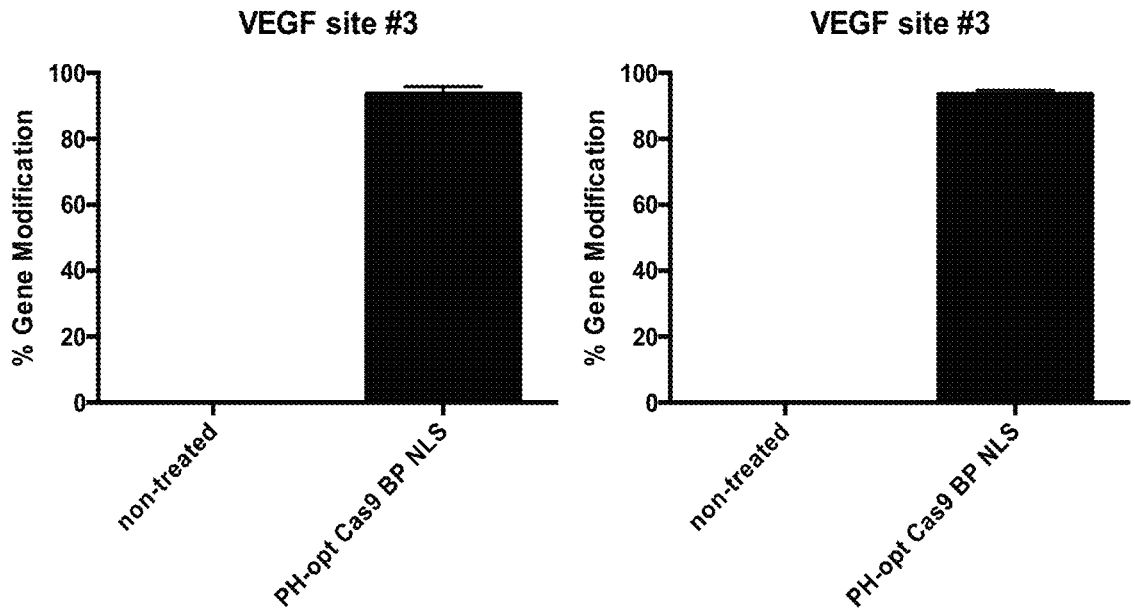
FIG. 7: Exemplary T1eVLP-delivered spCas9 genome editing in vitro. U2OS cells transduced with T1eVLPs containing PLC PH or hAkt PH fused to spCas9 targeted to VEGF site #3. eVLPs are pseudotyped with VSVG. Gene modification is measured by amplicon sequencing.

In FIG. 7, hPLCδ1 (left graph) or hAkt PH (right graph) fusions to codon optimized Cas9 with guide RNA targeting VEGF site #3 were packaged in T1eVLPs. U2OS cells were treated with these particles that were previously purified from HEK293T cell culture media (DMEM, 10% FBS) 48 hours after transfection of VSVG, Cas9 fusions and guide RNA expressing plasmids. Particle purification and concentration was performed by filtration and ultracentrifugation at 100,000×g for 2 hours. Gene modification frequencies were determined by amplicon sequencing.

Figure 8:
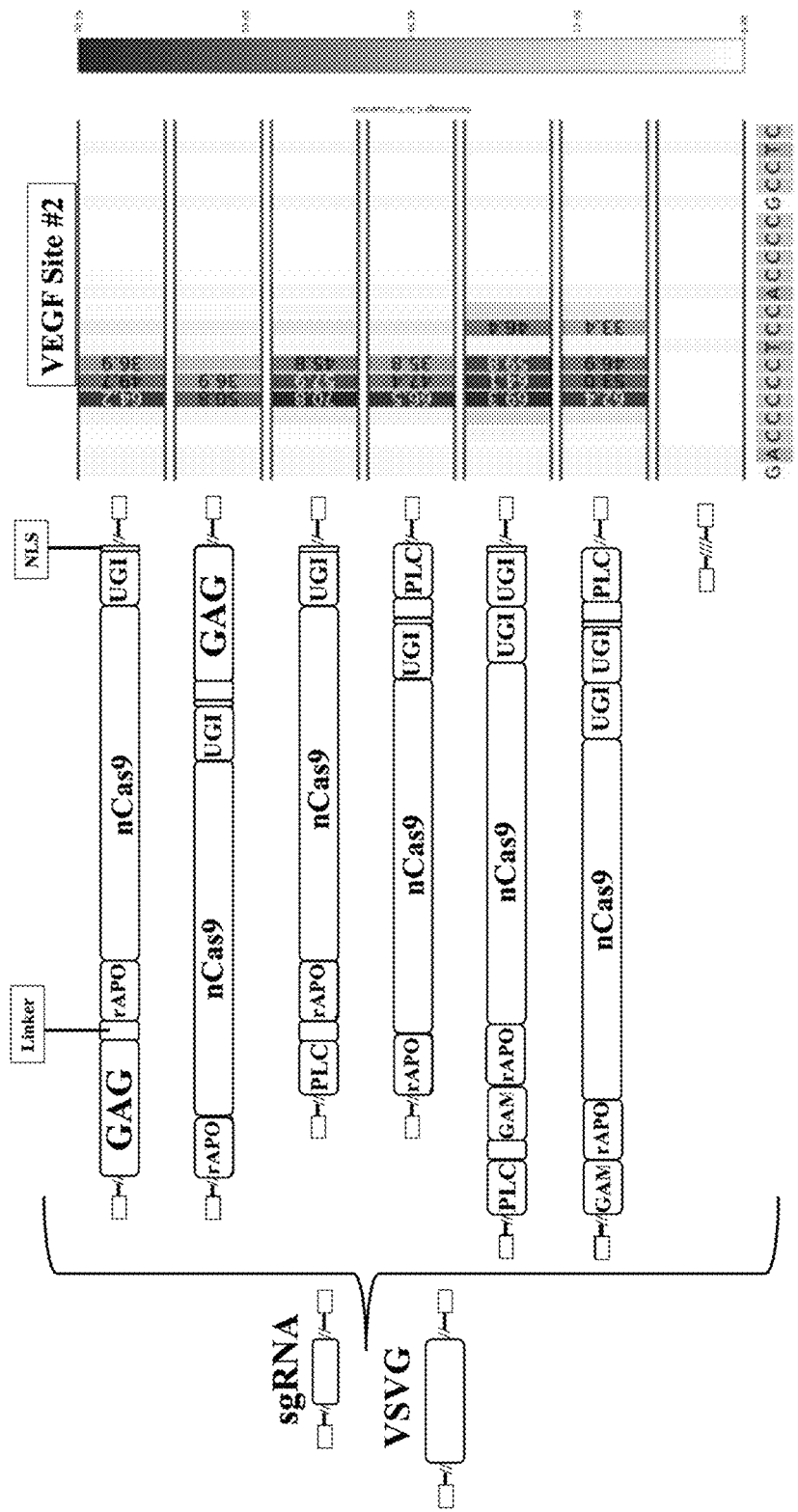
FIG. 8: Exemplary T1eVLP-delivered spCas9 base editing in vitro. HEK293T cells transduced with VLPs containing Rous sarcoma virus gag fused to spCas9 BE3 or Gam-BE4 with sgRNA targeted to VEGF site #2, or T1eVLPs containing PLC PH fused to spCas9 BE3 or Gam-BE4 with sgRNA targeted to VEGF site #2. eVLPs and VLPs are pseudotyped with VSVG Gene modification is measured by amplicon sequencing. The Rous sarcoma virus gag VLP serves as a positive control.

In FIG. 8, gag fusions to the N or C terminus of Cas9-based base editors (BE3 and BE4) or PH fusions to the N or C terminus of BE3 and BE4 with guide RNA targeting VEGF site #2 were packaged in VLPs and eVLPs, respectively. HEK293T cells were treated with these particles that were previously purified from HEK293T cell culture media (DMEM) 48 hours after transfection of VSVG, base editor fusions and guide RNA expressing plasmids. Particle purification and concentration was performed by filtration and ultracentrifugation at 100,000×g for 2 hours. Gene modification frequencies were determined by amplicon sequencing.

Figure 9:
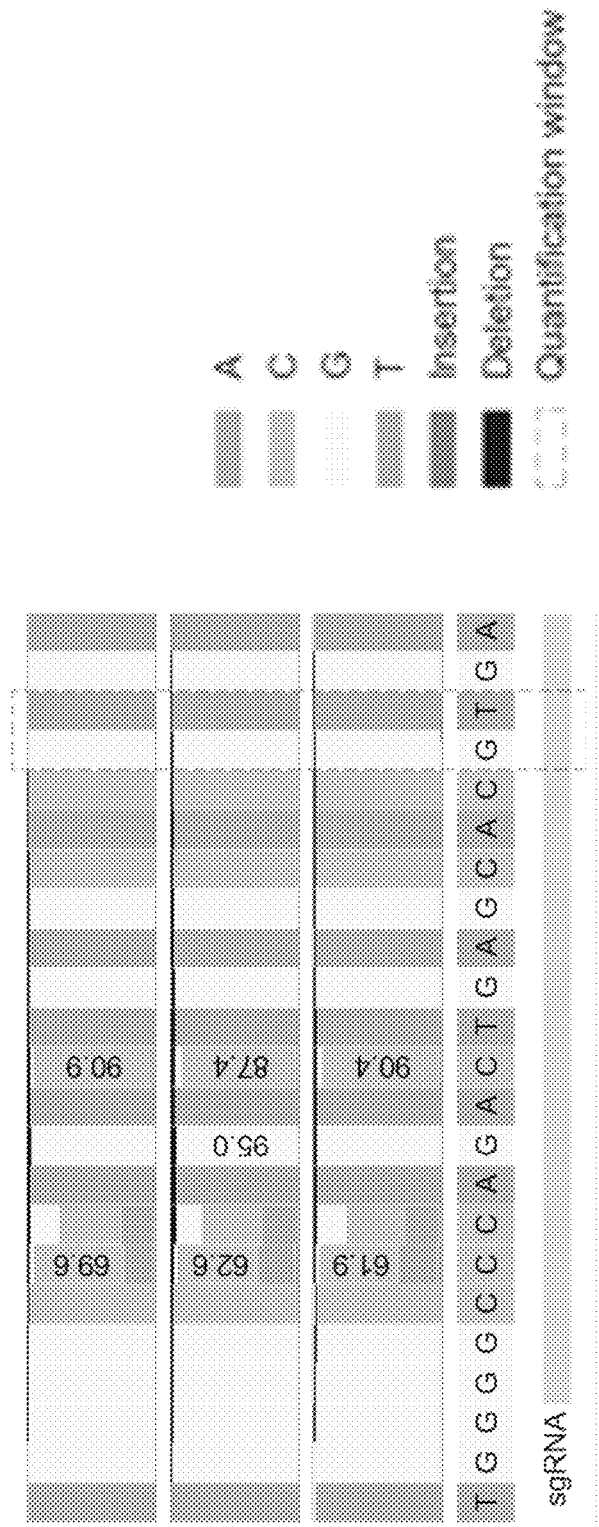
FIG. 9: Exemplary T1eVLP-delivered spCas9 base editing in vitro. HEK293T cells transduced with T1eVLPs containing PLC PH fused to codon optimized spCas9 BE4 targeted to HEK site #3. eVLPs are pseudotyped with VSVG. Gene modification is measured by amplicon sequencing.

In FIG. 9, hPLCδ1 fusions to the N terminus of Cas9-based base editors (codon optimized BE4) with guide RNA targeting HEK site #3 were packaged in eVLPs. HEK293T cells were treated with these particles that were previously purified from HEK293T cell culture media (DMEM) 48 hours after transfection of VSVG, base editor fusions and guide RNA expressing plasmids. Particle purification and concentration was performed by filtration and ultracentrifugation at 100,000×g for 2 hours. Gene modification frequencies were determined by amplicon sequencing.

Figure 10:
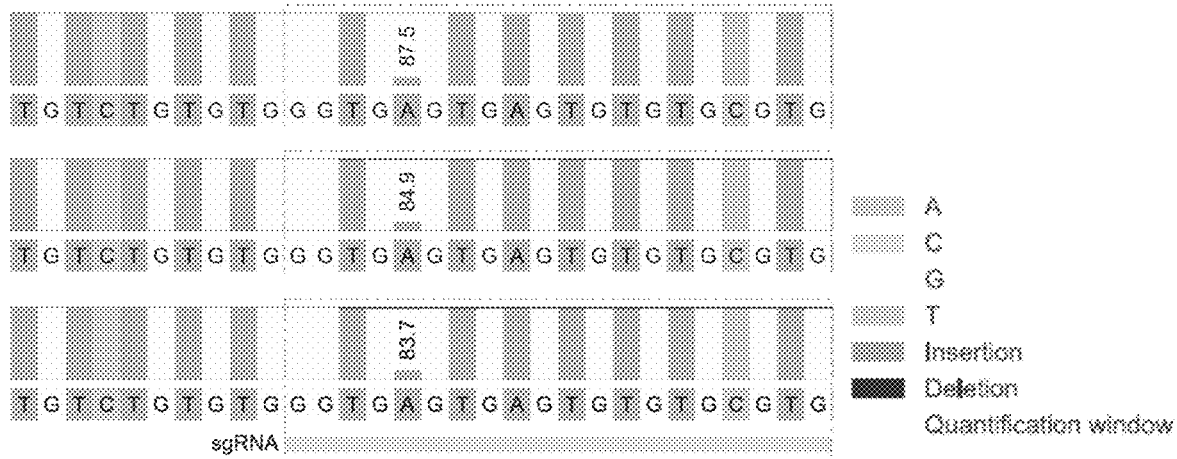
FIG. 10: Exemplary T1eVLP-delivered spCas9 base editing in vitro. HEK293T cells transduced with T1eVLPs containing PLC PH fused to codon optimized spCas9 ABE targeted to VEGF site #3. eVLPs are pseudotyped with VSVG Gene modification is measured by amplicon sequencing.

In FIG. 10, hPLCδ1 fusions to the N terminus of Cas9-based base editors (codon optimized ABE) with guide RNA targeting VEGF site #3 were packaged in eVLPs. HEK293T cells were treated with these particles that were previously purified from HEK293T cell culture media (DMEM) 48 hours after transfection of VSVG, base editor fusions and guide RNA expressing plasmids. Particle purification and concentration was performed by filtration and ultracentrifugation at 100,000×g for 2 hours. Gene modification frequencies were determined by amplicon sequencing.

Figure 11:
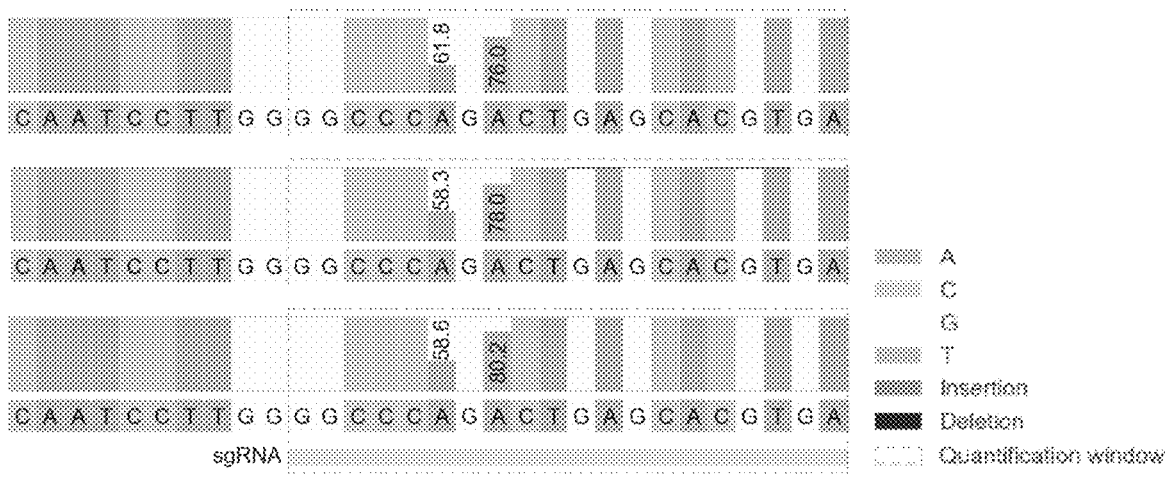
FIG. 11: Exemplary T1eVLP-delivered spCas9 base editing in vitro. HEK293T cells transduced with T1eVLPs containing PLC PH fused to codon optimized spCas9 ABE targeted to HEK site #3. eVLPs are pseudotyped with VSVG. Gene modification is measured by amplicon sequencing.
Figure 12:
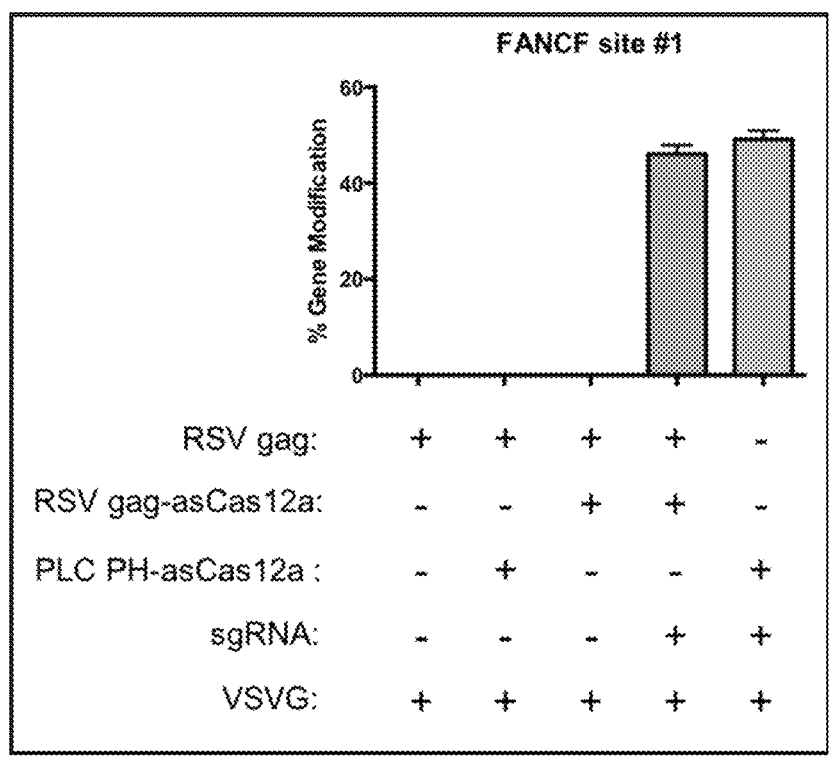
FIG. 12: Exemplary T1eVLP-delivered asCas12a genome editing in vitro. HEK293 cells transduced with VLPs containing Rous sarcoma virus gag or T1eVLPs containing PLC PH fused to asCas12a. VLPs and eVLPs are targeted to FANCF site #1 by crRNA. Gene modification is measured by T7E1. The Rous sarcoma virus gag VLP serves as a positive control.

In FIG. 11, hPLCδ1 fusions to the N terminus of Cas9-based base editors (codon optimized ABE) with guide RNA targeting HEK site #3 were packaged in eVLPs. HEK293T cells were treated with these particles that were previously purified from HEK293T cell culture media (DMEM) 48 hours after transfection of VSVG, base editor fusions and guide RNA expressing plasmids. Particle purification and concentration was performed by filtration and ultracentrifugation at 100,000×g for 2 hours. Gene modification frequencies were determined by amplicon sequencing.

In FIG. 12, gag fusions to Cas12a or hPLCδ1 PH fusions to Cas12a with guide RNA targeting FANCF site #1 were packaged in VLPs and eVLPs, respectively. HEK293 cells were treated with these particles that were previously purified from HEK293T cell culture media (DMEM) 48 hours after transfection of VSVG, Cas12a fusions and guide RNA expressing plasmids. Particle purification and concentration was performed by PVDF filtration and ultracentrifugation at 100,000×g for 2 hours. Gene modification frequencies were determined by T7E1.

Figure 13:
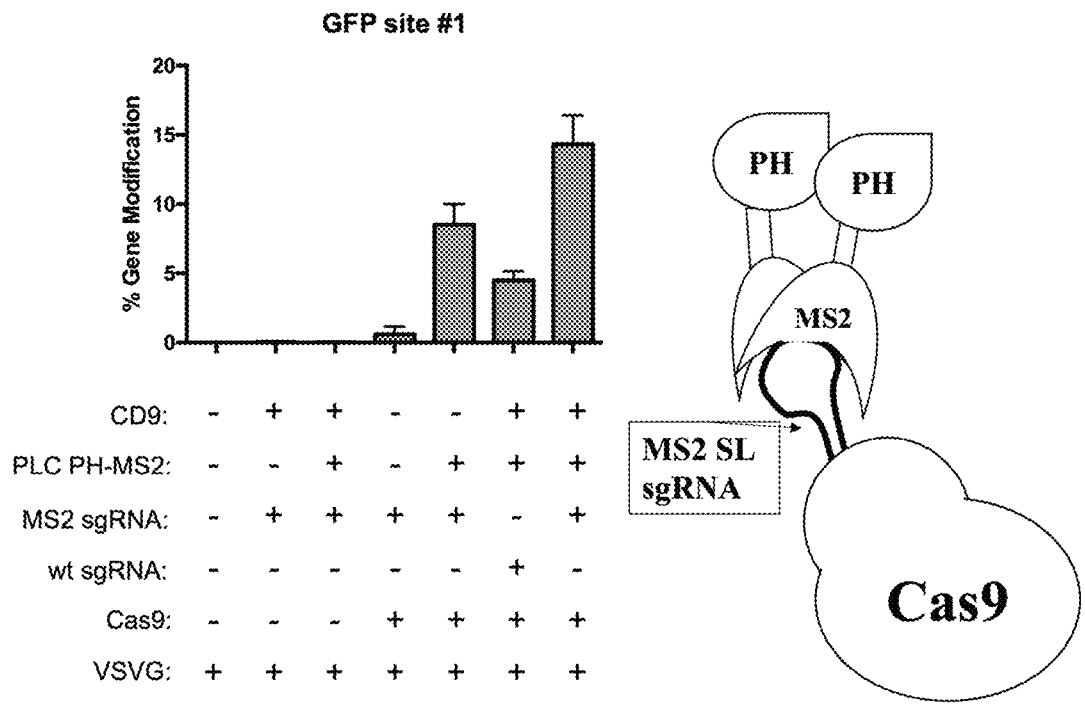
FIG. 13: Exemplary T1eVLP-delivered spCas9 genome editing in vitro. HEK293 cells transduced with T1eVLPs containing PLC PH fused to RNA binding protein MS2. MS2 binds to MS2 stem loops in the sgRNA, which is complexed with Cas9, and MS2 is fused to a PH domain for efficient eVLP loading. eVLPs are targeted to GFP site #1 by sgRNA. Gene modification is measured by T7E1.

In FIG. 13, hPLCδ1 PH fusions to MS2 with MS2-stem loop guide RNA targeting GFP site #1 were packaged in eVLPs with Cas9. HEK293 cells were treated with these particles that were previously purified from HEK293T cell culture media (DMEM) 48 hours after transfection of VSVG, Cas9, PH-MS2 fusions and MS2 stem loop guide RNA expressing plasmids. Particle purification and concentration was performed by PVDF filtration and ultracentrifugation at 100,000×g for 2 hours. Gene modification frequencies were determined by T7E1.

Figure 14:
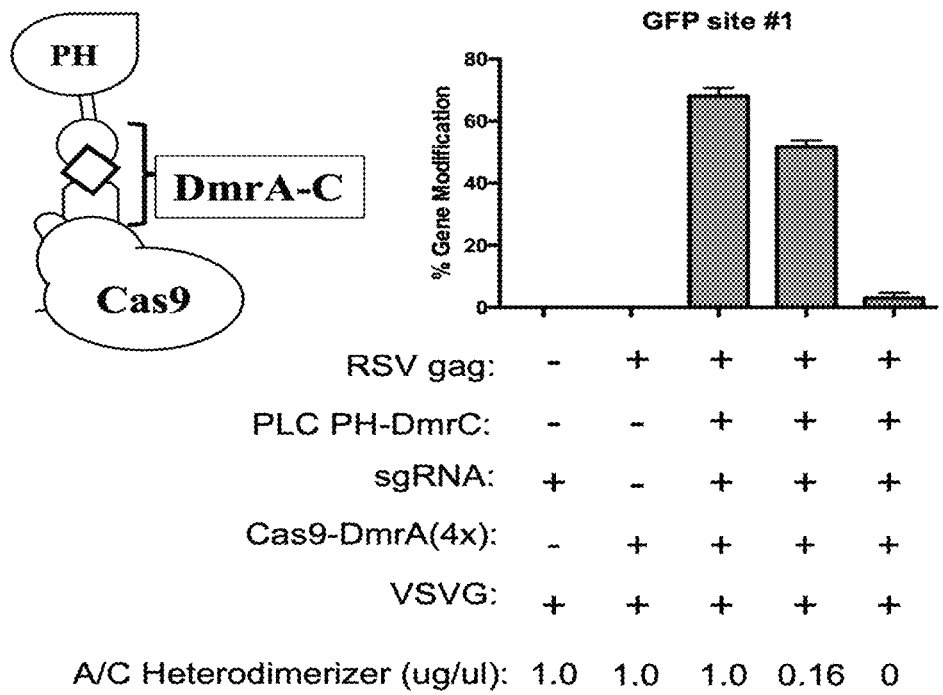
FIG. 14: Exemplary T1eVLP-delivered spCas9 genome editing in vitro. HEK293 cells transduced with T1eVLPs containing PLC PH fused to dimerization domain (DmrC). In the presence of A/C Heterodimerizer molecule, DmrC binds to DmrA which is directly fused to Cas9. eVLPs are targeted to GFP site #1 by sgRNA. Gene modification is measured by T7E1.

In FIG. 14, hPLCδ1 PH fusions to DmrC with guide RNA targeting GFP site #1 and Cas9 fused to DmrA repeats were packaged in eVLPs. HEK293 cells were treated with these particles that were previously purified from HEK293T cell culture media (DMEM) 48 hours after transfection of VSVG, DmrA-Cas9, PH-DmrC fusions and guide RNA expressing plasmids. Particle purification and concentration was performed by PVDF filtration and ultracentrifugation at 100,000×g for 2 hours. Gene modification frequencies were determined by T7E1.

Figure 15:
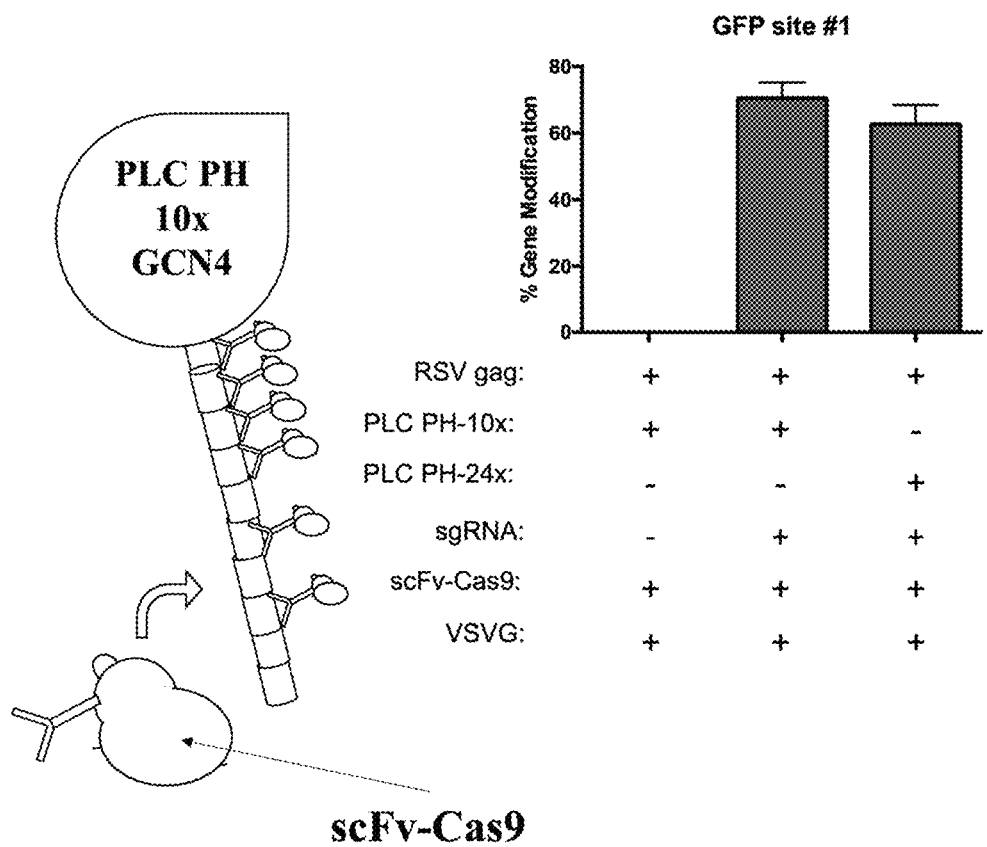
FIG. 15: Exemplary T1eVLP-delivered asCas9 genome editing in vitro. HEK293 cells transduced with T1eVLPs containing PLC PH fused to GNC4 protein domain repeats. An scFv binds to the GCN4 repeats, and scFvs are directly fused to Cas9. eVLPs are targeted to GFP site #1 by sgRNA. Gene modification is measured by T7E1.
Figure 16:
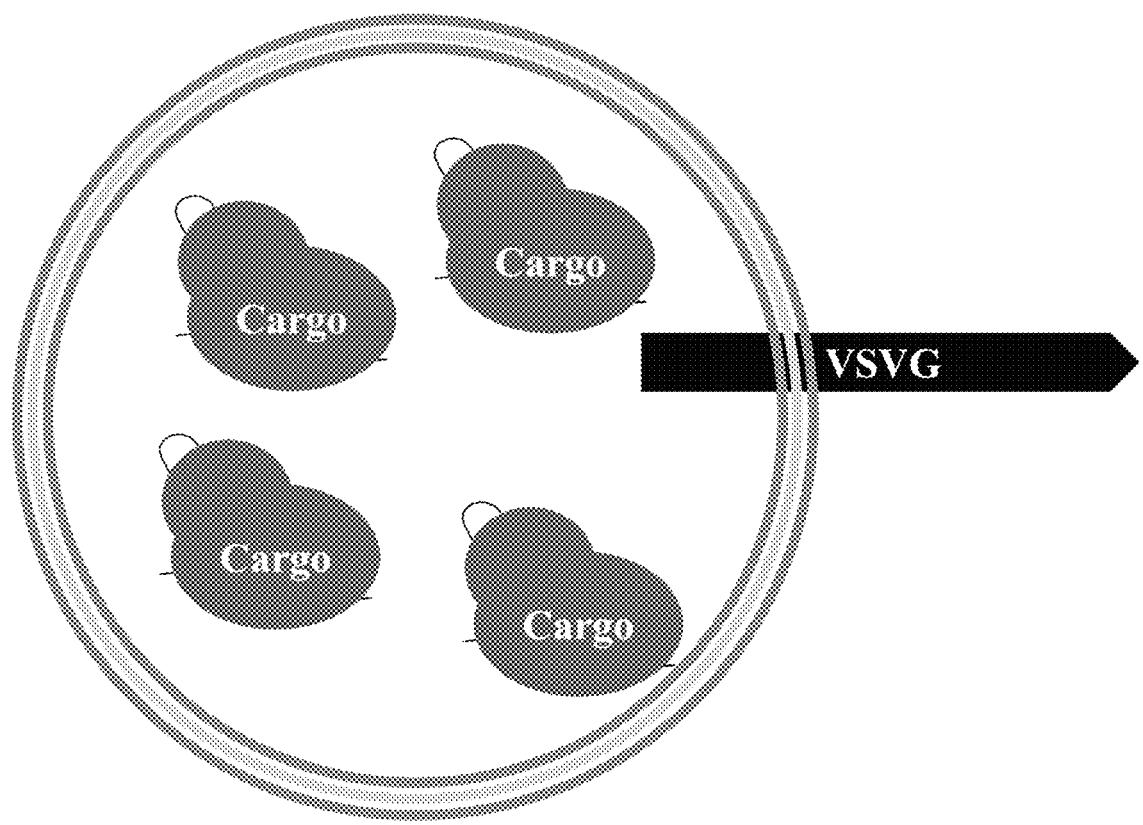
Figure 17:
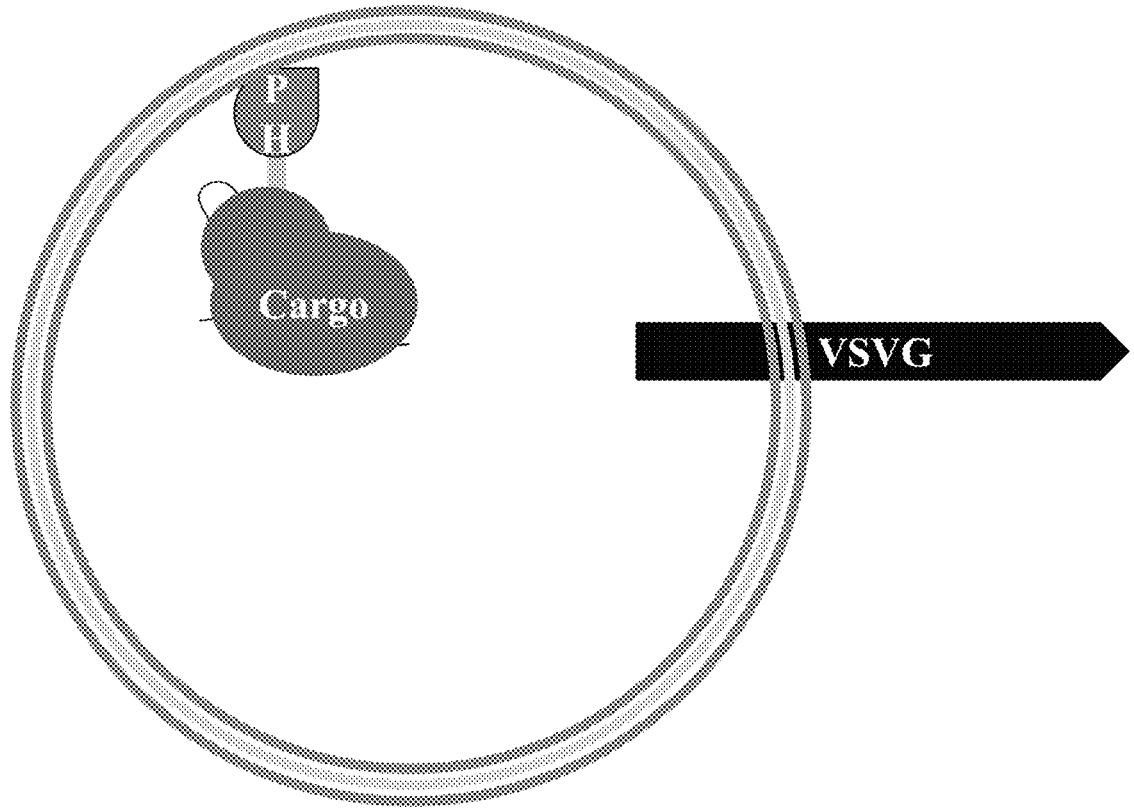
Figure 18:
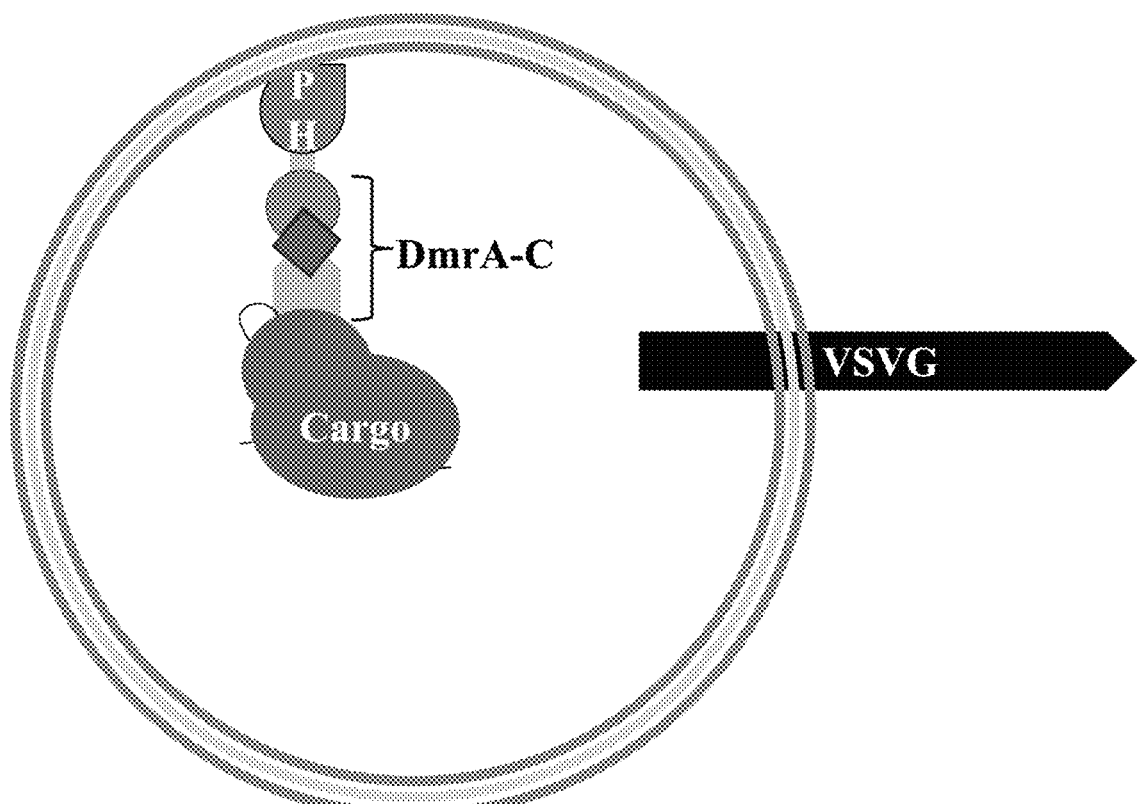
Figure 19:
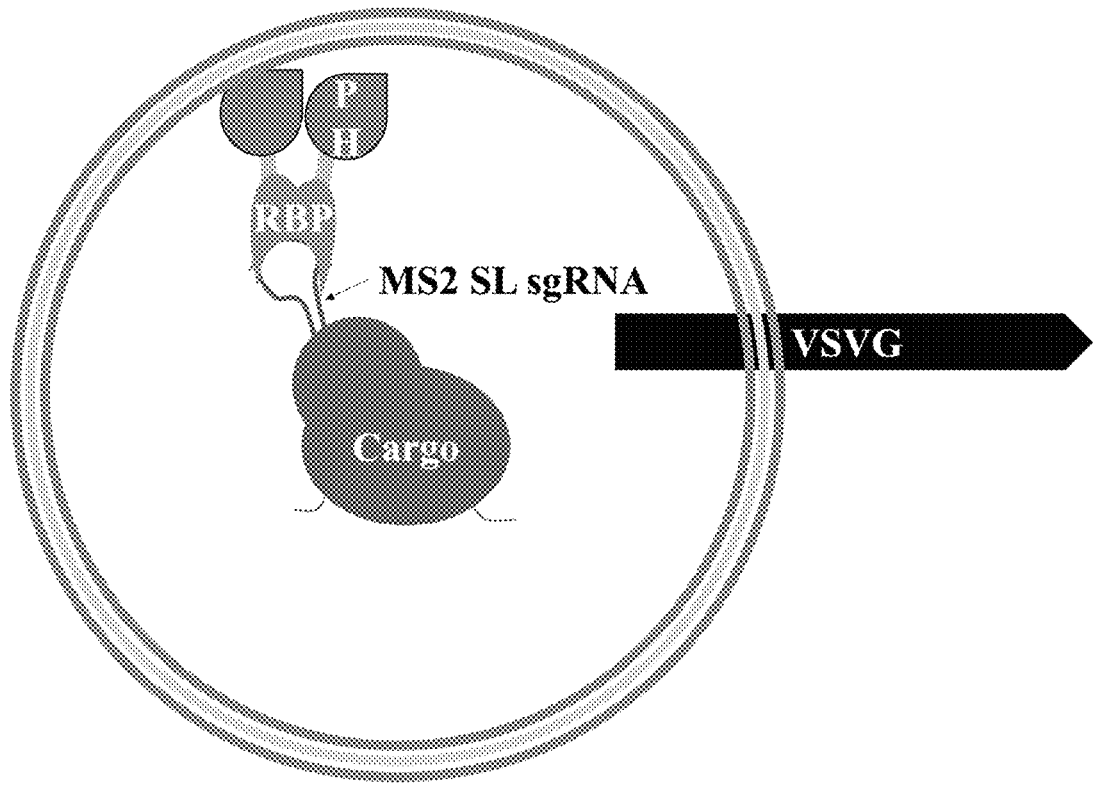
Figure 20:
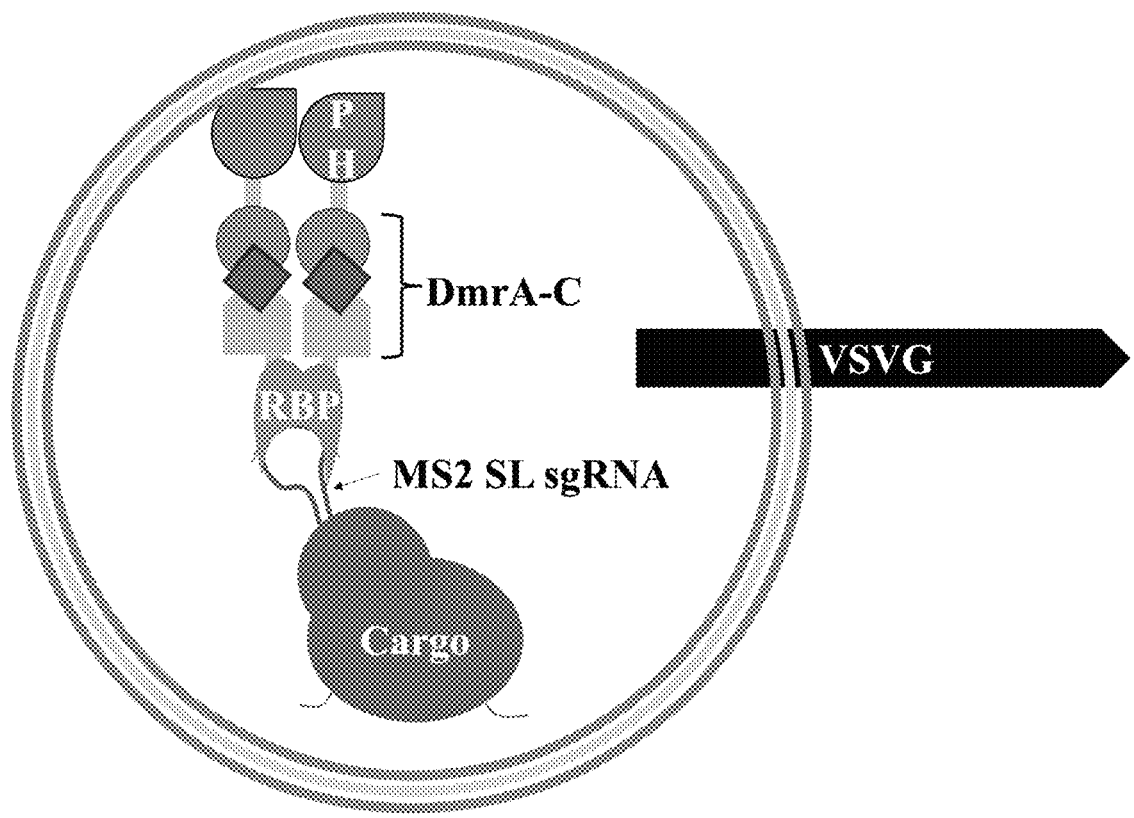
Figure 21:
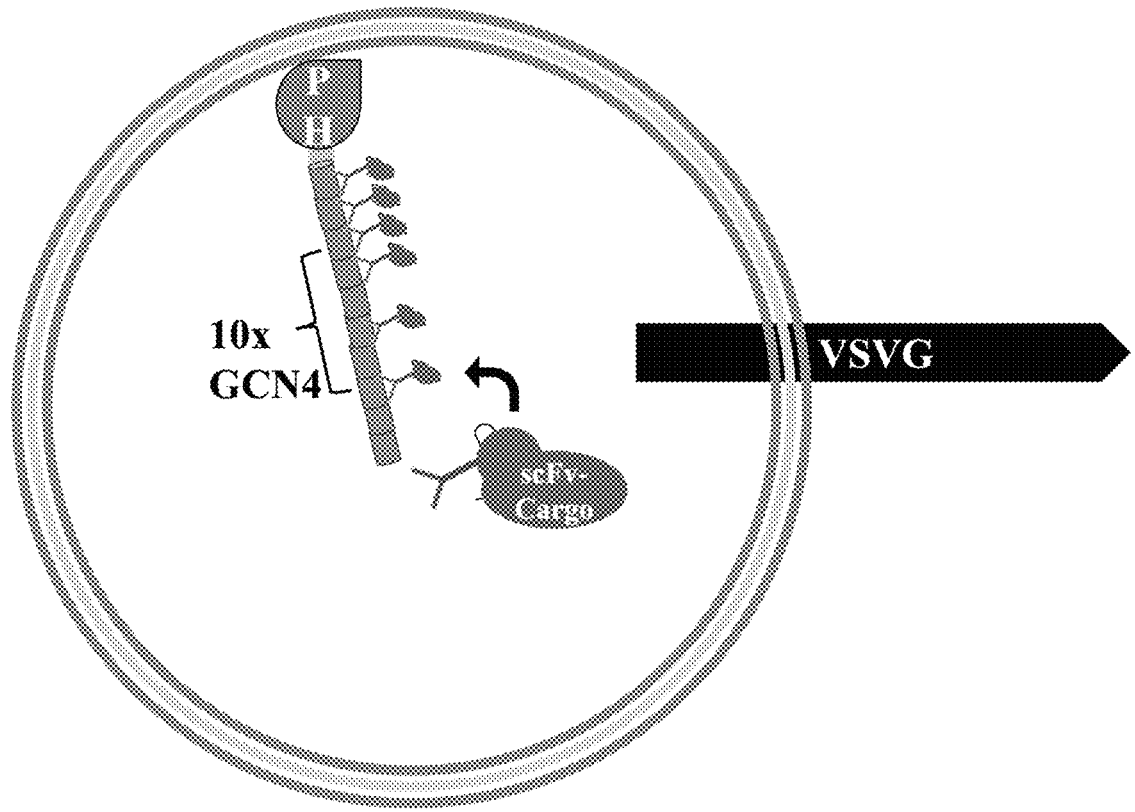
Figure 22:
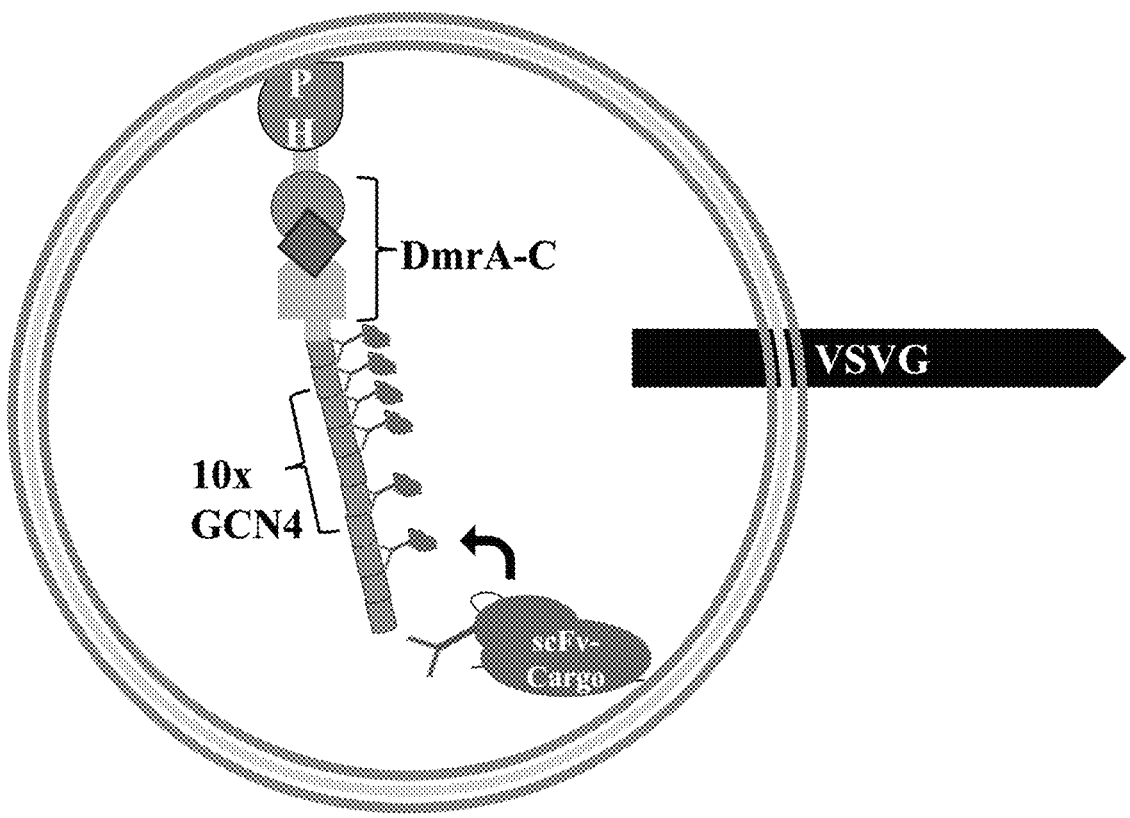
Figure 23:
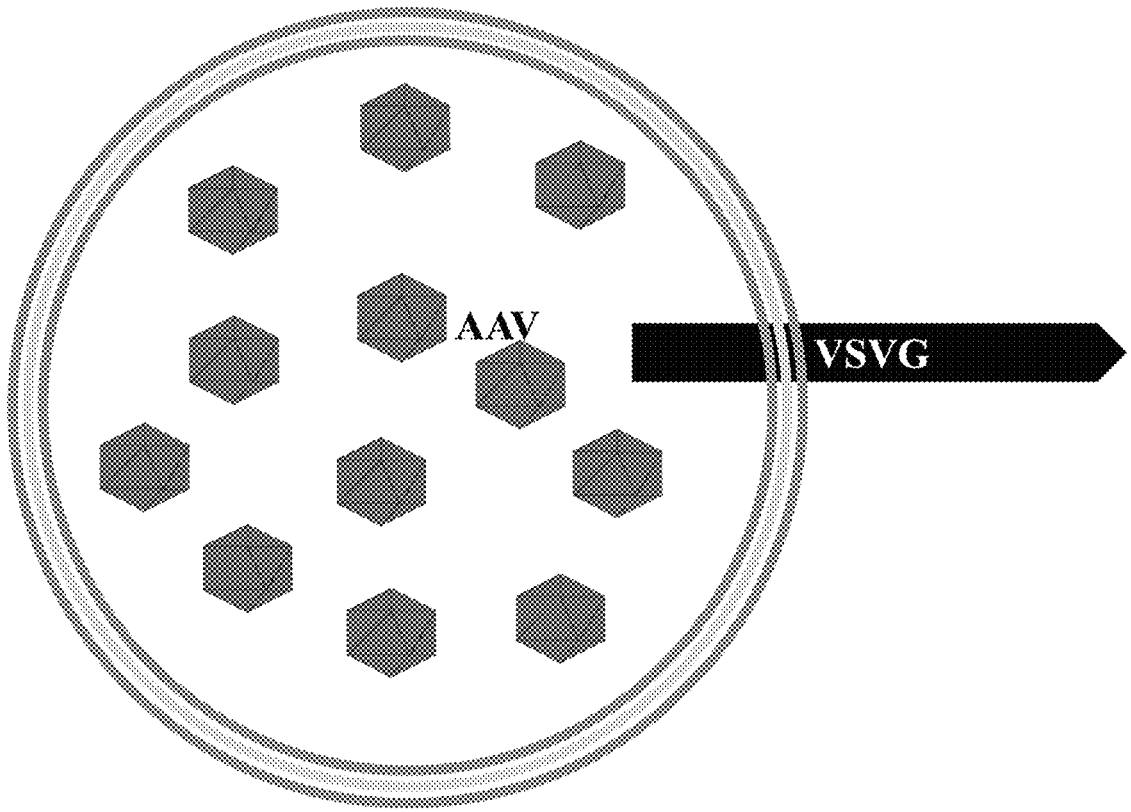
Figure 24:
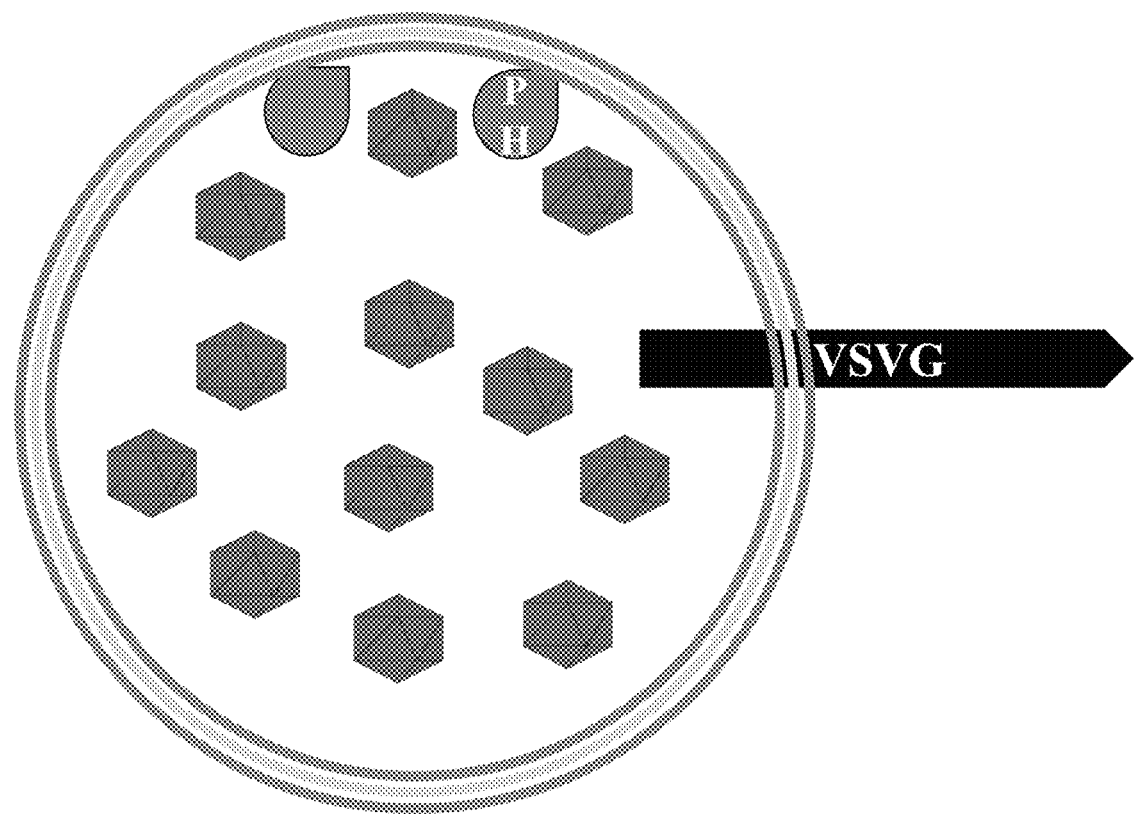
Figure 25:
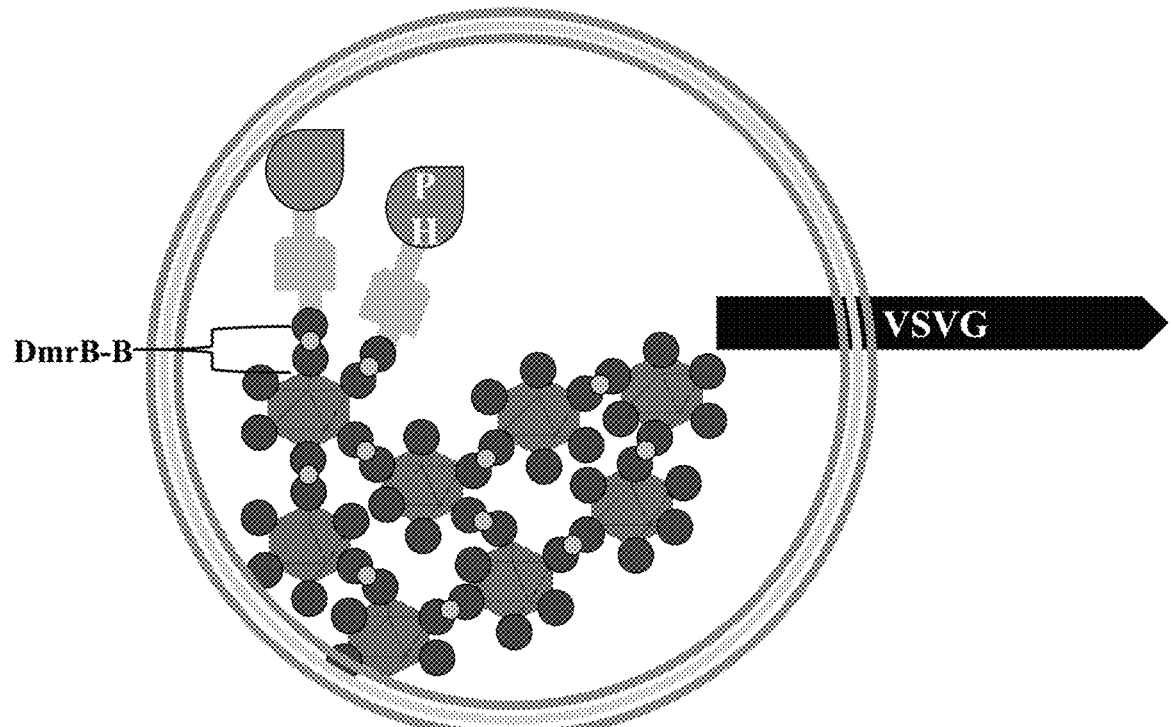
Figure 26:
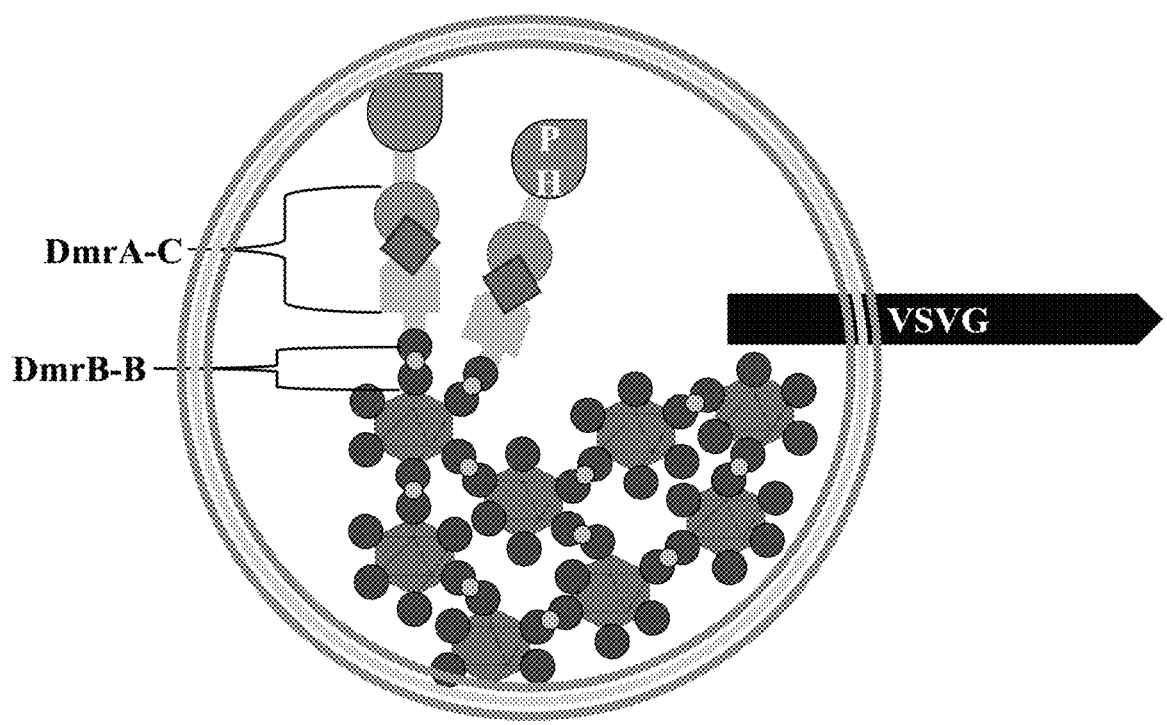
Figure 27:
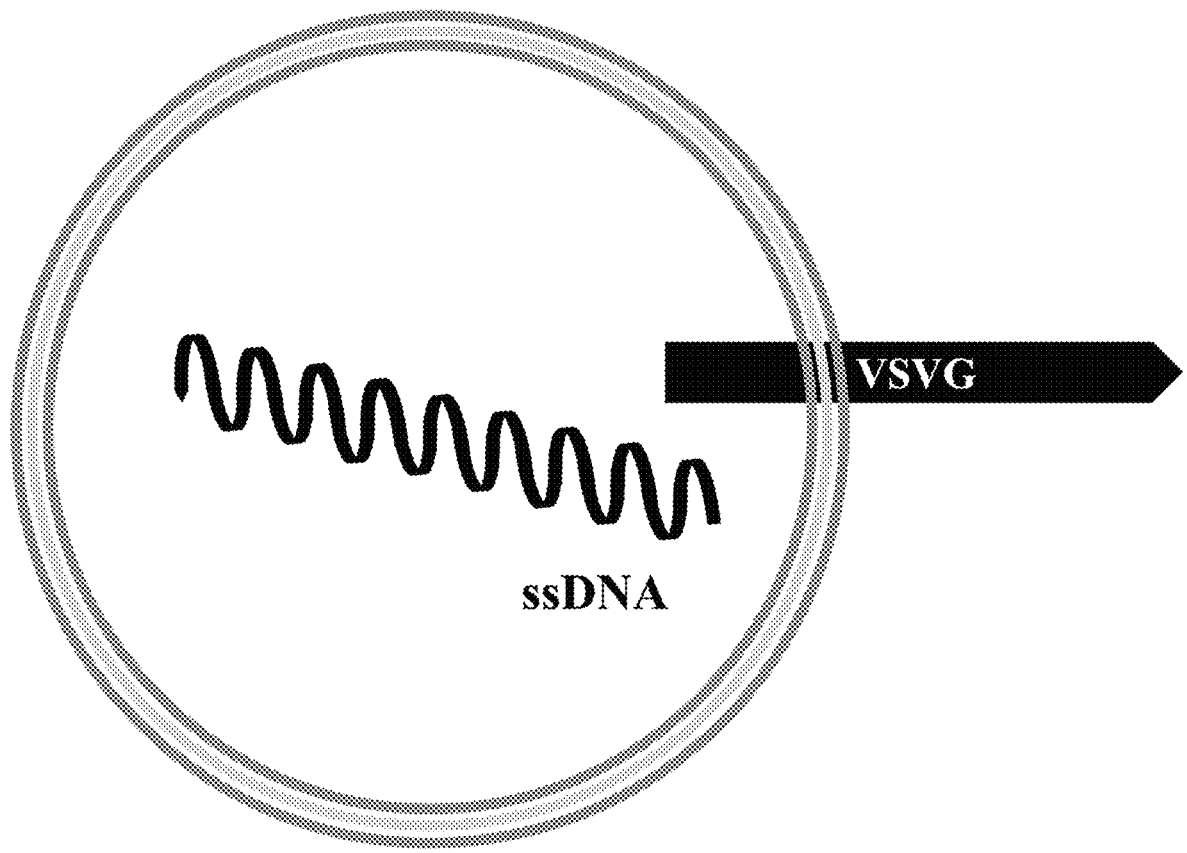
Figure 28:
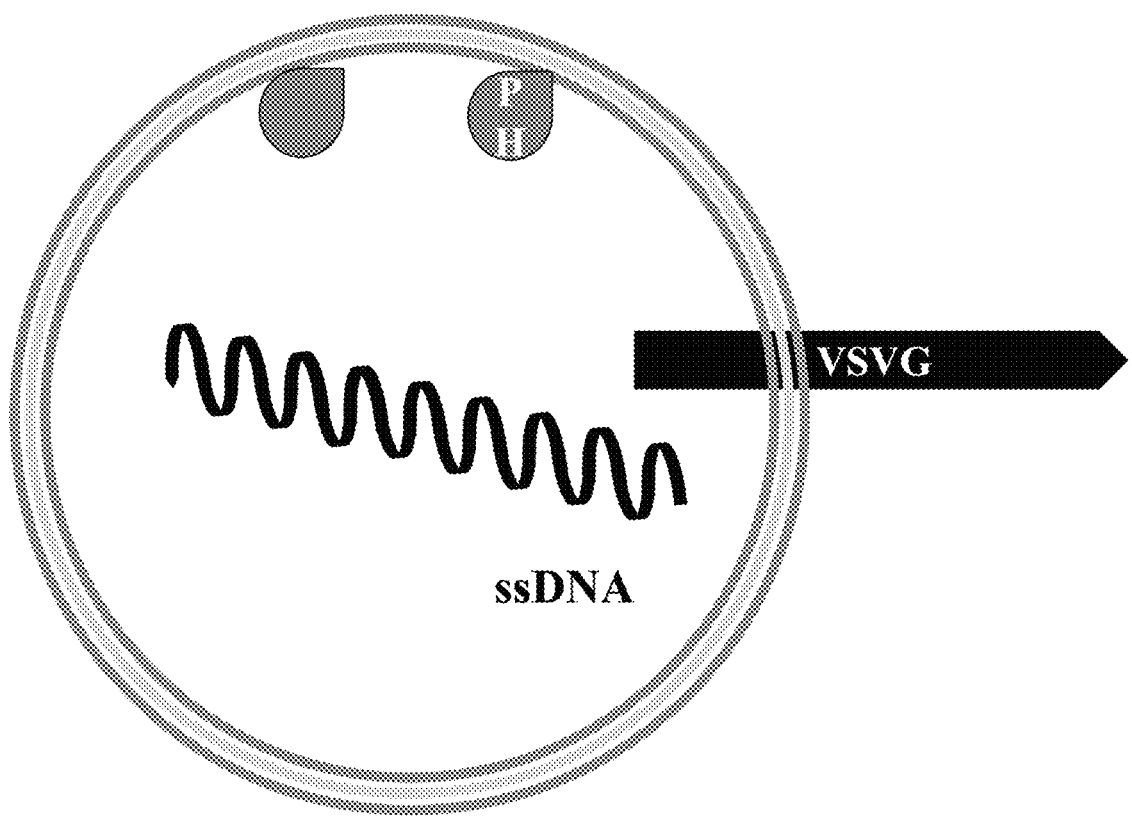
Figure 29:
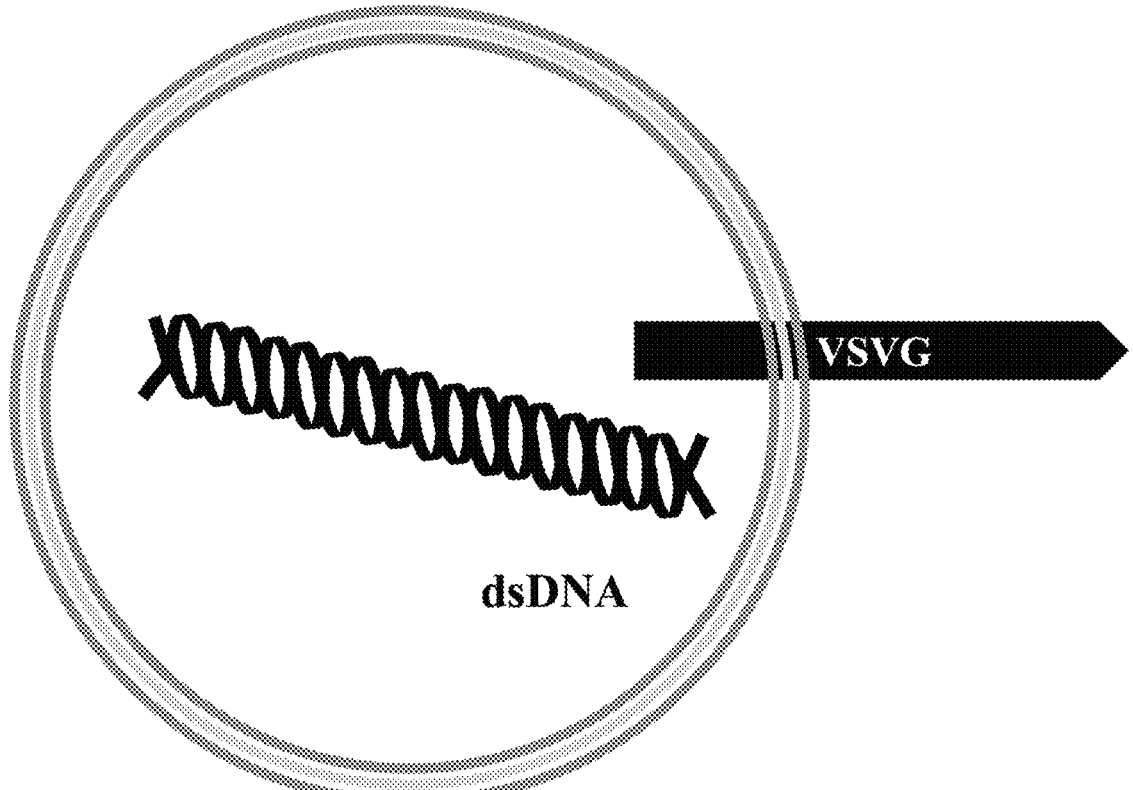
Figure 30:
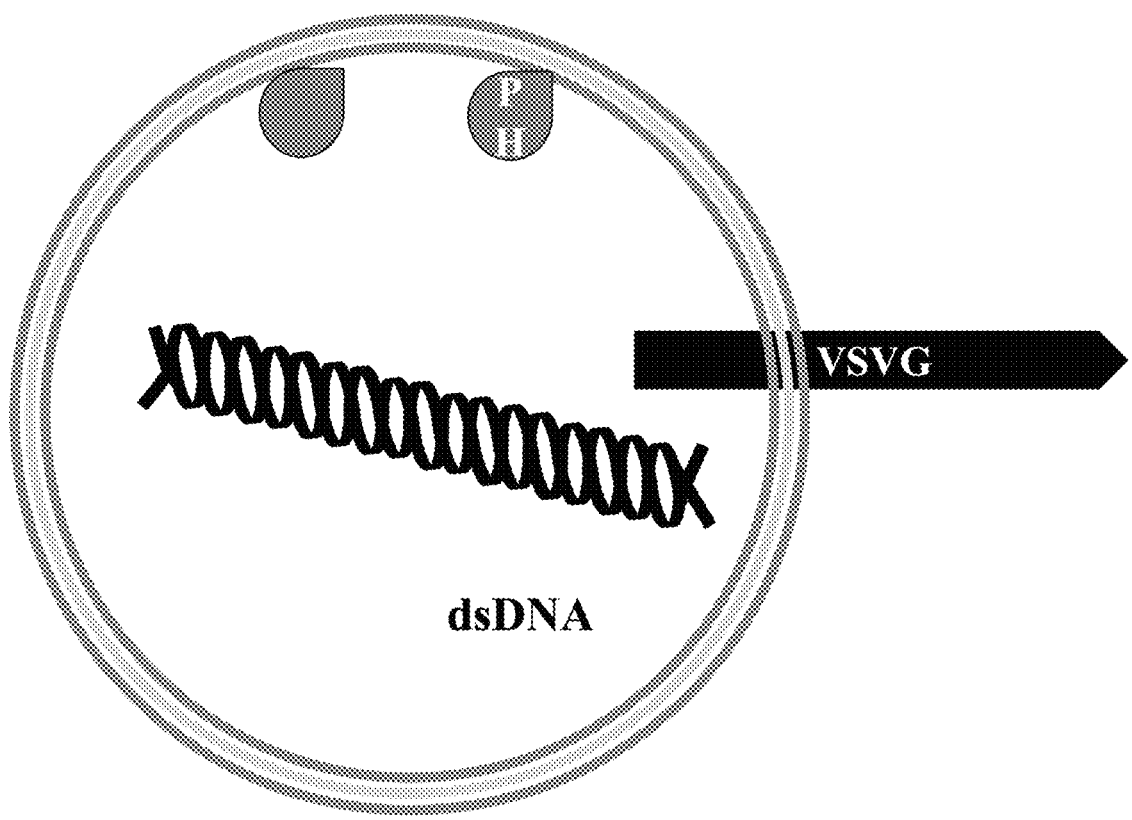
Figure 31:
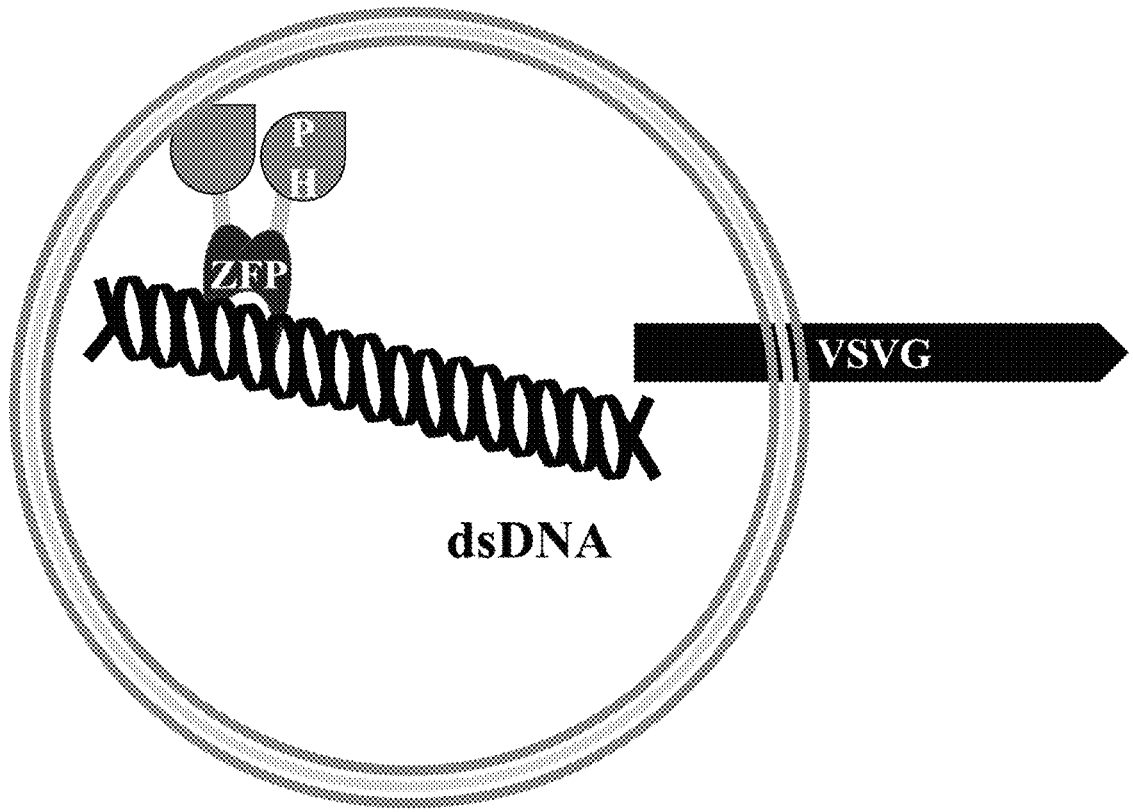
Figure 32:
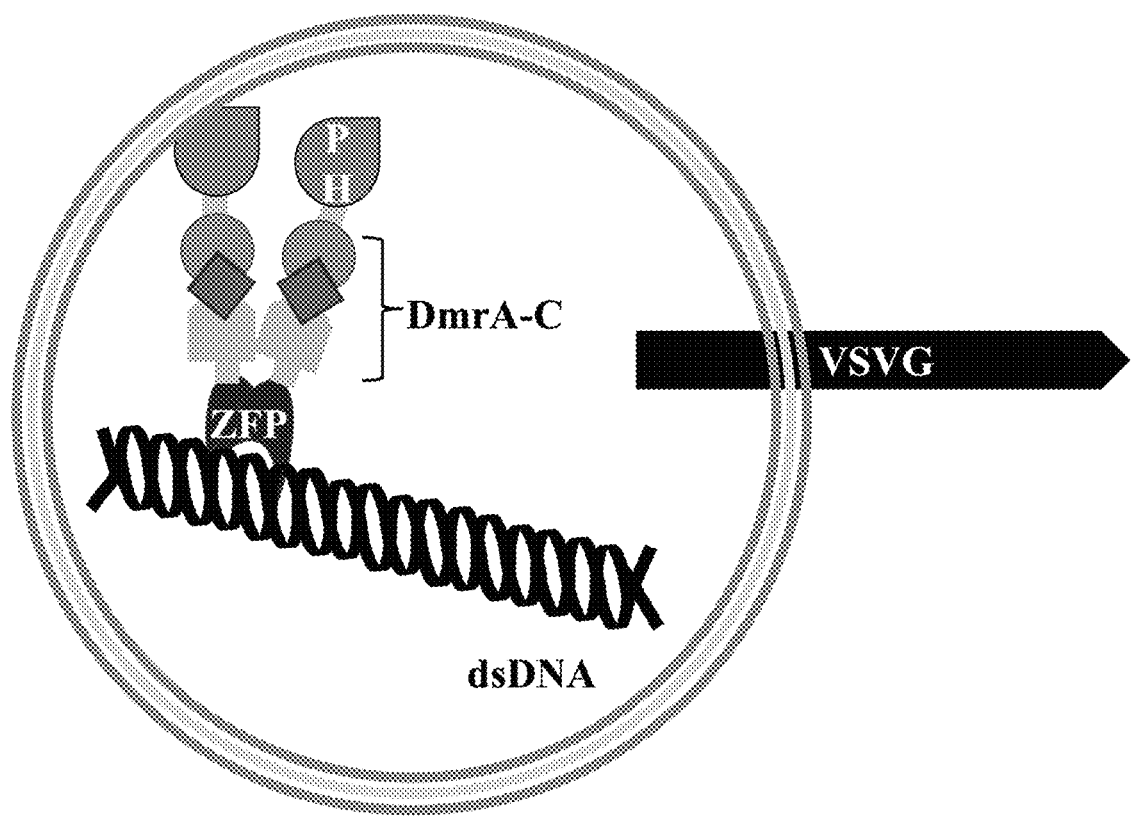
Figure 33:
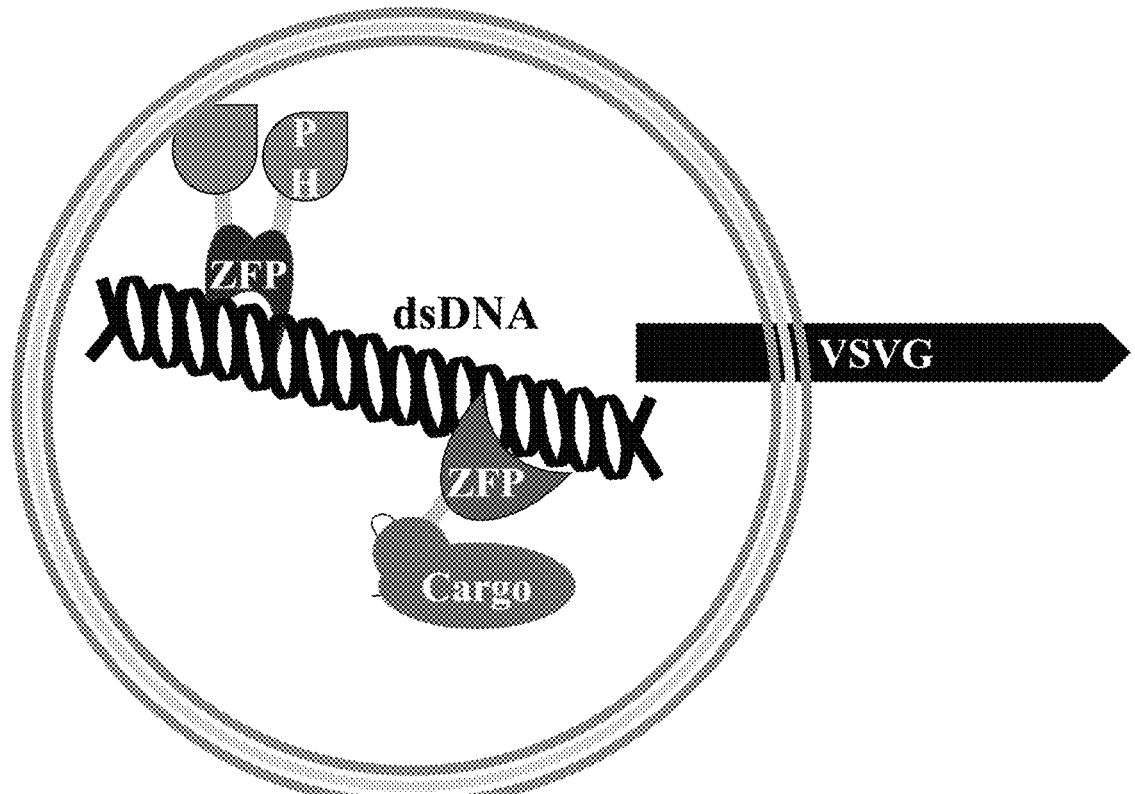
Figure 34:
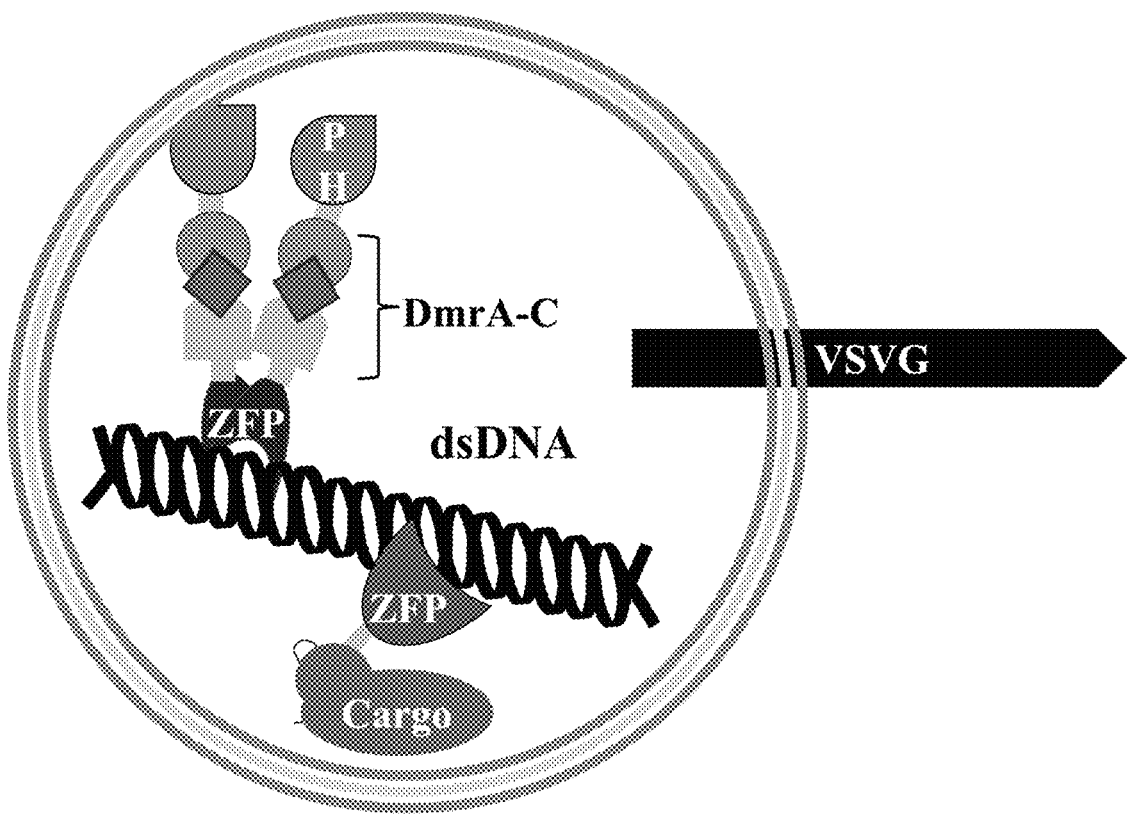
Figure 35:
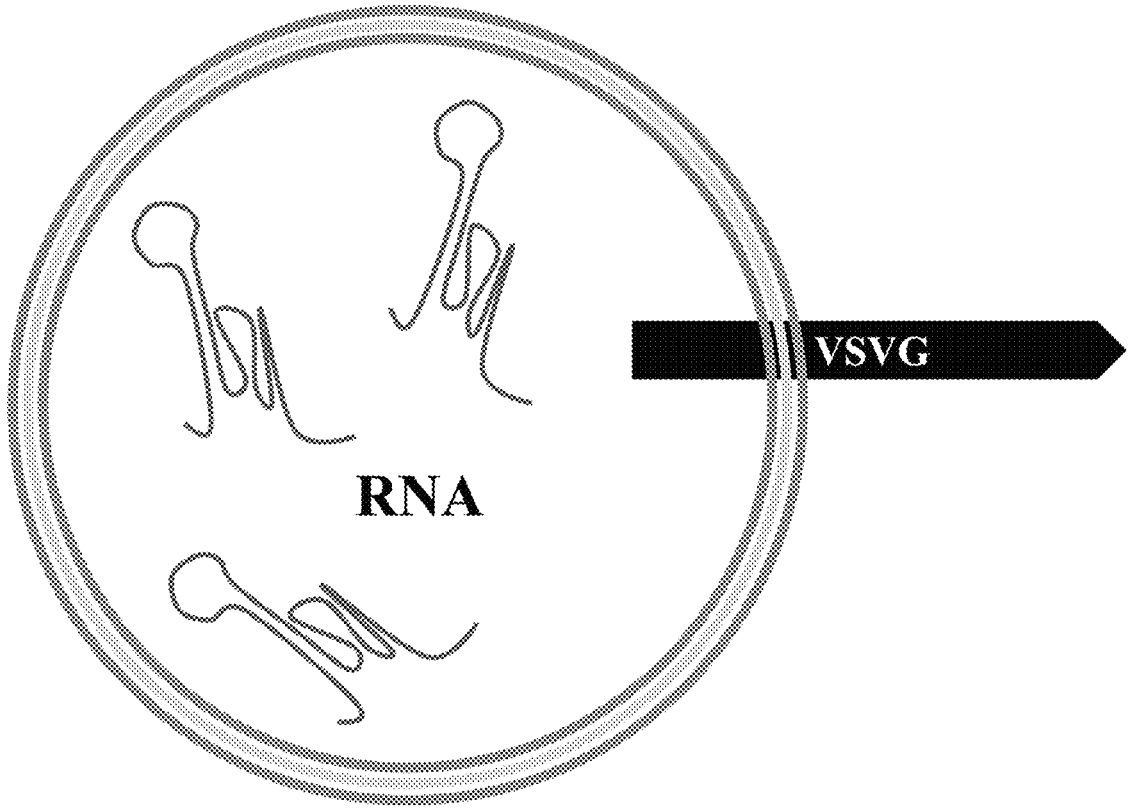
Figure 38:
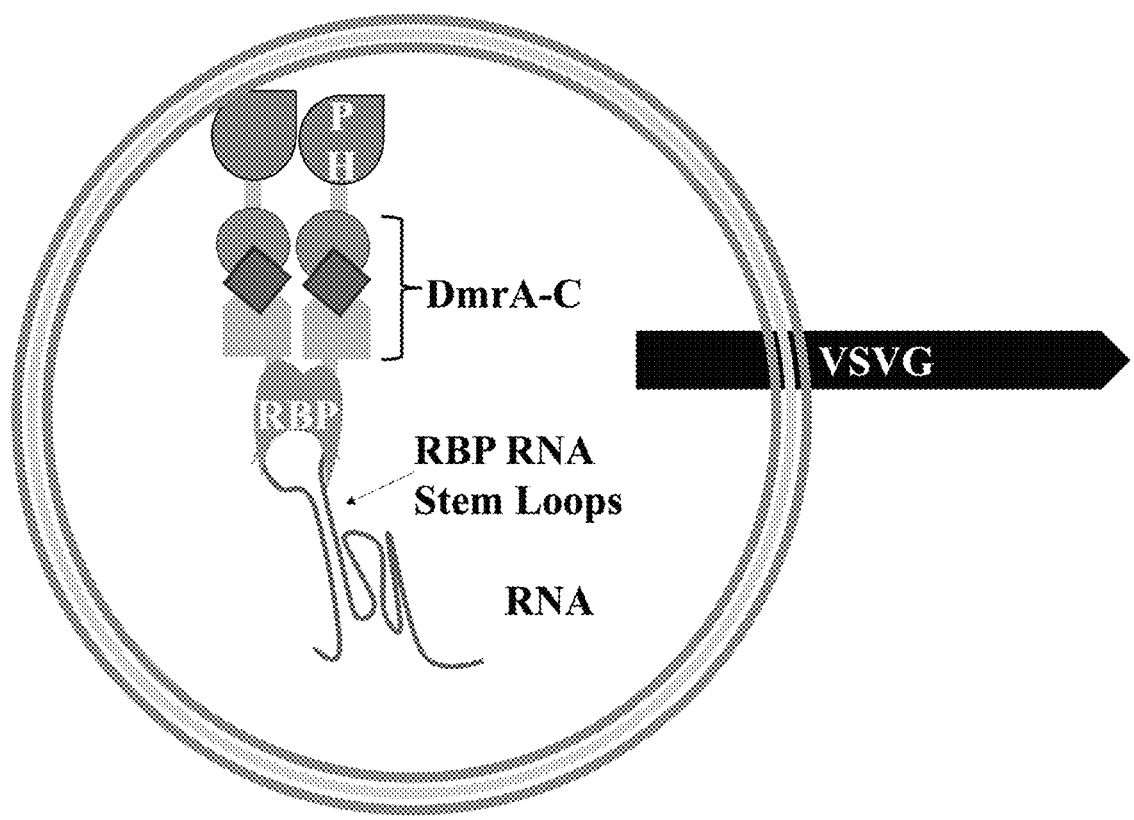
Figure 39:
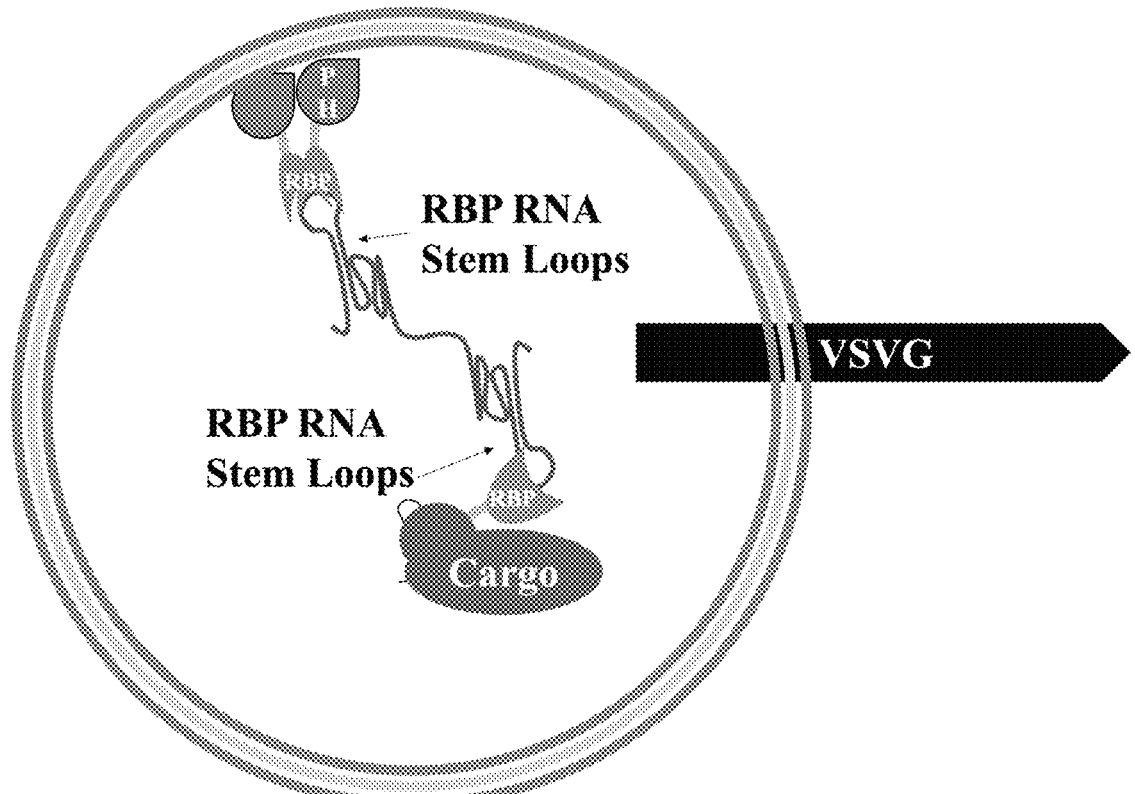
Figure 40:
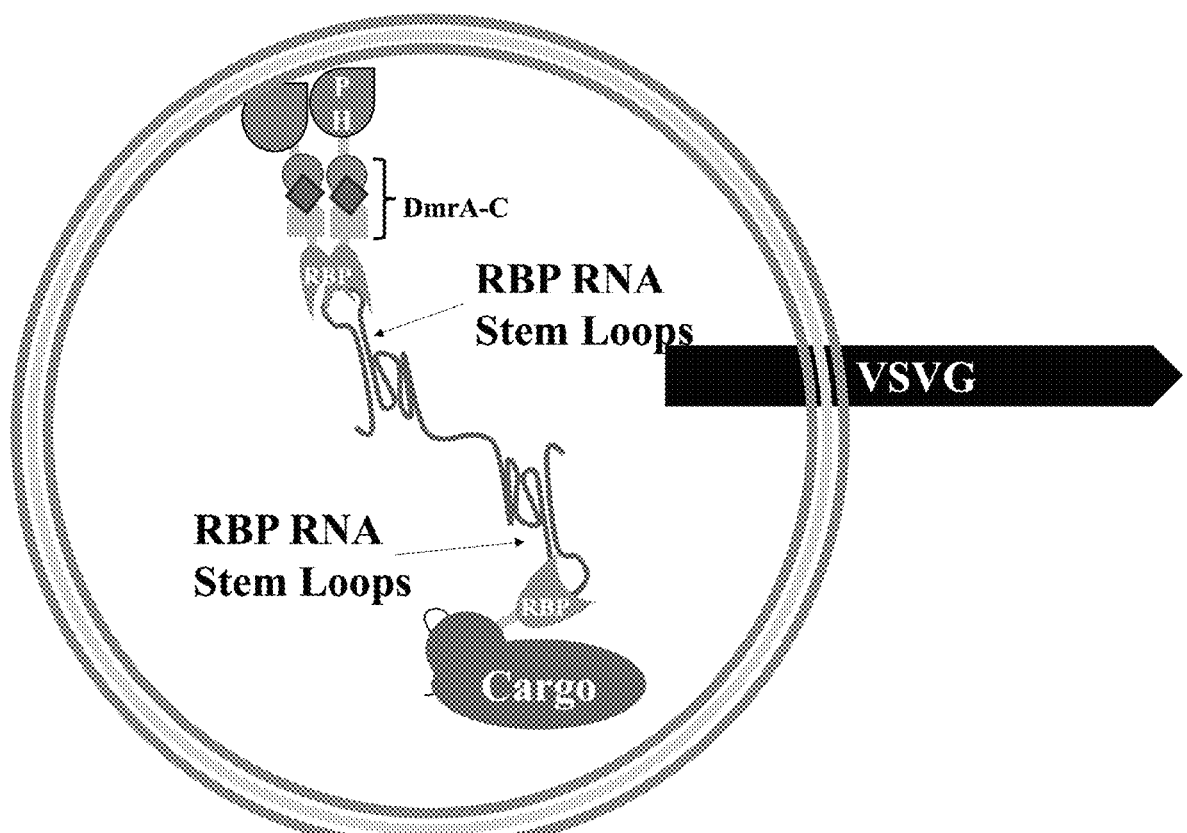

In FIG. 15, hPLCδ1 PH fusions to GCN4 repeats with guide RNA targeting GFP site #1 and Cas9 fused to scFv were packaged in eVLPs. HEK293 cells were treated with these particles that were previously purified from HEK293T cell culture media (DMEM) 48 hours after transfection of VSVG, scFv-Cas9, PH-GCN4 fusions and guide RNA expressing plasmids. Particle purification and concentration was performed by PVDF filtration and ultracentrifugation at 100,000×g for 2 hours. Gene modification frequencies were determined by T7E1.

FIGS. 16-40 show various non-limiting examples of eVLP configurations and possible cargo.

TABLE 1

Exemplary Virally-derived glycoproteins.

| Virally-derived glycoproteins |
|---|
| vesicular stomatitis virus glycoprotein (VSVG) |
| GP64 |
| GP160 |
| RD114 |
| BaEVTR |
| BaEVTRless |
| FuG-E |
| FuG-E (P440E) |
| MLV ENV (ecotropic) |
| MLV ENV (amphotropic) |
| MLV 10A1 |

TABLE 2

Exemplary Potential Cas9 and Cas12a orthologs

| DNA-binding Cas ortholog | Enzyme class | Nickase mutation | CI mutations |
|---|---|---|---|
| SpCas9 | Type II-A | D10A | D10A, H840A |
| SaCas9 | Type II-A | D10A | D10A |
| CjCas9 | Type II-C | D8A | D8A |
| NmeCas9 | Type II-C | D16A | D16A, H588A |
| asCas12a | Type II-C | | D908A, E993A |
| lbCas12a | Type II-C | | D832A, E925A |

Nickase mutation residues represents a position of the enzyme either known to be required for catalytic activity of the conserved RuvC nuclease domain or predicted to be required for this catalytic activity based on sequence alignment to CjCas9 where structural information is lacking. All positional information refers to the wild-type protein sequences acquired from uniprot.org.

TABLE 3

Exemplary Deaminase domains and their substrate sequence preferences.

| Deaminase | Nucleotide sequence preference |
|---|---|
| hAID | 5'-WRC |
| rAPOBEC1* | 5'-TC ≥ CC ≥ AC > GC |
| mAPOBEC3 | 5'-TYC |
| hAPOBEC3A | 5'-TCG̅ |
| hAPOBEC3B | 5'-TCR̅ > TCT |
| hAPOBEC3C | 5'-WYC̅ |
| hAPOBEC3F | 5'-TTC̅ |
| hAPOBEC3G | 5'-CCC̅ |
| hAPOBEC3H | 5'-TTCA~TCT̅~TTCG > AC̅CCA > TGCA̅ |
| ecTadA | |
| hAdar1 | |
| hAdar2 | |

Nucleotide positions that are poorly specified or are permissive of two or more nucleotides are annotated according to IUPAC codes, where W = A or T, R = A or G, and Y = C or T.

TABLE 4

Exemplary Epigenetic modulator domains.

| Epigenetic modulator | Epigenetic modulation |
|---|---|
| VP16 | transcriptional activation |
| VP64 | transcriptional activation |
| P65 | transcriptional activation |
| RTA | transcriptional activation |
| KRAB | transcriptional repression |
| MeCP2 | transcriptional repression |
| Tet1 | Methylation |
| Dnmt3a | Methylation |

TABLE 5

Exemplary CRISPR based RNA-guided RNA binding enzymes

| RNA-binding Cas ortholog | Enzyme class |
| --- | --- |
| LshCas13a | Type-VI |
| LwaCas13a | Type-VI |
| PspCas13b | Type-VI |
| RfxCas13d | Type-VI |

TABLE 6

Exemplary plasma membrane recruitment domains

| # | Plasma membrane recruitment domain | Substitution(s) |
| --- | --- | --- |
| 1. | Pleckstrin homology domain of human phospholipase Cδ1 (hPLCδ1) | |
| 2. | Pleckstrin homology domain of human Akt1 (hAkt1) | |
| 3. | Mutant Pleckstrin homology domain of human Akt1 | E17K |
| 4. | Pleckstrin homology domain of human 3-phosphoinositide-dependent protein kinase 1 (hPDPKI) | |
| 5. | Human CD9 | |
| 6. | Human CD47 | |
| 7. | Human CD63 | |
| 8. | Human CD81 | |
| 9. | Pleckstrin homology domain of Human Dapp1 | |
| 10. | Pleckstrin homology domain of Mouse Grp1 | |
| 11. | Pleckstrin homology domain of Human Grp1 | |
| 12. | Pleckstrin homology domain of Human OSBP | |
| 13. | Pleckstrin homology domain of Human Btk1 | |
| 14. | Pleckstrin homology domain of Human FAPP1 | |
| 15. | Pleckstrin homology domain of Human CERT | |
| 16. | Pleckstrin homology domain of Human PKD | |
| 17. | Pleckstrin homology domain of Human PHLPP1 | |
| 18. | Pleckstrin homology domain of Human SWAP70 | |
| 19. | Pleckstrin homology domain of Human MAPKAP1 | |

*Homo sapiens*: Pleckstrin homology
domain of Human Dapp1
(SEQ ID NO: 1)
MQTGRTEDDLVPTAPSLGTKEGYLTKQGGLVKTWKTRWFTLHRNELK

YFKDQMSPEPIRILDLTECSAVQFDYSQERVNCFCLVFPFRTFYLCA

KTGVEADEWIKILRWKLSQIRKQLNQGEGTIR

*Mus musculus*: Pleckstrin homology domain
of Mouse Grp1
(SEQ ID NO: 2)
PFKIPEDDGNDLTHTFFNPDREGWLLKLGGRVKTWKRRWFILTDNCL

YYFEYTTDKEPRGIIPLENLSIREVEDPRKPNCFELYNPSHKGQVIK

ACKTEADGRVVEGNHVVYRISAPSPEEKEEWMKSIKASISRDPFYDM

LATRKRRIANKK

*Homo sapiens*: Pleckstrin homology
domain of Human Grp1
(SEQ ID NO: 3)
NPDREGWLLKLGGGRVKTWKRRWFILTDNCLYYFEYTTDKEPRGIIP

LENLSIREVEDPRKPNCFELYNPSHKGQVIKACKTEADGRVVEGNHV

VYRISAPSPEEKEEWMKSIKASIS

*Homo sapiens*: Pleckstrin homology
domain of Human OSBP
(SEQ ID NO: 4)
SGSAREGWLFKWTNYIKGYQRRWFVLSNGLLSYYRSKAEMRHTCRGT

INLATANITVEDSCNFIISNGGAQTYHLKASSEVERQRWVTALELAK

AKAVK

*Homo sapiens*: Pleckstrin homology
domain of Human Btk1
(SEQ ID NO: 5)
MAAVILESIFLKRSQQKKKTSPLNFKKRLFLLTVHKLSYYEYDFERG

RRGSKKGSIDVEKITCVETVVPEKNPPPERQIPRRGEESSEMEQISI

IERFPYPFQVVYDEGPLYVFSPTEELRKRWIHQLKNVIRYNSDLVQK

YHPCFWIDGQYLCCSQTAKNAMGCQILENRNGSLKP

*Homo sapiens*: Pleckstrin homology
domain of Human FAPP1
(SEQ ID NO: 6)
MEGVLYKWTNYLTGWQPRWFVLDNGILSYYDSQDDVCKGSKGSIKMA

VCEIKVHSADNTRMELIIPGEQHFYMKAVNAAERQRWLVALGSSKAC

LTDT

*Homo sapiens*: Pleckstrin homology
domain of Human CERT
(SEQ ID NO: 7)
MSDNQSWNSSGSEEDPETESGPPVERCGVLSKWTNYIHGWQDRWVLK

NNALSYYKSEDETEYGCRGSICLSKAVITPHDFDECRFDISVNDSVW

YLRAQDPDHRQQWIDAIEQHKTESGYG

*Homo sapiens*: Pleckstrin homology
domain of Human PKD
(SEQ ID NO: 8)
TVMKEGWMVHYTSKDTLRKRHYWRLDSKCITLFQNDTGSRYYKEIPL

SEILSLEPVKTSALIPNGANPHCFEITTANVVYYVGENVVNPSSPSP

NNSVLTSGVGADVARMWEIAIQHALM

*Homo sapiens*: Pleckstrin homology
domain of Human PHLPP1
(SEQ ID NO: 9)
RIQLSGMYNVRKGKMQLPVNRWTRRQVILCGTCLIVSSVKDSLTGKM

HVLPLIGGKVEEVKKHQHCLAFSSSGPQSQTYYICFDTFTEYLRWLR

QVSKVAS

*Homo sapiens*: Pleckstrin homology
domain of Human SWAP70
(SEQ ID NO: 10)
DVLKQGYMMKKGHRRKNWTERWFVLKPNIISYYVSEDLKDKKGDILL

DENCCVESLPDKDGKKCLFLVKCFDKTFEISASDKKKKQEWIQAIHS

TIH

*Homo sapiens*: Pleckstrin homology
domain of Human MAPKAP1
(SEQ ID NO: 11)
DMLSSHHYKSFKVSMIHRLRFTTDVQLGISGDKVEIDPVTNQKASTK

FWIKQKPISIDSDLLCACDLAEEKSPSHAIFKLTYLSNHDYKHLYFE

SDAATVNEIVLKVNYILES

Baboon Endogenous Retrovirus glycoprotein
(BaEVTR)
(SEQ ID NO: 12)
MGFTTKIIFLYNLVLVYAGFDDPRKAIELVQKRYGRPCDCSGGQVSE

PPSDRVSQVTCSGKTAYLMPDQRWKCKSIPKDTSPSGPLQECPCNSY

QSSVHSSCYTSYQQCRSGNKTYYTATLLKTQTGGTSDVQVLGSTNKL

IQSPCNGIKGQSICWSTTAPIHVSDGGGPLDTTRIKSVQRKLEEIHK

ALYPELQYHPLAIPKVRDNLMVDAQTLNILNATYNLLLMSNTSLVDD

CWLCLKLGPPTPLAIPNFLLSYVTRSSDNISCLIIPPLLVQPMQFSN

SSCLFSPSYNSTEEIDLGHVAFSNCTSITNVTGPICAVNGSVFLCGN

NMAYTYLPTNWTGLCVLATLLPDIDIIPGDEPVPIPAIDHFIYRPKR

AIQFIPLLAGLGITAAFTTGATGLGVSVTQYTKLSNQLISDVQILSS

TIQDLQDQVDSLAEVVLQNRRGLDLLTAEQGGICLALQEKCCFYVNK

SGIVRDKIKTLQEELERRRKDLASNPLWTGLQGLLPYLLPFLGPLLT

LLLLLTIGPCIFNRLVQFVKDRISVVQALVLTQQYHQLKPLEYEP

Modified Baboon Endogenous Retrovirus
glycoprotein (BaEVTRless)
(SEQ ID NO: 13)
MGFTTKIIFLYNLVLVYAGFDDPRKAIELVQKRYGRPCDCSGGQVSE

PPSDRVSQVTCSGKTAYLMPDQRWKCKSIPKDTSPSGPLQECPCNSY

QSSVHSSCYTSYQQCRSGNKTYYTATLLKTQTGGTSDVQVLGSTNKL

IQSPCNGIKGQSICWSTTAPIHVSDGGGPLDTTRIKSVQRKLEEIHK

ALYPELQYHPLAIPKVRDNLMVDAQTLNILNATYNLLLMSNTSLVDD

CWLCLKLGPPTPLAIPNFLLSYVTRSSDNISCLIIPPLLVQPMQFSN

SSCLFSPSYNSTEEIDLGHVAFSNCTSITNVTGPICAVNGSVFLCGN

NMAYTYLPTNWTGLCVLATLLPDIDIIPGDEPVPIPAIDHFIYRPKR

AIQFIPLLAGLGITAAFTTGATGLGVSVTQYTKLSNQLISDVQILSS

TIQDLQDQVDSLAEVVLQNRRGLDLLTAEQGGICLALQEKCCFYVNK

SGIVRDKIKTLQEELERRRKDLASNPLWTGLQGLLPYLLPFLGPLLT

LLLLLTIGPCIFNRLTAFINDKLNIIHAM

Fusion protein of Vesicular stomatitis
Indiana virus and Rabies virus
Glycoproteins (FuG-E)
(SEQ ID NO: 14)

MVPQVLLFVLLLGFSLCFGKFPIYTIPDELGPWSPIDIHHLSCPNNL

WEDEGCTNLSEFSYMELKVGYISAIKVNGFTCTGWTEAETYTNFVGY

VTTTFKRKHFRPTPDACRAAYNWKMAGDPRYEESLHNPYPDYHWLRT

VRTTKESLIIISPSVTDLDPYDKSLHSRVFPGGKCSGITVSSTYCST

NHDYTIWMPENPRPRTPCDIFTNSRGKRASNGNKTCGFVDERGLYKS

LKGACRLKLCGVLGLRLMDGTWVAMQTSDETKWCPPDQLVNLHDFRS

DEIEHLVVEELVKKREECLDALESIMTTKSVSFRRLSHLRKLVPGFG

KAYTIFNKTLMEADAHYKSVRTWNEIIPSKGCLKVGGRCHPHVNGVF

FNGIILGPDDHVLIPEMQSSLLQQHMELLESSVIPLMHPLADPSTVF

KEGDEAEDFVEVHLPKNPIELVEGWFSSWKSSIASFFFIIGLIIGLF

LVLRVGIHLCIKLKHTKKRQIYTDIEMNRLGK

Modified Fusion protein of Vesicular stomatitis Indiana virus and Rabies virus Glycoproteins (FuG-E (P440E))

(SEQ ID NO: 15)

MVPQVLLFVLLLGFSLCFGKFPIYTIPDELGPWSPIDIHHLSCPNNL

VVEDEGCTNLSEFSYMELKVGYISAIKVNGFTCTGVVTEAETYTNFV

-continued

GYVTTTFKRKHFRPTPDACRAAYNWKMAGDPRYEESLHNPYPDYHWL

RTVRTTKESLIIISPSVTDLDPYDKSLHSRVFPGGKCSGITVSSTYC

STNHDYTIWMPENPRPRTPCDIFTNSRGKRASNGNKTCGFVDERGLY

KSLKGACRLKLCGVLGLRLMDGTWVAMQTSDETKWCPPDQLVNLHDF

RSDEIEHLVVEELVKKREECLDALESIMTTKSVSFRRLSHLRKLVPG

FGKAYTIFNKTLMEADAHYKSVRTWNEIIPSKGCLKVGGRCHPHVNG

VFFNGIILGPDDHVLIPEMQSSLLQQHMELLESSVIPLMHPLADPST

VFKEGDEAEDFVEVHLEKNPIELVEGWFSSWKSSIASFFFIIGLIIG

LFLVLRVGIHLCIKLKHTKKRQIYTDIEMNRLGK

Amphotrophic Murine Leukemia Virus (MLV ENV (amphotropic))

(SEQ ID NO: 16)

MARSTLSKPPQDKINPWKPLIVMGVLLGVGMAESPHQVFNVTWRVTN

LMTGRTANATSLLGTVQDAFPKLYFDLCDLVGEEWDPSDQEPYVGYG

CKYPAGRQRTRTFDFYVCPGHTVKSGCGGPGEGYCGKWGCETTGQAY

WKPTSSWDLISLKRGNTPWDTGCSKVACGPCYDLSKVSNSFQGATRG

GRCNPLVLEFTDAGKKANWDGPKSWGLRLYRTGTDPITMFSLTRQVL

NVGPRVPIGPNPVLPDQRLPSSPIEIVPAPQPPSPLNTSYPPSTTST

PSTSPTSPSVPQPPPGTGDRLLALVKGAYQALNLTNPDKTQECWLCL

VSGPPYYEGVAVVGTYTNHSTAPANCTATSQHKLTLSEVTGQGLCMG

AVPKTHQALCNTTQSAGSGSYYLAAPAGTMWACSTGLTPCLSTTVLN

LTTDYCVLVELWPRVIYHSPDYMYGQLEQRTKYKREPVSLTLALLLG

GLTMGGIAAGIGTGTTALIKTQQFEQLHAAIQTDLNEVEKSITNLEK

SLTSLSEVVLQNRRGLDLLFLKEGGLCAALKEECCFYADHTGLVRDS

MAKLRERLNQRQKLFETGQGWFEGLFNRSPWFTTLISTIMGPLIVLL

LILLFGPCILNRLVQFVKDRISVVQALVLTQQYHQLKPIEYEP

Ecotrophic Murine Leukemia Virus (MLV ENV (Ecotropic))

(SEQ ID NO: 17)

MARSTLSKPLKNKVNPRGPLIPLILLMLRGVSTASPGSSPHQVYNIT

WEVTNGDRETVWATSGNHPLWTWWPDLTPDLCMLAHHGPSYWGLEYQ

SPFSSPPGPPCCSGGSSPGCSRDCEEPLTSLTPRCNTAWNRLKLDQT

THKSNEGFYVCPGPHRPRESKSCGGPDSFYCAYWGCETTGRAYWKPS

SSWDFITVNNNLTSDQAVQVCKDNKWCNPLVIRFTDAGRRVTSWTTG

HYWGLRLYVSGQDPGLTFGIRLRYQNLGPRVPIGPNPVLADQQPLSK

PKPVKSPSVTKPPSGTPLSPTQLPPAGTENRLLNLVDGAYQALNLTS

PDKTQECWLCLVAGPPYYEGVAVLGTYSNHTSAPANCSVASQHKLTL

SEVTGQGLCIGAVPKTHQALCNTTQTSSRGSYYLVAPTGTMWACSTG

LTPCISTTILNLTTDYCVLVELWPRVTYHSPSYVYGLFERSNRHKRE

PVSLTLALLLGGLTMGGIAAGIGTGTTALMATQQFQQLQAAVQDDLR

EVEKSISNLEKSLTSLSEVVLQNRRGLDLLFLKEGGLCAALKEECCF

-continued

YADHTGLVRDSMAKLRERLNQRQKLFESTQGWFEGLFNRSPWFTTLI

STIMGPLIVLLMILLFGPCILNRLVQFVKDRISVVQALVLTQQYHQL

KPIEYEP

Moloney murine leukemia virus 10A1
strain Glycoprotein (MLV 10A1)
(SEQ ID NO: 18)
MARSTLSKPLKDKINPWKSLMVMGVLLRVGMAESPHQVFNVTWRVTN

LMTGRTANATSLLGTVQDAFPRLYFDLCDLVGEEWDPSDQEPYVGYG

CKYPGGRKRTRTFDFYVCPGHTVKSGCGGPREGYCGEWGCETTGQAY

WKPTSSWDLISLKRGNTPWDTGCSKMACGPCYDLSKVSNSFQGATRG

GRCNPLVLEFTDAGKKANWDGPKSWGLRLYRTGTDPITMFSLTRQVL

NIGPRIPIGPNPVITGQLPPSRPVQIRLPRPPQPPPTGAASIVPETA

PPSQQPGTGDRLLNLVEGAYRALNLTNPDKTQECWLCLVSGPPYYEG

VAVVGTYTNHSTAPASCTATSQHKLTLSEVTGQGLCMGAVPKTHQAL

CNTTQSAGSGSYYLAAPAGTMWACSTGLTPCLSTTMLNLTTDYCVLV

ELWPRIIYHSPDYMYGQLEQRTKYKREPVSLTLALLLGGLTMGGIAA

GIGTGTTALIKTQQFEQLHAAIQTDLNEVEKSITNLEKSLTSLSEVV

LQNRRGLDLLFLKEGGLCAALKEECCFYADHTGLVRDSMAKLRERLN

QRQKLFESGQGWFEGLFNRSPWFTTLISTIMGPLIVLLLILLFGPCI

LNRLVQFVKDRISVVQALVLTQQYHQLKPIEYEP

Rattus norvegicus & synthetic: APOBEC1-XTEN
L8-nspCas9-UGI-SV40 NLS
(SEQ ID NO: 19)
MSSETGPVAVDPTLRRRIEPHEFEVFFDPRELRKETCLLYEINWGGR

HSIWRHTSQNTNKHVEVNFIEKFTTERYFCPNTRCSITWFLSWSPCG

ECSRAITEFLSRYPHVTLFIYIARLYHHADPRNRQGLRDLISSGVTI

QIMTEQESGYCWRNFVNYSPSNEAHWPRYPHLWVRLYVLELYCIILG

LPPCLNILRRKQPQLTFFTIALQSCHYQRLPPHILWATGLKSGSETP

GTSESATPESDKKYSIGLAIGTNSVGWAVITDEYKVPSKKFKVLGNT

DRHSIKKNLIGALLFDSGETAEATRLKRTARRRYTRRKNRICYLQEI

FSNEMAKVDDSFFHRLEESFLVEEDKKHERHPIFGNIVDEVAYHEKY

PTIYHLRKKLVDSTDKADLRLIYLALAHMIKFRGHFLIEGDLNPDNS

DVDKLFIQLVQTYNQLFEENPINASGVDAKAILSARLSKSRRLENLI

AQLPGEKKNGLFGNLIALSLGLTPNFKSNFDLAEDAKLQLSKDTYDD

DLDNLLAQIGDQYADLFLAAKNLSDAILLSDILRVNTEITKAPLSAS

MIKRYDEHHQDLTLLKALVRQQLPEKYKEIFFDQSKNGYAGYIDGGA

SQEEFYKFIKPILEKMDGTEELLVKLNREDLLRKQRTFDNGSIPHQI

HLGELHAILRRQEDFYPFLKDNREKIEKILTFRIPYYVGPLARGNSR

FAWMTRKSEETITPWNFEEVVDKGASAQSFIERMTNFDKNLPNEKVL

PKHSLLYEYFTVYNELTKVKYVTEGMRKPAFLSGEQKKAIVDLLFKT

NRKVTVKQLKEDYFKKIECFDSVEISGVEDRFNASLGTYHDLLKIIK

DKDFLDNEENEDILEDIVLTLTLFEDREMIEERLKTYAHLFDDKVMK

QLKRRRYTGWGRLSRKLINGIRDKQSGKTILDFLKSDGFANRNFMQL

IHDDSLTFKEDIQKAQVSGQGDSLHEHIANLAGSPAIKKGILQTVKV

VDELVKVMGRHKPENIVIEMARENQTTQKGQKNSRERMKRIEEGIKE

LGSQILKEHPVENTQLQNEKLYLYYLQNGRDMYVDQELDINRLSDYD

VDHIVPQSFLKDDSIDNKVLTRSDKNRGKSDNVPSEEVVKKMKNYWR

QLLNAKLITQRKFDNLTKAERGGLSELDKAGFIKRQLVETRQITKHV

AQILDSRMNTKYDENDKLIREVKVITLKSKLVSDFRKDFQFYKVREI

NNYHHAHDAYLNAVVGTALIKKYPKLESEFVYGDYKVYDVRKMIAKS

EQEIGKATAKYFFYSNIMNFFKTEITLANGEIRKRPLIETNGETGEI

VWDKGRDFATVRKVLSMPQVNIVKKTEVQTGGFSKESILPKRNSDKL

IARKKDWDPKKYGGFDSPTVAYSVLVVAKVEKGKSKKLKSVKELLGI

TIMERSSFEKNPIDFLEAKGYKEVKKDLIIKLPKYSLFELENGRKRM

LASAGELQKGNELALPSKYVNFLYLASHYEKLKGSPEDNEQKQLFVE

QHKHYLDEIIEQISEFSKRVILADANLDKVLSAYNKHRDKPIREQAE

NIIHLFTLTNLGAPAAFKYFDTTIDRKRYTSTKEVLDATLIHQSITG

LYETRIDLSQLGGDSGGSTNLSDIIEKETGKQLVIQESILMLPEEVE

EVIGNKPESDILVHTAYDESTDENVMLLTSDAPEYKPWALVIQDSNG

ENKIKMLSGGSPKKKRKV

Homo sapiens: AID
(SEQ ID NO: 20)
MDSLLMNRRKFLYQFKNVRWAKGRRETYLCYVVKRRDSATSFSLDFG

YLRNKNGCHVELLFLRYISDWDLDPGRCYRVTWFTSWSPCYDCARHV

ADFLRGNPNLSLRIFTARLYFCEDRKAEPEGLRRLHRAGVQIAIMTF

KDYFYCWNTFVENHERTFKAWEGLHENSVRLSRQLRRILLPLYEVDD

LRDAFRTLGL

Homo sapiens: MDv solubility variant lacking
N-terminal RNA-binding region
(SEQ ID NO: 21)
LMDPHIFTSNFNNGIGRHKTYLCYEVERLDSATSFSLDFGYLRNKNG

CHVELLFLRYISDWDLDPGRCYRVTWFTSWSPCYDCARHVADFLRGN

PNLSLRIFTARLYFCEDRKAEPEGLRRLHRAGVQIAIMTFKDYFYCW

NTFVENHERTFKAWEGLHENSVRLSRQLRRILLPLYEVDDLRDAFRT

LGL

Homo sapiens: AIDv solubility variant
lacking N-terminal RNA-binding region and
the C-terminal poorly structured region
(SEQ ID NO: 22)
MDPHIFTSNFNNGIGRHKTYLCYEVERLDSATSFSLDFGYLRNKNGC

HVELLFLRYISDWDLDPGRCYRVTWFTSWSPCYDCARHVADFLRGNP

NLSLRIFTARLYFCEDRKAEPEGLRRLHRAGVQIAIMTFKDYFYCWN

TFVENHERTFKAWEGLHENSVRLSRQLRRILLPL

Rattus norvegicus: APOBEC1
(SEQ ID NO: 23)
MSSETGPVAVDPTLRRRIEPHEFEVFFDPRELRKETCLLYEINWGGR

HSIWRHTSQNTNKHVEVNFIEKFTTERYFCPNTRCSITWFLSWSPCG

-continued

ECSRAITEFLSRYPHVTLFIYIARLYHHADPRNRQGLRDLISSGVTI

QIMTEQESGYCWRNFVNYSPSNEAHWPRYPHLWVRLYVLELYCIILG

LPPCLNILRRKQPQLTFFTIALQSCHYQRLPPHILWATGLK

Mus musculus: APOBEC3
(SEQ ID NO: 24)
MGPFCLGCSHRKCYSPIRNLISQETFKFHFKNLGYAKGRKDTFLCYE

VTRKDCDSPVSLHHGVFKNKDNIHAEICFLYWFHDKVLKVLSPREEF

KITWYMSWSPCFECAEQIVRFLATHHNLSLDIFSSRLYNVQDPETQQ

NLCRLVQEGAQVAAMDLYEFKKCWKKFVDNGGRRFRPWKRLLTNFRY

QDSKLQEILRRMDPLSEEEFYSQFYNQRVKHLCYYHRMKPYLCYQLE

QFNGQAPLKGCLLSEKGKQHAEILFLDKIRSMELSQVTITCYLTWSP

CPNCAWQLAAFKRDRPDLILHIYTSRLYFHWKRPFQKGLCSLWQSGI

LVDVMDLPQFTDCWTNFVNPKRPFRPWKGLEIISRRTQRRLRRIKES

WGLQDLVNDFGNLQLGPPMSN

Mus musculus: APOBEC3 catalytic domain
(SEQ ID NO: 25)
MGPFCLGCSHRKCYSPIRNLISQETFKFHFKNLGYAKGRKDTFLCYE

VTRKDCDSPVSLHHGVFKNKDNIHAEICFLYWFHDKVLKVLSPREEF

KITWYMSWSPCFECAEQIVRFLATHHNLSLDIFSSRLYNVQDPETQQ

NLCRLVQEGAQVAAMDLYEFKKCWKKFVDNGGRRFRPWKRLLTNFRY

QDSKLQEILRR

Homo sapiens: APOBEC3A
(SEQ ID NO: 26)
MEASPASGPRHLMDPHIFTSNFNNGIGRHKTYLCYEVERLDNGTSVK

MDQHRGFLHNQAKNLLCGFYGRHAELRFLDLVPSLQLDPAQIYRVTW

FISWSPCFSWGCAGEVRAFLQENTHVRLRIFAARIYDYDPLYKEALQ

MLRDAGAQVSIMTYDEFKHCWDTFVDHQGCPFQPWDGLDEHSQALSG

RLRAILQNQGN

Homo sapiens: APOBEC3G
(SEQ ID NO: 27)
MKPHFRNTVERMYRDTFSYNFYNRPILSRRNTVWLCYEVKTKGPSRP

PLDAKIFRGQVYSELKYHPEMRFFHWFSKWRKLHRDQEYEVTWYISW

SPCTKCTRDMATFLAEDPKVTLTIFVARLYYFWDPDYQEALRSLCQK

RDGPRATMKIMNYDEFQHCWSKFVYSQRELFEPWNNLPKYYILLHIM

LGEILRHSMDPPTFTFNFNNEPWVRGRHETYLCYEVERMHNDTWVLL

NQRRGFLCNQAPHKHGFLEGRHAELCFLDVIPFWKLDLDQDYRVTCF

TSWSPCFSCAQEMAKFISKNKHVSLCIFTARIYDDQGRCQEGLRTLA

EAGAKISIMTYSEFKHCWDTFVDHQGCPFQPWDGLDEHSQDLSGRLR

AILQNQEN

Homo sapiens: APOBEC3G catalytic domain
(SEQ ID NO: 28)
PPTFTFNFNNEPWVRGRHETYLCYEVERMHNDTWVLLNQRRGFLCNQ

APHKHGFLEGRHAELCFLDVIPFWKLDLDQDYRVTCFTSWSPCFSCA

QEMAKFISKNKHVSLCIFTARIYDDQGRCQEGLRTLAEAGAKISIMT

YSEFKHCWDTFVDHQGCPFQPWDGLDEHSQDLSGRLRAILQNQEN

Homo sapiens: APOBEC3H
(SEQ ID NO: 29)
MALLTAETFRLQFNNKRRLRRPYYPRKALLCYQLTPQNGSTPTRGYF

ENKKKCHAEICFINEIKSMGLDETQCYQVTCYLTWSPCSSCAWELVD

FIKAHDHLNLGIFASRLYYHWCKPQQKGLRLLCGSQVPVEVMGFPKF

ADCWENFVDHEKPLSFNPYKMLEELDKNSRAIKRRLERIKIPGVRAQ

GRYMDILCDAEV

Homo sapiens: APOBEC3F
(SEQ ID NO: 30)
MKPHFRNTVERMYRDTFSYNFYNRPILSRRNTVWLCYEVKTKGPSRP

RLDAKIFRGQVYSQPEHHAEMCFLSWFCGNQLPAYKCFQITWFVSWT

PCPDCVAKLAEFLAEHPNVTLTISAARLYYYWERDYRRALCRLSQAG

ARVKIMDDEEFAYCWENFVYSEGQPFMPWYKFDDNYAFLHRTLKEIL

RNPMEAMYPHIFYFHFKNLRKAYGRNESWLCFTMEVVKHHSPVSWKR

GVFRNQVDPETHCHAERCFLSWFCDDILSPNTNYEVTWYTSWSPCPE

CAGEVAEFLARHSNVNLTIFTARLYYFWDTDYQEGLRSLSQEGASVE

IMGYKDFKYCWENFVYNDDEPFKPWKGLKYNFLFLDSKLQEILE

Homo sapiens: APOBEC3F catalytic domain
(SEQ ID NO: 31)
KEILRNPMEAMYPHIFYFHFKNLRKAYGRNESWLCFTMEVVKHHSPV

SWKRGVFRNQVDPETHCHAERCFLSWFCDDILSPNTNYEVTWYTSWS

PCPECAGEVAEFLARHSNVNLTIFTARLYYFWDTDYQEGLRSLSQEG

ASVEIMGYKDFKYCWENFVYNDDEPFKPWKGLKYNFLFLDSKLQEIL

E

Escherichia coli: TadA
(SEQ ID NO: 32)
MKRTADGSEFESPKKKRKVSEVEFSHEYWMRHALTLAKRAWDEREVP

VGAVLVHNNRVIGEGWNRPIGRHDPTAHAEIMALRQGGLVMQNYRLI

DATLYVTLEPCVMCAGAMIHSRIGRWFGARDAKTGAAGSLMDVLHHP

GMNHRVEITEGILADECAALLSDFFRMRRQEIKAQKKAQSSTDSGGS

SGGSSGSETPGTSESATPESSGGSSGGSSEVEFSHEYWMRHALTLAK

RARDEREVPVGAVLVLNNRVIGEGWNRAIGLHDPTAHAEIMALRQGG

LVMQNYRLIDATLYVTFEPCVMCAGAMIHSRIGRVVFGVRNAKTGAA

GSLMDVLHYPGMNHRVEITEGILADECAALLCYFFRMPRQVFNAQKK

AQSSTD

Homo sapiens: Adar1
(SEQ ID NO: 33)
MNPRQGYSLSGYYTHPFQGYEHRQLRYQQPGPGSSPSSFLLKQIEFL

KGQLPEAPVIGKQTPSLPPSLPGLRPRFPVLLASSTRGRQVDIRGVP

RGVHLGSQGLQRGFQHPSPRGRSLPQRGVDCLSSHFQELSIYQDQEQ

RILKFLEELGEGKATTAHDLSGKLGTPKKEINRVLYSLAKKGKLQKE

AGTPPLWKIAVSTQAWNQHSGVVRPDGHSQGAPNSDPSLEPEDRNST

SVSEDLLEPFIAVSAQAWNQHSGVVRPDSHSQGSPNSDPGLEPEDSN

```
STSALEDPLEFLDMAEIKEKICDYLFNVSDSSALNLAKNIGLTKARD
INAVLIDMERQGDVYRQGTTPPIWHLTDKKRERMQIKRNTNSVPETA
PAAIPETKRNAEFLTCNIPTSNASNNMVTTEKVENGQEPVIKLENRQ
EARPEPARLKPPVHYNGPSKAGYVDFENGQWATDDIPDDLNSIRAAP
GEFRAIMEMPSFYSHGLPRCSPYKKLTECQLKNPISGLLEYAQFASQ
TCEFNMIEQSGPPHEPRFKFQVVINGREFPPAEAGSKKVAKQDAAMK
AMTILLEEAKAKDSGKSEESSHYSTEKESEKTAESQTPTPSATSFFS
GKSPVTTLLECMHKLGNSCEFRLLSKEGPAHEPKFQYCVAVGAQTFP
SVSAPSKKVAKQMAAEEAMKALHGEATNSMASDNQPEGMISESLDNL
ESMMPNKVRKIGELVRYLNTNPVGGLLEYARSHGFAAEFKLVDQSGP
PHEPKFVYQAKVGGRWFPAVCAHSKKQGKQEAADAALRVLIGENEKA
ERMGFTEVTPVTGASLRRTMLLLSRSPEAQPKTLPLTGSTFHDQIAM
LSHRCFNTLTNSFQPSLLGRKILAAIIMKKDSEDMGVVVSLGTGNRC
VKGDSLSLKGETVNDCHAEIISRRGFIRFLYSELMKYNSQTAKDSIF
EPAKGGEKLQIKKTVSFHLYISTAPCGDGALFDKSCSDRAMESTESR
HYPVFENPKQGKLRTKVENGEGTIPVESSDIVPTWDGIRLGERLRTM
SCSDKILRWNVLGLQGALLTHFLQPIYLKSVTLGYLFSQGHLTRAIC
CRVTRDGSAFEDGLRHPFIVNHPKVGRVSIYDSKRQSGKTKETSVNW
CLADGYDLEILDGTRGTVDGPRNELSRVSKKNIFLLFKKLCSFRYRR
DLLRLSYGEAKKAARDYETAKNYFKKGLKDMGYGNWISKPQEEKNFY
LCPV
```

*Streptococcus pyogenes*: spCas9 Bipartite NLS
(SEQ ID NO: 34)
```
MDKKYSIGLDIGTNSVGWAVITDEYKVPSKKFKVLGNTDRHSIKKNL
IGALLFDSGETAEATRLKRTARRRYTRRKNRICYLQEIFSNEMAKVD
DSFFHRLEESFLVEEDKKHERHPIFGNIVDEVAYHEKYPTIYHLRKK
LVDSTDKADLRLIYLALAHMIKFRGHFLIEGDLNPDNSDVDKLFIQL
VQTYNQLFEENPINASGVDAKAILSARLSKSRRLENLIAQLPGEKKN
GLFGNLIALSLGLTPNFKSNFDLAEDAKLQLSKDTYDDDLDNLLAQI
GDQYADLFLAAKNLSDAILLSDILRVNTEITKAPLSASMIKRYDEHH
QDLTLLKALVRQQLPEKYKEIFFDQSKNGYAGYIDGGASQEEFYKFI
KPILEKMDGTEELLVKLNREDLLRKQRTFDNGSIPHQIHLGELHAIL
RRQEDFYPFLKDNREKIEKILTFRIPYYVGPLARGNSRFAWMTRKSE
ETITPWNFEEVVDKGASAQSFIERMTNFDKNLPNEKVLPKHSLLYEY
FTVYNELTKVKYVTEGMRKPAFLSGEQKKAIVDLLFKTNRKVTVKQL
KEDYFKKIECFDSVEISGVEDRFNASLGTYHDLLKIIKDKDFLDNEE
NEDILEDIVLTLTLFEDREMIEERLKTYAHLFDDKVMKQLKRRRYTG
WGRLSRKLINGIRDKQSGKTILDFLKSDGFANRNFMQLIHDDSLTFK
EDIQKAQVSGQGDSLHEHIANLAGSPAIKKGILQTVKVVDELVKVMG
RHKPENIVIEMARENQTTQKGQKNSRERMKRIEEGIKELGSQILKEH
PVENTQLQNEKLYLYYLQNGRDMYVDQELDINRLSDYDVDHIVPQSF
LKDDSIDNKVLTRSDKNRGKSDNVPSEEVVKKMKNYWRQLLNAKLIT
QRKFDNLTKAERGGLSELDKAGFIKRQLVETRQITKHVAQILDSRMN
TKYDENDKLIREVKVITLKSKLVSDFRKDFQFYKVREINNYHHAHDA
YLNAVVGTALIKKYPKLESEFVYGDYKVYDVRKMIAKSEQEIGKATA
KYFFYSNIMNFFKTEITLANGEIRKRPLIETNGETGEIVWDKGRDFA
TVRKVLSMPQVNIVKKTEVQTGGFSKESILPKRNSDKLIARKKDWDP
KKYGGFDSPTVAYSVLVVAKVEKGKSKKLKSVKELLGITIMERSSFE
KNPIDFLEAKGYKEVKKDLIIKLPKYSLFELENGRKRMLASAGELQK
GNELALPSKYVNFLYLASHYEKLKGSPEDNEQKQLFVEQHKHYLDEI
IEQISEFSKRVILADANLDKVLSAYNKHRDKPIREQAENIIHLFTLT
NLGAPAAFKYFDTTIDRKRYTSTKEVLDATLIHQSITGLYETRIDLS
QLGGDGSGGGGSGKRTADGSEFEPKKKRKVSSGGDYKDHDGDYKDHD
IDYKDDDDK
```

*Staphylococcus aureus*: saCas9
(SEQ ID NO: 35)
```
MKRNYILGLDIGITSVGYGIIDYETRDVIDAGVRLFKEANVENNEGR
RSKRGARRLKRRRHRIQRVKKLLFDYNLLTDHSELSGINPYEARVK
GLSQKLSEEEFSAALLHLAKRRGVHNVNEVEEDTGNELSTKEQISRN
SKALEEKYVAELQLERLKKDGEVRGSINRFKTSDYVKEAKQLLKVQK
AYHQLDQSFIDTYIDLLETRRTYYEGPGEGSPFGWKDIKEWYEMLMG
HCTYFPEELRSVKYAYNADLYNALNDLNNLVITRDENEKLEYYEKFQ
IIENVFKQKKKPTLKQIAKEILVNEEDIKGYRVTSTGKPEFTNLKVY
HDIKDITARKEIIENAELLDQIAKILTIYQSSEDIQEELTNLNSELT
QEEIEQISNLKGYTGTHNLSLKAINLILDELWHTNDNQIAIFNRLKL
VPKKVDLSQQKEIPTTLVDDFILSPVVKRSFIQSIKVINAIIKKYGL
PNDIIIELAREKNSKDAQKMINEMQKRNRQTNERIEEIIRTTGKENA
KYLIEKIKLHDMQEGKCLYSLEAIPLEDLLNNPFNYEVDHIIPRSVS
FDNSFNNKVLVKQEENSKKGNRTPFQYLSSSDSKISYETFKKHILNL
AKGKGRISKTKKEYLLEERDINRFSVQKDFINRNLVDTRYATRGLMN
LLRSYFRVNNLDVKVKSINGGFTSFLRRKWKFKKERNKGYKHHAEDA
LIIANADFIFKEWKKLDKAKKVMENQMFEEKQAESMPEIETEQEYKE
IFITPHQIKHIKDFKDYKYSHRVDKKPNRELINDTLYSTRKDDKGNT
LIVNNLNGLYDKDNDKLKKLINKSPEKLLMYHHDPQTYQKLKLIMEQ
YGDEKNPLYKYYEETGNYLTKYSKKDNGPVIKKIKYYGNKLNAHLDI
TDDYPNSRNKVVKLSLKPYRFDVYLDNGVYKFVTVKNLDVIKKENYY
EVNSKCYEEAKKLKKISNQAEFIASFYNNDLIKINGELYRVIGVNND
LLNRIEVNMIDITYREYLENMNDKRPPRIIKTIASKTQSIKKYSTDI
LGNLYEVKSKKHPQIIKKG
```

*Campylobacter jejuni*: cjCas9
(SEQ ID NO: 36)
```
MARILAFDIGISSIGWAFSENDELKDCGVRIFTKVENPKTGESLALP
RRLARSARKRLARRKARLNHLKHLIANEFKLNYEDYQSFDESLAKAY
KGSLISPYELRFRALNELLSKQDFARVILHIAKRRGYDDIKNSDDKE
```

KGAILKAIKQNEEKLANYQSVGEYLYKEYFQKFKENSKEFTNVRNKK
ESYERCIAQSFLKDELKLIFKKQREFGFSFSKKFEEEVLSVAFYKRA
LKDFSHLVGNCSFFTDEKRAPKNSPLAFMFVALTRIINLLNNLKNTE
GILYTKDDLNALLNEVLKNGTLTYKQTKKLLGLSDDYEFKGEKGTYF
IEFKKYKEFIKALGEHNLSQDDLNEIAKDITLIKDEIKLKKALAKYD
LNQNQIDSLSKLEFKDHLNISFKALKLVTPLMLEGKKYDEACNELNL
KVAINEDKKDFLPAFNETYYKDEVTNPVVLRAIKEYRKVLNALLKKY
GKVHKINIELAREVGKNHSQRAKIEKEQNENYKAKKDAELECEKLGL
KINSKNILKLRLFKEQKEFCAYSGEKIKISDLQDEKMLEIDHIYPYS
RSFDDSYMNKVLVFTKQNQEKLNQTPFEAFGNDSAKWQKIEVLAKNL
PTKKQKRILDKNYKDKEQKNFKDRNLNDTRYIARLVLNYTKDYLDFL
PLSDDENTKLNDTQKGSKVHVEAKSGMLTSALRHTWGFSAKDRNNHL
HHAIDAVIIAYANNSIVKAFSDFKKEQESNSAELYAKKISELDYKNK
RKFFEPFSGFRQKVLDKIDEIFVSKPERKKPSGALHEETFRKEEEFY
QSYGGKEGVLKALELGKIRKVNGKIVKNGDMFRVDIFKHKKTNKFYA
VPIYTMDFALKVLPNKAVARSKKGEIKDWILMDENYEFCFSLYKDSL
ILIQTKDMQEPEFVYYNAFTSSTVSLIVSKHDNKFETLSKNQKILFK
NANEKEVIAKSIGIQNLKVFEKYIVSALGEVTKAEFRQREDFKK

*Neisseria meningitidis*: nmeCas9
(SEQ ID NO: 37)
MAAFKPNSINYILGLDIGIASVGWAMVEIDEEENPIRLIDLGVRVFE
RAEVPKTGDSLAMARRLARSVRRLTRRRAHRLLRTRRLLKREGVLQA
ANFDENGLIKSLPNTPWQLRAAALDRKLTPLEWSAVLLHLIKHRGYL
SQRKNEGETADKELGALLKGVAGNAHALQTGDFRTPAELALNKFEKE
SGHIRNQRSDYSHTFSRKDLQAELILLFEKQKEFGNPHVSGGLKEGI
ETLLMTQRPALSGDAVQKMLGHCTFEPAEPKAAKNTYTAERFIWLTK
LNNLRILEQGSERPLTDTERATLMDEPYRKSKLTYAQARKLLGLEDT
AFFKGLRYGKDNAEASTLMEMKAYHAISRALEKEGLKDKKSPLNLSP
ELQDEIGTAFSLFKTDEDITGRLKDRIQPEILEALLKHISFDKFVQI
SLKALRRIVPLMEQGKRYDEACAEIYGDHYGKKNTEEKIYLPPIPAD
EIRNPWLRALSQARKVINGVVRRYGSPARIHIETAREVGKSFKDRKE
IEKRQEENRKDREKAAAKFREYFPNFVGEPKSKDILKLRLYEQQHGK
CLYSGKEINLGRLNEKGYVEIDHALPFSRTWDDSFNNKVLVLGSENQ
NKGNQTPYEYFNGKDNSREWQEFKARVETSRFPRSKKQRILLQKFDE
DGFKERNLNDTRYVNRFLCQFVADRMRLTGKGKKRVFASNGQITNLL
RGFWGLRKVRAENDRHHALDAVWACSTVAMQQKITRFVRYKEMNAFD
GKTIDKETGEVLHQKTHFPQPWEFFAQEVMIRVFGKPDGKPEFEEAD
TLEKLRTLLAEKLSSRPEAVHEYVTPLFVSRAPNRKMSGQGHMETVK
SAKRLDEGVSVLRVPLTQLKLKDLEKMVNREREPKLYEALKARLEAH
KDDPAKAFAEPFYKYDKAGNRTQQVKAVRVEQVQKTGVWWRNHNGIA
DNATMVRVDVFEKGDKYYLVPIYSWQVAKGILPDRAWQGKDEEDWQL IDDSFNFKFSLHPNDLVEVITKKARMFGYFASCHRGTGNINIRIHDL
DHKIGKNGILEGIGVKTALSFQKYQIDELGKEIRPCRLKKRPPVR

*Acidaminococcus* sp.: asCas12a
(SEQ ID NO: 38)
MTQFEGFTNLYQVSKTLRFELIPQGKTLKHIQEQGFIEEDKARNDHY
KELKPIIDRIYKTYADQCLQLVQLDWENLSAAIDSYRKEKTEETRNA
LIEEQATYRNAIHDYFIGRTDNLTDAINKRHAEIYKGLFKAELFNGK
VLKQLGTVTTTEHENALLRSFDKFTTYFSGFYENRKNVFSAEDISTA
IPHRIVQDNFPKFKENCHIFTRLITAVPSLREHFENVKKAIGIFVST
SIEEVFSFPPFYNQLLTQTQIDLYNQLLGGISREAGTEKIKGLNEVLN
LAIQKNDETAHIIASLPHRFIPLFKQILSDRNTLSFILEEFKSDEEV
IQSFCKYKTLLRNENVLETAEALFNELNSIDLTHIFISHKKLETISS
ALCDHWDTLRNALYERRISELTGKITKSAKEKVQRSLKHEDINLQEI
ISAAGKELSEAFKQKTSEILSHAHAALDQPLPTTLKKQEEKEILKSQ
LDSLLGLYHLLDWFAVDESNEVDPEFSARLTGIKLEMEPSLSFYNKA
RNYATKKPYSVEKFKLNFQMPTLASGWDVNKEKNNGAILFVKNGLYY
LGIMPKQKGRYKALSFEPTEKTSEGFDKMYYDYFPDAAKMIPKCSTQ
LKAVTAHFQTHTTPILLSNNFIEPLEITKEIYDLNNPEKEPKKFQTA
YAKKTGDQKGYREALCKWIDFTRDFLSKYTKTTSIDLSSLRPSSQYK
DLGEYYAELNPLLYHISFQRIAEKEIMDAVETGKLYLFQIYNKDFAK
GHHGKPNLHTLYWTGLFSPENLAKTSIKLNGQAELFYRPKSRMKRMA
HRLGEKMLNKKLKDQKTPIPDTLYQELYDYVNHRLSHDLSDEARALL
PNVITKEVSHEIIKDRRFTSDKFFFHVPITLNYQAANSPSKFNQRVN
AYLKEHPETPIIGIDRGERNLIYITVIDSTGKILEQRSLNTIQQFDY
QKKLDNREKERVAARQAWSVVGTIKDLKQGYLSQVIHEIVDLMIHYQ
AVWLENLNFGFKSKRTGIAEKAVYQQFEKMLIDKLNCLVLKDYPAEK
VGGVLNPYQLTDQFTSFAKMGTQSGFLFYVPAPYTSKIDPLTGFVDP
FVWKTIKNHESRKHFLEGFDFLHYDVKTGDFILHFKMNRNLSFQRGL
PGFMPAWDIVFEKNETQFDAKGTPFIAGKRIVPVIENHRFTGRYRDL
YPANELIALLEEKGIVFRDGSNILPKLLENDDSHAIDTMVALIRSVL
QMRNSNAATGEDYINSPVRDLNGVCFDSRFQNPEWPMDADANGAYHI
ALKGQLLLNHLKESKDLKLQNGISNQDWLAYIQELRN

*Lachnospiraceae bacterium*: lbCas12a:
(SEQ ID NO: 39)
MSKLEKFTNCYSLSKTLRFKAIPVGKTQENIDNKRLLVEDEKRAEDY
KGVKKLLDRYYLSFINDVLHSIKLKNLNNYISLFRKKTRTEKENKEL
ENLEINLRKEIAKAFKGNEGYKSLFKKDIIETILPEFLDDKDEIALV
NSFNGFTTAFTGFFDNRENMFSEEAKSTSIAFRCINENLTRYISNMD
IFEKVDAIFDKHEVQEIKEKILNSDYDVEDFFEGEFFNFVLTQEGID
VYNAIIGGFVTESGEKIKGLNEYINLYNQKTKQKLPKFKPLYKQVLS
DRESLSFYGEGYTSDEEVLEVFRNTLNKNSEIFSSIKKLEKLFKNFD
EYSSAGIFVKNGPAISTISKDIFGEWNVIRDKWNAEYDDIHLKKKAW

TEKYEDDRRKSFKKIGSFSLEQLQEYADADLSWEKLKEIIQKVDEI

YKVYGSSEKLFDADFVLEKSLKKNDAVVAIMKDLLDSVKSFENYIKA

FFGEGKETNRDESFYGDFVLAYDILLKVDHIYDAIRNYVTQKPYSKD

KFKLYFQNPQFMGGWDKDKETDYRATILRYGSKYYLAIMDKKYAKCL

QKIDKDDVNGNYEKINYKLLPGPNKMLPKVFFSKKWMAYYNPSEDIQ

KIYKNGTFKKGDMFNLNDCHKLIDFFKDSISRYPKWSNAYDFNFSET

EKYKDIAGFYREVEEQGYKVSFESASKKEVDKLVEEGKLYMFQIYNK

DFSDKSHGTPNLHTMYFKLLFDENNHGQIRLSGGAELFMRRASLKKE

ELVVHPANSPIANKNPDNPKKTTTLSYDVYKDKRFSEDQYELHIPIA

INKCPKNIFKINTEVRVLLKHDDNPYVIGIDRGERNLLYIVWVDGKG

NIVEQYSLNEIINNFNGIRIKTDYHSLLDKKEKERFEARQNWTSIEN

IKELKAGYISQVVHKICELVEKYDAVIALEDLNSGFKNSRVKVEKQV

YQKFEKMLIDKLNYMVDKKSNPCATGGALKGYQITNKFESFKSMSTQ

NGFIFYIPAWLTSKIDPSTGFVNLLKTKYTSIADSKKFISSFDRIMY

VPEEDLFEFALDYKNFSRTDADYIKKWKLYSYGNRIRIFRNPKKNNV

FDWEEVCLTSAYKELFNKYGINYQQGDIRALLCEQSDKAFYSSFMAL

MSLMLQMRNSITGRTDVDFLISPVKNSDGIFYDSRNYEAQENAILPK

NADANGAYNIARKVLWAIGQFKKAEDEKLDKVKIAISNKEWLEYAQT

SVKH

Leptotrichia shahii: LshCas13a
(SEQ ID NO: 40)
MGNLFGHKRWYEVRDKKDFKIKRKVKVKRNYDGNKYILNINENNNKE

KIDNNKFIRKYINYKKNDNILKEFTRKFHAGNILFKLKGKEGIIRIE

NNDDFLETEEEWLYIEAYGKSEKLKALGITKKKIIDEAIRQGITKDDK

KIEIKRQENEEEIEIDIRDEYTNKTLNDCSIILRIIENDELETKKSI

YEIFKNINMSLYKIIEKIIENETEKVFENRYYEEHLREKLLKDDKID

VILTNFMEIREKIKSNLEILGFVKFYLNVGGDKKKSKNKKMLVEKIL

NINVDLTVEDIADFVIKELEFWNITKRIEKVKKVNNEFLEKRRNRTY

IKSYVLLDKHEKFKIERENKKDKIVKFFVENIKNNSIKEKIEKILAE

FKIDELIKKLEKELKKGNCDTEIFGIFKKHYKVNFDSKKFSKKSDEE

KELYKIIYRYLKGRIEKILVNEQKVRLKKMEKIEIEKILNESILSEK

ILKRVKQYTLEHIMYLGKLRHNDIDMTTVNTDDFSRLHAKEELDLEL

ITFFASTNMELNKIFSRENINNDENIDFFGGDREKNYVLDKKILNSK

IKIIRDLDFIDNKNNITNNFIRKFTKIGTNERNRILHAISKERDLQG

TQDDYNKVINIIQNLKISDEEVSKALNLDVVFKDKKNIITKINDIKI

SEENNNDIKYLPSFSKVLPEILNLYRNNPKNEPFDTIETEKIVLNAL

IYVNKELYKKLILEDDLEENESKNIFLQELKKTLGNIDEIDENIIEN

YYKNAQISASKGNNKAIKKYQKKVIECYIGYLRKNYEELFDFSDFKM

NIQEIKKQIKDINDNKTYERITVKTSDKTIVINDDFEYIISIFALLN

SNAVINKIRNRFFATSVWLNTSEYQNIIDILDEIMQLNTLRNECITE

NWNLNLEEFIQKMKEIEKDFDDFKIQTKKEIFNNYYEDIKNNILTEF

KDDINGCDVLEKKLEKMFDDETKFEIDKKSNILQDEQRKLSNINKKD

LKKKVDQYIKDKDQEIKSKILCRIIFNSDFLKKYKKEIDNLIEDMES

ENENKFQEIYYPKERKNELYIYKKNLFLNIGNPNFDKIYGLISNDIK

MADAKFLFNIDGKNIRKNKISEIDAILKNLNDKLNGYSKEYKEKYIK

KLKENDDFFAKNIQNKNYKSFEKDYNRVSEYKKIRDLVEFNYLNKIE

SYLIDINWKLAIQMARFERDMHYIVNGLRELGIIKLSGYNTGISRAY

PKRNGSDGFYTTTAYYKFFDEESYKKFEKICYGFGIDLSENSEINKP

ENESIRNYISHFYIVRNPFADYSIAEQIDRVSNLLSYSTRYNNSTYA

SVFEVFKKDVNLDYDELKKKFKLIGNNDILERLMKPKKVSVLELESY

NSDYIKNLIIELLTKIENTNDTL

Leptotrichia wadeii: LwaCas13a
(SEQ ID NO: 41)
MKVTKVDGISHKKYIEEGKLVKSTSEENRTSERLSELLSIRLDIYIK

NPDNASEEENRIRRENLKKFFSNKVLHLKDSVLYLKNRKEKNAVQDK

NYSEEDISEYDLKNKNSFSVLKKILLNEDVNSEELEIFRKDVEAKLN

KINSLKYSFEENKANYQKINENNVEKVGGKSKRNIIYDYYRESAKRN

DYINNVQEAFDKLYKKEDIEKLFFLIENSKKHEKYKIREYYHKIIGR

KNDKENFAKIIYEEIQNVNNIKELIEKIPDMSELKKSQVFYKYYLDK

EELNDKNIKYAFCHFVEIEMSQLLKNYVYKRLSNISNDKIKIRFEYQ

NLKKLIENKLLNKLDTYVRNCGKYNYYLQVGEIATSDFIARNRQNEA

FLRNIIGVSSVAYFSLRNILETENENGITGRMRGKTVKNNKGEEKYV

SGEVDKIYNENKQNEVKENLKMFYSYDFNMDKNEIEDFFANIDEAI

SSIAHGIVHFNLELEGKDIFAFKNIAPSEISKKMFQNEINEKKLKLK

IFKQLNSANVFNYYEKDVIIKYLKNTKFNFVNKNIPFVPSFTKLYNK

IEDLRNTLKFFWSVPKDKEEKDAQIYLLKNIYYGEFLNKFVKNSKVF

FKITNEVIKINKQRNQKTGHYKYQKFENIEKTVPVEYLAIIQSREMI

NNQDKEEKNTYIDFIQQIFLKGFIDYLNKNNLKYIESNNNNDNNDIF

SKIKIKKDNKEKYDKILKNYEKHNRNKEIPHEINEFVREIKLGKILK

YTENLNMFYLILKLLNHKELTNLKGSLEKYQSANKEETFSDELELIN

LLNLDNNRVTEDFELEANEIGKFLDFNENKIKDRKELKKFDTNKIYF

DGENIIKHRAFYNIKKYGMLNLLEKIADKAKYKISLKELKEYSNKKN

EIEKNYTMQQNLHRKYARPKKDEKFNDEDYKEYEKAIGNIQKYTHLK

NKVEFNELNLLQGLLLKILHRLVGYTSIWERDLRFRLKGEFPENHYI

EEIFNFDNSKNVKYKSGQIVEKYINFYKELYKDNVEKRSIYSDKKVK

KLKQEKKDLYIANYIAHFNYIPHAEISLLEVLENLRKLLSYDRKLKN

AIMKSIVDILKEYGFVATFKIGADKKIEIQTLESEKIVHLKNLKKKK

LMTDRNSEELCELVKVMFEYKALE

Pleckstrin homology domain of Homo sapiens phospholipase Cδ1 (hPLCδ1)
(SEQ ID NO: 42)
MDSGRDFLTLHGLQDDEDLQALLKGSQLLKVKSSSWRRERFYKLQED

CKTIWQESRKVMRTPESQLFSIEDIQEVRMGHRTEGLEKFARDVPED

-continued

RCFSIVFKDQRNTLDLIAPSPADAQHWVLGLHKIIHHSGSMDQRQKL

QHWIHSCLRKADKNKDNKMSFKELQNFLKELNIQ

Pleckstrin homology domain of *Homo sapiens* Akt1 (hAkt)
(SEQ ID NO: 43)
MSDVAIVKEGWLHKRGEYIKTWRPRYFLLKNDGTFIGYKERPQDVDQ

REAPLNNFSVAQCQLMKTERPRPNTFIIRCLQWTTVIERTFHVETPE

EREEWTTAIQTVADGLKKQEEEEMDFRSGSPSDNSGAEEMEVSLAKP

KHRVTMNEFEYLKLLGKGTFGKVDPPV

Pleckstrin homology domain of *Homo sapiens* PDPK1 (hPDPKI)
(SEQ ID NO: 44)
KMGPVDKRKGLFARRRQLLLTEGPHLYYVDPVNKVLKGEIPWSQELR

PEAKNFKTFFVHTPNRTYYLMDPSGNAHKWCRKIQEVWRQRYQSH

Herpes simplex virus (HSV) type 1: VP16 Transcription Activation Domain
(SEQ ID NO: 45)
PTDALDDFDLDMLPADALDDFDLDMLPADALDDFDLDM Herpes simplex virus (HSV) type 1 & Synthetic: VP64
(SEQ ID NO: 46)
GRADALDDFDLDMLGSDALDDFDLDMLGSDALDDFDLDMLGSDALDD

FDLDML

*Homo sapiens*: P65
(SEQ ID NO: 47)
SQYLPDTDDRHRIEEKRKRTYETFKSIMKKSPFSGPTDPRPPPRRIA

VPSRSSASVPKPAPQPYPFTSSLSTINYDEFPTMVFPSGQISQASAL

APAPPQVLPQAPAPAPAPAMVSALAQAPAPVPVLAPGPPQAVAPPAP

KPTQAGEGTLSEALLQLQFDDEDLGALLGNSTDPAVFTDLASVDNSE

FQQLLNQGIPVAPHTTEPMLMEYPEAITRLVTGAQRPPDPAPAPLGA

PGLPNGLLSGDEDFSSIADMDFSALL

Kaposi's Sarcoma-Associated Herpesvirus Transactivator: RTA
(SEQ ID NO: 48)
RDSREGMFLPKPEAGSAISDVFEGREVCQPKRIRPFHPPGSPWANRP

LPASLAPTPTGPVHEPVGSLTPAPVPQPLDPAPAVTPEASHLLEDPD

EETSQAVKALREMADIVIPQKEEAAICGQMDLSHPPPRGHLDELIII

LESMIEDLNLDSPLIPELNEILDTFLNDECLLHAMHISTGLSIFDTS

LF

*Homo sapiens*: KRAB
(SEQ ID NO: 49)
MDAKSLTAWSRTLVTFKDVFVDFTREEWKLLDTAQQIVYRNVMLENY

KNLVSLGYQLTKPDVILRLEKGEEP

*Homo sapiens*. MeCP2
(SEQ ID NO: 50)
EASVQVKRVLEKSPGKLLVKMPFQASPGGKGEGGGATTSAQVMVIKR

PGRKRKAEADPQAIPKKRGRKPGSVVAAAAAEAKKKAVKESSIRSVQ

ETVLPIKKRKTRETVSIEVKEWKPLLVSTLGEKSGKGLKTCKSPGRK

SKESSPKGRSSSASSPPKKEHHHHHHHAESPKAPMPLLPPPPPPEPQ

SSEDPISPPEPQDLSSSICKEEKMPRAGSLESDGCPKEPAKIQPMVA

AAATTTTTTTTVAEKYKHRGEGERKDIVSSSMPRPNREEPVDSRTP

VTERVS

*Homo sapiens*: Tet1
(SEQ ID NO: 51)
LPTCSCLDRVIQKDKGPYYTHLGAGPSVAAVREIMENRYGQKGNAIR

IEIWYTGKEGKSSHGCPIAKWWLRRSSDEEKVLCLVRQRTGHHCPTA

VMVVLIMVWDGIPLPMADRLYTELTENLKSYNGHPTDRRCTLNENRT

CTCQGIDPETCGASFSFGCSWSMYFNGCKFGRSPSPRRFRIDPSSPL

HEKNLEDNLQSLATRLAPIYKQYAPVAYQNQVEYENVARECRLGSKE

GRPFSGVTACLDFCAHPHRDIHNMNNGSTVVCTLTREDNRSLGVIPQ

DEQLHVLPLYKLSDTDEFGSKEGMEAKIKSGAIEVLAPRRKKRTCFT

QPVPRSGKKRAAMMTEVLAHKIRAVEKKPIPRIKRKNNSTTTNNSKP

SSLPTLGSNTETVQPEVKSETEPHFILKSSDNTKTYSLMPSAPHPVK

EASPGFSWSPKTASATPAPLKNDATASCGFSERSSTPHCTMPSGRLS

GANAAAADGPGISQLGEVAPLPTLSAPVMEPLINSEPSTGVTEPLTP

HQPNHQPSFLTSPQDLASSPMEEDEQHSEADEPPSDEPLSDDPLSPA

EEKLPHIDEYWSDSEHIFLDANIGGVAIAPAHGSVLIECARRELHAT

TPVEHPNRNHPTRLSLVFYQHKNLNKPQHGFELNKIKFEAKEAKNKK

MKASEQKDQAANEGPEQSSEVNELNQIPSHKALTLTHDNVVTVSPYA

LTHVAGPYNHWW

*Homo sapiens*: Dnmt3a
(SEQ ID NO: 52)
MPAMPSSGPGDTSSSAAEREEDRKDGEEQEEPRGKEERQEPSTTARK

VGRPGRKRKHPPVESGDTPKDPAVISKSPSMAQDSGASELLPNGDLE

KRSEPQPEEGSPAGGQKGGAPAEGEGAAETLPEASRAVENGCCTPKE

GRGAPAEAGKEQKETNIESMKMEGSRGRLRGGLGWESSLRQRPMPRL

TFQAGDPYYISKRKRDEWLARWKREAEKKAKVIAGMNAVEENQGPGE

SQKVEEASPPAVQQPTDPASPTVATTPEPVGSDAGDKNATKAGDDEP

EYEDGRGFGIGELVWGKLRGFSWWPGRIVSWWMTGRSRAAEGTRWWM

WFGDGKFSVVCVEKLMPLSSFCSAFHQATYNKQPMYRKAIYEVLQVA

SSRAGKLFPVCHDSDESDTAKAVEVQNKPMIEWALGGFQPSGPKGLE

PPEEEKNPYKEVYTDMWVEPEAAAYAPPPPAKKPRKSTAEKPKVKEI

IDERTRERLVYEVRQKCRNIEDICISCGSLNVTLEHPLFVGGMCQNC

KNCFLECAYQYDDDGYQSYCTICCGGREVLMCGNNNCCRCFCVECVD

LLVGPGAAQAAIKEDPWNCYMCGHKGTYGLLRRREDWPSRLQMFFAN

NHDQEFDPPKVYPPVPAEKRKPIRVLSLFDGIATGLLVLKDLGIQVD

RYIASEVCEDSITVGMVRHQGKIMYVGDVRSVTQKHIQEWGPFDLVI

GGSPCNDLSIVNPARKGLYEGTGRLFFEFYRLLHDARPKEGDDRPFF

```
WLFENVVAMGVSDKRDISRFLESNPVMIDAKEVSAAHRARYFWGNLP

GMNRPLASTVNDKLELQECLEHGRIAKFSKVRTITTRSNSIKQGKDQ

HFPVFMNEKEDILWCTEMERVFGFPVHYTDVSNMSRLARQRLLGRSW

SVPVIRHLFAPLKEYFACV
```

Indiana vesiculovirus, formerly Vesicular
stomatitis Indiana virus G Protein: VSVG
(SEQ ID NO: 53)
```
MKCLLYLAFLFIGVNCKFTIVFPHNQKGNWKNVPSNYHYCPSSSDLN

WHNDLIGTALQVKMPKSHKAIQADGWMCHASKWVTTCDFRWYGPKYI

THSIRSFTPSVEQCKESIEQTKQGTWLNPGFPPQSCGYATVTDAEAV

IVQVTPHHVLVDEYTGEWVDSQFINGKCSNYICPTVHNSTTWHSDYK

VKGLCDSNLISMDITFFSEDGELSSLGKEGTGFRSNYFAYETGGKAC

KMQYCKHWGVRLPSGVWFEMADKDLFAAARFPECPEGSSISAPSQTS

VDVSLIQDVERILDYSLCQETWSKIRAGLPISPVDLSYLAPKNPGTG

PAFTIINGTLKYFETRYIRVDIAAPILSRMVGMISGTTTERELWDDW

APYEDVEIGPNGVLRTSSGYKFPLYMIGHGMLDSDLHLSSKAQVFEH

PHIQDAASQLPDDESLFFGDTGLSKNPIELVEGWFSSWKSSIASFFF

IIGLIIGLFLVLRVGIHLCIKLKHTKKRQIYTDIEMNRLGK
```

Baculovirus envelope glycoprotein GP64
(SEQ ID NO: 54)
```
MVSAIVLYVLLAAAAHSAFAAEHCNAQMKTGPYKIKNLDITPPKETL

QKDVEITIVETDYNENVIIGYKGYYQAYAYNGGSLDPNTRVEETMKT

LNVGKEDLLMWSIRQQCEVGEELIDRWGSDSDDCFRDNEGRGQWVKG

KELVKRQNNNHFAHHTCNKSWRCGISTSKMYSRLECQDDTDECQVYI

LDAEGNPINVTVDTVLHRDGVSMILKQKSTFTTRQIKAACLLIKDDK

NNPESVTREHCLIDNDIYDLSKNTWNCKFNRCIKRKVEHRVKKRPPT

WRHNVRAKYTEGDTATKGDLMHIQEELMYENDLLKMNIELMHAHINK

LNNMLHDLIVSVAKVDERLIGNLMNNSVSSTFLSDDTFLLMPCTNPP

AHTSNCYNNSIYKEGRWVANTDSSQCIDFSNYKELAIDDDVEFWIPT

IGNTTYHDSWKDASGWSFIAQQKSNLITTMENTKFGGVGTSLSDITS

MAEGELAAKLTSFMFGHVVNFVIILIVILFLYCMIRNRNRQY
```

Human immunodeficiency virus gp160
(SEQ ID NO: 55)
```
MRVKEKYQHLWRWGWRWGTMLLGMLMICSATEKLWVTVYYGVPVWKE

ATTTLFCASDAKAYDTEVHNVWATHACVPTDPNPQEVVLVNVTENFN

MWKNDMVEQMHEDIISLWDQSLKPCVKLTPLCVSLKCTDLKNDTNTN

SSSGRMIMEKGEIKNCSFNISTSIRGKVQKEYAFFYKLDIIPIDNDT

TSYKLTSCNTSVITQACPKVSFEPIPIHYCAPAGFAILKCNNKTFNG

TGPCTNVSTVQCTHGIRPVVSTQLLLNGSLAEEEVVIRSVNFTDNAK

TIIVQLNTSVEINCTRPNNNTRKRIRIQRGPGRAFVTIGKIGNMRQA

HCNISRAKWNNTLKQIASKLREQFGNNKTIIFKQSSGGDPEIVTHSF

NCGGEFFYCNSTQLFNSTWFNSTWSTEGSNNTEGSDTITLPCRIKQI

INMWQKVGKAMYAPPISGQIRCSSNITGLLLTRDGGNSNNESEIFRP

GGGDMRDNWRSELYKYKVVKIEPLGVAPTKAKRRVVQREKRAVGIGA

LFLGFLGAAGSTMGAASMTLTVQARQLLSGIVQQQNNLLRAIEAQQH

LLQLTVWGIKQLQARILAVERYLKDQQLLGIWGCSGKLICTTAVPWN

ASWSNKSLEQIWNHTTWMEWDREINNYTSLIHSLIEESQNQQEKNEQ

ELLELDKWASLWNWFNITNWLWYIKLFIMIVGGLVGLRIVFAVLSIV

NRVRQGYSPLSFQTHLPTPRGPDRPEGIEEEGGERDRDRSIRLVNGS

LALIWDDLRSLCLFSYHRLRDLLLIVTRIVELLGRRGWEALKYWWNL

LQYWSQELKNSAVSLLNATAIAVAEGTDRVIEVQGACRAIRHIPRRI

RQGLERILL
```

Endogenous feline virus RD114 ENV
(SEQ ID NO: 56)
```
MKLPTGMVILCSLIIVRAGFDDPRKAIALVQKQHGKPCECSGGQVSE

APPNSIQQVTCPGKTAYLMTNQKWKCRVTPKISPSGGELQNCPCNTF

QDSMHSSCYTEYRQCRRINKTYYTATLLKIRSGSLNEVQILQNPNQL

LQSPCRGSINQPVCWSATAPIHISDGGGPLDTKRVWTVQKRLEQIHK

AMTPELQYHPLALPKVRDDLSLDARTFDILNTTFRLLQMSNFSLAQD

CWLCLKLGTPTPLAIPTPSLTYSLADSLANASCQIIPPLLVQPMQFS

NSSCLSSPFINDTEQIDLGAVTFTNCTSVANVSSPLCALNGSVFLCG

NNMAYTYLPQNWTRLCVQASLLPDIDINPGDEPVPIPAIDHYIHRPK

RAVQFIPLLAGLGITAAFTTGATGLGVSVTQYTKLSHQLISDVQVLS

GTIQDLQDQVDSLAEWLQNRRGLDLLTAEQGGICLALQEKCCFYANK

SGIVRNKIRTLQEELQKRRESLATNPLWTGLQGFLPYLLPLLGPLLT

LLLILTIGPCVFSRLMAFINDRLNVVHAMVLAQQYQALKAEEEAQD
```

Homo sapiens: CD9 Complete Protein
(SEQ ID NO: 57)
```
MSPVKGGTKCIKYLLFGFNFIFWLAGIAVLAIGLWLRFDSQTKSIFE

QETNNNNSSFYTGVYILIGAGALMMLVGFLGCCGAVQESQCMLGLFF

GFLLVIFAIEIAAAIWGYSHKDEVIKEVQEFYKDTYNKLKTKDEPQR

ETLKAIHYALNCCGLAGGVEQFISDICPKKDVLETFTVKSCPDAIKE

VFDNKFHIIGAVGIGIAVVMIFGMIFSMILCCAIRRNREMV
```

Homo sapiens: CD63 Complete Protein
(SEQ ID NO: 58)
```
MAVEGGMKCVKFLLYVLLLAFCACAVGLIAVGVGAQLVLSQTIIQGA

TPGSLLPVVIIAVGVFLFLVAFVGCCGACKENYCLMITFAIFLSLIM

LVEVAAAIAGYVFRDKVMSEFNNNFRQQMENYPKNNHTASILDRMQA

DFKCCGAANYTDWEKIPSMSKNRVPDSCCINVTVGCGINFNEKAIHK

EGCVEKIGGWLRKNVLVVAAAALGIAFVEVLGIVFACCLVKSIRSGY

EVM
```

Homo sapiens: CD81 Complete Protein
(SEQ ID NO: 59)
```
MGVEGCTKCIKYLLFVFNFVFWLAGGVILGVALWLRHDPQTTNLLYL

ELGDKPAPNTFYVGIYILIAVGAVMMFVGFLGCYGAIQESQCLLGTF

FTCLVILFACEVAAGIWGFVNKDQIAKDVKQFYDQALQQAWDDDANN

AKAVVKTFHETLDCCGSSTLTALTTSVLKNNLCPSGSNIISNLFKED

CHQKIDDLFSGKLYLIGIAAIWAVIMIFEMILSMVLCCGIRNSSVY
```

*Homo sapiens*: CD47 "Self Hairpin" 10 Amino Acids (SEQ ID NO: 60)

EVTELTREGE

*Homo sapiens*: CD47 "Self Hairpin" 21 Amino Acids (SEQ ID NO: 61)

GNYTCEVTELTREGETIIELK

*Homo sapiens*: CD47 Complete Protein (SEQ ID NO: 62)

MWPLVAALLLGSACCGSAQLLFNKTKSVEFTFCNDTVVIPCFVTNME
AQNTTEVYVKWKFKGRDIYTFDGALNKSTVPTDFSSAKIEVSQLLKG
DASLKMDKSDAVSHTGNYTCEVTELTREGETIIELKYRVVSWFSPNE
NILIVIFPIFAILLFWGQFGIKTLKYRSGGMDEKTIALLVAGLVITV
IVIVGAILFVPGEYSLKNATGLGLIVTSTGILILLHYYVFSTAIGLT
SFVIAILVIQVIAYILAVGLSLCIAACIPMHGPLLISGLSILALAQL
LGLVYMKFVE

AAV2: REP52

(SEQ ID NO: 63)

MELVGWLVDKGITSEKQWIQEDQASYISFNAASNSRSQIKAALDNAG
KIMSLTKTAPDYLVGQQPVEDISSNRIYKILELNGYDPQYAASVFLG
WATKKFGKRNTIWLFGPATTGKTNIAEAIAHTVPFYGCVNWTNENFP
FNDCVDKMVIWWEEGKMTAKWVESAKAILGGSKVRVDQKCKSSAQID
PTPVIVTSNTNMCAVIDGNSTTFEHQQPLQDRMFKFELTRRLDHDFG
KVTKQEVKDFFRWAKDHWEVEHEFYVKKGGAKKRPAPSDADISEPKR
VRESVAQPSTSDAEASINYADRYQNKCSRHVGMNLMLFPCRQCERMN
QNSNICFTHGQKDCLECFPVSESQPVSWKKAYQKLCYIHHIMGKVPD
ACTACDLVNVDLDDCIFEQ

AAV2: REP78

(SEQ ID NO: 64)

MPGFYEIVIKVPSDLDEHLPGISDSFVNWAEKEWELPPDSDMDLNLI
EQAPLTVAEKLQRDFLTEWRRVSKAPEALFFVQFEKGESYFHMHVLV
ETTGVKSMVLGRFLSQIREKLIQRIYRGIEPTLPNWFAVTKTRNGAG
GGNKWDECYIPNYLLPKTQPELQWAWTNMEQYLSACLNLTERKRLVA
QHLTHVSQTQEQNKENQNPNSDAPVIRSKTSARYMELVGWLVDKGIT
SEKQWIQEDQASYISFNAASNSRSQIKAALDNAGKIMSLTKTAPDYL
VGQQPVEDISSNRIYKILELNGYDPQYAASVFLGWATKKFGKRNTIW
LFGPATTGKTNIAEAIAHTVPFYGCVNWTNENFPFNDCVDKMVIWWE
EGKMTAKVVESAKAILGGSKVRVDQKCKSSAQIDPTPVIVTSNTNMC
AVIDGNSTTFEHQQPLQDRMFKFELTRRLDHDFGKVTKQEVKDFFRW
AKDHWEVEHEFYVKKGGAKKRPAPSDADISEPKRVRESVAQPSTSDA
EASINYADRYQNKCSRHVGMNLMLFPCRQCERMNQNSNICFTHGQKD
CLECFPVSESQPVSVVKKAYQKLCYIHHIMGKVPDACTACDLVNVDL
DDCIFEQ

AAV2: VP1

(SEQ ID NO: 65)

MAADGYLPDWLEDTLSEGIRQWWKLKPGPPPPKPAERHKDDSRGLVL
PGYKYLGPFNGLDKGEPVNEADAAALEHDKAYDRQLDSGDNPYLKYN
HADAEFQERLKEDTSFGGNLGRAVFQAKKRVLEPLGLVEEPVKTAPG
KKRPVEHSPVEPDSSSGTGKAGQQPARKRLNFGQTGDADSVPDPQPL
GQPPAAPSGLGTNTMATGSGAPMADNNEGADGVGNSSGNWHCDSTWM
GDRVITTSTRTWALPTYNNHLYKQISSQSGASNDNHYFGYSTPWGYF
DFNRFHCHFSPRDWQRLINNNWGFRPKRLNFKLFNIQVKEVTQNDGT
TTIANNLTSTVQVFTDSEYQLPYVLGSAHQGCLPPFPADVFMVPQYG
YLTLNNGSQAVGRSSFYCLEYFPSQMLRTGNNFTFSYTFEDVPFHSS
YAHSQSLDRLMNPLIDQYLYYLSRTNTPSGTTTQSRLQFSQAGASDI
RDQSRNWLPGPCYRQQRVSKTSADNNNSEYSWTGATKYHLNGRDSLV
NPGPAMASHKDDEEKFFPQSGVLIFGKQGSEKTNVDIEKVMITDEEE
IRTTNPVATEQYGSVSTNLQRGNRQAATADVNTQGVLPGMVWQDRDV
YLQGPIWAKIPHTDGHFHPSPLMGGFGLKHPPPQILIKNTPVPANPS
TTFSAAKFASFITQYSTGQVSVEIEWELQKENSKRWNPEIQYTSNYN
KSVNVDFTVDTNGVYSEPRPIGTRYLTRNL

AAV2: VP2

(SEQ ID NO: 66)

APGKKRPVEHSPVEPDSSSGTGKAGQQPARKRLNFGQTGDADSVPDP
QPLGQPPAAPSGLGTNTMATGSGAPMADNNEGADGVGNSSGNWHCDS
TWMGDRVITTSTRTWALPTYNNHLYKQISSQSGASNDNHYFGYSTPW
GYFDFNRFHCHFSPRDWQRLINNNWGFRPKRLNFKLFNIQVKEVTQN
DGTTTIANNLTSTVQVFTDSEYQLPYVLGSAHQGCLPPFPADVFMVP
QYGYLTLNNGSQAVGRSSFYCLEYFPSQMLRTGNNFTFSYTFEDVPF
HSSYAHSQSLDRLMNPLIDQYLYYLSRTNTPSGTTTQSRLQFSQAGA
SDIRDQSRNWLPGPCYRQQRVSKTSADNNNSEYSWTGATKYHLNGRD
SLVNPGPAMASHKDDEEKFFPQSGVLIFGKQGSEKTNVDIEKVMITD
EEEIRTTNPVATEQYGSVSTNLQRGNRQAATADVNTQGVLPGMVWQD
RDVYLQGPIWAKIPHTDGHFHPSPLMGGFGLKHPPPQILIKNTPVPA
NPSTTFSAAKFASFITQYSTGQVSVEIEWELQKENSKRWNPEIQYTS
NYNKSVNVDFTVDTNGVYSEPRPIGTRYLTRNL

AAV2: VP3

(SEQ ID NO: 67)

MATGSGAPMADNNEGADGVGNSSGNWHCDSTWMGDRVITTSTRTWAL
PTYNNHLYKQISSQSGASNDNHYFGYSTPWGYFDFNRFHCHFSPRDW
QRLINNNWGFRPKRLNFKLFNIQVKEVTQNDGTTTIANNLTSTVQVF
TDSEYQLPYVLGSAHQGCLPPFPADVFMVPQYGYLTLNNGSQAVGRS
SFYCLEYFPSQMLRTGNNFTFSYTFEDVPFHSSYAHSQSLDRLMNPL
IDQYLYYLSRTNTPSGTTTQSRLQFSQAGASDIRDQSRNWLPGPCYR
QQRVSKTSADNNNSEYSWTGATKYHLNGRDSLVNPGPAMASHKDDEE
KFFPQSGVLIFGKQGSEKTNVDIEKVMITDEEEIRTTNPVATEQYGS
VSTNLQRGNRQAATADVNTQGVLPGMVWQDRDVYLQGPIWAKIPHTD

-continued

GHFHPSPLMGGFGLKHPPPQILIKNTPVPANPSTTFSAAKFASFITQ

YSTGQVSVEIEWELQKENSKRWNPEIQYTSNYNKSVNVDFTVDTNGV

YSEPRPIGTRYLTRNL

Synthetic: Myc-Tagged Anti CD19 scFv
(SEQ ID NO: 68)
EQKLISEEDLDIQMTQTTSSLSASLGDRVTISCRASQDISKYLNWYQ

QKPDGTVKLLIYHTSRLHSGVPSRFSGSGSGTDYSLTISNLEQEDIA

TYFCQQGNTLPYTFGGGTKLEITGGGGSGGGGSGGGGSEVKLQESGP

GLVAPSQSLSVTCTVSGVSLPDYGVSWIRQPPRKGLEWLGVIWGSET

TYYNSALKSRLTIIKDNSKSQVFLKMNSLQTDDTAIYYCAKHYYYGG

SYAMDYWGQGTSVTVSS

Synthetic: dDZF1
(SEQ ID NO: 69)
FKCEHCRILFLDHVMFTIHMGCHGFRDPFKCNMCGEKCDGPVGLFVH

MARNAHGEKPFYCEHCEITFRDWMYSLHKGYHGFRDPFECNICGYHS

QDRYEFSSHIVRGEH

Synthetic: dDZF2
(SEQ ID NO: 70)
HHCQHCDMYFADNILYTIHMGCHSCDDVFKCNMCGEKCDGPVGLFVH

MARNAHGEKPTKCVHCGIVFLDEVMYALHMSCHGFRDPFECNICGYH

SQDRYEFSSHIVRGEH

Synthetic: DmrA
(SEQ ID NO: 71)
MGRGVQVETISPGDGRTFPKRGQTCVHYTGMLEDGKKFDSSRDRNKP

FKFMLGKQEVIRGWEEGVAQMSVGQRAKLTISPDYAYGATGHPGIIP

PHATLVFDVELLKLE

Synthetic: DmrB
(SEQ ID NO: 72)
MASRGVQVETISPGDGRTFPKRGQTCWHYTGMLEDGKKVDSSRDRNK

PFKFMLGKQEVIRGWEEGVAQMSVGQRAKLTISPDYAYGATGHPGII

PPHATLVFDVELLKLE

Synthetic: DmrC
(SEQ ID NO: 73)
MGSRILWHEMWHEGLEEASRLYFGERNVKGMFEVLEPLHAMMERGPQ

TLKETSFNQAYGRDLMEAQEWCRKYMKSGNVKDLLQAWDLYYHVFRR

ISK

Homo sapiens/Synthetic: FKBP
(SEQ ID NO: 74)
MGVQVETISPGDGRTFPKRGQTCWHYTGMLEDGKKFDSSRDRNKPFK

FMLGKQEVIRGWEEGVAQMSVGQRAKLTISPDYAYGATGHPGIIPPH

ATLVFDVELLKLE

Homo sapiens/Synthetic: FRB
(SEQ ID NO: 75)
QGMLEMWHEGLEEASRLYFGERNVKGMFEVLEPLHAMMERGPQTLKE

TSFNQAYGRDLMEAQEWCRKYMKSGNVKDLLQAWDLYYHVFRRISK+0

Synthetic: Anti-GCN4 scFv
(SEQ ID NO: 76)
MGPDIVMTQSPSSLSASVGDRVTITCRSSTGAVTTSNYASWVQEKPG

KLFKGLIGGTNNRAPGVPSRFSGSLIGDKATLTISSLQPEDFATYFC

ALWYSNHWVFGQGTKVELKRGGGGSGGGGSGGGGSSGGGSEVKLLES

GGGLVQPGGSLKLSCAVSGFSLTDYGVNVWRQAPGRGLEWIGVIWGD

GITDYNSALKDRFIISKDNGKNTVYLQMSKVRSDDTALYYCVTGLFD

YWGQGTLVTVSSYPYDVPDYAGGGGSGGGGSGGGGSGGGGS

Synthetic: 10x-GCN4 Repeats
(SEQ ID NO: 77)
EELLSKNYHLENEVARLKKGSGSGEELLSKNYHLENEVARLKKGSGS

GEELLSKNYHLENEVARLKKGSGSGEELLSKNYHLENEVARLKKGSG

SGEELLSKNYHLENEVARLKKGSGSGEELLSKNYHLENEVARLKKGS

GSGEELLSKNYHLENEVARLKKGSGSGEELLSKNYHLENEVARLKKG

SGSGEELLSKNYHLENEVARLKKGSGSGEELLSKNYHLENEVARLKK

GS

Synthetic: 24x-GCN4 Repeats
(SEQ ID NO: 78)
EELLSKNYHLENEVARLKKGSGSGEELLSKNYHLENEVARLKKGSGS

GEELLSKNYHLENEVARLKKGSGSGEELLSKNYHLENEVARLKKGSG

SGEELLSKNYHLENEVARLKKGSGSGEELLSKNYHLENEVARLKKGS

GSGEELLSKNYHLENEVARLKKGSGSGEELLSKNYHLENEVARLKKG

SGSGEELLSKNYHLENEVARLKKGSGSGEELLSKNYHLENEVARLKK

GSGSGEELLSKNYHLENEVARLKKGSGSGEELLSKNYHLENEVARLK

KGSGSGEELLSKNYHLENEVARLKKGSGSGEELLSKNYHLENEVARL

KKGSGSGEELLSKNYHLENEVARLKKGSGSGEELLSKNYHLENEVAR

LKKGSGSGEELLSKNYHLENEVARLKKGSGSGEELLSKNYHLENEVA

RLKKGSGSGEELLSKNYHLENEVARLKKGSGSGEELLSKNYHLENEV

ARLKKGSGSGEELLSKNYHLENEVARLKKGSGSGEELLSKNYHLENE

VARLKKGSGSGEELLSKDYHLENEVARLKKGSGSGEELLSKNYHLEN

EVARLKKGS

Synthetic: GFP-targeting Nanobody
(SEQ ID NO: 79)
VQLVESGGALVQPGGSLRLSCAASGFPVNRYSMRWYRQAPGKEREVW

AGMSSAGDRSSYEDSVKGRFTISRDDARNTVYLQMNSLKPEDTAVYY

SNVNVGFEYWGQGTQVTVSS

Nostoc punctiforme: Npu DnaE N-terminal
Split Intein
(SEQ ID NO: 80)
CLSYETEILTVEYGLLPIGKIVEKRIECTVYSVDNNGNIYTQPVAQW

HDRGEQEVFEYCLEDGSLIRATKDHKFMTVDGQMLPIDEIFERELDL

MRVDNLPN

Nostoc punctiforme: Npu DnaE C-terminal
Split Intein
(SEQ ID NO: 81)
MIKIATRKYLGKQNVYDIGVERDHNFALKNGFIASNCFN Synthetic: Cfa N-Terminal Split Intein
(SEQ ID NO: 82)
CLSYDTEILTVEYGFLPIGKIVEERIECTVYTVDKNGFVYTQPIAQW

HNRGEQEVFEYCLEDGSIIRATKDHKFMTTDGQMLPIDEIFERGLDL

KQVDGLP

Synthetic: Cfa C-Terminal Split Intein
(SEQ ID NO: 83)
MVKIISRKSLGTQNVYDIGVEKDHNFLLKNGLVASN

*Saccharomyces cerevisiae*: Vma N-terminal
Split Intein
(SEQ ID NO: 84)
CFAKGTNVLMADGSIECIENIEVGNKVMGKDGRPREVIKLPRGRETM

YSWQKSQHRAHKSDSSREVPELLKFTCNATHELWRTPRSVRRLSRTI

KGVEYFEVITFEMGQKKAPDGRIVELVKEVSKSYPISEGPERANELV

ESYRKASNKAYFEWTIEARDLSLLGSHVRKATYQTYAPILY

*Saccharomyces cerevisiae*: Vma C-terminal
Split Intein
(SEQ ID NO: 85)
VLLNVLSKCAGSKKFRPAPAAAFARECRGFYFELQELKEDDYYGITL

SDDSDHQFLLANQVWHN

*Synechocystis* sp. PCC 6803: Ssp DnaE
N-terminal Split Intein
(SEQ ID NO: 86)
CLSFGTEILTVEYGPLPIGKIVSEEINCSVYSVDPEGRVYTQAIAQW

HDRGEQEVLEYELEDGSVIRATSDHRFLTTDYQLLAIEEIFARQLDL

LTLENIKQTEEALDNHRLPFPLLDAGTIK

*Synechocystis* sp. PCC 6803: Ssp DnaE
C-terminal Split Intein
(SEQ ID NO: 87)
MVKVIGRRSLGVQRIFDIGLPQDHNFLLANGAIAAN Synthetic: Spy Tag
(SEQ ID NO: 88)
VPTIVMVDAYKRYK Synthetic: Spy Catcher
(SEQ ID NO: 89)
MVTTLSGLSGEQGPSGDMTTEEDSATHIKFSKRDEDGRELAGATMEL

RDSSGKTISTWISDGHVKDFYLYPGKYTFVETAAPDGYEVATAITFT

VNEQGQVTVNGEATKGDAHTGSSGS

Bacteriophage MS2: MS2 RNA Binding Protein
(SEQ ID NO: 90)
MASNFTQFVLVDNGGTGDVTVAPSNFANGVAEWISSNSRSQAYKVTC

SVRQSSAQNRKYTIKVEVPKVATQTVGGVELPVAAWRSYLNMELTIP

IFATNSDCELIVKAMQGLLKDGNPIPSAIAANSGIY

Bacteriophage MS2: MS2 (N55K) RNA
Binding Protein
(SEQ ID NO: 91)
MASNFTQFVLVDNGGTGDVTVAPSNFANGVAEWISSNSRSQAYKVTCS

VRQSSAQKRKYTIKVEVPKVATQTVGGVELPVAAWRSYLNMELTIPI

FATNSDCELIVKAMQGLLKDGNPIPSAIAANSGIY

Bacteriophage MS2: MS2 (N55K)(V29I) RNA
Binding Protein
(SEQ ID NO: 92)
MASNFTQFVLVDNGGTGDVTVAPSNFANGIAEWISSNSRSQAYKVTC

SVRQSSAQKRKYTIKVEVPKVATQTVGGVELPVAAWRSYLNMELTIP

IFATNSDCELIVKAMQGLLKDGNPIPSAIAANSGIY

Bacteriophage PP7: PP7 RNA Binding Protein
(SEQ ID NO: 93)
KTIVLSVGEATRTLTEIQSTADRQIFEEKVGPLVGRLRLTASLRQNG

AKTAYRVNLKLDQADVVDSGLPKVRYTQVWSHDVTIVANSTEASRKS

LYDLTKSLVATSQVEDLWNLVPLGRS

Bacteriophage Mu: COM RNA Binding Protein
(SEQ ID NO: 94)
MKSIRCKNCNKLLFKADSFDHIEIRCPRCKRHIIMLNACEHPTEKHC

GKREKITHSDETVRY

Synthetic: Zinc Finger ZF6/10
(SEQ ID NO: 95)
STRPGERPFQCRICMRNFSIPNHLARHTRTHTGEKPFQCRICMRNFS

QSAHLKRHLRTHTGEKPFQCRICMRNFSQDVSLVRHLKTHLRQKDGE

RPFQCRICMRNFSSAQALARHTRTHTGEKPFQCRICMRNFSQGGNLT

RHLRTHTGEKPFQCRICMRNFSQHPNLTRHLKTHLRGS

Synthetic: Zinc Finger ZF8/7
(SEQ ID NO: 96)
SRPGERPFQCRICMRNFSTMAVLRRHTRTHTGEKPFQCRICMRNFSR

REVLENHLRTHTGEKPFQCRICMRNFSQTVNLDRHLKTHLRQKDGER

PFQCRICMRNFSKKDHLHRHTRTHTGEKPFQCRICMRNFSQRPHLTN

HLRTHTGEKPFQCRICMRNFSVGASLKRHLKTHLRGS

Synthetic: Zinc Finger ZF9
(SEQ ID NO: 97)
SRPGERPFQCRICMRNFSDKTKLRVHTRTHTGEKPFQCRICMRNFSV

RHNLTRHLRTHTGEKPFQCRICMRNFSQSTSLQRHLKTHLRGF

Synthetic: Zinc Finger MK10
(SEQ ID NO: 98)
SRPGERPFQCRICMRNFSRRHGLDRHTRTHTGEKPFQCRICMRNFSD

HSSLKRHLRTHTGSQKPFQCRICMRNFSVRHNLTRHLRTHTGEKPFQ

CRICMRNFSDHSNLSRHLKTHTGSQKPFQCRICMRNFSQRSSLVRHL

RTHTGEKPFQCRICMRNFSESGHLKRHLRTHLRGS

Synthetic: Zinc Finger 268
(SEQ ID NO: 99)
YACPVESCDRRFSRSDELTRHIRIHTGQKPFQCRICMRNFSRSDHLT

THIRTHTGEKPFACDICGRKFARSDERKRHTKIHLRQKD

Synthetic: Zinc Finger NRE
(SEQ ID NO: 100)
YACPVESCDRRFSQSHDLTKHIRIHTGQKPFQCRICMRNFSDSSKLS

RHIRTHTGEKPFACDICGRKFARLDNRTAHTKIHLRQKD

Synthetic: Zinc Finger 268/NRE
(SEQ ID NO: 101)
YACPVESCDRRFSRSDELTRHIRIHTGQKPFQCRICMRNFSRSDHLT

THIRTHTGEKPFACDICGRKFARSDERKRHTKIHLRQKDGERPYACP

VESCDRRFSQSHDLTKHIRIHTGQKPFQCRICMRNFSDSSKLSRHIR

THTGEKPFACDICGRKFARLDNRTAHTKIHLRQKD

Synthetic: Zinc Finger 268//NRE
(SEQ ID NO: 102)
YACPVESCDRRFSRSDELTRHIRIHTGQKPFQCRICMRNFSRSDHLT

THIRTHTGEKPFACDICGRKFARSDERKRHTKIHLRQKDGGGSERPY

ACPVESCDRRFSQSHDLTKHIRIHTGQKPFQCRICMRNFSDSSKLSR

HIRTHTGEKPFACDICGRKFARLDNRTAHTKIHLRQKD

Synthetic: FokI Zinc Finger Nuclease
17-2 Targeting GFP
(SEQ ID NO: 103)
SRPGERPFQCRICMRNFSTRQNLDTHTRTHTGEKPFQCRICMRNFSR

RDTLERHLRTHTGEKPFQCRICMRNFSRPDALPRHLKTHLRGSQLVK

SELEEKKSELRHKLKYVPHEYIELIEIARNSTQDRILEMKVMEFFMK

VYGYRGKHLGGSRKPDGAIYTVGSPIDYGVIVDTKAYSGGYNLPIGQ

ADEMQRYVEENQTRNKHINPNEWWKVYPSSVTEFKFLFVSGHFKGNY

KAQLTRLNHITNCNGAVLSVEELLIGGEMIKAGTLTLEEVRRKFNNG

EINF

Synthetic: FokI Zinc Finger Nuclease
18-2 Targeting GFP
(SEQ ID NO: 104)
SRPGERPFQCRICMRNFSSPSKLIRHTRTHTGEKPFQCRICMRNFSD

GSNLARHLRTHTGEKPFQCRICMRNFSRVDNLPRHLKTHLRGSQLVK

SELEEKKSELRHKLKYVPHEYIELIEIARNSTQDRILEMKVMEFFMK

VYGYRGKHLGGSRKPDGAIYTVGSPIDYGVIVDTKAYSGGYNLPIGQ

ADEMQRYVEENQTRNKHINPNEWWKVYPSSVTEFKFLFVSGHFKGNY

KAQLTRLNHITNCNGAVLSVEELLIGGEMIKAGTLTLEEVRRKFNNG

EINF

Synthetic: Left FokI Zinc Finger Nuclease
Targeting CCR5
(SEQ ID NO: 105)
MDYKDHDGDYKDHDIDYKDDDDKMAPKKKRKVGIHGVPAAMAERPFQ

CRICMRNFSDRSNLSRHIRTHTGEKPFACDICGRKFAISSNLNSHTK

IHTGSQKPFQCRICMRNFSRSDNLARHIRTHTGEKPFACDICGRKFA

TSGNLTRHTKIHLRGSQLVKSELEEKKSELRHKLKYVPHEYIELIEI

ARNSTQDRILEMKVMEFFMKVYGYRGKHLGGSRKPDGAIYTVGSPID

YGVIVDTKAYSGGYNLPIGQADEMQRYVEENQTRNKHINPNEWWKVY

PSSVTEFKFLFVSGHFKGNYKAQLTRLNHITNCNGAVLSVEELLIGG

EMIKAGTLTLEEVRRKFNNGEINF

Synthetic: Right FokI Zinc Finger Nuclease
Targeting CCR5
(SEQ ID NO: 106)
MDYKDHDGDYKDHDIDYKDDDDKMAPKKKRKVGIHGVPAAMAERPFQ

CRICMRNFSRSDNLSVHIRTHTGEKPFACDICGRKFAQKINLQVHTK

IHTGEKPFQCRICMRNFSRSDVLSEHIRTHTGEKPFACDICGRKFAQ

RNHRTTHTKIHLRGSQLVKSELEEKKSELRHKLKYVPHEYIELIEIA

RNSTQDRILEMKVMEFFMKVYGYRGKHLGGSRKPDGAIYTVGSPIDY

GVIVDTKAYSGGYNLPIGQADEMQRYVEENQTRNKHINPNEWWKVYP

SSVTEFKFLFVSGHFKGNYKAQLTRLNHITNCNGAVLSVEELLIGGE

MIKAGTLTLEEVRRKFNNGEINF

Synthetic: FokI Nuclease Domain
(SEQ ID NO: 107)
QLVKSELEEKKSELRHKLKYVPHEYIELIEIARNSTQDRILEMKVME

FFMKVYGYRGKHLGGSRKPDGAIYTVGSPIDYGVIVDTKAYSGGYNL

PIGQADEMQRYVEENQTRNKHINPNEWWKVYPSSVTEFKFLFVSGHF

KGNYKAQLTRLNHITNCNGAVLSVEELLIGGEMIKAGTLTLEEVRRK

FNNGEINF

Synthetic: AcuI Nuclease Domain
(SEQ ID NO: 108)
VHDHKLELAKLIRNYETNRKECLNSRYNETLLRSDYLDPFFELLGWD

IKNKAGKPTNEREVVLEEALKASASEHSKKPDYTFRLFSERKFFLEA

KKPSVHIESDNETAKQVRRYGFTAKLKISVLSNFEYLVIYDTSVKVD

GDDTFNKARIKKYHYTEYETHFDEICDLLGRESVYSGNFDKEWLSIE

NKINHFSVDTL

Synthetic: Truncated AcuI Nuclease Domain
(SEQ ID NO: 109)
YNETLLRSDYLDPFFELLGWDIKNKAGKPTNEREWLEEALKASASEH

SKKPDYTFRLFSERKFFLEAKKPSVHIESDNETAKQVRRYGFTAKLK

ISVLSNFEYLVIYDTSVKVDGDDT

Escherichia coli: Ferritin
(SEQ ID NO: 110)
MLKPEMIEKLNEQMNLELYSSLLYQQMSAWCSYHTFEGAAAFLRRHA

QEEMTHMQRLFDYLTDTGNLPRINTVESPFAEYSSLDELFQETYKHE

QLITQKINELAHAAMTNQDYPTFNFLQWYVSEQHEEEKLFKSIIDKL

SLAGKSGEGLYFIDKELSTLDTQN

Escherichia coli: Ferritin (H34L)(T64I)
(SEQ ID NO: 111)
MLKPEMIEKLNEQMNLELYSSLLYQQMSAWCSYLTFEGAAAFLRRHA

QEEMTHMQRLFDYLTDIGNLPRINTVESPFAEYSSLDELFQETYKHE

QLITQKINELAHAAMTNQDYPTFNFLQWYVSEQHEEEKLFKSIIDKL

SLAGKSGEGLYFIDKELSTLDTQN

Mus musculus & Synthetic: Light & Heavy
Chain Ferritin Chimera
(SEQ ID NO: 112)
MTSQIRQNYSTEVEAAVNRLVNLHLRASYTYLSLGFFFDRDDVALEG

VGHFFRELAEEKREGAERLLEFQNDRGGRALFQDVQKPSQDEWGKTQ

EAMEAALAMEKNLNQALLDLHALGSARADPHLCDFLESHYLDKEVKL

IKKMGNHLTNLRRVAGPQPAQTGAPQGSLGEYLFERLTLKHDARGGG

GSDYKDDDDKGGGGSRVMTTASPSQVRQNYHQDAEAAINRQINLELY

ASYVYLSMSCYFDRDDVALKNFAKYFLHQSHEEREHAEKLMKLQNQR

GGRIFLQDIKKPDRDDWESGLNAMECALHLEKSVNQSLLELHKLATD

KNDPHLCDFIETYYLSEQVKSIKELGDHVTNLRKMGAPEAGMAEYLF

DKHTLGHGDESTR

Homo sapiens & Synthetic: Light & Heavy
Chain Ferritin Chimera
(SEQ ID NO: 113)
SQIRQNYSTDVEAAVNSLVNLYLQASYTYLSLGFYFDRDDVALEGVS

HFFRELAEEKREGYERLLKMQNQRGGRALFQDIKKPAEDEWGKTPDA

```
MKAAMALEKKLNQALLDLHALGSARTDPHLCDFLETHFLDEEVKLIK
KMGDHLTNLHRLGGPEAGLGEYLFERLTLKHDARGGGGSDYKDDDDK
GGGGSRVMTTASTSQVRQNYHQDSEAAINRQINLELYASYVYLSMSY
YFDRDDVALKNFAKYFLHQSHEEREHAEKLMKLQNQRGGRIFLQDIK
KPDCDDWESGLNAMECALHLEKNVQSLLELHKLATDKNDPHLCDFI
ETHYLNEQVKAIKELGDHVTNLRKMGAPESGLAEYLFDKHTLGDSDN
ES
```

*Arabidopsis thaliana*: Cry2

(SEQ ID NO: 114)
```
MKMDKKTIVWFRRDLRIEDNPALAAAAHEGSVFPVFIWCPEEEGQFY
PGRASRWWMKQSLAHLSQSLKALGSDLTLIKTHNTISAILDCIRVTG
ATKVVFNHLYDPVSLVRDHTVKEKLVERGISVQSYNGDLLYEPWEIY
CEKGKPFTSFNSYWKKCLDMSIESVMLPPPWRLMPITAAAEAIWACS
IEELGLENEAEKPSNALLTRAWSPGWSNADKLLNEFIEKQLIDYAKN
SKKWGNSTSLLSPYLHFGEISVRHVFQCARMKQIIWARDKNSEGEES
ADLFLRGIGLREYSRYICFNFPFTHEQSLLSHLRFFPWDADVDKFKA
WRQGRTGYPLVDAGMRELWATGWMHNRIRVIVSSFAVKFLLLPWKWG
MKYFWDTLLDADLECDILGWQYISGSIPDGHELDRLDNPALQGAKYD
PEGEYIRQWLPELARLPTEWIHHPWDAPLTVLKASGVELGTNYAKPI
VDIDTARELLAKAISRTREAQIMIGAAPDEIVADSFEALGANTIKEP
GLCPSVSSNDQQVPSAVRYNGSAAVKPEEEEERDMKKSRGFDERELF
STAESSSSSSVFFVSQSCSLASEGKNLEGIQDSSDQITTSLGKNGCK
```

*Arabidopsis thaliana*: CIBN (SEQ ID NO: 115)
```
MNGAIGGDLLLNFPDMSVLERQRAHLKYLNPTFDSPLAGFFADSSMI
TGGEMDSYLSTAGLNLPMMYGETTVEGDSRLSISPETTLGTGNFKAA
KFDTETKDCNEAAKKMTMNRDDLVEEGEEEKSKITEQNNGSTKSIKK
MKHKAKKEENNFSNDSSKVTKELEKTDYI
```

Synthetic: LoV2-Ja (SEQ ID NO: 116)
```
SLATTLERIEKNFVITDPRLPDNPIIFASDSFLQLTEYSREEILGRN
CRFLQGPETDRATVRKIRDAIDNQTEVTVQLINYTKSGKKFWNLFHL
QPMRDQKGDVQYFIGVQLDGTEHVRDAAEREGVMLIKKTAENIDEAA
KEL
```

*Homo sapiens*: Full Length WT ADAR2

(SEQ ID NO: 117)
```
DIEDEENMSSSSTDVKENRNLDNVSPKDGSTPGPGEGSQLSNGGGGG
PGRKRPLEEGSNGHSKYRLKKRRKTPGPVLPKNALMQLNEIKPGLQY
TLLSQTGPVHAPLFVMSVEVNGQVFEGSGPTKKKAKLHAAEKALRSF
VQFPNASEAHLAMGRTLSVNTDFTSDQADFPDTLFNGFETPDKAEPP
FYVGSNGDDSFSSSGDLSLSASPVPASLAQPPLPVLPPFPPPSGKNP
VMILNELRPGLKYDFLSESGESHAKSFVMSVWDGQFFEGSGRNKKLA
KARAAQSALAAIFNLHLDQTPSRQPIPSEGLQLHLPQVLADAVSRLV
LGKFGDLTDNFSSPHARRKVLAGVVMTTGTDVKDAKVISVSTGTKCI
NGEYMSDRGLALNDCHAEIISRRSLLRFLYTQLELYLNNKDDQKRSI
FQKSERGGFRLKENVQFHLYISTSPCGDARIFSPHEPILEGSRSYTQ
AGVQWCNHGSLQPRPPGLLSDPSTSTFQGAGTTEPADRHPNRKARGQ
LRTKIESGEGTIPVRSNASIQTWDGVLQGERLLTMSCSDKIARWNWG
IQGSLLSIFVEPIYFSSIILGSLYHGDHLSRAMYQRISNIEDLPPLY
TLNKPLLSGISNAEARQPGKAPNFSVNWTVGDSAIEVINATTGKDEL
GRASRLCKHALYCRWMRVHGKVPSHLLRSKITKPNVYHESKLAAKEY
QAAKARLFTAFIKAGLGAVWEKPTEQDQFSLTP
```

*Homo sapiens*: Full Length WT ADAR2 (E488Q)

(SEQ ID NO: 118)
```
DIEDEENMSSSSTDVKENRNLDNVSPKDGSTPGPGEGSQLSNGGGGG
PGRKRPLEEGSNGHSKYRLKKRRKTPGPVLPKNALMQLNEIKPGLQY
TLLSQTGPVHAPLFVMSVEVNGQVFEGSGPTKKKAKLHAAEKALRSF
VQFPNASEAHLAMGRTLSVNTDFTSDQADFPDTLFNGFETPDKAEPP
FYVGSNGDDSFSSSGDLSLSASPVPASLAQPPLPVLPPFPPPSGKNP
VMILNELRPGLKYDFLSESGESHAKSFVMSVWDGQFFEGSGRNKKLA
KARAAQSALAAIFNLHLDQTPSRQPIPSEGLQLHLPQVLADAVSRLV
LGKFGDLTDNFSSPHARRKVLAGVVMTTGTDVKDAKVISVSTGTKCI
NGEYMSDRGLALNDCHAEIISRRSLLRFLYTQLELYLNNKDDQKRSI
FQKSERGGFRLKENVQFHLYISTSPCGDARIFSPHEPILEGSRSYTQ
AGVQWCNHGSLQPRPPGLLSDPSTSTFQGAGTTEPADRHPNRKARGQ
LRTKIESGQGTIPVRSNASIQTWDGVLQGERLLTMSCSDKIARWNWG
IQGSLLSIFVEPIYFSSIILGSLYHGDHLSRAMYQRISNIEDLPPLY
TLNKPLLSGISNAEARQPGKAPNFSVNWTVGDSAIEVINATTGKDEL
GRASRLCKHALYCRWMRVHGKVPSHLLRSKITKPNVYHESKLAAKEY
QAAKARLFTAFIKAGLGAVWEKPTEQDQFSLTP
```

*Homo sapiens*: Truncated WT ADAR2

(SEQ ID NO: 119)
```
VLADAVSRLVLGKFGDLTDNFSSPHARRKVLAGWMTTGTDVKDAKVI
SVSTGTKCINGEYMSDRGLALNDCHAEIISRRSLLRFLYTQLELYLN
NKDDQKRSIFQKSERGGFRLKENVQFHLYISTSPCGDARIFSPHEPI
LEGSRSYTQAGVQWCNHGSLQPRPPGLLSDPSTSTFQGAGTTEPADR
HPNRKARGQLRTKIESGEGTIPVRSNASIQTWDGVLQGERLLTMSCS
DKIARWNWGIQGSLLSIFVEPIYFSSIILGSLYHGDHLSRAMYQRIS
NIEDLPPLYTLNKPLLSGISNAEARQPGKAPNFSVNWTVGDSAIEVI
NATTGKDELGRASRLCKHALYCRWMRVHGKVPSHLLRSKITKPNVYH
ESKLAAKEYQAAKARLFTAFIKAGLGAVWEKPTEQDQFSLTP
```

*Homo sapiens*: Truncated WT ADAR2 (E488Q)

(SEQ ID NO: 120)
```
VLADAVSRLVLGKFGDLTDNFSSPHARRKVLAGVMTTGTDVKDAKVI
SVSTGTKCINGEYMSDRGLALNDCHAEIISRRSLLRFLYTQLELYLN
NKDDQKRSIFQKSERGGFRLKENVQFHLYISTSPCGDARIFSPHEPI
LEGSRSYTQAGVQWCNHGSLQPRPPGLLSDPSTSTFQGAGTTEPADR
HPNRKARGQLRTKIESGQGTIPVRSNASIQTWDGVLQGERLLTMSCS
```

```
DKIARWNWGIQGSLLSIFVEPIYFSSIILGSLYHGDHLSRAMYQRIS

NIEDLPPLYTLNKPLLSGISNAEARQPGKAPNFSVNWTVGDSAIEVI

NATTGKDELGRASRLCKHALYCRWMRVHGKVPSHLLRSKITKPNVYH

ESKLAAKEYQAAKARLFTAFIKAGLGAWWEKPTEQDQFSLTP
```

Homo sapiens & Synthetic: MS2-ADAR1 Deaminase
Domain-Nuclear Exclusion Signal
(SEQ ID NO: 121)
```
MASNFTQFVLVDNGGTGDVTVAPSNFANGIAEWISSNSRSQAYKVTC

SVRQSSAQNRKYTIKVEVPKGAWRSYLNMELTIPIFATNSDCELIVK

AMQGLLKDGNPIPSAIAANSGIYGGSGSGAGSGSPAGGGAPGSGGGS

KAERMGFTEVTPVTGASLRRTMLLLSRSPEAQPKTLPLTGSTFHDQI

AMLSHRCFNTLTNSFQPSLLGRKILAAIIMKKDSEDMGVWVSLGTGN

RCVKGDSLSLKGETVNDCHAEIISRRGFIRFLYSELMKYNSQTAKDS

IFEPAKGGEKLQIKKTVSFHLYISTAPCGDGALFDKSCSDRAMESTE

SRHYPVFENPKQGKLRTKVENGEGTIPVESSDIVPTWDGIRLGERLR

TMSCSDKILRWNVLGLQGALLTHFLQPIYLKSVTLGYLFSQGHLTRA

ICCRVTRDGSAFEDGLRHPFIVNHPKVGRVSIYDSKRQSGKTKETSV

NWCLADGYDLEILDGTRGTVDGPRNELSRVSKKNIFLLFKKLCSFRY

RRDLLRLSYGEAKKAARDYETAKNYFKKGLKDMGYGNWISKPQEEKN

FYLCPVGSGSGSLPPLERLT
```

Homo sapiens & Synthetic: MS2-ADAR1 Deaminase
Domain (E1008Q)-
Nuclear Exclusion Signal
(SEQ ID NO: 122)
```
MASNFTQFVLVDNGGTGDVTVAPSNFANGIAEWISSNSRSQAYKVTC

SVRQSSAQNRKYTIKVEVPKGAWRSYLNMELTIPIFATNSDCELIVK

AMQGLLKDGNPIPSAIAANSGIYGGSGSGAGSGSPAGGGAPGSGGGS

KAERMGFTEVTPVTGASLRRTMLLLSRSPEAQPKTLPLTGSTFHDQI

AMLSHRCFNTLTNSFQPSLLGRKILAAIIMKKDSEDMGVWVSLGTGN

RCVKGDSLSLKGETVNDCHAEIISRRGFIRFLYSELMKYNSQTAKDS

IFEPAKGGEKLQIKKTVSFHLYISTAPCGDGALFDKSCSDRAMESTE

SRHYPVFENPKQGKLRTKVENGQGTIPVESSDIVPTWDGIRLGERLR

TMSCSDKILRWNVLGLQGALLTHFLQPIYLKSVTLGYLFSQGHLTRA

ICCRVTRDGSAFEDGLRHPFIVNHPKVGRVSIYDSKRQSGKTKETSV

NWCLADGYDLEILDGTRGTVDGPRNELSRVSKKNIFLLFKKLCSFRY

RRDLLRLSYGEAKKAARDYETAKNYFKKGLKDMGYGNWISKPQEEKN

FYLCPVGSGSGSLPPLERLTL
```

Ruminococcus flavefaciens: RfxCas13d (CasRx)
(SEQ ID NO: 123)
```
EASIEKKKSFAKGMGVKSTLVSGSKVYMTTFAEGSDARLEKIVEGDS

IRSVNEGEAFSAEMADKNAGYKIGNAKFSHPKGYAVVANNPLYTGPV

QQDMLGLKETLEKRYFGESADGNDNICIQVIHNILDIEKILAEYITN

AAYAVNNISGLDKDIIGFGKFSTVYTYDEFKDPEHHRAAFNNNDKLI

NAIKAQYDEFDNFLDNPRLGYFGQAFFSKEGRNYIINYGNECYDILA

LLSGLRHWVVHNNEEESRISRTWLYNLDKNLDNEYISTLNYLYDRIT

NELTNSFSKNSAANVNYIAETLGINPAEFAEQYFRFSIMKEQKNLGF

NITKLREVMLDRKDMSEIRKNHKVFDSIRTKVYTMMDFVIYRYYIEE

DAKVAAANKSLPDNEKSLSEKDIFVINLRGSFNDDQKDALYYDEANR

IWRKLENIMHNIKEFRGNKTREYKKKDAPRLPRILPAGRDVSAFSKL

MYALTMFLDGKEINDLLTTLINKFDNIQSFLKVMPLIGVNAKFVEEY

AFFKDSAKIADELRLIKSFARMGEPIADARRAMYIDAIRILGTNLSY

DELKALADTFSLDENGNKLKKGKHGMRNFIINNVISNKRFHYLIRYG

DPAHLHEIAKNEAVKFVLGRIADIQKKQGQNGKNQIDRYYETCIGKD

KGKSVSEKVDALTKIITGMNYDQFDKKRSVIEDTGRENAEREKFKKI

ISLYLTVIYHILKNIVNINARYVIGFHCVERDAQLYKEKGYDINLKK

LEEKGFSSVTKLCAGIDETAPDKRKDVEKEMAERAKESIDSLESANP

KLYANYIKYSDEKKAEEFTRQINREKAKTALNAYLRNTKWNVIIRED

LLRIDNKTCTLFRNKAVHLEVARYVHAYINDIAEVNSYFQLYHYIMQ

RIIMNERYEKSSGKVSEYFDAVNDEKKYNDRLLKLLCVPFGYCIPRF

KNLSIEALFDRNEAAKFDKEKKKVSGNSGSG
```

Ruminococcus flavefaciens & Synthetic: dead
RfxCas13d (dCasRx)
(SEQ ID NO: 124)
```
EASIEKKKSFAKGMGVKSTLVSGSKVYMTTFAEGSDARLEKIVEGDS

IRSVNEGEAFSAEMADKNAGYKIGNAKFSHPKGYAVVANNPLYTGPV

QQDMLGLKETLEKRYFGESADGNDNICIQVIHNILDIEKILAEYITN

AAYAVNNISGLDKDIIGFGKFSTVYTYDEFKDPEHHRAAFNNNDKLI

NAIKAQYDEFDNFLDNPRLGYFGQAFFSKEGRNYIINYGNECYDILA

LLSGLAHWWANNEEESRISRTWLYNLDKNLDNEYISTLNYLYDRITN

ELTNSFSKNSAANVNYIAETLGINPAEFAEQYFRFSIMKEQKNLGFN

ITKLREVMLDRKDMSEIRKNHKVFDSIRTKVYTMMDFVIYRYYIEED

AKVAAANKSLPDNEKSLSEKDIFVINLRGSFNDDQKDALYYDEANRI

WRKLENIMHNIKEFRGNKTREYKKKDAPRLPRILPAGRDVSAFSKLM

YALTMFLDGKEINDLLTTLINKFDNIQSFLKVMPLIGVNAKFVEEYA

FFKDSAKIADELRLIKSFARMGEPIADARRAMYIDAIRILGTNLSYD

ELKALADTFSLDENGNKLKKGKHGMRNFIINNVISNKRFHYLIRYGD

PAHLHEIAKNEAWKFVLGRIADIQKKQGQNGKNQIDRYYETCIGKDK

GKSVSEKVDALTKIITGMNYDQFDKKRSVIEDTGRENAEREKFKKII

SLYLTVIYHILKNIVNINARYVIGFHCVERDAQLYKEKGYDINLKKL

EEKGFSSVTKLCAGIDETAPDKRKDVEKEMAERAKESIDSLESANPK

LYANYIKYSDEKKAEEFTRQINREKAKTALNAYLRNTKWNVIIREDL

LRIDNKTCTLFANKAVALEVARYVHAYINDIAEVNSYFQLYHYIMQR

IIMNERYEKSSGKVSEYFDAVNDEKKYNDRLLKLLCVPFGYCIPRFK

NLSIEALFDRNEAAKFDKEKKKVSGNSGSGPKKKRKVAAAYPYDVPD

YA
```

-continued

Prevotella sp. P5-125: PspCas13b
(SEQ ID NO: 125)
MNIPALVENQKKYFGTYSVMAMLNAQTVLDHIQKVADIEGEQNENNE

NLWFHPVMSHLYNAKNGYDKQPEKTMFIIERLQSYFPPFLKIMAENQR

EYSNGKYKQNRVEVNSNDIFEVLKRAFGVLKMYRDLTNHYKTYEEKL

NDGCEFLTSTEQPLSGMINNYYTVALRNMNERYGYKTEDLAFIQDKR

FKFVKDAYGKKKSQVNTGFFLSLQDYNGDTQKKLHLSGVGIALLICL

FLDKQYINIFLSRLPIFSSYNAQSEERRIIRSFGINSIKLPKDRIH

SEKSNKSVAMDMLNEVKRCPDELFTTLSAEKQSRFRIISDDHNEVLM

KRSSDRFVPLLLQYIDYGKLFDHIRFHVNMGKLRYLLKADKTCIDGQ

TRVRVIEQPLNGFGRLEEAETMRKQENGTFGNSGIRIRDFENMKRDD

ANPANYPYIVDTYTHYILENNKVEMFINDKEDSAPLLPVIEDDRYVV

KTIPSCRMSTLEIPAMAFHMFLFGSKKTEKLIVDVHNRYKRLFQAMQ

KEEVTAENIASFGIAESDLPQKILDLISGNAHGKDVDAFIRLTVDDM

LTDTERRIKRFKDDRKSIRSADNKMGKRGFKQISTGKLADFLAKDIV

LFQPSVNDGENKITGLNYRIMQSAIAVYDSGDDYEAKQQFKLMFEKA

RLIGKGTTEPHPFLYKVFARSIPANAVEFYERYLIERKFYLTGLSNE

IKKGNRVDVPFIRRDQNKWKTPAMKTLGRIYSEDLPVELPRQMFDNE

IKSHLKSLPQMEGIDFNNANVTYLIAEYMKRVLDDDFQTFYQWNRNY

RYMDMLKGEYDRKGSLQHCFTSVEEREGLWKERASRTERYRKQASNK

IRSNRQMRNASSEEIETILDKRLSNSRNEYQKSEKVIRRYRVQDALL

FLLAKKTLTELADFDGERFKLKEIMPDAEKGILSEIMPMSFTFEKGG

KKYTITSEGMKLKNYGDFFVLASDKRIGNLLELVGSDIVSKEDIMEE

FNKYDQCRPEISSIVFNLEKWAFDTYPELSARVDREEKVDFKSILKI

LLNNKNINKEQSDILRKIRNAFDHNNYPDKGVEIKALPEIAMSIKKA

FGEYAIMKGSLQ

Synthetic: L17E
(SEQ ID NO: 126)
IWLTALKFLGKHAAKHEAKQQLSKL

Synthetic: L17E-Transmembrane
(SEQ ID NO: 127)
IWLTALKFLGKHAAKHEAKQQLSKLNAVGQDTQEVIVPHSLPFKVVV

ISAILALVVLTIISLHLIMLWQKKPR

Synthetic: KALA
(SEQ ID NO: 128)
WEAKLAKALAKALAKHLAKALAKALKACEA

Synthetic: KALA-Transmembrane
(SEQ ID NO: 129)
WEAKLAKALAKALAKHLAKALAKALKACEANAVGQDTQEVIVVPHSL

PFKVWISAILALVVLTIISLIILIMLWQKKPR

Synthetic: Vectofusin
(SEQ ID NO: 130)
KKALLHAALAHLLALAHHLLALLKKA

Synthetic: Vectofusin-Transmembrane
(SEQ ID NO: 131)
KKALLHAALAHLLALAHHLLALLKKANAVGQDTQEVIVVPHSLPFKW

VISAILALVVLTIISLIILIMLWQKKPR

Synthetic: Transmembrane Domain
(SEQ ID NO: 132)
NAVGQDTQEVIVVPHSLPFKVWVISAILALVVLTIISLIILIMLWQK

KPR

Lactococcus lactis: Nisin A
(SEQ ID NO: 133)
ITSISLCTPGCKTGALMGCNMKTATCHCSIHVSK

Lactococcus lactis NIZO 22186: Nisin Z
(SEQ ID NO: 134)
ITSISLCTPGCKTGALMGCNMKTATCNCSIHVSK Lactococcus lactis subsp. lactis F10: Nisin F
(SEQ ID NO: 135)
ITSISLCTPGCKTGALMGCNMKTATCNCSVHVSK Lactococcus lactis 61-14: Nisin Q
(SEQ ID NO: 136)
ITSISLCTPGCKTGVLMGCNLKTATCNCSVHVSK Streptococcus hyointestinalis: Nisin H
(SEQ ID NO: 137)
FTSISMCTPGCKTGALMTCNYKTATCHCSIKVSK Streptococcus uberis: Nisin U
(SEQ ID NO: 138)
ITSKSLCTPGCKTGILMTCPLKTATCGCHFG Streptococcus uberis: Nisin U2
(SEQ ID NO: 139)
VTSKSLCTPGCKTGILMTCPLKTATCGCHFG Streptococcus galloyticus subsp. pasteurianus: Nisin P
(SEQ ID NO: 140)
VTSKSLCTPGCKTGILMTCAIKTATCGCHFG L. lactis NZ9800: Nisin A S29A
(SEQ ID NO: 141)
ITSISLCTPGCKTGALMGCNMKTATCHCAIHVSK L. lactis NZ9800: Nisin A S29D
(SEQ ID NO: 142)
ITSISLCTPGCKTGALMGCNMKTATCHCDIHVSK L. lactis NZ9800: Nisin A S29E
(SEQ ID NO: 143)
ITSISLCTPGCKTGALMGCNMKTATCHCEIHVSK L. lactis NZ9800: Nisin A S29G
(SEQ ID NO: 144)
ITSISLCTPGCKTGALMGCNMKTATCHCGIHVSK L. lactis NZ9800: Nisin A K22T
(SEQ ID NO: 145)
ITSISLCTPGCKTGALMGCNMTTATCHCSIHVSK L. lactis NZ9800: Nisin A N20P
(SEQ ID NO: 146)
ITSISLCTPGCKTGALMGCPMKTATCHCSIHVSK L. lactis NZ9800: Nisin A M21V
(SEQ ID NO: 147)
ITSISLCTPGCKTGALMGCNVKTATCHCSIHVSK L. lactis NZ9800: Nisin A K22S
(SEQ ID NO: 148)
ITSISLCTPGCKTGALMGCNMSTATCHCSIHVSK L. lactis NZ9800: Nisin Z N20K
(SEQ ID NO: 149)
ITSISLCTPGCKTGALMGCKMKTATCNCSIHVSK L. lactis NZ9800: Nisin Z M21K
(SEQ ID NO: 150)
ITSISLCTPGCKTGALMGCNKKTATCNCSIHVSK Relevant RNA Sequences (5'-3')

Synthetic: MS2 Stem Loop spCas9 Scaffold RNA for sgRNA with Terminator Example 1
(SEQ ID NO: 151)
GUUUUAGAGCUAGGCCAACAUGAGGAUCACCCAUGUCUGCAGGGCCU

AGCAAGUUAAAAUAAGGCUAGUCCGUUAUCAACUUGGCCAACAUGAG

GAUCACCCAUGUCUGCAGGGCCAAGUGGCACCGAGUCGGUGCUUUUU

UU

Synthetic: MS2 Stem Loop spCas9 Scaffold RNA for sgRNA with Terminator Example 2
(SEQ ID NO: 152)
GUUUUAGAGCUAGGCCAACAUGAGGAUCACCCAUGUCUGCAGGGCCU

AGCAAGUUAAAAUAAGGCUAGUCCGUUAUCAACUUGGCCAACAUGAG

GAUCACCCAUGUCUGCAGGGCCAAGUGGCACCGAGUCGGUGCGGGAG

CACAUGAGGAUCACCCAUGUGCGACUCCCACAGUCACUGGGGAGUCU

UCCCUUUUUUU

Synthetic: MS2 Stem Loop spCas9 Scaffold RNA for sgRNA with Terminator Example 3
(SEQ ID NO: 153)
GUUUAAGAGCUAUGCUGGAAACAGCAUAGCAAGUUUAAAUAAGGCUA

GUCCGUUAUCAACUUGAAAAAGUGGCACCGAGUCGGUGCGGGAGCAC

AUGAGGAUCACCCAUGUGCGACUCCCACAGUCACUGGGGAGUCUUCC

CUUUUUUU

Synthetic: 4xMS2 Stem Loop RNA Scaffold Example
(SEQ ID NO: 154)
UUCUAGAUCAUCGAAACAUGAGGAUCACCCAUAUCUGCAGUCGACAU

CGAAACAUGAGGAUCACCCAUGUCUGCAGUCGACAUCGAAACAUGAG

GAUCACCCAUGUCUGCAGUCGACAUCGAAACAUGAGGAUCACCCAUG

UCUGCAGUCGACAUCGAAAUCGAUAAGCUUCAGAUCAGAUCCUAG

Synthetic: MS2 Stem Loop Example 1
(SEQ ID NO: 155)
ACAUGAGGAUCACCCAUGU

Synthetic: MS2 Stem Loop Example 2
(SEQ ID NO: 156)
ACAUGAGGAUCACCCAUAU

Synthetic: MS2 Stem Loop Example 3
(SEQ ID NO: 157)
CCACAGUCACUGGG

Synthetic: 2xMS2 Stem Loop Example
(SEQ ID NO: 158)
ACAUGAGGAUCACCCAUGUCUGCAGGGCCUAGCAAGUUAAAAUAAGG

CUAGUCCGUUAUCAACUUGGCCAACAUGAGGAUCACCCAUGU

Synthetic: 2xPP7 Stem Loop spCas9 Scaffold RNA for sgRNA with Terminator Example
(SEQ ID NO: 159)
GUUUUAGAGCUAGGCCGGAGCAGACGAUAUGGCGUCGCUCCGGCCUA

GCAAGUUAAAAUAAGGCUAGUCCGUUAUCAACUUGGCCGGAGCAGAC

GAUAUGGCGUCGCUCCGGCCAAGUGGCACCGAGUCGGUGCUUUUUUU

Synthetic: PP7 Stem Loop Example
(SEQ ID NO: 160)
GCCGGAGCAGACGAUAUGGCGUCGCUCCGGCC Synthetic: COM Stem Loop spCas9 Scaffold RNA for sgRNA with Terminator Example
(SEQ ID NO: 161)
GUUUAAGAGCUAUGCUGGAAACAGCAUAGCAAGUUUAAAUAAGGCUA

GUCCGUUAUCAACUUGAAAAAGUGGCACCGAGUCGGUGCCUGAAUGC

CUGCGAGCAUCUUUUUUU

Synthetic: COM Stem Loop Example
(SEQ ID NO: 162)
CUGAAUGCCUGCGAGCAUC

Synthetic ZKSCAN1 Circular Splice RNA: Upstream Intron
(SEQ ID NO: 163)
AGUGACAGUGGAGAUUGUACAGUUUUUUCCUCGAUUUGUCAGGAUUU

UUUUUUUUGACGGAGUUUAACUUCUUGUCUCCCAGGUAGGAAGUGC

AGUGGCGUAAUCUCGGCUCACUACAACCUCCACCUCCUGGGUUCAAG

CGUUUCUCCUGCCUCAGCUUUCCGAGUAGCUGGGAUUACAGGCGCCU

GCCACCAUGCCCUGCUGACUUUUGUAUUUUUAGUAGAGACGGGGUUU

CACCAUGUUGGCCAGGCUGGUCUUGAACUCCUGACCGCAGGCGAUUG

GCCUGCCUCGGCCUCCCAAAGUGCUGAGAUUACAGGCGUGAGCCACC

ACCCCCGGCCUCAGGAGCGUUCUGAUAGUGCCUCGAUGUGCUGCCUC

CUAUAAAGUGUUAGCAGCACAGAUCACUUUUUGUAAAGGUACGUACU

AAUGACUUUUUUUUUAUACUUCAGG

Synthetic ZKSCAN1 Circular Splice RNA: Downstream Intron
(SEQ ID NO: 164)
UAAGAAGCAAGGUUUCAUUUAGGGGAAGGGAAAUGAUUCAGGACGAG

AGUCUUUGUGCUGCUGAGUGCCUGUGAUGAAGAAGCAUGUUAGUCCU

GGGCAACGUAGCGAGACCCCAUCUCUACAAAAAAUAGAAAAAUUAGC

CAGGUAUAGUGGCGCACACCUGUGAUUCCAGCUACGCAGGAGGCUGA

GGUGGGAGGAUUGCUUGAGCCCAGGAGGUUGAGGCUGCAGUGAGCUG

UAAUCAUGCCACUACUCCAACCUGGGCAACACAGCAAGGACCCUGUC

UCAAAGCUACUUACAGAAAAGAAUUAGGCUCGGCACGGUAGCUCAC

ACCUGUAAUCCCAGCACUUUGGGAGGCUGAGGCGGGCAGAUCACUUG

AGGUCAGGAGUUUGAGACCAGCCUGGCCAACAUGGUGAAACCUUGUC

UCUACUAAAAAUAUGAAAAUUAGCCAGGCAUGGUGGCACAUUCCUGU

AAUCCCAGCUACUCGGGAGGCUGAGGCAGGAGAAUCACUUGAACCCA

GGAGGUGGAGGUUGCAGUAAGCCGAGAUCGUACCACUGUGCUCUAGC

CUUGGUGACAGAGCGAGACUGUCUUAAAAAAAAAAAAAAAAAAAAAA

GAAUUAAUUAAAAAUUUAAAAAAAAAUGAAAAAAAGCUGCAUGCUUG

UUUUUUGUUUUUAGUUAUUCUACAUUGUUGUCAUUAUUACCAAAUAU

UGGGGAAAAUACAACUUACAGACCAAUCUCAGGAGUUAAAUGUUACU

ACGAAGGCAAAUGAACUAUGCGUAAUGAACCUGGUAGGCAUUAG

*Homo sapiens* Beta-globin and Immunoglobulin
Heavy Chain Genes: Linear
Splice RNA Intron (SEQ ID NO: 165)
GUAAGUAUCAAGGUUACAAGACAGGUUUAAGGAGACCAAUAGAAACU

GGGCUUGUCGAGACAGAGAAGACUCUUGCGUUUCUGAUAGGCACCUA

UUGGUCUUACUGACAUCCACUUUGCCUUUCUCUCCACAG

Relevant DNA Sequences (5'-3')
Synthetic: Zinc Finger ZF6/10 Binding Site (SEQ ID NO: 166)
GAAGAAGCTGCAGGAGGT Synthetic: Zinc Finger ZF8/7 Binding Site (SEQ ID NO: 167)
GCTGGAGGGGAAGTGGTC Synthetic: Zinc Finger ZF6/10 & ZF8/7
Binding Site (SEQ ID NO: 168)
GAAGAAGCTGCAGGAGGTGCTGGAGGGGAAGTGGTC Synthetic: Zinc Finger ZF6/10 & ZF8/7
Binding Site 8x Repeat Example (SEQ ID NO: 169)
TGAAGAAGCTGCAGGAGGTGCTGGAGGGGAAGTGGTCCGGATCTTGA

AGAAGCTGCAGGAGGTGCTGGAGGGGAAGTGGTCCGGATCTTGAAGA

AGCTGCAGGAGGTGCTGGAGGGGAAGTGGTCCGGATCTTGAAGAAGC

TGCAGGAGGTGCTGGAGGGGAAGTGGTCCGGATCTTGAAGAAGCTGC

AGGAGGTGCTGGAGGGGAAGTGGTCCGGATCTTGAAGAAGCTGCAGG

AGGTGCTGGAGGGGAAGTGGTCCGGATCTTGAAGAAGCTGCAGGAGG

TGCTGGAGGGGAAGTGGTCCGGATCTTGAAGAAGCTGCAGGAGGTGC

TGGAGGGGAAGTGGTCC

Synthetic: Zinc Finger ZF9 Binding Site (SEQ ID NO: 170)
GTAGATGGA

Synthetic: Zinc Finger MK10 Binding Site (SEQ ID NO: 171)
CGGCGTAGCCGATGTCGCGC

Synthetic: Zinc Finger 268 Binding Site (SEQ ID NO: 172)
AAGGGTTCA

Synthetic: Zinc Finger NRE Binding Site (SEQ ID NO: 173)
GCGTGGGCG

Synthetic: Zinc Finger 268/NRE or
268//NRE Binding Site Example 1

(SEQ ID NO: 174)
AAGGGTTCAGCGTGGGCG

Synthetic: Zinc Finger 268/NRE or
268//NRE Binding Site Example 2

(SEQ ID NO: 175)
AAGGGTTCAGGCGTGGGCG

Synthetic: Zinc Finger 268/NRE or
268//NRE Binding Site Example 3

(SEQ ID NO: 176)
AAGGGTTCAGTGCGTGGGCG

Synthetic: FokI Zinc Finger Nuclease
17-2 & 18-2 Binding Site in GFP (SEQ ID NO: 177)
GATCCGCCACAACATCGAGGACGGCA Human codon optimized *Streptococcus pyogenes*
Cas9 (spCas9) NLS (SEQ ID NO: 178)
ATGGACAAGAAGTACAGCATCGGCCTGGACATCGGC

ACCAACTCTGTGGGCTGGGC

CGTGATCACCGACGAGTACAAGGTGCCCAGCAAGAAATTCA

AGGTGCTGGGCAACACCGACCGGCACAGCATCAAGAAGAACCTGATC

GGAGCCCTGCTGTTCGACAGCGGCGAAACAGCCGAGGCCACCCGGCT

GAAGAGAACCGCCAGAAGAAGATACACCAGACGGAAGAACCGGATCT

GCTATCTGCAAGAGATCTTCAGCAACGAGATGGCCAAGGTGGACGAC

AGCTTCTTCCACAGACTGGAAGAGTCCTTCCTGGTGGAAGAGGATAA

GAAGCACGAGCGGCACCCCATCTTCGGCAACATCGTGGACGAGGTGG

CCTACCACGAGAAGTACCCCACCATCTACCACCTGAGAAAGAAACTG

GTGGACAGCACCGACAAGGCCGACCTGCGGCTGATCTATCTGGCCCT

GGCCCACATGATCAAGTTCCGGGGCCACTTCCTGATCGAGGGCGACC

TGAACCCCGACAACAGCGACGTGGACAAGCTGTTCATCCAGCTGGTG

CAGACCTACAACCAGCTGTTCGAGGAAAACCCCATCAACGCCAGCGG

CGTGGACGCCAAGGCCATCCTGTCTGCCAGACTGAGCAAGAGCAGAC

GGCTGGAAAATCTGATCGCCCAGCTGCCCGGCGAGAAGAAGAATGGC

CTGTTCGGAAACCTGATTGCCCTGAGCCTGGGCCTGACCCCCAACTT

CAAGAGCAACTTCGACCTGGCCGAGGATGCCAAACTGCAGCTGAGCA

AGGACACCTACGACGACGACCTGGACAACCTGCTGGCCCAGATCGGC

GACCAGTACGCCGACCTGTTTCTGGCCGCCAAGAACCTGTCCGACGC

CATCCTGCTGAGCGACATCCTGAGAGTGAACACCGAGATCACCAAGG

CCCCCCTGAGCGCCTCTATGATCAAGAGATACGACGAGCACCACCAG

GACCTGACCCTGCTGAAAGCTCTCGTGCGGCAGCAGCTGCCTGAGAA

GTACAAAGAGATTTTCTTCGACCAGAGCAAGAACGGCTACGCCGGCT

ACATTGACGGCGGAGCCAGCCAGGAAGAGTTCTACAAGTTCATCAAG

CCCATCCTGGAAAAGATGGACGGCACCGAGGAACTGCTCGTGAAGCT

GAACAGAGAGGACCTGCTGCGGAAGCAGCGGACCTTCGACAACGGCA

GCATCCCCCACCAGATCCACCTGGGAGAGCTGCACGCCATTCTGCGG

CGGCAGGAAGATTTTTACCCATTCCTGAAGGACAACCGGGAAAAGAT

CGAGAAGATCCTGACCTTCCGCATCCCCTACTACGTGGGCCCTCTGG

CCAGGGGAAACAGCAGATTCGCCTGGATGACCAGAAAGAGCGAGGAA

ACCATCACCCCCTGGAACTTCGAGGAAGTGGTGGACAAGGGCGCTTC

CGCCCAGAGCTTCATCGAGCGGATGACCAACTTCGATAAGAACCTGC

CCAACGAGAAGGTGCTGCCCAAGCACAGCCTGCTGTACGAGTACTTC

ACCGTGTATAACGAGCTGACCAAAGTGAAATACGTGACCGAGGGAAT

GAGAAAGCCCGCCTTCCTGAGCGGCGAGCAGAAAAAGGCCATCGTGG

ACCTGCTGTTCAAGACCAACCGGAAAGTGACCGTGAAGCAGCTGAAA

GAGGACTACTTCAAGAAAATCGAGTGCTTCGACTCCGTGGAAATCTC

CGGCGTGGAAGATCGGTTCAACGCCTCCCTGGGCACATACCACGATC

TGCTGAAAATTATCAAGGACAAGGACTTCCTGGACAATGAGGAAAAC

```
GAGGACATTCTGGAAGATATCGTGCTGACCCTGACACTGTTTGAGGA
CAGAGAGATGATCGAGGAACGGCTGAAAACCTATGCCCACCTGTTCG
ACGACAAAGTGATGAAGCAGCTGAAGCGGCGGAGATACACCGGCTGG
GGCAGGCTGAGCCGGAAGCTGATCAACGGCATCCGGGACAAGCAGTC
CGGCAAGACAATCCTGGATTTCCTGAAGTCCGACGGCTTCGCCAACA
GAAACTTCATGCAGCTGATCCACGACGACAGCCTGACCTTTAAAGAG
GACATCCAGAAAGCCCAGGTGTCCGGCCAGGGCGATAGCCTGCACGA
GCACATTGCCAATCTGGCCGGCAGCCCCGCCATTAAGAAGGGCATCC
TGCAGACAGTGAAGGTGGTGGACGAGCTCGTGAAAGTGATGGGCCGG
CACAAGCCCGAGAACATCGTGATCGAAATGGCCAGAGAGAACCAGAC
CACCCAGAAGGGACAGAAGAACAGCCGCGAGAGAATGAAGCGGATCG
AAGAGGGCATCAAAGAGCTGGCAGCCAGATCCTGAAAGAACACCCC
GTGGAAAACACCCAGCTGCAGAACGAGAAGCTGTACCTGTACTACCT
GCAGAATGGCCGGGATATGTACGTGGACCAGGAACTGGACATCAACC
GGCTGTCCGACTACGATGTGGACCATATCGTGCCTCAGAGCTTTCTG
AAGGACGACTCCATCGACAACAAGGTGCTGACCAGAAGCGACAAGAA
CCGGGGCAAGAGCGACAACGTGCCCTCCGAAGAGGTCGTGAAGAAGA
TGAAGAACTACTGGCGGCAGCTGCTGAACGCCAAGCTGATTACCCAG
AGAAAGTTCGACAATCTGACCAAGGCCGAGAGAGGCGGCCTGAGCGA
ACTGGATAAGGCCGGCTTCATCAAGAGACAGCTGGTGGAAACCCGGC
AGATCACAAAGCACGTGGCACAGATCCTGGACTCCCGGATGAACACT
AAGTACGACGAGAATGACAAGCTGATCCGGGAAGTGAAAGTGATCAC
CCTGAAGTCCAAGCTGGTGTCCGATTTCCGGAAGGATTTCCAGTTTT
ACAAAGTGCGCGAGATCAACAACTACCACCACGCCCACGACGCCTAC
CTGAACGCCGTCGTGGGAACCGCCCTGATCAAAAAGTACCCTAAGCT
GGAAAGCGAGTTCGTGTACGGCGACTACAAGGTGTACGACGTGCGGA
AGATGATCGCCAAGAGCGAGCAGGAAATCGGCAAGGCTACCGCCAAG
TACTTCTTCTACAGCAACATCATGAACTTTTTCAAGACCGAGATTAC
CCTGGCCAACGGCGAGATCCGGAAGCGGCCTCTGATCGAGACAAACG
GCGAAACCGGGGAGATCGTGTGGGATAAGGGCCGGGATTTTGCCACC
GTGCGGAAAGTGCTGAGCATGCCCCAAGTGAATATCGTGAAAAAGAC
CGAGGTGCAGACAGGCGGCTTCAGCAAAGAGTCTATCCTGCCCAAGA
GGAACAGCGATAAGCTGATCGCCAGAAAGAAGGACTGGGACCCTAAG
AAGTACGGCGGCTTCGACAGCCCCACCGTGGCCTATTCTGTGCTGGT
GGTGGCCAAAGTGGAAAAGGGCAAGTCCAAGAAACTGAAGAGTGTGA
AAGAGCTGCTGGGGATCACCATCATGGAAAGAAGCAGCTTCGAGAAG
AATCCCATCGACTTTCTGGAAGCCAAGGGCTACAAAGAAGTAAAAA
GGACCTGATCATCAAGCTGCCTAAGTACTCCCTGTTCGAGCTGGAAA
ACGGCCGGAAGAGAATGCTGGCCTCTGCCGGCGAACTGCAGAAGGGA
AACGAACTGGCCCTGCCCTCCAAATATGTGAACTTCCTGTACCTGGC
```

```
CAGCCACTATGAGAAGCTGAAGGGCTCCCCCGAGGATAATGAGCAGA
AACAGCTGTTTGTGGAACAGCACAAGCACTACCTGGACGAGATCATC
GAGCAGATCAGCGAGTTCTCCAAGAGAGTGATCCTGGCCGACGCTAA
TCTGGACAAAGTGCTGTCCGCCTACAACAAGCACCGGGATAAGCCCA
TCAGAGAGCAGGCCGAGAATATCATCCACCTGTTTACCCTGACCAAT
CTGGGAGCCCCTGCCGCCTTCAAGTACTTTGACACCACCATCGACCG
GAAGAGGTACACCAGCACCAAAGAGGTGCTGGACGCCACCCTGATCC
ACCAGAGCATCACCGGCCTGTACGAGACACGGATCGACCTGTCTCAG
CTGGGAGGCGACGGATCCCCCAAGAAGAAGAGGAAAGTCTCGAGCGA
CTACAAAGACCATGACGGTGATTATAAAGATCATGACATCGATTACA
AGGATGACGATGACAAGGCTGCAGGATGA
```

Human codon optimized *Streptococcus pyogenes*
Cas9 (spCas9) Bipartite (BP) NLS
(SEQ ID NO: 179)

```
ATGGACAAGAAGTACAGCATCGGCCTGGACATCGGCACCAACTCTGT
GGGCTGGGCCGTGATCACCGACGAGTACAAGGTGCCCAGCAAGAAAT
TCAAGGTGCTGGGCAACACCGACCGGCACAGCATCAAGAAGAACCTG
ATCGGAGCCCTGCTGTTCGACAGCGGCGAAACAGCCGAGGCCACCCG
GCTGAAGAGAACCGCCAGAAGAAGATACACCAGACGGAAGAACCGGA
TCTGCTATCTGCAAGAGATCTTCAGCAACGAGATGGCCAAGGTGGAC
GACAGCTTCTTCCACAGACTGGAAGAGTCCTTCCTGGTGGAAGAGGA
TAAGAAGCACGAGCGGCACCCCATCTTCGGCAACATCGTGGACGAGG
TGGCCTACCACGAGAAGTACCCCACCATCTACCACCTGAGAAAGAAA
CTGGTGGACAGCACCGACAAGGCCGACCTGCGGCTGATCTATCTGGC
CCTGGCCCACATGATCAAGTTCCGGGGCCACTTCCTGATCGAGGGCG
ACCTGAACCCCGACAACAGCGACGTGGACAAGCTGTTCATCCAGCTG
GTGCAGACCTACAACCAGCTGTTCGAGGAAAACCCCATCAACGCCAG
CGGCGTGGACGCCAAGGCCATCCTGTCTGCCAGACTGAGCAAGAGCA
GACGGCTGGAAAATCTGATCGCCCAGCTGCCCGGCGAGAAGAAGAAT
GGCCTGTTCGGAAACCTGATTGCCCTGAGCCTGGGCCTGACCCCCAA
CTTCAAGAGCAACTTCGACCTGGCCGAGGATGCCAAACTGCAGCTGA
GCAAGGACACCTACGACGACGACCTGGACAACCTGCTGGCCCAGATC
GGCGACCAGTACGCCGACCTGTTTCTGGCCGCCAAGAACCTGTCCGA
CGCCATCCTGCTGAGCGACATCCTGAGAGTGAACACCGAGATCACCA
AGGCCCCCCTGAGCGCCTCTATGATCAAGAGATACGACGAGCACCAC
CAGGACCTGACCCTGCTGAAAGCTCTCGTGCGGCAGCAGCTGCCTGA
GAAGTACAAAGAGATTTTCTTCGACCAGAGCAAGAACGGCTACGCCG
GCTACATTGACGGCGGAGCCAGCCAGGAAGAGTTCTACAAGTTCATC
AAGCCCATCCTGGAAAAGATGGACGGCACCGAGGAACTGCTCGTGAA
GCTGAACAGAGAGGACCTGCTGCGGAAGCAGCGGACCTTCGACAACG
GCAGCATCCCCCACCAGATCCACCTGGGAGAGCTGCACGCCATTCTG
CGGCGGCAGGAAGATTTTTACCCATTCCTGAAGGACAACCGGGAAAA
```

```
GATCGAGAAGATCCTGACCTTCCGCATCCCCTACTACGTGGGCCCTC
TGGCCAGGGGAAACAGCCAGATTCGCCTGGATGACCAGAAAGAGCGAG
GAAACCATCACCCCCTGGAACTTCGAGGAAGTGGTGGACAAGGGCGC
TTCCGCCCAGAGCTTCATCGAGCGGATGACCAACTTCGATAAGAACC
TGCCCAACGAGAAGGTGCTGCCCAAGCACAGCCTGCTGTACGAGTAC
TTCACCGTGTATAACGAGCTGACCAAAGTGAAATACGTGACCGAGGG
AATGAGAAAGCCCGCCTTCCTGAGCGGCGAGCAGAAAAAGGCCATCG
TGGACCTGCTGTTCAAGACCAACCGGAAAGTGACCGTGAAGCAGCTG
AAAGAGGACTACTTCAAGAAAATCGAGTGCTTCGACTCCGTGGAAAT
CTCCGGCGTGGAAGATCGGTTCAACGCCTCCCTGGGCACATACCACG
ATCTGCTGAAAATTATCAAGGACAAGGACTTCCTGGACAATGAGGAA
AACGAGGACATTCTGGAAGATATCGTGCTGACCCTGACACTGTTTGA
GGACAGAGAGATGATCGAGGAACGGCTGAAAACCTATGCCCACCTGT
TCGACGACAAAGTGATGAAGCAGCTGAAGCGGCGGAGATACACCGGC
TGGGGCAGGCTGAGCCGGAAGCTGATCAACGGCATCCGGGACAAGCA
GTCCGGCAAGACAATCCTGGATTTCCTGAAGTCCGACGGCTTCGCCA
ACAGAAACTTCATGCAGCTGATCCACGACGACAGCCTGACCTTTAAA
GAGGACATCCAGAAAGCCCAGGTGTCCGGCCAGGGCGATAGCCTGCA
CGAGCACATTGCCAATCTGGCCGGCAGCCCCGCCATTAAGAAGGGCA
TCCTGCAGACAGTGAAGGTGGTGGACGAGCTCGTGAAAGTGATGGGC
CGGCACAAGCCCGAGAACATCGTGATCGAAATGGCCAGAGAGAACCA
GACCACCCAGAAGGGACAGAAGAACAGCCGCGAGAGAATGAAGCGGA
TCGAAGAGGGCATCAAAGAGCTGGGCAGCCAGATCCTGAAAGAACAC
CCCGTGGAAAACACCCAGCTGCAGAACGAGAAGCTGTACCTGTACTA
CCTGCAGAATGGGCGGGATATGTACGTGGACCAGGAACTGGACATCA
ACCGGCTGTCCGACTACGATGTGGACCATATCGTGCCTCAGAGCTTT
CTGAAGGACGACTCCATCGACAACAAGGTGCTGACCAGAAGCGACAA
GAACCGGGGCAAGAGCGACAACGTGCCCTCCGAAGAGGTCGTGAAGA
AGATGAAGAACTACTGGCGGCAGCTGCTGAACGCCAAGCTGATTACC
CAGAGAAAGTTCGACAATCTGACCAAGGCCGAGAGAGGCGGCCTGAG
CGAACTGGATAAGGCCGGCTTCATCAAGAGACAGCTGGTGGAAACCC
GGCAGATCACAAAGCACGTGGCACAGATCCTGGACTCCCGGATGAAC
ACTAAGTACGACGAGAATGACAAGCTGATCCGGGAAGTGAAAGTGAT
CACCCTGAAGTCCAAGCTGGTGTCCGATTTCCGGAAGGATTTCCAGT
TTTACAAAGTGCGCGAGATCAACAACTACCACCACGCCCACGACGCC
TACCTGAACGCCGTCGTGGGAACCGCCCTGATCAAAAAGTACCCTAA
GCTGGAAAGCGAGTTCGTGTACGGCGACTACAAGGTGTACGACGTGC
GGAAGATGATCGCCAAGAGCGAGCAGGAAATCGGCAAGGCTACCGCC
AAGTACTTCTTCTACAGCAACATCATGAACTTTTTCAAGACCGAGAT
TACCCTGGCCAACGGCGAGATCCGGAAGCGGCCTCTGATCGAGACAA
ACGGCGAAACCGGGGAGATCGTGTGGGATAAGGGCCGGGATTTTGCC
ACCGTGCGGAAAGTGCTGAGCATGCCCCAAGTGAATATCGTGAAAAA
GACCGAGGTGCAGACAGGCGGCTTCAGCAAAGAGTCTATCCTGCCCA
AGAGGAACAGCGATAAGCTGATCGCCAGAAAGAAGGACTGGGACCCT
AAGAAGTACGGCGGCTTCGACAGCCCCACCGTGGCCTATTCTGTGCT
GGTGGTGGCCAAAGTGGAAAAGGGCAAGTCCAAGAAACTGAAGAGTG
TGAAAGAGCTGCTGGGGATCACCATCATGGAAAGAAGCAGCTTCGAG
AAGAATCCCATCGACTTTCTGGAAGCCAAGGGCTACAAAGAAGTGAA
AAAGGACCTGATCATCAAGCTGCCTAAGTACTCCCTGTTCGAGCTGG
AAAACGGCCGGAAGAGAATGCTGGCCTCTGCCGGCGAACTGCAGAAG
GGAAACGAACTGGCCCTGCCCTCCAAATATGTGAACTTCCTGTACCT
GGCCAGCCACTATGAGAAGCTGAAGGGCTCCCCCGAGGATAATGAGC
AGAAACAGCTGTTTGTGGAACAGCACAAGCACTACCTGGACGAGATC
ATCGAGCAGATCAGCGAGTTCTCCAAGAGAGTGATCCTGGCCGACGC
TAATCTGGACAAAGTGCTGTCCGCCTACAACAAGCACCGGGATAAGC
CCATCAGAGAGCAGGCCGAGAATATCATCCACCTGTTTACCCTGACC
AATCTGGGAGCCCCTGCCGCCTTCAAGTACTTTGACACCACCATCGA
CCGGAAGAGGTACACCAGCACCAAAGAGGTGCTGGACGCCACCCTGA
TCCACCAGAGCATCACCGGCCTGTACGAGACACGGATCGACCTGTCT
CAGCTGGGAGGCGACGGATCCGGCGGAGGCGGAAGCGGGAAAAGAAC
CGCCGACGGCAGCGAATTCGAGCCCAAGAAGAAGAGGAAAGTCTCGA
GCGGAGGCGACTACAAAGACCATGACGGTGATTATAAAGATCATGAC
ATCGATTACAAGGATGACGATGACAAGTGA
Human codon optimized Streptococcus pyogenes
Cas9 (spCas9) BE4
                                    (SEQ ID NO: 180)
ATGAAACGGACAGCCGACGGAAGCGAGTTCGAGTCACCAAAGAAGAA
GCGGAAAGTCTCCTCAGAGACTGGGCCTGTCGCCGTCGATCCAACCC
TGCGCCGCCGGATTGAACCTCACGAGTTTGAAGTGTTCTTTGACCCC
CGGGAGCTGAGAAAGGAGACATGCCTGCTGTACGAGATCAACTGGGG
AGGCAGGCACTCCATCTGGAGGCACACCTCTCAGAACACAAATAAGC
ACGTGGAGGTGAACTTCATCGAGAAGTTTACCACAGAGCGGTACTTC
TGCCCCAATACCAGATGTAGCATCACATGGTTTCTGAGCTGGTCCCC
TTGCGGAGAGTGTAGCAGGGCCATCACCGAGTTCCTGTCCAGATATC
CACACGTGACACTGTTTATCTACATCGCCAGGCTGTATCACCACGCA
GACCCAAGGAATAGGCAGGGCCTGCGCGATCTGATCAGCTCCGGCGT
GACCATCCAGATCATGACAGAGCAGGAGTCCGGCTACTGCTGGCGGA
ACTTCGTGAATTATTCTCCTAGCAACGAGGCCCACTGGCCTAGGTAC
CCACACCTGTGGGTGCGCCTGTACGTGCTGGAGCTGTATTGCATCAT
CCTGGGCCTGCCCCCTTGTCTGAATATCCTGCGGAGAAAGCAGCCCC
AGCTGACCTTCTTTACAATCGCCCTGCAGTCTTGTCACTATCAGAGG
CTGCCACCCCACATCCTGTGGGCCACAGGCCTGAAGTCTGGAGGATC
TAGCGGAGGATCCTCTGGCAGCGAGACACCAGGAACAAGCGAGTCAG
```

-continued

CAACACCAGAGAGCAGTGGCGGCAGCAGCGGCGGCAGCGACAAGAAG

TACAGCATCGGCCTGGACATCGGCACCAACTCTGTGGGCTGGGCCGT

GATCACCGACGAGTACAAGGTGCCCAGCAAGAAATTCAAGGTGCTGG

GCAACACCGACCGGCACAGCATCAAGAAGAACCTGATCGGAGCCCTG

CTGTTCGACAGCGGCGAAACAGCCGAGGCCACCCGGCTGAAGAGAAC

CGCCAGAAGAAGATACACCAGACGGAAGAACCGGATCTGCTATCTGC

AAGAGATCTTCAGCAACGAGATGGCCAAGGTGGACGACAGCTTCTTC

CACAGACTGGAAGAGTCCTTCCTGGTGGAAGAGGATAAGAAGCACGA

GCGGCACCCCATCTTCGGCAACATCGTGGACGAGGTGGCCTACCACG

AGAAGTACCCCACCATCTACCACCTGAGAAAGAAACTGGTGGACAGC

ACCGACAAGGCCGACCTGCGGCTGATCTATCTGGCCCTGGCCCACAT

GATCAAGTTCCGGGGCCACTTCCTGATCGAGGGCGACCTGAACCCCG

ACAACAGCGACGTGGACAAGCTGTTCATCCAGCTGGTGCAGACCTAC

AACCAGCTGTTCGAGGAAAACCCCATCAACGCCAGCGGCGTGGACGC

CAAGGCCATCCTGTCTGCCAGACTGAGCAAGAGCAGACGGCTGGAAA

ATCTGATCGCCCAGCTGCCCGGCGAGAAGAAGAATGGCCTGTTCGGA

AACCTGATTGCCCTGAGCCTGGGCCTGACCCCCAACTTCAAGAGCAA

CTTCGACCTGGCCGAGGATGCCAAACTGCAGCTGAGCAAGGACACCT

ACGACGACGACCTGGACAACCTGCTGGCCCAGATCGGCGACCAGTAC

GCCGACCTGTTTCTGGCCGCCAAGAACCTGTCCGACGCCATCCTGCT

GAGCGACATCCTGAGAGTGAACACCGAGATCACCAAGGCCCCCCTGA

GCGCCTCTATGATCAAGAGATACGACGAGCACCACCAGGACCTGACC

CTGCTGAAAGCTCTCGTGCGGCAGCAGCTGCCTGAGAAGTACAAAGA

GATTTTCTTCGACCAGAGCAAGAACGGCTACGCCGGCTACATTGACG

GCGGAGCCAGCCAGGAAGAGTTCTACAAGTTCATCAAGCCCATCCTG

GAAAAGATGGACGGCACCGAGGAACTGCTCGTGAAGCTGAACAGAGA

GGACCTGCTGCGGAAGCAGCGGACCTTCGACAACGGCAGCATCCCCC

ACCAGATCCACCTGGGAGAGCTGCACGCCATTCTGCGCGGCGGAGGAA

GATTTTTACCCATTCCTGAAGGACAACCGGGAAAAGATCGAGAAGAT

CCTGACCTTCCGCATCCCCTACTACGTGGGCCCTCTGGCCAGGGGAA

ACAGCAGATTCGCCTGGATGACCAGAAAGAGCGAGGAAACCATCACC

CCCTGGAACTTCGAGGAAGTGGTGGACAAGGGCGCTTCCGCCCAGAG

CTTCATCGAGCGGATGACCAACTTCGATAAGAACCTGCCCAACGAGA

AGGTGCTGCCCAAGCACAGCCTGCTGTACGAGTACTTCACCGTGTAT

AACGAGCTGACCAAAGTGAAATACGTGACCGAGGGAATGAGAAAGCC

CGCCTTCCTGAGCGGCGAGCAGAAAAAGGCCATCGTGGACCTGCTGT

TCAAGACCAACCGGAAAGTGACCGTGAAGCAGCTGAAAGAGGACTAC

TTCAAGAAAATCGAGTGCTTCGACTCCGTGGAAATCTCCGGCGTGGA

AGATCGGTTCAACGCCTCCCTGGGCACATACCACGATCTGCTGAAAA

TTATCAAGGACAAGGACTTCCTGGACAATGAGGAAAACGAGGACATT

-continued

CTGGAAGATATCGTGCTGACCCTGACACTGTTTGAGGACAGAGAGAT

GATCGAGGAACGGCTGAAAACCTATGCCCACCTGTTCGACGACAAAG

TGATGAAGCAGCTGAAGCGGCGGAGATACACCGGCTGGGGCAGGCTG

AGCCGGAAGCTGATCAACGGCATCCGGGACAAGCAGTCCGGCAAGAC

AATCCTGGATTTCCTGAAGTCCGACGGCTTCGCCAACAGAAACTTCA

TGCAGCTGATCCACGACGACAGCCTGACCTTTAAAGAGGACATCCAG

AAAGCCCAGGTGTCCGGCCAGGGCGATAGCCTGCACGAGCACATTGC

CAATCTGGCCGGCAGCCCCGCCATTAAGAAGGGCATCCTGCAGACAG

TGAAGGTGGTGGACGAGCTCGTGAAAGTGATGGGCCGGCACAAGCCC

GAGAACATCGTGATCGAAATGGCCAGAGAGAACCAGACCACCCAGAA

GGGACAGAAGAACAGCCGCGAGAGAATGAAGCGGATCGAAGAGGGCA

TCAAAGAGCTGGGCAGCCAGATCCTGAAAGAACACCCCGTGGAAAAC

ACCCAGCTGCAGAACGAGAAGCTGTACCTGTACTACCTGCAGAATGG

GCGGGATATGTACGTGGACCAGGAACTGGACATCAACCGGCTGTCCG

ACTACGATGTGGACCATATCGTGCCTCAGAGCTTTCTGAAGGACGAC

TCCATCGACAACAAGGTGCTGACCAGAAGCGACAAGAACCGGGGCAA

GAGCGACAACGTGCCCTCCGAAGAGGTCGTGAAGAAGATGAAGAACT

ACTGGCGGCAGCTGCTGAACGCCAAGCTGATTACCCAGAGAAAGTTC

GACAATCTGACCAAGGCCGAGAGAGGCGGCCTGAGCGAACTGGATAA

GGCCGGCTTCATCAAGAGACAGCTGGTGGAAACCCGGCAGATCACAA

AGCACGTGGCACAGATCCTGGACTCCCGGATGAACACTAAGTACGAC

GAGAATGACAAGCTGATCCGGGAAGTGAAAGTGATCACCCTGAAGTC

CAAGCTGGTGTCCGATTTCCGGAAGGATTTCCAGTTTTACAAAGTGC

GCGAGATCAACAACTACCACCACGCCCACGACGCCTACCTGAACGCC

GTCGTGGGAACCGCCCTGATCAAAAAGTACCCTAAGCTGGAAAGCGA

GTTCGTGTACGGCGACTACAAGGTGTACGACGTGCGGAAGATGATCG

CCAAGAGCGAGCAGGAAATCGGCAAGGCTACCGCCAAGTACTTCTTC

TACAGCAACATCATGAACTTTTTCAAGACCGAGATTACCCTGGCCAA

CGGCGAGATCCGGAAGCGGCCTCTGATCGAGACAAACGGCGAAACCG

GGGAGATCGTGTGGGATAAGGGCCGGGATTTTGCCACCGTGCGGAAA

GTGCTGAGCATGCCCCAAGTGAATATCGTGAAAAAGACCGAGGTGCA

GACAGGCGGCTTCAGCAAAGAGTCTATCCTGCCCAAGAGGAACAGCG

ATAAGCTGATCGCCAGAAAGAAGGACTGGGACCCTAAGAAGTACGGC

GGCTTCGACAGCCCCACCGTGGCCTATTCTGTGCTGGTGGTGGCCAA

AGTGGAAAAGGGCAAGTCCAAGAAACTGAAGAGTGTGAAAGAGCTGC

TGGGGATCACCATCATGGAAAGAAGCAGCTTCGAGAAGAATCCCATC

GACTTTCTGGAAGCCAAGGGCTACAAAGAAGTGAAAAAGGACCTGAT

CATCAAGCTGCCTAAGTACTCCCTGTTCGAGCTGGAAAACGGCCGGA

AGAGAATGCTGGCCTCTGCCGGCGAACTGCAGAAGGGAAACGAACTG

GCCCTGCCCTCCAAATATGTGAACTTCCTGTACCTGGCCAGCCACTA

TGAGAAGCTGAAGGGCTCCCCCGAGGATAATGAGCAGAAACAGCTGT

TTGTGGAACAGCACAAGCACTACCTGGACGAGATCATCGAGCAGATC
AGCGAGTTCTCCAAGAGAGTGATCCTGGCCGACGCTAATCTGGACAA
AGTGCTGTCCGCCTACAACAAGCACCGGGATAAGCCCATCAGAGAGC
AGGCCGAGAATATCATCCACCTGTTTACCCTGACCAATCTGGGAGCC
CCTGCCGCCTTCAAGTACTTTGACACCACCATCGACCGGAAGAGGTA
CACCAGCACCAAAGAGGTGCTGGACGCCACCCTGATCCACCAGAGCA
TCACCGGCCTGTACGAGACACGGATCGACCTGTCTCAGCTGGGAGGT
GACAGCGGCGGGAGCGGCGGGAGCGGGGGGAGCACTAATCTGAGCGA
CATCATTGAGAAGGAGACTGGGAAACAGCTGGTCATTCAGGAGTCCA
TCCTGATGCTGCCTGAGGAGGTGGAGGAAGTGATCGGCAACAAGCCA
GAGTCTGACATCCTGGTGCACACCGCCTACGACGAGTCCACAGATGA
GAATGTGATGCTGCTGACCTCTGACGCCCCCGAGTATAAGCCTTGGG
CCCTGGTCATCCAGGATTCTAACGGCGAGAATAAGATCAAGATGCTG
AGCGGAGGATCCGGAGGATCTGGAGGCAGCACCAACCTGTCTGACAT
CATCGAGAAGGAGACAGGCAAGCAGCTGGTCATCCAGGAGAGCATCC
TGATGCTGCCCGAAGAAGTCGAAGAAGTGATCGGAAACAAGCCTGAG
AGCGATATCCTGGTCCATACCGCCTACGACGAGAGTACCGACGAAAA
TGTGATGCTGCTGACATCCGACGCCCCAGAGTATAAGCCCTGGGCTC
TGGTCATCCAGGATTCCAACGGAGAGAACAAAATCAAAATGCTGTCT
GGCGGCTCAAAAAGAACCGCCGACGGCAGCGAATTCGAGCCCAAGAA
GAAGAGGAAAGTCTAA

Human codon optimized *Streptococcus pyogenes*
Cas9 (spCas9) ABE (SEQ ID NO: 181)
ATGAAACGGACAGCCGACGGAAGCGAGTTCGAGTCACCAAAGAAGAAGC
GGAAAGTCTCTGAAGTCGAGTTTAGCCACGAGTATTGGATGAGGCACG
CACTGACCCTGGCAAAGCGAGCATGGGATGAAAGAGAAGTCCCCGTG
GGCGCCGTGCTGGTGCACAACAATAGAGTGATCGGAGAGGGATGGAA
CAGGCCAATCGGCCGCCACGACCCTACCGCACACGCAGAGATCATGG
CACTGAGGCAGGGAGGCCTGGTCATGCAGAATTACCGCCTGATCGAT
GCCACCCTGTATGTGACACTGGAGCCATGCGTGATGTGCGCAGGAGC
AATGATCCACAGCAGGATCGGAAGAGTGGTGTTCGGAGCACGGGACG
CCAAGACCGGCGCAGCAGGCTCCCTGATGGATGTGCTGCACCACCCC
GGCATGAACCACCGGGTGGAGATCACAGAGGGAATCCTGGCAGACGA
GTGCGCCGCCCTGCTGAGCGATTTCTTTAGAATGCGGAGACAGGAGA
TCAAGGCCCAGAAGAAGGCACAGAGCTCCACCGACTCTGGAGGATCT
AGCGGAGGATCCTCTGGAAGCGAGACACCAGGCACAAGCGAGTCCGC
CACACCAGAGAGCTCCGGCGGCTCCTCCGGAGGATCCTCTGAGGTGG
AGTTTTCCCACGAGTACTGGATGAGACATGCCCTGACCCTGGCCAAG
AGGGCACGCGATGAGAGGGAGGTGCCTGTGGGAGCCGTGCTGGTGCT
GAACAATAGAGTGATCGGCGAGGGCTGGAACAGAGCCATCGGCCTGC
ACGACCCAACAGCCCATGCCGAAATTATGGCCCTGAGACAGGGCGGC CTGGTCATGCAGAACTACAGACTGATTGACGCCACCCTGTACGTGAC
ATTCGAGCCTTGCGTGATGTGCGCCGGCGCCATGATCCACTCTAGGA
TCGGCCGCGTGGTGTTTGGCGTGAGGAACGCAAAAACCGGCGCCGCA
GGCTCCCTGATGGACGTGCTGCACTACCCCGGCATGAATCACCGCGT
CGAAATTACCGAGGGAATCCTGGCAGATGAATGTGCCGCCCTGCTGT
GCTATTTCTTTCGGATGCCTAGACAGGTGTTCAATGCTCAGAAGAAG
GCCCAGAGCTCCACCGACTCCGGAGGATCTAGCGGAGGCTCCTCTGG
CTCTGAGACACCTGGCACAAGCGAGAGCGCAACACCTGAAAGCAGCG
GGGGCAGCAGCGGGGGGTCAGACAAGAAGTACAGCATCGGCCTGGCC
ATCGGCACCAACTCTGTGGGCTGGGCCGTGATCACCGACGAGTACAA
GGTGCCCAGCAAGAAATTCAAGGTGCTGGGCAACACCGACCGGCACA
GCATCAAGAAGAACCTGATCGGAGCCCTGCTGTTCGACAGCGGCGAA
ACAGCCGAGGCCACCCGGCTGAAGAGAACCGCCAGAAGAAGATACAC
CAGAAGGAAGAACCGGATCTGCTATCTGCAAGAGATCTTCAGCAACG
AGATGGCCAAGGTGGACGACAGCTTCTTCCACAGACTGGAAGAGTCC
TTCCTGGTGGAAGAGGATAAGAAGCACGAGCGGCACCCCATCTTCGG
CAACATCGTGGACGAGGTGGCCTACCACGAGAAGTACCCCACCATCT
ACCACCTGAGAAAGAAACTGGTGGACAGCACCGACAAGGCCGACCTG
CGGCTGATCTATCTGGCCCTGGCCCACATGATCAAGTTCCGGGGCCA
CTTCCTGATCGAGGGCGACCTGAACCCCGACAACAGCGACGTGGACA
AGCTGTTCATCCAGCTGGTGCAGACCTACAACCAGCTGTTCGAGGAA
AACCCCATCAACGCCAGCGGCGTGGACGCCAAGGCCATCCTGTCTGC
CAGACTGAGCAAGAGCAGACGGCTGGAAAATCTGATCGCCCAGCTGC
CCGGCGAGAAGAAGAATGGCCTGTTCGGAAACCTGATTGCCCTGAGC
CTGGGCCTGACCCCCAACTTCAAGAGCAACTTCGACCTGGCCGAGGA
TGCCAAACTGCAGCTGAGCAAGGACACCTACGACGACGACCTGGACA
ACCTGCTGGCCCAGATCGGCGACCAGTACGCCGACCTGTTTCTGGCC
GCCAAGAACCTGTCCGACGCCATCCTGCTGAGCGACATCCTGAGAGT
GAACACCGAGATCACCAAGGCCCCCCTGAGCGCCTCTATGATCAAGA
GATACGACGAGCACCACCAGGACCTGACCCTGCTGAAAGCTCTCGTG
CGGCAGCAGCTGCCTGAAAAGTACAAAGAGATTTTCTTCGACCAGAG
CAAGAACGGCTACGCCGGCTACATTGACGGCGGAGCCAGCCAGGAAG
AGTTCTACAAGTTCATCAAGCCCATCCTGGAAAAGATGGACGGCACC
GAGGAACTGCTCGTGAAGCTGAACAGAGAGGACCTGCTGCGGAAGCA
GCGGACCTTCGACAACGGCAGCATCCCCCACCAGATCCACCTGGGAG
AGCTGCACGCCATTCTGCGGCGGCAGGAAGATTTTTACCCATTCCTG
AAGGACAACCGGGAAAAGATCGAGAAGATCCTGACCTTCCGCATCCC
CTACTACGTGGGCCCTCTGGCCAGGGGAAACAGCAGATTCGCCTGGA
TGACCAGAAAGAGCGAGGAAACCATCACCCCCTGGAACTTCGAGGAA
GTGGTGGACAAGGGCGCTTCCGCCCAGAGCTTCATCGAGCGGATGAC CAACTTCGATAAGAACCTGCCCAACGAGAAGGTGCTGCCCAAGCACA
GCCTGCTGTACGAGTACTTCACCGTGTATAACGAGCTGACCAAAGTG
AAATACGTGACCGAGGGAATGAGAAAGCCCGCCTTCCTGAGCGGCGA
GCAGAAAAAGGCCATCGTGGACCTGCTGTTCAAGACCAACCGGAAAG
TGACCGTGAAGCAGCTGAAAGAGGACTACTTCAAGAAAATCGAGTGC
TTCGACTCCGTGGAAATCTCCGGCGTGGAAGATCGGTTCAACGCCTC
CCTGGGCACATACCACGATCTGCTGAAAATTATCAAGGACAAGGACT
TCCTGGACAATGAGGAAAACGAGGACATTCTGGAAGATATCGTGCTG
ACCCTGACACTGTTTGAGGACAGAGAGATGATCGAGGAACGGCTGAA
AACCTATGCCCACCTGTTCGACGACAAAGTGATGAAGCAGCTGAAGC
GGCGGAGATACACCGGCTGGGGCAGGCTGAGCCGGAAGCTGATCAAC
GGCATCCGGGACAAGCAGTCCGGCAAGACAATCCTGGATTTCCTGAA
GTCCGACGGCTTCGCCAACAGAAACTTCATGCAGCTGATCCACGACG
ACAGCCTGACCTTTAAAGAGGACATCCAGAAAGCCCAGGTGTCCGGC
CAGGGCGATAGCCTGCACGAGCACATTGCCAATCTGGCCGGCAGCCC
CGCCATTAAGAAGGGCATCCTGCAGACAGTGAAGGTGGTGGACGAGC
TCGTGAAAGTGATGGGCCGGCACAAGCCCGAGAACATCGTGATCGAA
ATGGCCAGAGAGAACCAGACCACCCAGAAGGGACAGAAGAACAGCCG
CGAGAGAATGAAGCGGATCGAAGAGGGCATCAAAGAGCTGGGCAGCC
AGATCCTGAAAGAACACCCCGTGGAAAACACCCAGCTGCAGAACGAG
AAGCTGTACCTGTACTACCTGCAGAATGGGCGGGATATGTACGTGGA
CCAGGAACTGGACATCAACCGGCTGTCCGACTACGATGTGGACCATA
TCGTGCCTCAGAGCTTTCTGAAGGACGACTCCATCGACAACAAGGTG
CTGACCAGAAGCGACAAGAACCGGGGCAAGAGCGACAACGTGCCCTC
CGAAGAGGTCGTGAAGAAGATGAAGAACTACTGGCGGCAGCTGCTGA
ACGCCAAGCTGATTACCCAGAGAAAGTTCGACAATCTGACCAAGGCC
GAGAGAGGCGGCCTGAGCGAACTGGATAAGGCCGGCTTCATCAAGAG
ACAGCTGGTGGAAACCCGGCAGATCACAAAGCACGTGGCACAGATCC
TGGACTCCCGGATGAACACTAAGTACGACGAGAATGACAAGCTGATC
CGGGAAGTGAAAGTGATCACCCTGAAGTCCAAGCTGGTGTCCGATTT
CCGGAAGGATTTCCAGTTTTACAAAGTGCGCGAGATCAACAACTACC
ACCACGCCCACGACGCCTACCTGAACGCCGTCGTGGGAACCGCCCTG
ATCAAAAAGTACCCTAAGCTGGAAAGCGAGTTCGTGTACGGCGACTA
CAAGGTGTACGACGTGCGGAAGATGATCGCCAAGAGCGAGCAGGAAA
TCGGCAAGGCTACCGCCAAGTACTTCTTCTACAGCAACATCATGAAC
TTTTTCAAGACCGAGATTACCCTGGCCAACGGCGAGATCCGGAAGCG
GCCTCTGATCGAGACAAACGGCGAAACCGGGGAGATCGTGTGGGATA
AGGGCCGGGATTTTGCCACCGTGCGGAAAGTGCTGAGCATGCCCCAA
GTGAATATCGTGAAAAAGACCGAGGTGCAGACAGGCGGCTTCAGCAA
AGAGTCTATCCTGCCCAAGAGGAACAGCGATAAGCTGATCGCCAGAA
AGAAGGACTGGGACCCTAAGAAGTACGGCGGCTTCGACAGCCCCACC GTGGCCTATTCTGTGCTGGTGGTGGCCAAAGTGGAAAAGGGCAAGTC
CAAGAAACTGAAGAGTGTGAAAGAGCTGCTGGGGATCACCATCATGG
AAAGAAGCAGCTTCGAGAAGAATCCCATCGACTTTCTGGAAGCCAAG
GGCTACAAAGAAGTGAAAAAGGACCTGATCATCAAGCTGCCTAAGTA
CTCCCTGTTCGAGCTGGAAAACGGCCGGAAGAGAATGCTGGCCTCTG
CCGGCGAACTGCAGAAGGGAAACGAACTGGCCCTGCCCTCCAAATAT
GTGAACTTCCTGTACCTGGCCAGCCACTATGAGAAGCTGAAGGGCTC
CCCCGAGGATAATGAGCAGAAACAGCTGTTTGTGGAACAGCACAAGC
ACTACCTGGACGAGATCATCGAGCAGATCAGCGAGTTCTCCAAGAGA
GTGATCCTGGCCGACGCTAATCTGGACAAAGTGCTGTCCGCCTACAA
CAAGCACCGGGATAAGCCCATCAGAGAGCAGGCCGAGAATATCATCC
ACCTGTTTACCCTGACCAATCTGGGAGCCCCTGCCGCCTTCAAGTAC
TTTGACACCACCATCGACCGGAAGAGGTACACCAGCACCAAAGAGGT
GCTGGACGCCACCCTGATCCACCAGAGCATCACCGGCCTGTACGAGA
CACGGATCGACCTGTCTCAGCTGGGAGGTGACTCTGGCGGCTCAAAA
AGAACCGCCGACGGCAGCGAATTCGAGCCCAAGAAGAAGAGGAAAGT
CTAA Human codon optimized VSVG (SEQ ID NO: 182)

ATGAAATGTCTGCTGTACCTGGCTTTCCTGTTCATCGGCGTGAACTG
CAAGTTCACCATCGTGTTCCCTCACAACCAGAAGGGCAACTGGAAAA
ATGTGCCTAGCAACTACCACTACTGTCCTAGCTCTAGCGACCTTAAT
TGGCATAACGACCTGATCGGCACAGCCCTGCAGGTGAAGATGCCTAA
GAGCCACAAGGCCATCCAGGCCGACGGATGGATGTGCCACGCCAGCA
AGTGGGTCACAACCTGTGACTTCAGATGGTACGGCCCTAAATACATT
ACCCACTCTATCAGAAGCTTCACCCCTTCTGTGGAACAATGTAAAGA
GTCCATTGAGCAGACAAAGCAGGGCACCTGGCTGAACCCCGGCTTCC
CCCCCCAGAGCTGCGGCTACGCCACCGTTACCGATGCCGAGGCCGTG
ATCGTGCAGGTGACACCTCACCACGTGCTGGTCGATGAGTACACCGG
CGAATGGGTGGACAGCCAATTTATCAACGGCAAATGCAGCAATTACA
TCTGCCCCACCGTGCACAACAGCACCACCTGGCACAGCGATTACAAG
GTGAAAGGCCTGTGCGACAGCAACCTGATCTCTATGGACATCACCTT
CTTCAGCGAGGACGGCGAGCTGTCTAGTCTGGGCAAGGAAGGCACAG
GTTTTCGGAGCAACTACTTCGCCTACGAGACTGGCGGCAAGGCCTGC
AAGATGCAGTACTGCAAGCACTGGGGCGTTAGACTGCCTTCAGGCGT
GTGGTTCGAGATGGCCGATAAGGACCTGTTCGCCGCTGCCAGATTCC
CAGAGTGCCCTGAGGGCAGCTCCATCAGCGCCCCTTCCCAGACCTCC
GTGGATGTGTCCCTGATCCAGGACGTGGAAAGAATCCTGGACTACAG
CCTCTGTCAGGAGACATGGTCCAAAATCAGAGCCGGACTCCCCATTA
GCCCTGTGGACCTGAGCTACCTGGCCCCCAAGAATCCTGGAACCGGC
CCCGCCTTCACAATCATTAACGGCACCCTGAAATACTTCGAGACCAG

-continued
```
ATACATCCGGGTGGACATCGCCGCTCCTATCCTGTCAAGAATGGTGG

GCATGATTTCTGGCACAACAACAGAGAGGGAACTGTGGGACGACTGG

GCCCCTTACGAGGATGTGGAAATCGGCCCAAACGGCGTGCTGCGGAC

CAGCTCAGGCTATAAGTTCCCCCTGTACATGATCGGCCACGGCATGC

TGGATTCTGACCTGCACCTGAGCAGCAAGGCCCAGGTCTTTGAGCAC

CCTCATATCCAAGACGCCGCCAGCCAGCTGCCTGATGACGAGAGCCT

GTTTTTTGGAGATACAGGACTGAGCAAGAACCCCATCGAGCTGGTGG

AAGGCTGGTTTAGCAGCTGGAAGTCCAGCATAGCTAGCTTCTTCTTC

ATCATCGGCCTGATCATCGGACTGTTCCTGGTGCTGAGAGTGGGGAT

CCACCTGTGCATCAAGCTGAAGCACACCAAAAAGAGACAGATCTACA

CCGACATCGAGATGAACCGGCTGGGGAAGTGA
```

LITERATURE CITED

1. Parseval, N. et al. Survey of human genes of retroviral origin: identification and transcriptome of the genes with coding capacity for complete envelope proteins. Journal of Virology 77, 10414-10422, (2003).
2. Okimoto, T. et al. VSV-G envelope glycoprotein forms complexes with plasmid DNA and MLV retrovirus-like particles in cell-free conditions and enhances DNA transfection. Molecular Therapy 4, 232-238, (2001).
3. Mangeot, P. et al. Protein transfer into human cells by VSV-G-induced nanovesicles. Molecular Therapy 19, 1656-1666, (2011).
4. Wagner, D. et al. High prevalence of Streptococcus pyogenes Cas9-reactive T cells within the adult human population. Nature Medicine 25, 242-248 (2019)
5. Kim, S. et al. CRISPR RNAs trigger innate immune responses in human cells. Genome Research 28, 1-7 (2018).
6. Charlesworth, C. et al. Identification of preexisting adaptive immunity to Cas9 proteins in humans. Nature Medicine 25, 249-254 (2019)
7. Ferdosi, S. et al. Multifunctional CRISPR-Cas9 with engineered immunosilenced human T cell epitopes. Nature Communications 10, Article number: 1842 (2019).
8. Wang, D. et al. Adenovirus-mediated somatic genome editing of Pten by CRISPR/Cas9 in mouse liver in spite of Cas9-specific immune responses. Human Gene Therapy 26, 432-442 (2015).
9. Devanabanda, M. et al. Immunotoxic effects of gold and silver nanoparticles: Inhibition of mitogen-induced proliferative responses and viability of human and murine lymphocytes in vitro. Journal of Immunotoxicology 13, 1547-6901 (2016).
10. Mout, R. et al. Direct cytosolic delivery of CRISPR/Cas9-ribonucleoprotein for efficient gene editing. ACS Nano 11, 2452-2458 (2017).
11. Yin, H. et al. structure-guided chemical modification of guide RNA enables potent non-viral in vivo genome editing. Nature Biotechnology 35, 1179-1187 (2017).
12. Qiao, J. et al. Cytosolic delivery of CRISPR/Cas9 ribonucleoproteins for genome editing using chitosan-coated red fluorescent protein. Chemical Communications 55, 4707-4710 (2019).
13. Li, L. et al. A rationally designed semiconducting polymer brush for NIR-II imaging guided light-triggered remote control of CRISPR/Cas9 genome editing. Advanced Materials 1901187, 1-9 (2019).
14. Gao, X. et al. Treatment of autosomal dominant hearing loss by in vivo delivery of genome editing agents. Nature 553, 217-221 (2018)
15. Lee, K. et al. Nanoparticle delivery of Cas9 ribonucleoprotein and donor DNA in vivo induces homology-directed DNA repair. Nature Biomedical Engineering 1, 889-901 (2017).
16. Staahl, B. et al. Efficient genome editing in the mouse brain by local delivery of engineered Cas9 ribonucleoprotein complexes. Nature Biotechnology 35, 431-433 (2017).
17. Zuris, J. et al. Cationic lipid-mediated delivery of proteins enables efficient protein-based genome editing in vitro and in vivo. Nature Biotechnology 33, 73-79 (2015).
18. Finn, J. et al. A single administration of CRISPR/Cas9 lipid nanoparticles achieves robust and persistent in vivo genome editing. Cell Reports 22, 2227-2235 (2018).
19. Wang, H. et al. Nonviral gene editing via CRISPR/Cas9 delivery by membrane-disruptive and endosomolytic helical polypeptide. PNAS 115, 4903-4908 (2018).
20. Del'Guidice, T. et al. Membrane permeabilizing amphiphilic peptide delivers recombinant transcription factor and CRISPR-Cas9/Cpf1 ribonucleoproteins in hard-to-modify cells. PLOS ONE 13, e0195558 (2018).
21. Colella, P. et al. Emerging Issues in AAV-Mediated In Vivo Gene Therapy. Molecular Therapy: Methods & Clinical Development 8, 87-104 (2018).
22. Naso, F. et al. Adeno-Associated Virus (AAV) as a Vector for Gene Therapy. BioDrugs 31, 317-334 (2017).
23. Handel, E. et al. Versatile and efficient genome editing in human cells by combining zinc-finger nucleases with adeno-associated viral vectors. Human Gene Therapy 23, 321-329 (2012).
24. Chadwick, A. et al. Reduced Blood Lipid Levels With In Vivo CRISPR-Cas9 Base Editing of ANGPTL3. Circulation 137, 975-977 (2018).
25. Schenkwein, D. et al. Production of HIV-1 Integrase Fusion Protein-Carrying Lentiviral Vectors for Gene Therapy and Protein Transduction. Human Gene Therapy 21, 589-602 (2010).
26. Cai, Y. et al. Targeted genome editing by lentiviral protein transduction of zinc-finger and TAL-effector nucleases. eLife 3, e01911 (2014).
27. Choi, J. et al. Lentivirus pre-packed with Cas9 protein for safer gene editing. Gene Therapy 23, 627-633 (2016).
28. Meyer, C. et al. Pseudotyping exosomes for enhanced protein delivery in mammalian cells. International Journal of Nanomedicine 12, 3153-3170 (2017).
29. Mangeot, P. et al. Genome editing in primary cells and in vivo using viral-derived Nanoblades loaded with Cas9-sgRNA ribonucleoproteins. Nature Communications 10, Article number: 45 (2019).
30. Lu, B. et al. Delivering SaCas9 mRNA by lentivirus-like bionanoparticles for transient expression and efficient genome editing. Nucleic Acids Research 47, e44 (2019).
31. Wang, Q. et al. ARMMs as a versatile platform for intracellular delivery of macromolecules. Nature Communications 9, 1-7 (2018).
32. Lainscek, D. et al. Delivery of an Artificial Transcription Regulator dCas9-VPR by Extracellular Vesicles for Therapeutic Gene Activation. ACS Synthetic Biology 7, 2715-2725 (2018).
33. Fuchs, J. et al. First-in-Human Evaluation of the Safety and Immunogenicity of a Recombinant Vesicular Stoma- 34. Cong, L. et al. Multiplex Genome Engineering Using CRISPR/Cas Systems. Science 339, 819-823, (2013).
35. Ran, F. et al. In vivo genome editing using *Staphylococcus aureus* Cas9. Nature 520, 186-191, (2015).
36. Zetsche, B. et al. Cpf1 Is a Single RNA-Guided Endonuclease of a Class 2 CRISPR-Cas System. Cell 163, 759-771, (2015).
37. Komor, A. et al. Programmable editing of a target base in genomic DNA without double-stranded DNA cleavage. Nature 533, 420-424, (2016).
38. Gaudelli, N. et al. Programmable base editing of A•T to G•C in genomic DNA without DNA cleavage. Nature 551, 464-471, (2017).
39. Voelkel, C. et al. Protein transduction from retroviral Gag precursors. Proc Natl Acad Sci USA 107, 7805-7810, (2010).
40. Kaczmarczyk, S. et al. Protein delivery using engineered virus-like particles. Proc Natl Acad Sci USA 108, 16998-17003, (2011).
41. Ebner, M. et al. PI (3,4,5)P$_3$ Engagement Restricts Akt Activity to Cellular Membranes. Mol Cell 65, 416-431, (2017).
42. Urano, E. et al. Substitution of the myristoylation signal of human immunodeficiency virus type 1 Pr55Gag with the phospholipase C-d1pleckstrin homology domain results in infectious pseudovirion production. J. Gen Virology 89, 3144-3149, (2008).
43. Pastuzyn, E. et al. The Neuronal Gene Arc Encodes a Repurposed Retrotransposon Gag Protein that Mediates Intercellular RNA Transfer. Cell 172, 275-288, (2018).
44. Lukacs, G. et al. Size-dependent DNA Mobility in Cytoplasm and Nucleus. Journal of Biological Chemistry 275, 1625-1629, (1999).
45. Kreiss, P. et al. Plasmid DNA size does not affect the physicochemical properties of lipoplexes but modulates gene transfer efficiency. Nucleic Acids Research 27, 3792-3798 (1999).
46. Nafissi, N. et al. DNA Ministrings: Highly Safe and Effective Gene Delivery Vectors. Molecular Therapy—Nucleic Acids 3, e165, (2014).
47. Fujimoto, T. et al. Selective EGLN Inhibition Enables Ablative Radiotherapy and Improves Survival in Unresectable Pancreatic Cancer. Cancer Research 79, 2327-2338 (2019).
48. Tai, S. et al. Differential Expression of Metallothionein 1 and 2 Isoforms in Breast Cancer Lines with Different Invasive Potential: Identification of a Novel Nonsilent Metallothionein-1H Mutant Variant. American Journal of Pathology 163, 2009-2019 (2003).
49. Caussinus, E. et al. Fluorescent fusion protein knockout mediated by anti-GFP nanobody. Nature Structural & Molecular Biology 19, 117-121, (2012).
50. Zhao, W. et al. Quantitatively Predictable Control of Cellular Protein Levels through Proteasomal Degradation. ACS Synthetic Biology 7, 540-552, (2018).
51. Clift, D. et al. A Method for the Acute and Rapid Degradation of Endogenous Proteins. Cell 171, 1692-1706, (2017).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A particle for delivering a CRISPR-based genome editing protein to a nucleus of a target cell, the particle comprising:
   (a) a membrane comprising a phospholipid bilayer with a glycoprotein on an external side; and
   (b) a fusion protein comprising the CRISPR-based genome editing protein fused via a linker with a non-viral plasma membrane recruitment domain comprising a pleckstrin homology (PH) domain disposed in a core of the particle, and
   wherein the fusion protein does not comprise a Gag protein.

2. The particle of claim 1, wherein the PH domain is a human PH domain.

3. The particle of claim 1, wherein the PH domain is selected from the group consisting of a pleckstrin homology domain of phospholipase CM (PLC61), pleckstrin homology domain of Aktl (Aktl) or a mutant thereof, pleckstrin homology domain of PDPK1 (PDPKI), pleckstrin homology domain of Dappl, pleckstrin homology domain of Grpl, pleckstrin homology domain of OSBP, pleckstrin homology domain of Btkl, pleckstrin homology domain of FAPP1, pleckstrin homology domain of PKD, pleckstrin homology domain of PHLPP1, pleckstrin homology domain of SWAP70, and a pleckstrin homology domain of MAPKAP1.

4. The particle of claim 1, wherein the PH domain is selected from the group consisting of a pleckstrin homology domain of human phospholipase CM (hPLC61), pleckstrin homology domain of human Aktl (hAktl) or a mutant thereof, pleckstrin homology domain of Homo sapiens PDPK1 (hPDPKI), pleckstrin homology domain of Human Dappl, pleckstrin homology domain of Mouse Grpl, pleckstrin homology domain of Human Grpl, pleckstrin homology domain of Human OSBP, pleckstrin homology domain of Human Btkl, pleckstrin homology domain of Human FAPP1, pleckstrin homology domain of Human PKD, pleckstrin homology domain of Human PHLPP1, pleckstrin homology domain of Human SWAP70, and a pleckstrin homology domain of Human MAPKAP1.

5. The particle of claim 1, wherein the PH domain is a pleckstrin homology (PH) domain of Aktl or a pleckstrin homology domain of phospholipase CM (PLC61).

6. The particle of claim 1, wherein the PH domain is a mutant pleckstrin homology domain of AKT that comprises an amino acid substitution relative to a corresponding wild type pleckstrin homology domain of Aktl.

7. The particle of claim 1, wherein the plasma membrane recruitment domain comprises the amino acid sequence set forth in any one of SEQ ID NOs: 1-11 or 42-44.

8. The particle of claim 1, wherein the glycoprotein is a viral glycoprotein.

9. The particle of claim 8, wherein the viral glycoprotein comprises a viral envelope protein.

10. The particle of claim 9, wherein the viral envelope protein is selected from the group consisting of a vesicular stomatitis virus glycoprotein (VSVG), GP64, GP160, RD114, BaEVTR, BaEVTRless, FuG-E, FuG-E (P440E), ecotropic MLV ENV, amphotropic MLV ENV, and a MLV10A1.

11. The particle of claim 9, wherein the viral envelope protein comprises a vesicular stomatitis virus glycoprotein VSVG.

12. The particle of claim 9, wherein the viral envelope protein comprises the amino acid sequence set forth in any one of SEQ ID NOs: 12-18, 54, or 55.

13. The particle of claim 1, wherein the particle further comprises a single-chain variable fragment, a nanobody, or a darpin on the external side.

14. The particle of claim 1, wherein the particle does not comprise a Gag protein.

15. The particle of claim 1, wherein the particle does not further comprise a viral protein or a polynucleotide encoding the viral protein.

16. The particle of claim 1, wherein the particle does not comprise an exogenous GAG protein, an exogenous Pol protein, a polynucleotide encoding the exogenous GAG protein, or a polynucleotide encoding the exogenous Pol protein.

17. The particle of claim 1, wherein the CRISPR-based genome editing protein further comprises a nuclear localization sequence.

18. The particle of claim 1, wherein the CRISPR-based genome editing protein is complexed with a guide RNA.

19. The particle of claim 1, wherein the CRISPR-based genome editing protein is fused N-terminal to N-terminus or C-terminus of the non-viral plasma membrane recruitment domain.

20. A method of engineering a target cell, the method comprising contacting the target cell with the particle of claim 1.

21. A method of engineering a population of target cells, the method comprising contacting the population of target cells with the particle of claim 1.

22. The method of claim 21, wherein the contacting results in an increased delivery of the CRISPR-based genome editing protein relative to that upon contacting with a corresponding particle that lacks a fusion of the CRISPR-based genome editing protein to the non-viral plasma membrane recruitment domain.

23. The method of claim 22, wherein the delivery results in an increased modification of the population of target cells relative to that upon contacting with a corresponding particle that lacks a fusion of the CRISPR-based genome editing protein to the non-viral plasma membrane recruitment domain.

24. The particle of claim 1, wherein the CRISPR-based genome editing protein comprises Cas9.

25. The particle of claim 24, wherein the Cas9 comprises *Streptococcus pyogenes* Cas9 (spCas9).

26. The particle of claim 1, wherein the CRISPR-based genome editing protein comprises Cas12a.

27. The particle of claim 1, wherein the CRISPR-based genome editing protein comprises a deaminase.

28. The particle of claim 27, wherein the CRISPR-based genome editing protein comprises a uracil glycosylase inhibitor (UGI).

29. The particle of claim 1, wherein the CRISPR-based genome editing protein is wild-type, a nickase, or catalytically inactive.

30. The particle of claim 1, wherein the PH domain is a human PH domain, wherein the linker comprises a 10 amino acid glycine/serine polypeptide linker, wherein the plasma membrane recruitment domain is N-terminal to the CRISPR-based genome editing protein, wherein the CRISPR-based genome editing protein comprises Cas9, wherein the Cas9 is complexed with a sgRNA, wherein the particle does not comprise a Gag protein, and wherein the glycoprotein is fusogenic.

31. The particle of claim 1, further comprising a targeting peptide to enable cell-specific entry.

32. The particle of claim 1, wherein the CRISPR-based genome editing protein is fused C-terminal to the non-viral plasma membrane recruitment domain.

33. The particle of claim 1, wherein the linker is a polypeptide linker.

34. The particle of claim 33, wherein the polypeptide linker is 5-20 amino acids in length.

35. The particle of claim 33, wherein the polypeptide linker is 8-12 amino acids in length.

36. The particle of claim 33, wherein the polypeptide linker comprises a glycine/serine polypeptide linker.

37. The particle of claim 33, wherein the polypeptide linker comprises a 10 amino acid glycine/serine polypeptide linker.

\* \* \* \* \*

SEQUENCE LISTING

```
Sequence total quantity: 186
SEQ ID NO: 1              moltype = AA  length = 126
FEATURE                   Location/Qualifiers
source                    1..126
                          mol_type = protein
                          organism = Homo sapiens
SEQUENCE: 1
MQTGRTEDDL VPTAPSLGTK EGYLTKQGGL VKTWKTRWFT LHRNELKYFK DQMSPEPIRI  60
LDLTECSAVQ FDYSQERVNC FCLVFPFRTF YLCAKTGVEA DEWIKILRWK LSQIRKQLNQ  120
GEGTIR                                                             126

SEQ ID NO: 2              moltype = AA  length = 153
FEATURE                   Location/Qualifiers
source                    1..153
                          mol_type = protein
                          organism = Mus musculus
SEQUENCE: 2
PFKIPEDDGN DLTHTFFNPD REGWLLKLGG RVKTWKRRWF ILTDNCLYYF EYTTDKEPRG  60
IIPLENLSIR EVEDPRKPNC FELYNPSHKG QVIKACKTEA DGRVVEGNHV VYRISAPSPE  120
EKEEWMKSIK ASISRDPFYD MLATRKRRIA NKK                               153

SEQ ID NO: 3              moltype = AA  length = 118
FEATURE                   Location/Qualifiers
source                    1..118
                          mol_type = protein
                          organism = Homo sapiens
SEQUENCE: 3
NPDREGWLLK LGGGRVKTWK RRWFILTDNC LYYFEYTTDK EPRGIIPLEN LSIREVEDPR  60
KPNCFELYNP SHKGQVIKAC KTEADGRVVE GNHVVYRISA PSPEEKEEWM KSIKASIS    118

SEQ ID NO: 4              moltype = AA  length = 99
FEATURE                   Location/Qualifiers
source                    1..99
```

```
                        mol_type = protein
                        organism = Homo sapiens
SEQUENCE: 4
SGSAREGWLF KWTNYIKGYQ RRWFVLSNGL LSYYRSKAEM RHTCRGTINL ATANITVEDS    60
CNFIISNGGA QTYHLKASSE VERQRWVTAL ELAKAKAVK                           99

SEQ ID NO: 5            moltype = AA  length = 177
FEATURE                 Location/Qualifiers
source                  1..177
                        mol_type = protein
                        organism = Homo sapiens
SEQUENCE: 5
MAAVILESIF LKRSQQKKKT SPLNFKKRLF LLTVHKLSYY EYDFERGRRG SKKGSIDVEK    60
ITCVETVVPE KNPPPERQIP RRGEESSEME QISIIERFPY PFQVVYDEGP LYVFSPTEEL   120
RKRWIHQLKN VIRYNSDLVQ KYHPCFWIDG QYLCCSQTAK NAMGCQILEN RNGSLKP      177

SEQ ID NO: 6            moltype = AA  length = 98
FEATURE                 Location/Qualifiers
source                  1..98
                        mol_type = protein
                        organism = Homo sapiens
SEQUENCE: 6
MEGVLYKWTN YLTGWQPRWF VLDNGILSYY DSQDDVCKGS KGSIKMAVCE IKVHSADNTR    60
MELIIPGEQH FYMKAVNAAE RQRWLVALGS SKACLTDT                           98

SEQ ID NO: 7            moltype = AA  length = 122
FEATURE                 Location/Qualifiers
source                  1..122
                        mol_type = protein
                        organism = Homo sapiens
SEQUENCE: 7
MSDNQSWNSS GSEEDPETES GPPVERCGVL SKWTNYIHGW QDRWVVLKNN ALSYYKSEDE    60
TEYGCRGSIC LSKAVITPHD FDECRFDISV NDSVWYLRAQ DPDHRQQWID AIEQHKTESG   120
YG                                                                 122

SEQ ID NO: 8            moltype = AA  length = 120
FEATURE                 Location/Qualifiers
source                  1..120
                        mol_type = protein
                        organism = Homo sapiens
SEQUENCE: 8
TVMKEGWMVH YTSKDTLRKR HYWRLDSKCI TLFQNDTGSR YYKEIPLSEI LSLEPVKTSA    60
LIPNGANPHC FEITTANVVY YVGENVVNPS SPSPNNSVLT SGVGADVARM WEIAIQHALM   120

SEQ ID NO: 9            moltype = AA  length = 101
FEATURE                 Location/Qualifiers
source                  1..101
                        mol_type = protein
                        organism = Homo sapiens
SEQUENCE: 9
RIQLSGMYNV RKGKMQLPVN RWTRRQVILC GTCLIVSSVK DSLTGKMHVL PLIGGKVEEV    60
KKHQHCLAFS SSGPQSQTYY ICFDTFTEYL RWLRQVSKVA S                       101

SEQ ID NO: 10           moltype = AA  length = 97
FEATURE                 Location/Qualifiers
source                  1..97
                        mol_type = protein
                        organism = Homo sapiens
SEQUENCE: 10
DVLKQGYMMK KGHRRKNWTE RWFVLKPNII SYYVSEDLKD KKGDILLDEN CCVESLPDKD    60
GKKCLFLVKC FDKTFEISAS DKKKKQEWIQ AIHSTIH                            97

SEQ ID NO: 11           moltype = AA  length = 113
FEATURE                 Location/Qualifiers
source                  1..113
                        mol_type = protein
                        organism = Homo sapiens
SEQUENCE: 11
DMLSSHHYKS FKVSMIHRLR FTTDVQLGIS GDKVEIDPVT NQKASTKFWI KQKPISIDSD    60
LLCACDLAEE KSPSHAIFKL TYLSNHDYKH LYFESDAATV NEIVLKVNYI LES         113

SEQ ID NO: 12           moltype = AA  length = 562
FEATURE                 Location/Qualifiers
REGION                  1..562
                        note = Description of Unknown:Baboon endogenous virus
                        sequence
source                  1..562
                        mol_type = protein
                        organism = unidentified
```

```
SEQUENCE: 12
MGFTTKIIFL YNLVLVYAGF DDPRKAIELV QKRYGRPCDC SGGQVSEPPS DRVSQVTCSG    60
KTAYLMPDQR WKCKSIPKDT SPSGPLQECP CNSYQSSVHS SCYTSYQQCR SGNKTYYTAT   120
LLKTQTGGTS DVQVLGSTNK LIQSPCNGIK GQSICWSTTA PIHVSDGGGP LDTTRIKSVQ   180
RKLEEIHKAL YPELQYHPLA IPKVRDNLMV DAQTLNILAG TYNLLLMSNT SLVDDCWLCL   240
KLGPPTPLAI PNFLLSYVTR SSDNISCLII PPLLVQPMQF SNSSCLFSPS YNSTEEIDLG   300
HVAFSNCTSI TNVTGPICAV NGSVFLCGNN MAYTYLPTNW TGLCVLATLL PDIDIIPGDE   360
PVPIPAIDHF IYRPKRAIQF IPLLAGLGIT AAFTTGATGL GVSVTQYTKL SNQLISDVQI   420
LSSTIQDLQD QVDSLAEVVL QNRRGLDLLT AEQGGICLAL QEKCCFYVNK SGIVRDKIKT   480
LQEELERRRK DLASNPLWTG LQGLLPYLLP FLGPLLTLLL LLTIGPCIFN RLVQFVKDRI   540
SVVQALVLTQ QYHQLKPLEY EP                                           562

SEQ ID NO: 13         moltype = AA  length = 546
FEATURE               Location/Qualifiers
REGION                1..546
                      note = Description of Artificial Sequence:
                      Syntheticpolypeptide
source                1..546
                      mol_type = protein
                      organism = synthetic construct
SEQUENCE: 13
MGFTTKIIFL YNLVLVYAGF DDPRKAIELV QKRYGRPCDC SGGQVSEPPS DRVSQVTCSG    60
KTAYLMPDQR WKCKSIPKDT SPSGPLQECP CNSYQSSVHS SCYTSYQQCR SGNKTYYTAT   120
LLKTQTGGTS DVQVLGSTNK LIQSPCNGIK GQSICWSTTA PIHVSDGGGP LDTTRIKSVQ   180
RKLEEIHKAL YPELQYHPLA IPKVRDNLMV DAQTLNILA TYNLLLMSNT SLVDDCWLCL    240
KLGPPTPLAI PNFLLSYVTR SSDNISCLII PPLLVQPMQF SNSSCLFSPS YNSTEEIDLG   300
HVAFSNCTSI TNVTGPICAV NGSVFLCGNN MAYTYLPTNW TGLCVLATLL PDIDIIPGDE   360
PVPIPAIDHF IYRPKRAIQF IPLLAGLGIT AAFTTGATGL GVSVTQYTKL SNQLISDVQI   420
LSSTIQDLQD QVDSLAEVVL QNRRGLDLLT AEQGGICLAL QEKCCFYVNK SGIVRDKIKT   480
LQEELERRRK DLASNPLWTG LQGLLPYLLP FLGPLLTLLL LLTIGPCIFN RLTAFINDKL   540
NIIHAM                                                             546

SEQ ID NO: 14         moltype = AA  length = 504
FEATURE               Location/Qualifiers
REGION                1..504
                      note = Description of Artificial Sequence:
                      Syntheticpolypeptide
source                1..504
                      mol_type = protein
                      organism = synthetic construct
SEQUENCE: 14
MVPQVLLFVL LLGFSLCFGK FPIYTIPDEL GPWSPIDIHH LSCPNNLVVE DEGCTNLSEF    60
SYMELKVGYI SAIKVNGFTC TGVVTEAETY TNFVGYVTTT FKRKHFRPTP DACRAAYNWK   120
MAGDPRYEES LHNPYPDYHW LRTVRTTKES LIIISPSVTD LDPYDKSLHS RVFPGGKCSG   180
ITVSSTYCST NHDYTIWMPE NPRPRTPCDI FTNSRGKRAS NGNKTCGFVD ERGLYKSLKG   240
ACRLKLCGVL GLRLMDGTWV AMQTSDETKW CPPDQLVNLH DFRSDEIEHL VVEELVKKRE   300
ECLDALESIM TTKSVSFRRL SHLRKLVPGF GKAYTIFNKT LMEADAHYKS VRTWNEIIPS   360
KGCLKVGGRC HPHVNGVFFN GIILGPDDHV LIPEMQSSLL QQHMELLESS VIPLMHPLAD   420
PSTVFKEGDE AEDFVEVHLP KNPIELVEGW FSSWKSSIAS FFFIIGLIIG LFLVLRVGIH   480
LCIKLKHTKK RQIYTDIEMN RLGK                                         504

SEQ ID NO: 15         moltype = AA  length = 504
FEATURE               Location/Qualifiers
REGION                1..504
                      note = Description of Artificial Sequence:
                      Syntheticpolypeptide
source                1..504
                      mol_type = protein
                      organism = synthetic construct
SEQUENCE: 15
MVPQVLLFVL LLGFSLCFGK FPIYTIPDEL GPWSPIDIHH LSCPNNLVVE DEGCTNLSEF    60
SYMELKVGYI SAIKVNGFTC TGVVTEAETY TNFVGYVTTT FKRKHFRPTP DACRAAYNWK   120
MAGDPRYEES LHNPYPDYHW LRTVRTTKES LIIISPSVTD LDPYDKSLHS RVFPGGKCSG   180
ITVSSTYCST NHDYTIWMPE NPRPRTPCDI FTNSRGKRAS NGNKTCGFVD ERGLYKSLKG   240
ACRLKLCGVL GLRLMDGTWV AMQTSDETKW CPPDQLVNLH DFRSDEIEHL VVEELVKKRE   300
ECLDALESIM TTKSVSFRRL SHLRKLVPGF GKAYTIFNKT LMEADAHYKS VRTWNEIIPS   360
KGCLKVGGRC HPHVNGVFFN GIILGPDDHV LIPEMQSSLL QQHMELLESS VIPLMHPLAD   420
PSTVFKEGDE AEDFVEVHLE KNPIELVEGW FSSWKSSIAS FFFIIGLIIG LFLVLRVGIH   480
LCIKLKHTKK RQIYTDIEMN RLGK                                         504

SEQ ID NO: 16         moltype = AA  length = 654
FEATURE               Location/Qualifiers
source                1..654
                      mol_type = protein
                      organism = Murine leukemia virus
SEQUENCE: 16
MARSTLSKPP QDKINPWKPL IVMGVLLGVG MAESPHQVFN VTWRVTNLMT GRTANATSLL    60
GTVQDAFPKL YFDLCDLVGE EWDPSDQEPY VGYGCKYPAG RQRTRTFDFY VCPGHTVKSG   120
CGGPGEGYCG KWGCETTGQA YWKPTSSWDL ISLKRGNTPW DTGCSKVACG PCYDLSKVSN   180
```

```
SFQGATRGGR CNPLVLEFTD AGKKANWDGP KSWGLRLYRT GTDPITMFSL TRQVLNVGPR  240
VPIGPNPVLP DQRLPSSPIE IVPAPQPPSP LNTSYPPSTT STPSTSPTSP SVPQPPPGTG  300
DRLLALVKGA YQALNLTNPD KTQECWLCLV SGPPYYEGVA VVGTYTNHST APANCTATSQ  360
HKLTLSEVTG QGLCMGAVPK THQALCNTTQ SAGSGSYYLA APAGTMWACS TGLTPCLSTT  420
VLNLTTDYCV LVELWPRVIY HSPDYMYGQL EQRTKYKREP VSLTLALLLG GLTMGGIAAG  480
IGTGTTALIK TQQFEQLHAA IQTDLNEVEK SITNLEKSLT SLSEVVLQNR RGLDLLFLKE  540
GGLCAALKEE CCFYADHTGL VRDSMAKLRE RLNQRQKLFE TGQGWFEGLF NRSPWFTTLI  600
STIMGPLIVL LLILLFGPCI LNRLVQFVKD RISVVQALVL TQQYHQLKPI EYEP        654

SEQ ID NO: 17           moltype = AA  length = 665
FEATURE                 Location/Qualifiers
source                  1..665
                        mol_type = protein
                        organism = Murine leukemia virus
SEQUENCE: 17
MARSTLSKPL KNKVNPRGPL IPLILLMLRG VSTASPGSSP HQVYNITWEV TNGDRETVWA   60
TSGNHPLWTW WPDLTPDLCM LAHHGPSYWG LEYQSPFSRP PGPPCCSGGS SPGCSRDCEE  120
PLTSLTPRCN TAWNRLKLDQ TTHKSNEGFY VCPGPHRPRE SKSCGGPDSF YCAYWGCETT  180
GRAYWKPSSS WDFITVNNNL TSDQAVQVCK DNKWCNPLVI RFTDAGRRVT SWTTGHYWGL  240
RLYVSGQDPG LTFGIRLRYQ NLGPRVPIGP NPVLADQQPL SKPKPVKSPS VTKPPSGTPL  300
SPTQLPPAGT ENRLLNLVDG AYQALNLTSP DKTQECWLCL VAGPPYYEGV AVLGTYSNHT  360
SAPANCSVAS QHKLTLSEVT GQGLCIGAVP KTHQALCNTT QTSSRGSYYL VAPTGTMWAC  420
STGLTPCIST TILNLTTDYC VLVELWPRVT YHSPSYVYGL FERSNRHKRE PVSLTLALLL  480
GGLTMGGIAA GIGTGTTALM ATQQFQQLQA AVQDDLREVE KSISNLEKSL TSLSEVVLQN  540
RRGLDLLFLK EGGLCAALKE ECCFYADHTG LVRDSMAKLR ERLNQRQKLF ESTQGWFEGL  600
FNRSPWFTTL ISTIMGPLIV LLMILLFGPC ILNRLVQFVK DRISVVQALV LTQQYHQLKP  660
IEYEP                                                             665

SEQ ID NO: 18           moltype = AA  length = 645
FEATURE                 Location/Qualifiers
source                  1..645
                        mol_type = protein
                        organism = Murine leukemia virus
SEQUENCE: 18
MARSTLSKPL KDKINPWKSL MVMGVLLRVG MAESPHQVFN VTWRVTNLMT GRTANATSLL   60
GTVQDAFPRL YFDLCDLVGE EWDPSDQEPY VGYGCKYPGG RKRTRTFDFY VCPGHTVKSG  120
CGGPREGYCG EWGCETTGQA YWKPTSSWDL ISLKRGNTPW DTGCSKMACG PCYDLSKVSN  180
SFQGATRGGR CNPLVLEFTD AGKKANWDGP KSWGLRLYRT GTDPITMFSL TRQVLNIGPR  240
IPIGPNPVIT GQLPPSRPVQ IRLPRPPQPP PTGAASIVPE TAPPSQQPGT GDRLLNLVEG  300
AYRALNLTNP DKTQECWLCL VSGPPYYEGV AVVGTYTNHS TAPASCTATS QHKLTLSEVT  360
GQGLCMGAVP KTHQALCNTT QSAGSGSYYL AAPAGTMWAC STGLTPCLST TMLNLTTDYC  420
VLVELWPRII YHSPDYMYGQ LEQRTKYKRE PVSLTLALLL GGLTMGGIAA GIGTGTTALI  480
KTQQFEQLHA AIQTDLNEVE KSITNLEKSL TSLSEVVLQN RRGLDLLFLK EGGLCAALKE  540
ECCFYADHTG LVRDSMAKLR ERLNQRQKLF ESGQGWFEGL FNRSPWFTTL ISTIMGPLIV  600
LLLILLFGPC ILNRLVQFVK DRISVVQALV LTQQYHQLKP IEYEP                 645

SEQ ID NO: 19           moltype = AA  length = 1710
FEATURE                 Location/Qualifiers
REGION                  1..1710
                        note = Description of Artificial Sequence:
                        Syntheticpolypeptide
source                  1..1710
                        mol_type = protein
                        organism = synthetic construct
SEQUENCE: 19
MSSETGPVAV DPTLRRRIEP HEFEVFFDPR ELRKETCLLY EINWGGRHSI WRHTSQNTNK   60
HVEVNFIEKF TTERYFCPNT RCSITWFLSW SPCGECSRAI TEFLSRYPHV TLFIYIARLY  120
HHADPRNRQG LRDLISSGVT IQIMTEQESG YCWRNFVNYS PSNEAHWPRY PHLWVRLYVL  180
ELYCIILGLP PCLNILRRKQ PQLTFFTIAL QSCHYQRLFP HILWATGLKS GSETPGTSES  240
ATPESDKKYS IGLAIGTNSV GWAVITDEYK VPSKKFKVLG NTDRHSIKKN LIGALLFDSG  300
ETAEATRLKR TARRRYTRRK NRICYLQEIF SNEMAKVDDS FPHRLEESFL VEEDKKHERH  360
PIFGNIVDEV AYHEKYPTIY HLRKKLVDST DKADLRLIYL ALAHMIKFRG HFLIEGDLNP  420
DNSDVDKLFI QLVQTYNQLF EENPINASGV DAKAILSARL SKSRRLENLI AQLPGEKKNG  480
LFGNLIALSL GLTPNFKSNF DLAEDAKLQL SKDTYDDDLD NLLAQIGDQY ADLFLAAKNL  540
SDAILLSDIL RVNTEITKAP LSASMIKRYD EHHQDLTLLK ALVRQQLPEK YKEIFFDQSK  600
NGYAGYIDGG ASQEEFYKFI KPILEKMDGT EELLVKLNRE DLLRKQRTFD NGSIPHQIHL  660
GELHAILRRQ EDFYPFLKDN REKIEKILTF RIPYYVGPLA RGNSRFAWMT RKSEETITPW  720
NFEEVVDKGA SAQSFIERMT NFDKNLPNEK VLPKHSLLYE YFTVYNELTK VKYVTEGMRK  780
PAFLSGEQKK AIVDLLFKTN RKVTVKQLKE DYFKKIECFD SVEISGVEDR FNASLGTYHD  840
LLKIIKDKDF LDNEENEDIL EDIVLTLTLF EDREMIEERL KTYAHLFDDK VMKQLKRRRY  900
TGWGRLSRKL INGIRDKQSG KTILDFLKSD GFANRNFMQL IHDDSLTFKE DIQKAQVSGQ  960
GDSLHEHIAN LAGSPAIKKG ILQTVKVVDE LVKVMGRHKP ENIVIEMARE NQTTQKGQKN 1020
SRERMKRIEE GIKELGSQIL KEHPVENTQL QNEKLYLYYL QNGRDMYVDQ ELDINRLSDY 1080
DVDHIVPQSF LKDDSIDNKV LTRSDKNRGK SDNVPSEEVV KKMKNYWRQL LNAKLITQRK 1140
FDNLTKAERG GLSELDKAGF IKRQLVETRQ ITKHVAQILD SRMNTKYDEN DKLIREVKVI 1200
TLKSKLVSDF RKDFQFYKVR EINNYHHAHD AYLNAVVGTA LIKKYPKLES EFVYGDYKVY 1260
DVRKMIAKSE QEIGKATAKY FFYSNIMNFF KTEITLANGE IRKRPLIETN GETGEIVWDK 1320
GRDFATVRKV LSMPQVNIVK KTEVQTGGFS KESILPKRNS DKLIARKKDW DPKKYGGFDS 1380
PTVAYSVLVV AKVEKGKSKK LKSVKELLGI TIMERSSFEK NPIDFLEAKG YKEVKKDLII 1440
```

```
KLPKYSLFEL ENGRKRMLAS AGELQKGNEL ALPSKYVNFL YLASHYEKLK GSPEDNEQKQ    1500
LFVEQHKHYL DEIIEQISEF SKRVILADAN LDKVLSAYNK HRDKPIREQA ENIIHLFTLT    1560
NLGAPAAFKY FDTTIDRKRY TSTKEVLDAT LIHQSITGLY ETRIDLSQLG GDSGGSTNLS    1620
DIIEKETGKQ LVIQESILML PEEVEEVIGN KPESDILVHT AYDESTDENV MLLTSDAPEY    1680
KPWALVIQDS NGENKIKMLS GGSPKKKRKV                                    1710

SEQ ID NO: 20            moltype = AA   length = 198
FEATURE                  Location/Qualifiers
source                   1..198
                         mol_type = protein
                         organism = Homo sapiens
SEQUENCE: 20
MDSLLMNRRK FLYQFKNVRW AKGRRETYLC YVVKRRDSAT SFSLDFGYLR NKNGCHVELL    60
FLRYISDWDL DPGRCYRVTW FTSWSPCYDC ARHVADFLRG NPNLSLRIFT ARLYFCEDRK    120
AEPEGLRRLH RAGVQIAIMT FKDYFYCWNT FVENHERTFK AWEGLHENSV RLSRQLRRIL    180
LPLYEVDDLR DAFRTLGL                                                 198

SEQ ID NO: 21            moltype = AA   length = 191
FEATURE                  Location/Qualifiers
REGION                   1..191
                         note = Description of Artificial Sequence:
                         Syntheticpolypeptide
source                   1..191
                         mol_type = protein
                         organism = synthetic construct
SEQUENCE: 21
LMDPHIFTSN FNNGIGRHKT YLCYEVERLD SATSFSLDFG YLRNKNGCHV ELLFLRYISD    60
WDLDPGRCYR VTWFTSWSPC YDCARHVADF LRGNPNLSLR IFTARLYFCE DRKAEPEGLR    120
RLHRAGVQIA IMTFKDYFYC WNTFVENHER TFKAWEGLHE NSVRLSRQLR RILLPLYEVD    180
DLRDAFRTLG L                                                        191

SEQ ID NO: 22            moltype = AA   length = 175
FEATURE                  Location/Qualifiers
REGION                   1..175
                         note = Description of Artificial Sequence:
                         Syntheticpolypeptide
source                   1..175
                         mol_type = protein
                         organism = synthetic construct
SEQUENCE: 22
MDPHIFTSNF NNGIGRHKTY LCYEVERLDS ATSFSLDFGY LRNKNGCHVE LLFLRYISDW    60
DLDPGRCYRV TWFTSWSPCY DCARHVADFL RGNPNLSLRI FTARLYFCED RKAEPEGLRR    120
LHRAGVQIAI MTFKDYFYCW NTFVENHERT FKAWEGLHEN SVRLSRQLRR ILLPL         175

SEQ ID NO: 23            moltype = AA   length = 229
FEATURE                  Location/Qualifiers
source                   1..229
                         mol_type = protein
                         organism = Rattus norvegicus
SEQUENCE: 23
MSSETGPVAV DPTLRRRIEP HEFEVFFDPR ELRKETCLLY EINWGGRHSI WRHTSQNTNK    60
HVEVNFIEKF TTERYFCPNT RCSITWFLSW SPCGECSRAI TEFLSRYPHV TLFIYIARLY    120
HHADPRNRQG LRDLISSGVT IQIMTEQESG YCWRNFVNYS PSNEAHWPRY PHLWVRLYVL    180
ELYCIILGLP PCLNILRRKQ PQLTFFTIAL QSCHYQRLPP HILWATGLK                229

SEQ ID NO: 24            moltype = AA   length = 397
FEATURE                  Location/Qualifiers
source                   1..397
                         mol_type = protein
                         organism = Mus musculus
SEQUENCE: 24
MGPFCLGCSH RKCYSPIRNL ISQETFKFHF KNLGYAKGRK DTFLCYEVTR KDCDSPVSLH    60
HGVFKNKDNI HAEICFLYWF HDKVLKVLSP REEFKITWYM SWSPCFECAE QIVRFLATHH    120
NLSLDIFSSR LYNVQDPETQ QNLCRLVQEG AQVAAMDLYE FKKCWKKFVD NGGRRFRPWK    180
RLLTNFRYQD SKLQEILRRM DPLSEEEFYS QFYNQRVKHL CYYHRMKPYL CYQLEQFNGQ    240
APLKGCLLSE KGKQHAEILF LDKIRSMELS QVTITCYLTW SPCPNCAWQL AAFKRDRPDL    300
ILHIYTSRLY FHWKRPFQKG LCSLWQSGIL VDVMDLPQFT DCWTNFVNPK RPFRPWKGLE    360
IISRRTQRRL RRIKESWGLQ DLVNDFGNLQ LGPPMSN                             397

SEQ ID NO: 25            moltype = AA   length = 199
FEATURE                  Location/Qualifiers
source                   1..199
                         mol_type = protein
                         organism = Mus musculus
SEQUENCE: 25
MGPFCLGCSH RKCYSPIRNL ISQETFKFHF KNLGYAKGRK DTFLCYEVTR KDCDSPVSLH    60
HGVFKNKDNI HAEICFLYWF HDKVLKVLSP REEFKITWYM SWSPCFECAE QIVRFLATHH    120
NLSLDIFSSR LYNVQDPETQ QNLCRLVQEG AQVAAMDLYE FKKCWKKFVD NGGRRFRPWK    180
RLLTNFRYQD SKLQEILRR                                                199
```

```
SEQ ID NO: 26            moltype = AA   length = 199
FEATURE                  Location/Qualifiers
source                   1..199
                         mol_type = protein
                         organism = Homo sapiens
SEQUENCE: 26
MEASPASGPR HLMDPHIFTS NFNNGIRHK  TYLCYEVERL DNGTSVKMDQ HRGFLHNQAK   60
NLLCGFYGRH AELRFLDLVP SLQLDPAQIY RVTWFISWSP CFSWGCAGEV RAFLQENTHV  120
RLRIFAARIY DYDPLYKEAL QMLRDAGAQV SIMTYDEFKH CWDTFVDHQG CPFQPWDGLD  180
EHSQALSGRL RAILQNQGN                                               199

SEQ ID NO: 27            moltype = AA   length = 384
FEATURE                  Location/Qualifiers
source                   1..384
                         mol_type = protein
                         organism = Homo sapiens
SEQUENCE: 27
MKPHFRNTVE RMYRDTFSYN FYNRPILSRR NTVWLCYEVK TKGPSRPPLD AKIFRGQVYS   60
ELKYHPEMRF FHWFSKWRKL HRDQEYEVTW YISWSPCTKC TRDMATFLAE DPKVTLTIFV  120
ARLYYFWDPD YQEALRSLCQ KRDGPRATMK IMNYDEFQHC WSKFVYSQRE LFEPWNNLPK  180
YYILLHIMLG EILRHSMDPP TFTFNFNNEP WVRGRHETYL CYEVERMHND TWVLLNQRPG  240
FLCNQAPHKH GFLEGRHAEL CFLDVIPFWK LDLDQDYRVT CFTSWSPCFS CAQEMAKFIS  300
KNKHVSLCIF TARIYDDQGR CQEGLRTLAE AGAKISIMTY SEFKHCWDTF VDHQGCPFQP  360
WDGLDEHSQD LSGRLRAILQ NQEN                                         384

SEQ ID NO: 28            moltype = AA   length = 186
FEATURE                  Location/Qualifiers
source                   1..186
                         mol_type = protein
                         organism = Homo sapiens
SEQUENCE: 28
PPTFTFNFNN EPWVRGRHET YLCYEVERMH NDTWVLLNQR RGFLCNQAPH KHGFLEGRHA   60
ELCFLDVIPF WKLDLDQDYR VTCFTSWSPC FSCAQEMAKF ISKNKHVSLC IPTARIYDDQ  120
GRCQEGLRTL AEAGAKISIM TYSEFKHCWD TFVDHQGCPF QPWDGLDEHS QDLSGRLRAI  180
LQNQEN                                                             186

SEQ ID NO: 29            moltype = AA   length = 200
FEATURE                  Location/Qualifiers
source                   1..200
                         mol_type = protein
                         organism = Homo sapiens
SEQUENCE: 29
MALLTAETFR LQFNNKRRLR RPYYPRKALL CYQLTPQNGS TPTRGYFENK KKCHAEICFI   60
NEIKSMGLDE TQCYQVTCYL TWSPCSSCAW ELVDFIKAHD HLNLGIFASR LYYHWCKPQQ  120
KGLRLLCGSQ VPVEVMGFPK FADCWENFVD HEKPLSFNPY KMLEELDKNS RAIKRRLERI  180
KIPGVRAQGR YMDILCDAEV                                              200

SEQ ID NO: 30            moltype = AA   length = 373
FEATURE                  Location/Qualifiers
source                   1..373
                         mol_type = protein
                         organism = Homo sapiens
SEQUENCE: 30
MKPHFRNTVE RMYRDTFSYN FYNRPILSRR NTVWLCYEVK TKGPSRPRLD AKIFRGQVYS   60
QPEHHAEMCF LSWFCGNQLP AYKCFQITWF VSWTPCPDCV AKLAEFLAEH PNVTLTISAA  120
RLYYYWERDY RRALCRLSQA GARVKIMDDE EFAYCWENFV YSEGQPFMPW YKFDDNYAFL  180
HRTLKEILRN PMEAMYPHIF YFHFKNLRKA YGRNESWLCF TMEVVKHHSP VSWKRGVFRN  240
QVDPETHCHA ERCFLSWFCD DILSPNTNYE VTWYTSWSPC PECAGEVAEF LARHSNVNLT  300
IFTARLYYFW DTDYQEGLRS LSQEGASVEI MGYKDFKYCW ENFVYNDDEP FKPWKGLKYN  360
FLFLDSKLQE ILE                                                     373

SEQ ID NO: 31            moltype = AA   length = 189
FEATURE                  Location/Qualifiers
source                   1..189
                         mol_type = protein
                         organism = Homo sapiens
SEQUENCE: 31
KEILRNPMEA MYPHIFYFHF KNLRKAYGRN ESWLCFTMEV VKHHSPVSWK RGVFRNQVDP   60
ETHCHAERCF LSWFCDDILS PNTNYEVTWY TSWSPCPECA GEVAEFLARH SNVNLTIFTA  120
RLYYFWDTDY QEGLRSLSQE GASVEIMGYK DFKYCWENFV YNDDEPFKPW KGLKYNFLFL  180
DSKLQEILE                                                          189

SEQ ID NO: 32            moltype = AA   length = 383
FEATURE                  Location/Qualifiers
source                   1..383
                         mol_type = protein
                         organism = Escherichia coli
SEQUENCE: 32
```

```
MKRTADGSEF ESPKKKRKVS EVEFSHEYWM RHALTLAKRA WDEREVPVGA VLVHNNRVIG     60
EGWNRPIGRH DPTAHAEIMA LRQGGLVMQN YRLIDATLYV TLEPCVMCAG AMIHSRIGRV    120
VFGARDAKTG AAGSLMDVLH HPGMNHRVEI TEGILADECA ALLSDFFRMR RQEIKAQKKA    180
QSSTDSGGSS GGSSGSETPG TSESATPESS GGSSGGSSEV EFSHEYWMRH ALTLAKRARD    240
EREVPVGAVL VLNNRVIGEG WNRAIGLHDP TAHAEIMALR QGGLVMQNYR LIDATLYVTF    300
EPCVMCAGAM IHSRIGRVVF GVRNAKTGAA GSLMDVLHYP GMNHRVEITE GILADECAAL    360
LCYFFRMPRQ VFNAQKKAQS STD                                           383

SEQ ID NO: 33           moltype = AA   length = 1226
FEATURE                 Location/Qualifiers
source                  1..1226
                        mol_type = protein
                        organism = Homo sapiens
SEQUENCE: 33
MNPRQGYSLS GYYTHPFQGY EHRQLRYQQP GPGSSPSSFL LKQIEFLKGQ LPEAPVIGKQ     60
TPSLPPSLPG LRPRFPVLLA SSTRGRQVDI RGVPRGVHLG SQGLQRGFQH PSPRGRSLPQ    120
RGVDCLSSHF QELSIYQDQE QRILKFLEEL GEGKATTAHD LSGKLGTPKK EINRVLYSLA    180
KKGKLQKEAG TPPLWKIAVS TQAWNQHSGV VRPDGHSQGA PNSDPSLEPE DRNSTSVSED    240
LLEPFIAVSA QAWNQHSGVV RPDSHSQGSP NSDPGLEPED SNSTSALEDP LEFLDMAEIK    300
EKICDYLFNV SDSSALNLAK NIGLTKARDI NAVLIDMERQ GDVYRQGTTP PIWHLTDKKR    360
ERMQIKRNTN SVPETAPAAI PETKRNAEFL TCNIPTSNAS NNMVTTEKVE NGQEPVIKLE    420
NRQEARPEPA RLKPPVHYNG PSKAGYVDFE NGQWATDDIP DDLNSIRAAP GEFRAIMEMP    480
SFYSHGLPRC SPYKKLTECQ LKNPISGLLE YAQFASQTCE FNMIEQSGPP HEPRFKFQVV    540
INGREFPPAE AGSKKVAKQD AAMKAMTILL EEAKAKDSGK SEESSHYSTE KESEKTAESQ    600
TPTPSATSFF SGKSPVTTLL ECMHKLGNSC EFRLLSKEGP AHEPKFQYCV AVGAQTFPSV    660
SAPSKKVAKQ MAAEEAMKAL HGEATNSMAS DNQPEGMISE SLDNLESMMP NKVRKIGELV    720
RYLNTNPVGG LLEYARSHGF AAEFKLVDQS GPPHEPKFVY QAKVGGRWFP AVCAHSKKQG    780
KQEAADAALR VLIGENEKAE RMGFTEVTPV TGASLRRTML LLSRSPEAQP KTLPLTGSTF    840
HDQIAMLSHR CFNTLTNSFQ PSLLGRKILA AIIMKKDSED MGVVVSLGTG NRCVKGDSLS    900
LKGETVNDCH AEIISRRGFI RFLYSELMKY NSQTAKDSIF EPAKGGEKLQ IKKTVSFHLY    960
ISTAPCGDGA LFDKSCSDRA MESTESRHYP VFENPKQGKL RTKVENGEGT IPVESSDIVP   1020
TWDGIRLGER LRTMSCSDKI LRWNVLGLQG ALLTHFLQPI YLKSVTLGYL FSQGHLTRAI   1080
CCRVTRDGSA FEDGLRHPFI VNHPKVGRVS IYDSKRQSGK TKETSVNWCL ADGYDLEILD   1140
GTRGTVDGPR NELSRVSKKN IFLLFKKLCS FRYRRDLLRL SYGEAKKAAR DYETAKNYFK   1200
KGLKDMGYGN WISKPQEEKN FYLCPV                                       1226

SEQ ID NO: 34           moltype = AA   length = 1419
FEATURE                 Location/Qualifiers
source                  1..1419
                        mol_type = protein
                        organism = Streptococcus pyogenes
SEQUENCE: 34
MDKKYSIGLD IGTNSVGWAV ITDEYKVPSK KFKVLGNTDR HSIKKNLIGA LLFDSGETAE     60
ATRLKRTARR RYTRRKNRIC YLQEIFSNEM AKVDDSFFHR LEESFLVEED KKHERHPIFG    120
NIVDEVAYHE KYPTIYHLRK KLVDSTDKAD LRLIYLALAH MIKFRGHFLI EGDLNPDNSD    180
VDKLFIQLVQ TYNQLFEENP INASGVDAKA ILSARLSKSR RLENLIAQLP GEKKNGLFGN    240
LIALSLGLTP NFKSNFDLAE DAKLQLSKDT YDDDLDNLLA QIGDQYADLF LAAKNLSDAI    300
LLSDILRVNT EITKAPLSAS MIKRYDEHHQ DLTLLKALVR QQLPEKYKEI FFDQSKNGYA    360
GYIDGGASQE EFYKFIKPIL EKMDGTEELL VKLNREDLLR KQRTFDNGSI PHQIHLGELH    420
AILRRQEDFY PFLKDNREKI EKILTFRIPY YVGPLARGNS RFAWMTRKSE ETITPWNFEE    480
VVDKGASAQS FIERMTNFDK NLPNEKVLPK HSLLYEYFTV YNELTKVKYV TEGMRKPAFL    540
SGEQKKAIVD LLFKTNRKVT VKQLKEDYFK KIECFDSVEI SGVEDRFNAS LGTYHDLLKI    600
IKDKDFLDNE ENEDILEDIV LTLTLFEDRE MIEERLKTYA HLFDDKVMKQ LKRRRYTGWG    660
RLSRKLINGI RDKQSGKTIL DFLKSDGFAN RNFMQLIHDD SLTFKEDIQK AQVSGQGDSL    720
HEHIANLAGS PAIKKGILQT VKVVDELVKV MGRHKPENIV IEMARENQTT QKGQKNSRER    780
MKRIEEGIKE LGSQILKEHP VENTQLQNEK LYLYYLQNGR DMYVDQELDI NRLSDYDVDH    840
IVPQSFLKDD SIDNKVLTRS DKNRGKSDNV PSEEVVKKMK NYWRQLLNAK LITQRKFDNL    900
TKAERGGLSE LDKAGFIKRQ LVETRQITKH VAQILDSRMN TKYDENDKLI REVKVITLKS    960
KLVSDFRKDF QFYKVREINN YHHAHDAYLN AVVGTALIKK YPKLESEFVY GDYKVYDVRK   1020
MIAKSEQEIG KATAKYFFYS NIMNFFKTEI TLANGEIRKR PLIETNGETG EIVWDKGRDF   1080
ATVRKVLSMP QVNIVKKTEV QTGGFSKESI LPKRNSDKLI ARKKDWDPKK YGGFDSPTVA   1140
YSVLVVAKVE KGKSKKLKSV KELLGITIME RSSFEKNPID FLEAKGYKEV KKDLIIKLPK   1200
YSLFELENGR KRMLASAGEL QKGNELALPS KYVNFLYLAS HYEKLKGSPE DNEQKQLFVE   1260
QHKHYLDEII EQISEFSKRV ILADANLDKV LSAYNKHRDK PIREQAENII HLFTLTNLGA   1320
PAAFKYFDTT IDRKRYTSTK EVLDATLIHQ SITGLYETRI DLSQLGGDGS GGGGSGKRTA   1380
DGSEFEPKKK RKVSSGGDYK DHDGDYKDHD IDYKDDDDK                         1419

SEQ ID NO: 35           moltype = AA   length = 1053
FEATURE                 Location/Qualifiers
source                  1..1053
                        mol_type = protein
                        organism = Staphylococcus aureus
SEQUENCE: 35
MKRNYILGLD IGITSVGYGI IDYETRDVID AGVRLFKEAN VENNEGRRSK RGARRLKRRR     60
RHRIQRVKKL LFDYNLLTDH SELSGINPYE ARVKGLSQKL SEEEFSAALL HLAKRRGVHN    120
VNEVEEDTGN ELSTKEQISR NSKALEEKYV AELQLERLKK DGEVRGSINR FKTSDYVKEA    180
KQLLKVQKAY HQLDQSFIDT YIDLLETRRT YYEGPGEGSP FGWKDIKEWY EMLMGHCTYF    240
PEELRSVKYA YNADLYNALN DLNNLVITRD ENEKLEYYEK FQIIENVFKQ KKKPTLKQIA    300
KEILVNEEDI KGYRVTSTGK PEFTNLKVYH DIKDITARKE IIENAELLDQ IAKILTIYQS    360
```

```
SEDIQEELTN LNSELTQEEI EQISNLKGYT GTHNLSLKAI NLILDELWHT NDNQIAIFNR   420
LKLVPKKVDL SQQKEIPTTL VDDFILSPVV KRSFIQSIKV INAIIKKYGL PNDIIIELAR   480
EKNSKDAQKM INEMQKRNRQ TNERIEEIIR TTGKENAKYL IEKIKLHDMQ EGKCLYSLEA   540
IPLEDLLNNP FNYEVDHIIP RSVSFDNSFN NKVLVKQEEN SKKGNRTPFQ YLSSSDSKIS   600
YETFKKHILN LAKGKGRISK TKKEYLLEER DINRFSVQKD FINRNLVDTR YATRGLMNLL   660
RSYFRVNNLD VKVKSINGGF TSFLRRKWKF KKERNKGYKH HAEDALIIAN ADFIFKEWKK   720
LDKAKKVMEN QMFEEKQAES MPEIETEQEY KEIFITPHQI KHIKDFKDYK YSHRVDKKPN   780
RELINDTLYS TRKDDKGNTL IVNNLNGLYD KDNDKLKKLI NKSPEKLLMY HHDPQTYQKL   840
KLIMEQYGDE KNPLYKYYEE TGNYLTKYSK KDNGPVIKKI KYYGNKLNAH LDITDDYPNS   900
RNKVVKLSLK PYRFDVYLDN GVYKFVTVKN LDVIKKENYY EVNSKCYEEA KKLKKISNQA   960
EFIASFYNND LIKINGELYR VIGVNNDLLN RIEVNMIDIT YREYLENMND KRPPRIIKTI   1020
ASKTQSIKKY STDILGNLYE VKSKKHPQII KKG                                1053

SEQ ID NO: 36           moltype = AA  length = 984
FEATURE                 Location/Qualifiers
source                  1..984
                        mol_type = protein
                        organism = Campylobacter jejuni
SEQUENCE: 36
MARILAFDIG ISSIGWAFSE NDELKDCGVR IFTKVENPKT GESLALPRRL ARSARKRLAR   60
RKARLNHLKH LIANEFKLNY EDYQSFDESL AKAYKGSLIS PYELRFRALN ELLSKQDFAR   120
VILHIAKRRG YDDIKNSDDK EKGAILKAIK QNEEKLANYQ SVGEYLYKEY FQKFKENSKE   180
FTNVRNKKES YERCIAQSFL KDELKLIFKK QREFGFSFSK KFEEEVLSVA FYKRALKDFS   240
HLVGNCSFFT DEKRAPKNSP LAFMFVALTR IINLLNNLKN TEGILYTKDD LNALLNEVLK   300
NGTLTYKQTK KLLGLSDDYE FKGEKGTYFI EFKKYKEFIK ALGEHNLSQD DLNEIAKDIT   360
LIKDEIKLKK ALAKYDLNQN QIDSLSKLEF KDHLNIVKLT VKTVPLMLE GKKYDEACNE   420
LNLKVAINED KKDFLPAFNE TYYKDEVTNP VVLRAIKEYR KVLNALLKKY GKVHKINIEL   480
AREVGKNHSQ RAKIEKEQNE NYKAKKDAEL ECEKLGLKIN SKNILKLRLF KEQKEFCAYS   540
GEKIKISDLQ DEKMLEIDHI YPYSRSFDDS YMNKVLVFTK QNQEKLNQTP FEAFGNDSAK   600
WQKIEVLAKN LPTKKQKRIL DKNYKDKEQK NFKDRNLNDT RYIARLVLNY TKDYLDFLPL   660
SDDENTKLND TQKGSKVHVE AKSGMLTSAL RHTWGFSAKD RNNHLHHAID AVIIAYANNS   720
IVKAFSDFKK EQESNSAELY AKKISELDYK NKRKFFEPPS GFRQKVLDKI DEIFVSKPER   780
KKPSGALHEE TFRKEEEFYQ SYGGKEGVLK ALELGKIRKV NGKIVKNGDM FRVDIFKHKK   840
TNKFYAVPIY TMDFALKVLP NKAVARSKKG EIKDWILMDE NYEFCFSLYK DSLILIQTKD   900
MQEPEPEFVYYN AFTSSTVSLI VSKHDNKFET LSKNQKILFK NANEKEVIAK SIGIQNLKVF   960
EKYIVSALGE VTKAEFRQRE DFKK                                          984

SEQ ID NO: 37           moltype = AA  length = 1082
FEATURE                 Location/Qualifiers
source                  1..1082
                        mol_type = protein
                        organism = Neisseria meningitidis
SEQUENCE: 37
MAAFKPNSIN YILGLDIGIA SVGWAMVEID EEENPIRLID LGVRVFERAE VPKTGDSLAM   60
ARRLARSVRR LTRRRAHRLL RTRRLLKREG VLQAANFDEN GLIKSLPNTP WQLRAAALDR   120
KLTPLEWSAV LLHLIKHRGY LSQRKNEGET ADKELGALLK GVAGNAHALQ TGDFRTPAEL   180
ALNKFEKESG HIRNQRSDYS HTFSRKDLQA ELILLFEKQK EFGNPHVSGG LKEGIETLLM   240
TQRPALSGDA VQKMLGHCTF EPAEPKAAKN TYTAERFIWL TKLNNLRILE QGSERPLTDT   300
ERATLMDEPY RKSKLTYAQA RKLLGLEDTA FFKGLRYGKD NAEASTLMEM KAYHAISRAL   360
EKEGLKDKKS PLNLSPELQD EIGTAFSLFK TDEDITGRLK DRIQPEILEA LLKHISFDKF   420
VQISLKALRR IVPLMEQGKR YDEACAEIYG DHYGKKNTEE KIYLPPIPAD EIRNPVVLRA   480
LSQARKVING VVRRYGSPAR IHIETAREVG KSFKDRKEIE KRQEENRKDR EKAAAKFREY   540
FPNFVGEPKS KDILKLRLYE QQHGKCLYSG KEINLGRLNE KGYVEIDHAL PFSRTWDDSF   600
NNKVLVLGSE NQNKGNQTPY EYFNGKDNSR EWQEFKARVE TSRFPRSKKQ RILLQKFDED   660
GFKERNLNDT RYVNRFLCQF VADRMRLTGK GKKRVFASNG QITNLLRGFW GLRKVRAEND   720
RHHALDAVVV ACSTVAMQQK ITRFVRYKEM NAFDGKTIDK ETGEVLHQKT HFPQPWEFFA   780
QEVMIRVFGK PDGKPEFEEA DTLEKLRTLL AEKLSSRPEA VHEYVTPLFV SRAPNRKMSG   840
QGHMETVKSA KRLDEGVSVL RVPLTQLKLK DLEKMVNRER EPKLYEALKA RLEAHKDDPA   900
KAFAEPFYKY DKAGNRTQQV KAVRVEQVQK TGVWVRNHNG IADNATMVRV DVFEKGKYY    960
LVPIYSWQVA KGILPDRAVV QGKDEEDWQL IDDSFNFKFS LHPNDLVEVI TKKARMFGYF   1020
ASCHRGTGNI NIRIHDLDHK IGKNGILEGI GVKTALSFQK YQIDELGKEI RPCRLKKRPP   1080
VR                                                                  1082

SEQ ID NO: 38           moltype = AA  length = 1307
FEATURE                 Location/Qualifiers
source                  1..1307
                        mol_type = protein
                        organism = Acidaminococcus sp.
SEQUENCE: 38
MTQFEGFTNL YQVSKTLRFE LIPQGKTLKH IQEQGFIEED KARNDHYKEL KPIIDRIYKT   60
YADQCLQLVQ LDWENLSAAI DSYRKEKTEE TRNALIEEQA TYRNAIHDYF IGRTDNLTDA   120
INKRHAEIYK GLFKAELFNG KVLKQLGTVT TTEHENALLR SFDKFTTYFS GFYENRKNVF   180
SAEDISTAIP HRIVQDNFPK FKENCHIFTR LITAVPSLRE HFENVKKAIG IFVSTSIEEV   240
FSFPFYNQLL TQTQIDLYNQ LLGGISREAG TEKIKGLNEV LNLAIQKNDE TAHIIASLPH   300
RFIPLFKQIL SDRNTLSFIL EEFKSDEEVI QSFCKYKTLL RNENVLETAE ALFNELNSID   360
LTHIFISHKK LETISSALCD HWDTLRNALY ERRISELTGK ITKSAKEVQ RSLKHEDINL   420
QEIISAAGKE LSEAFKQKTS EILSHAHAAL DQPLPTTLKK QEEKEILKSQ LDSLLGLYHL   480
LDWFAVDESN EVDPEFSARL TGIKLEMEPS LSFYNKARNY ATKKPYSVEK FKLNFQMPTL   540
ASGWDVNKEK NNGAILFVKN GLYYLGIMPK QKGRYKALSF EPTEKTSEGF DKMYYDYFPD   600
```

```
AAKMIPKCST QLKAVTAHFQ THTTPILLSN NFIEPLEITK EIYDLNNPEK EPKKFQTAYA   660
KKTGDQKGYR EALCKWIDFT RDFLSKYTKT TSIDLSSLRP SSQYKDLGEY YAELNPLLYH   720
ISFQRIAEKE IMDAVETGKL YLFQIYNKDF AKGHHGKPNL HTLYWTGLFS PENLAKTSIK   780
LNGQAELFYR PKSRMKRMAH RLGEKMLNKK LKDQKTPIPD TLYQELYDYV NHRLSHDLSD   840
EARALLPNVI TKEVSHEIIK DRRFTSDKFF FHVPITLNYQ AANSPSKFNQ RVNAYLKEHP   900
ETPIIGIDRG ERNLIYITVI DSTGKILEQR SLNTIQQFDY QKKLDNREKE RVAARQAWSV   960
VGTIKDLKQG YLSQVIHEIV DLMIHYQAVV VLENLNFGFK SKRTGIAEKA VYQQFEKMLI  1020
DKLNCLVLKD YPAEKVGGVL NPYQLTDQFT SFAKMGTQSG FLFYVPAPYT SKIDPLTGFV  1080
DPFVWKTIKN HESRKHFLEG FDFLHYDVKT GDFILHFKMN RNLSFQRGLP GPMPAWDIVF  1140
EKNETQFDAK GTPFIAGKRI VPVIENHRFT GRYRDLYPAN ELIALLEEKG IVFRDGSNIL  1200
PKLLENDDSH AIDTMVALIR SVLQMRNSNA ATGEDYINSP VRDLNGVCFD SRFQNPEWPM  1260
DADANGAYHI ALKGQLLLNH LKESKDLKLQ NGISNQDWLA YIQELRN                1307

SEQ ID NO: 39          moltype = AA   length = 1228
FEATURE                Location/Qualifiers
REGION                 1..1228
                       note = Description of Unknown:Lachnospiraceae bacterium
                        sequence
source                 1..1228
                       mol_type = protein
                       organism = unidentified
SEQUENCE: 39
MSKLEKFTNC YSLSKTLRFK AIPVGKTQEN IDNKRLLVED EKRAEDYKGV KKLLDRYYLS    60
FINDVLHSIK LKNLNNYISL FRKKTRTEKE NKELENLEIN LRKEIAKAFK GNEGYKSLFK   120
KDIIETILPE FLDDKDEIAL VNSFNGFTTA FTGFFDNREN MFSEEAKSTS IAFRCINENL   180
TRYISNMDIF EKVDAIFDKH EVQEIKEKIL NSDYDVEDFF EGEFFNFVLT QEGIDVYNAI   240
IGGFVTESGE KIKGLNEYIN LYNQKTKQPL PKFKPLYKQV LSDRESLSFY GEGYTSDEEV   300
LEVFRNTLNK NSEIFSSIKK LEKLFKNFDE YSSAGIFVKN GPAISTISKD IPGEWNVIRD   360
KWNAEYDDIH LKKKAVVTEK YEDDRRKSFK KIGSFSLEQL QEYADADLSV VEKLKEIIIQ   420
KVDEIYKVYG SSEKLFDADF VLEKSLKKND AVVAIMKDLL DSVKSFENYI KAFFGEGKET   480
NRDESFYGDF VLAYDILLKV DHIYDAIRNY VTQKPYSKDK FKLYFQNPQF MGGWDKDKET   540
DYRATILRYG SKYYLAIMDK KYAKCLQKID KDDVNGNYEK INYKLLPGPN KMLPKVFFSK   600
KWMAYYNPSE DIQKIYKNGT FKKGDMFNLN DCHKLIDFFK DSISRYPKWS NAYDFNFSET   660
EKYKDIAGFY REVEEQGYKV SFESASKKEV DKLVEEGKLY MFQIYNKDFS DKSHGTPNLH   720
TMYFKLLFDE NNHGQIRLSG GAELFMRRAS LKKEELVVHP ANSPIANKNP DNPKKTTTLS   780
YDVYKDKRFS EDQYELHIPI AINKCPKNIF KINTEVRVLL KHDDNPYVIG IDRGERNLLY   840
IVVVDGKGNI VEQYSLNEII NNFNGIRIKT DYHSLLDKKE KERFEARQNW TSIENIKELK   900
AGYISQVVHK ICELVEKYDA VIALEDLNSG FKNSRVKVEK QVYQKFEKML IDKLNYMVDK   960
KSNPCATGGA LKGYQITNKF ESFKSMSTQN GFIFYIPAWL TSKIDPSTGF VNLLKTKYTS  1020
IADSKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAFYSSFMAL MSLMLQMRNS  1140
ITGRTDVDFL ISPVKNSDGI FYDSRNYEAQ ENAILPKNAD ANGAYNIARK VLWAIGQFKK  1200
AEDEKLDKVK IAISNKEWLE YAQTSVKH                                    1228

SEQ ID NO: 40          moltype = AA   length = 1389
FEATURE                Location/Qualifiers
source                 1..1389
                       mol_type = protein
                       organism = Leptotrichia shahii
SEQUENCE: 40
MGNLFGHKRW YEVRDKKDFK IKRKVKVKRN YDGNKYILNI NENNNKEKID NNKFIRKYIN    60
YKKNDNILKE FTRKFHAGNI LFKLKGKEGI IRIENNDDFL ETEEVVLYIE AYGKSEKLKA   120
LGITKKKIID EAIRQGITKD DKKIEIKRQE NEEEIEIDIR DEYTNKTLND CSIILRIIEN   180
DELETKKSIY EIFKNINMSL YKIIEKIIEN ETEKVFENRY YEEHLREKLL KDDKIDVILT   240
NFMEIREKIK SNLEILGFVK FYLNVGGDKK KSKNKKMLVE KILNINVDLT VEDIADFVIE   300
ELEFWNITKR IEKVKKVNNE FLEKRRNRTY IKSYVLLDKH EKFKIERENK KDKIVKFFVE   360
NIKNNSIKEK IEKILAEFKI DELIKKLEKE LKKGNCDTEI FGIFKKHYKV NFDSKKFSKK   420
SDEEKELYKI IYRYLKGRIE KILVNEQKVR LKKMEKIEIE KILNESILSE KILKRVKQYT   480
LEHIMYLGKL RHNDIDMTTV NTDDFSRLHA KEELDLELIT FFASTNMELN KIFSRENINN   540
DENIDFFGGD REKNYVLDKK ILNSKIKIIR DLDFIDNKNN ITNNFIRKFT KIGTNERNRI   600
LHAISKERDL QGTQDDYNKV INIIQNLKIS DEEVSKALNL DVVFKDKKNI ITKINDIKIS   660
EENNNDIKYL PSFSKVLPEI LNLYRNNPKN EPFDTIETEK IVLNALIYVN KELYKKLILE   720
DDLEENESKN IFLQELKKTL GNIDEIDENI IENYYKNAQI SASKGNNKAI KKYQKKVIEC   780
YIGYLRKNYE ELFDFSDFKM NIQEIKKQIK DINDNKTYER ITVKTSDKTI VINDDFEYII   840
SIFALLNSNA VINKIRNRFF ATSVWLNTSE YQNIIDILDE IMQLNTLRNE CITENWNLNL   900
EEFIQKMKEI EKDFDDFKIQ TKKEIFNNYY EDIKNNILTE FKDDINGCDV LEKKLEKIVI   960
FDDETKFEID KKSNILQDEQ RKLSNINKKD LKKKVDQYIK DKDQEIKSKI LCRIIFNSDF  1020
LKKYKKEIDN LIEDMESENE NKFQEIYYPK ERKNELYIYK KNFLNIGNP NPDKIYGLIS  1080
NDIKMADAKF LFNIDGKNIR KNKISEIDAI LKNLNDKLNG YSKEYKEKYI KKLKENDDFF  1140
AKNIQNKNYK SFEKDYNRVS EYKKIRDLVE FNYLNKIESY LIDINWKLAI QMARFERDMH  1200
YIVNGLRELG IIKLSGYNTG ISRAYPKRNG SDGFYTTTAY YKFFDEESYK KFEKICYGFG  1260
IDLSENSEIN KPENESIRNY ISHFYIVRNP FADYSIAEQI DRVSNLLSYS TRYNNSTYAS  1320
VFEVFKKDVN LDYDELKKKF KLIGNNDILE RLMKPKKVSV LELESYNSDY IKNLIIELLT  1380
KIENTNDTL                                                         1389

SEQ ID NO: 41          moltype = AA   length = 1152
FEATURE                Location/Qualifiers
source                 1..1152
                       mol_type = protein
```

```
                        organism = Leptotrichia wadei
SEQUENCE: 41
MKVTKVDGIS HKKYIEEGKL VKSTSEENRT SERLSELLSI RLDIYIKNPD NASEEENRIR    60
RENLKKFFSN KVLHLKDSVL YLKNRKEKNA VQDKNYSEED ISEYDLKNKN SFSVLKKILL   120
NEDVNSEELE IFRKDVEAKL NKINSLKYSF EENKANYQKI NENNVEKVGG KSKRNIIYDY   180
YRESAKRNDY INNVQEAFDK LYKKEDIEKL FFLIENSKKH EKYKIREYYH KIIGRKNDKE   240
NPAKIIYEEI QNVNNIKELI EKIPDMSELK KSQVFYKYYL DKEELNDKNI KYAFCHFVEI   300
EMSQLLKNYV YKRLSNISND KIKRIFEYQN LKKLIENKLL NKLDTYVRNC GKYNYYLQVG   360
EIATSDFIAR NRQNEAFLRN IIGVSSVAYF SLRNILETEN ENGITGRMRG KTVKNNKGEE   420
KYVSGEVDKI YNENKQNEVK ENLKMFYSYD FNMDNKNEIE DFFANIDEAI SSIAHGIVHF   480
NLELEGKDIF AFKNIAPSEI SKKMFQNEIN EKKLKLKIFK QLNSANVFNY YEKDVIIKYL   540
KNTKFNFVNK NIPFVPSFTK LYNKIEDLRN TLKFFWSVPK DKEEKDAQIY LLKNIYYGEF   600
LNKFVKNSKV FFKITNEVIK INKQRNQKTG HYKYQKFENI EKTVPVEYLA IIQSREMINN   660
QDKEEKNTYI DFIQQIFLKG FIDYLNKNNL KYIESNNNND NNDIFSKIKI KKDNKEKYDK   720
ILKNYEKHNR NKEIPHEINE FVREIKLGKI LKYTENLNMF YLILKLLNHK ELTNLKGSLE   780
KYQSANKEET FSDELELINL LNLDNNRVTE DFELEANEIG KFLDFNENKI KDRKELKKFD   840
TNKIYFDGEN IIKHRAFYNI KKYGMLNLLE KIADKAKYKI SLKELKEYSN KKNEIEKNYT   900
MQQNLHRKYA RPKKDEKFND EDYKEYEKAI GNIQKYTHLK NKVEFNELNL LQGLLLKILH   960
RLVGYTSIWE RDLRFRLKGE FPENHYIEEI FNFDNSKNVK YKSGQIVEKY INFYKELYKD  1020
NVEKRSIYSD KKVKKLKQEK KDLYIANYIA HFNYIPHAEI SLLEVLENLR KLLSYDRKLK  1080
NAIMKSIVDI LKEYGFVATF KIGADKKIEI QTLESEKIVH LKNLKKKKLM TDRNSEELCE  1140
LVKVMFEYKA LE                                                     1152

SEQ ID NO: 42            moltype = AA  length = 175
FEATURE                  Location/Qualifiers
source                   1..175
                         mol_type = protein
                         organism = Homo sapiens
SEQUENCE: 42
MDSGRDFLTL HGLQDDEDLQ ALLKGSQLLK VKSSSWRRER FYKLQEDCKT IWQESRKVMR    60
TPESQLFSIE DIQEVRMGHR TEGLEKFARD VPEDRCFSIV FKDQRNTLDL IAPSPADAQH   120
WVLGLHKIIH HSGSMDQRQK LQHWIHSCLR KADKNKDNKM SFKELQNFLK ELNIQ        175

SEQ ID NO: 43            moltype = AA  length = 168
FEATURE                  Location/Qualifiers
source                   1..168
                         mol_type = protein
                         organism = Homo sapiens
SEQUENCE: 43
MSDVAIVKEG WLHKRGEYIK TWRPRYFLLK NDGTFIGYKE RPQDVDQREA PLNNFSVAQC    60
QLMKTERPRP NTFIIRCLQW TTVIERTFHV ETPEEREEWT TAIQTVADGL KKQEEEEMDF   120
RSGSPSDNSG AEEMEVSLAK PKHRVTMNEF EYLKLLGKGT FGKVDPPV                168

SEQ ID NO: 44            moltype = AA  length = 92
FEATURE                  Location/Qualifiers
source                   1..92
                         mol_type = protein
                         organism = Homo sapiens
SEQUENCE: 44
KMGPVDKRKG LFARRRQLLL TEGPHLYYVD PVNKVLKGEI PWSQELRPEA KNFKTFFVHT    60
PNRTYYLMDP SGNAHKWCRK IQEVWRQRYQ SH                                  92

SEQ ID NO: 45            moltype = AA  length = 38
FEATURE                  Location/Qualifiers
source                   1..38
                         mol_type = protein
                         organism = Human alphaherpesvirus 1
SEQUENCE: 45
PTDALDDFDL DMLPADALDD FDLDMLPADA LDDFDLDM                            38

SEQ ID NO: 46            moltype = AA  length = 53
FEATURE                  Location/Qualifiers
REGION                   1..53
                         note = Description of Artificial Sequence:
                         Syntheticpolypeptide
source                   1..53
                         mol_type = protein
                         organism = synthetic construct
SEQUENCE: 46
GRADALDDFD LDMLGSDALD DFDLDMLGSD ALDDFDLDML GSDALDDFDL DML           53

SEQ ID NO: 47            moltype = AA  length = 261
FEATURE                  Location/Qualifiers
source                   1..261
                         mol_type = protein
                         organism = Homo sapiens
SEQUENCE: 47
SQYLPDTDDR HRIEEKRKRT YETFKSIMKK SPFSGPTDPR PPPRRIAVPS RSSASVPKPA    60
PQPYPFTSSL STINYDEFPT MVFPSGQISQ ASALAPAPPQ VLPQAPAPAP APAMVSALAQ   120
```

```
APAPVPVLAP GPPQAVAPPA PKPTQAGEGT LSEALLQLQF DDEDLGALLG NSTDPAVFTD    180
LASVDNSEFQ QLLNQGIPVA PHTTEPMLME YPEAITRLVT GAQRPPDPAP APLGAPGLPN    240
GLLSGDEDFS SIADMDFSAL L                                             261

SEQ ID NO: 48            moltype = AA  length = 190
FEATURE                  Location/Qualifiers
source                   1..190
                         mol_type = protein
                         organism = Human gammaherpesvirus 8
SEQUENCE: 48
RDSREGMFLP KPEAGSAISD VFEGREVCQP KRIRPFHPPG SPWANRPLPA SLAPTPTGPV    60
HEPVGSLTPA PVPQPLDPAP AVTPEASHLL EDPDEETSQA VKALREMADT VIPQKEEAAI    120
CGQMDLSHPP PRGHLDELTT TLESMTEDLN LDSPLTPELN EILDTFLNDE CLLHAMHIST    180
GLSIFDTSLF                                                          190

SEQ ID NO: 49            moltype = AA  length = 72
FEATURE                  Location/Qualifiers
source                   1..72
                         mol_type = protein
                         organism = Homo sapiens
SEQUENCE: 49
MDAKSLTAWS RTLVTFKDVF VDFTREEWKL LDTAQQIVYR NVMLENYKNL VSLGYQLTKP    60
DVILRLEKGE EP                                                       72

SEQ ID NO: 50            moltype = AA  length = 289
FEATURE                  Location/Qualifiers
source                   1..289
                         mol_type = protein
                         organism = Homo sapiens
SEQUENCE: 50
EASVQVKRVL EKSPGKLLVK MPFQASPGGK GEGGGATTSA QVMVIKRPGR KRKAEADPQA    60
IPKKRGRKPG SVVAAAAAEA KKKAVKESSI RSVQETVLPI KKRKTRETVS IEVKEVVKPL    120
LVSTLGEKSG KGLKTCKSPG RKSKESSPKG RSSSASSPPK KEHHHHHHA ESPKAMPPLL    180
PPPPPPPEPQS SEDPISPPEP QDLSSSICKE EKMPRAGSLE SDGCPKEPAK TQPMVAAAAT   240
TTTTTTTTVA EKYKHRGEGE RKDIVSSSMP RPNREEPVDS RTPVTERVS               289

SEQ ID NO: 51            moltype = AA  length = 718
FEATURE                  Location/Qualifiers
source                   1..718
                         mol_type = protein
                         organism = Homo sapiens
SEQUENCE: 51
LPTCSCLDRV IQKDKGPYYT HLGAGPSVAA VREIMENRYG QKGNAIRIEI VVYTGKEGKS    60
SHGCPIAKWV LRRSSDEEKV LCLVRQRTGH HCPTAVMVVL IMVWDGIPLP MADRLYTELT    120
ENLKSYNGHP TDRRCTLNEN RTCTCQGIDP ETCGASFSFG CSWSMYFNGC KFGRSPSPRR    180
FRIDPSSPLH EKNLEDNLQS LATRLAPIYK QYAPVAYQNQ VEYENVAREC RLGSKEGRPF    240
SGVTACLDFC AHPHRDIHNM NNGSTVVCTL TREDNRSLGV IPQDEQLHVL PLYKLSDTDE    300
FGSKEGMEAK IKSGAIEVLA PRRKKRTCFT QPVPRSGKKR AAMMTEVLAH KIRAVEKKPI    360
PRIKRKNNST TTNNSKPSSL PTLGSNTETV QPEVKSETEP HFILKSSDNT KTYSLMPSAP    420
HPVKEASPGF SWSPKTASAT PAPLKNDATA SCGFSERSST PHCTMPSGRL SGANAAAADG    480
PGISQLGEVA PLPTLSAPVM EPLINSEPST GVTEPLTPHQ PNHQPSFLTS PQDLASSPME    540
EDEQHSEADE PPSDEPLSDD PLSPAEEKLP HIDEYWSDSE HIFLDANIGG VAIAPAHGSV    600
LIECARRELH ATTPVEHPNR NHPTRLSLVF YQHKNLNKPQ HGFELNKIKF EAKEAKNKKM    660
KASEQKDQAA NEGPEQSSEV NELNQIPSHK ALTLTHDNVV TVSPYALTHV AGPYNHWV     718

SEQ ID NO: 52            moltype = AA  length = 912
FEATURE                  Location/Qualifiers
source                   1..912
                         mol_type = protein
                         organism = Homo sapiens
SEQUENCE: 52
MPAMPSSGPG DTSSSAAERE EDRKDGEEQE EPRGKEERQE PSTTARKVGR PGRKRKHPPV    60
ESGDTPKDPA VISKSPSMAQ DSGASELLPN GDLEKRSEPQ PEEGSPAGGQ KGGAPAEGEG    120
AAETLPEASR AVENGCCTPK EGRGAPAEAG KEQKETNIES MKMEGSRGRL RGGLGWESSL    180
RQRPMPRLTF QAGDPYYISK RKRDEWLARW KREAEKKAKV IAGMNAVEEN QGPGESQKVE    240
EASPPAVQQP TDPASPTVAT TPEPVGSDAG DKNATKAGDD EPEYEDGRGF GIGELVWGKL    300
RGFSWWPGRI VSWWMTGRSR AAEGTRWVMW FGDGKFSVVC VEKLMPLSSF CSAFHQATYN    360
KQPMYRKAIY EVLQVASSRA GKLFPVCHDS DESDTAKAVE VQNKPMIEWA LGGFQPSGPK    420
GLEPPEEEKN PYKEVYTDMW VEPEAAAYAP PPPAKKPRKS TAEKPKVKEI IDERTRERLV    480
YEVRQKCRNI EDICISCGSL NVTLEHPLFV GGMCQNCKNC FLECAYQYDD DGYQSYCTIC    540
CGGREVLMCG NNNCCRCFCV ECVDLLVGPG AAQAAIKEDP WNCYMCGHKG TYGLLRRRED    600
WPSRLQMFFA NNHDQEFDPP KVYPPVPAEK RKPIRVLSLF DGIATGLLVL KDLGIQVDRY    660
IASEVCEDSI TVGMVRHQGK IMYVGDVRSV TQKHIQEWGP FDLVIGGSPC NDLSIVNPAR    720
KGLYEGTGRL FFEFYRLLHD ARPKEGDDRP FFWLFENVVA MGVSDKRDIS RFLESNPVMI    780
DAKEVSAAHR ARYFWGNLPG MNRPLASTVN DKLELQECLE HGRIAKFSKV RTITTRSNSI    840
KQGKDQHFPV FMNEKEDILW CTEMERVFGF PVHYTDVSNM SRLARQRLLG RSWSVPVIRH    900
LFAPLKEYFA CV                                                       912

SEQ ID NO: 53            moltype = AA  length = 511
```

```
FEATURE                   Location/Qualifiers
source                    1..511
                          mol_type = protein
                          organism = Indiana vesiculovirus
SEQUENCE: 53
MKCLLYLAFL FIGVNCKFTI VFPHNQKGNW KNVPSNYHYC PSSSDLNWHN DLIGTALQVK    60
MPKSHKAIQA DGWMCHASKW VTTCDFRWYG PKYITHSIRS FTPSVEQCKE SIEQTKQGTW   120
LNPGFPPQSC GYATVTDAEA VIVQVTPHHV LVDEYTGEWV DSQFINGKCS NYICPTVHNS   180
TTWHSDYKVK GLCDSNLISM DITFFSEDGE LSSLGKEGTG FRSNYFAYET GGKACKMQYC   240
KHWGVRLPSG VWFEMADKDL FAAARFPECP EGSSISAPSQ TSVDVSLIQD VERILDYSLC   300
QETWSKIRAG LPISPVDLSY LAPKNPGTGP AFTIINGTLK YFETRYIRVD IAAPILSRMV   360
GMISGTTTER ELWDDWAPYE DVEIGPNGVL RTSSGYKFPL YMIGHGMLDS DLHLSSKAQV   420
FEHPHIQDAA SQLPDDESLF FGDTGLSKNP IELVEGWFSS WKSSIASFFF IIGLIIGLFL   480
VLRVGIHLCI KLKHTKKRQI YTDIEMNRLG K                                  511

SEQ ID NO: 54             moltype = AA  length = 512
FEATURE                   Location/Qualifiers
REGION                    1..512
                          note = Description of Unknown:Baculovirus envelope
                          glycoprotein GP64 sequence
source                    1..512
                          mol_type = protein
                          organism = unidentified
SEQUENCE: 54
MVSAIVLYVL LAAAAHSAFA AEHCNAQMKT GPYKIKNLDI TPPKETLQKD VEITIVETDY    60
NENVIIGYKG YYQAYAYNGG SLDPNTRVEE TMKTLNVGKE DLLMWSIRQQ CEVGEELIDR   120
WGSDSDDCFR DNEGRGQWVK GKELVKRQNN NHFAHHTCNK SWRCGISTSK MYSRLECQDD   180
TDECQVYILD AEGNPINVTV DTVLHRDGVS MILKQKSTFT TRQIKAACLL IKDDKNNPES   240
VTREHCLIDN DIYDLSKNTW NCKFNRCIKR KVEHRVKKRP PTWRHNVRAK YTEGDTATKG   300
DLMHIQEELM YENDLLKMNI ELMHAHINKL NNMLHDLIVS VAKVDERLIG NLMNNSVSST   360
FLSDDTFLLM PCTNPPAHTS NCYNNSIYKE GRWVANTDSS QCIDFSNYKE LAIDDDVEFW   420
IPTIGNTTYH DSWKDASGWS FIAQQKSNLI TTMENTKFGG VGTSLSDITS MAEGELAAKL   480
TSFMFGHVVN FVIILIVILF LYCMIRNRNR QY                                 512

SEQ ID NO: 55             moltype = AA  length = 856
FEATURE                   Location/Qualifiers
source                    1..856
                          mol_type = protein
                          organism = Human immunodeficiency virus 1
SEQUENCE: 55
MRVKEKYQHL WRWGWRWGTM LLGMLMICSA TEKLWVTVYY GVPVWKEATT TLFCASDAKA    60
YDTEVHNVWA THACVPTDPN PQEVVLVNVT ENFNMWKNDM VEQMHEDIIS LWDQSLKPCV   120
KLTPLCVSLK CTDLKNDTNT NSSSGRMIME KGEIKNCSFN ISTSIRGKVQ KEYAFFYKLD   180
IIPIDNDTTS YKLTSCNTSV ITQACPKVSF EPIPIHYCAP AGFAILKCNN KTFNGTGPCT   240
NVSTVQCTHG IRPVVSTQLL LNGSLAEEEV VIRSVNFTDN AKTIIVQLNT SVEINCTRPN   300
NNTRKRIRIQ RGPGRAFVTI GKIGNMRQAH CNISRAKWNN TLKQIASKLR EQFGNNKTII   360
FKQSSGGDPE IVTHSFNCGG EFFYCNSTQL FNSTWFNSTW STEGSNNTEG SDTITLPCRI   420
KQIINMWQKV GKAMYAPPIS GQIRCSSNIT GLLLTRDGGN SNNESEIFRP GGGDMRDNWR   480
SELYKYKVVK IEPLGVAPTK AKRRVVQREK RAVGIGALFL GFLGAAGSTM GAASMTLTVQ   540
ARQLLSGIVQ QQNNLLRAIE AQQHLLQLTV WGIKQLQARI LAVERYLKDQ QLLGIWGCSG   600
KLICTTAVPW NASWSNKSLE QIWNHTTWME WDREINNYTS LIHSLIEESQ NQQEKNEQEL   660
LELDKWASLW NWFNITNWLW YIKLFIMIVG GLVGLRIVFA VLSIVNRVRQ GYSPLSFQTH   720
LPTPRGPDRP EGIEEEGGER DRDRSIRLVG GSLALIWDDL RSLCLFSYHR LRDLLLIVTR   780
IVELLGRRGW EALKYWWNLL QYWSQELKNS AVSLLNATAI AVAEGTDRVI EVVQGACRAI   840
RHIPRRIRQG LERILL                                                   856

SEQ ID NO: 56             moltype = AA  length = 564
FEATURE                   Location/Qualifiers
REGION                    1..564
                          note = Description of Unknown:Endogenous feline virus
                          sequence
source                    1..564
                          mol_type = protein
                          organism = unidentified
SEQUENCE: 56
MKLPTGMVIL CSLIIVRAGF DDPRKAIALV QKQHGKPCEC SGGQVSEAPP NSIQQVTCPG    60
KTAYLMTNQK WKCRVTPKIS PSGGELQNCP CNTFQDSMHS SCYTEYRQCR RINKTYYTAT   120
LLKIRSGSLN EVQILQNPNQ LLQSPCRGSI NQPVCWSATA PIHISDGGGP LDTKRVMTVQ   180
KRLEQIHKAM TPELQYHPLA LPKVRDDLSL DARTFDILNT TFRLLQMSNF SLAQDCWLCL   240
KLGTPTPLAI PTPSLTYSLA DSLANASCQI IPPLLVQPMQ FSNSSCLSSP FINDTEQIDL   300
GAVTFTNCTS VANVSSPLCA LNGSVFLCGN NMAYTYLPQN WTRLCVQASL LPDIDINPGD   360
EPVPIPAIDH YIHRPKRAVQ FIPLLAGLGI TAAFTTGATG LGVSVTQYTK LSHQLISDVQ   420
VLSGTIQDLQ DQVDSLAEVV LQNRRGLDLL TAEQGGICLA LQEKCCFYAN KSGIVRNKIR   480
TLQEELQKRR ESLATNPLWT GLQGFLPYLL PLLGPLLTLL LILTIGPCVF SRLMAFINDR   540
LNVVHAMVLA QQYQALKAEE EAQD                                          564

SEQ ID NO: 57             moltype = AA  length = 229
FEATURE                   Location/Qualifiers
source                    1..229
```

```
                        mol_type = protein
                        organism = Homo sapiens
SEQUENCE: 57
MSPVKGGTKC IKYLLFGFNF IFWLAGIAVL AIGLWLRFDS QTKSIFEQET NNNNSSFYTG    60
VYILIGAGAL MMLVGFLGCC GAVQESQCML GLFFGFLLVI FAIEIAAAIW GYSHKDEVIK   120
EVQEFYKDTY NKLKTKDEPQ RETLKAIHYA LNCCGLAGGV EQFISDICPK KDVLETFTVK   180
SCPDAIKEVF DNKFHIIGAV GIGIAVVMIF GMIFSMILCC AIRRNREMV               229

SEQ ID NO: 58           moltype = AA  length = 238
FEATURE                 Location/Qualifiers
source                  1..238
                        mol_type = protein
                        organism = Homo sapiens
SEQUENCE: 58
MAVEGGMKCV KFLLYVLLLA FCACAVGLIA VGVGAQLVLS QTIIQGATPG SLLPVVIIAV    60
GVFLFLVAFV GCCGACKENY CLMITFAIFL SLIMLVEVAA AIAGYVFRDK VMSEFNNNFR   120
QQMENYPKNN HTASILDRMQ ADFKCCGAAN YTDWEKIPSM SKNRVPDSCC INVTVGCGIN   180
FNEKAIHKEG CVEKIGGWLR KNVLVVAAAA LGIAFVEVLG IVFACCLVKS IRSGYEVM     238

SEQ ID NO: 59           moltype = AA  length = 236
FEATURE                 Location/Qualifiers
source                  1..236
                        mol_type = protein
                        organism = Homo sapiens
SEQUENCE: 59
MGVEGCTKCI KYLLFVFNFV FWLAGGVILG VALWLRHDPQ TTNLLYLELG DKPAPNTFYV    60
GIYILIAVGA VMMFVGFLGC YGAIQESQCL LGTFFTCLVI LFACEVAAGI WGFVNKDQIA   120
KDVKQFYDQA LQQAVVDDDA NNAKAVVKTF HETLDCCGSS TLTALTTSVL KNNLCPSGSN   180
IISNLFKEDC HQKIDDLFSG KLYLIGIAAI VVAVIMIFEM ILSMVLCCGI RNSSVY       236

SEQ ID NO: 60           moltype = AA  length = 10
FEATURE                 Location/Qualifiers
source                  1..10
                        mol_type = protein
                        organism = Homo sapiens
SEQUENCE: 60
EVTELTREGE                                                          10

SEQ ID NO: 61           moltype = AA  length = 21
FEATURE                 Location/Qualifiers
source                  1..21
                        mol_type = protein
                        organism = Homo sapiens
SEQUENCE: 61
GNYTCEVTEL TREGETIIEL K                                             21

SEQ ID NO: 62           moltype = AA  length = 293
FEATURE                 Location/Qualifiers
source                  1..293
                        mol_type = protein
                        organism = Homo sapiens
SEQUENCE: 62
MWPLVAALLL GSACCGSAQL LFNKTKSVEF TFCNDTVVIP CFVTNMEAQN TTEVYVKWKF    60
KGRDIYTFDG ALNKSTVPTD FSSAKIEVSQ LLKGDASLKM DKSDAVSHTG NYTCEVTELT   120
REGETIIELK YRVVSWFSPN ENILIVIFPI FAILLFWGQF GIKTLKYRSG GMDEKTIALL   180
VAGLVITVIV IVGAILFVPG EYSLKNATGL GLIVTSTGIL ILLHYYVFST AIGLTSFVIA   240
ILVIQVIAYI LAVVGLSLCI AACIPMHGPL LISGLSILAL AQLLGLVYMK FVE          293

SEQ ID NO: 63           moltype = AA  length = 397
FEATURE                 Location/Qualifiers
source                  1..397
                        mol_type = protein
                        organism = Adeno-associated virus 2
SEQUENCE: 63
MELVGWLVDK GITSEKQWIQ EDQASYISFN AASNSRSQIK AALDNAGKIM SLTKTAPDYL    60
VGQQPVEDIS SNRIYKILEL NGYDPQYAAS VFLGWATKKF GKRNTIWLFG PATTGKTNIA   120
EAIAHTVPFY GCVNWTNENF PFNDCVDKMV IWWEEGKMTA KVVESAKAIL GGSKVRVDQK   180
CKSSAQIDPT PVIVTSNTNM CAVIDGNSTT FEHQQPLSDR MPKFELTRRL DHDFGKVTKQ   240
EVKDFFRWAK DHVVEVEHEF YVKKGGAKKR PAPSDADISE PKRVRESVAQ PSTSDAEASI   300
NYADRYQNKC SRHVGMNLML FPCRQCERMN QNSNICFTHG QKDCLECFPV SESQPVSVVK   360
KAYQKLCYIH HIMGKVPDAC TACDLVNVDL DDCIFEQ                            397

SEQ ID NO: 64           moltype = AA  length = 621
FEATURE                 Location/Qualifiers
source                  1..621
                        mol_type = protein
                        organism = Adeno-associated virus 2
SEQUENCE: 64
MPGFYEIVIK VPSDLDEHLP GISDSFVNWV AEKEWELPPD SDMDLNLIEQ APLTVAEKLQ    60
```

```
RDFLTEWRRV SKAPEALFFV QFEKGESYFH MHVLVETTGV KSMVLGRFLS QIREKLIQRI    120
YRGIEPTLPN WFAVTKTRNG AGGGNKVVDE CYIPNYLLPK TQPELQWAWT NMEQYLSACL    180
NLTERKRLVA QHLTHVSQTQ EQNKENQNPN SDAPVIRSKT SARYMELVGW LVDKGITSEK    240
QWIQEDQASY ISFNAASNSR SQIKAALDNA GKIMSLTKTA PDYLVGQQPV EDISSNRIYK    300
ILELNGYDPQ YAASVFLGWA TKKFGKRNTI WLFGPATTGK TNIAEAIAHT VPFYGCVNWT    360
NENFPFNDCV DKMVIWWEEG KMTAKVVESA KAILGGSKVR VDQKCKSSAQ IDPTPVIVTS    420
NTNMCAVIDG NSTTFEHQQP LQDRMFKFEL TRRLDHDFGK VTKQEVKDFF RWAKDHVVEV    480
EHEFYVKKGG AKKRPAPSDA DISEPKRVRE SVAQPSTSDA EASINYADRY QNKCSRHVGM    540
NLMLFPCRQC ERMNQNSNIC FTHGQKDCLE CFPVSESQPV SVVKKAYQKL CYIHHIMGKV    600
PDACTACDLV NVDLDDCIFE Q                                              621

SEQ ID NO: 65          moltype = AA  length = 735
FEATURE                Location/Qualifiers
source                 1..735
                       mol_type = protein
                       organism = Adeno-associated virus 2
SEQUENCE: 65
MAADGYLPDW LEDTLSEGIR QWWKLKPGPP PPKPAERHKD DSRGLVLPGY KYLGPFNGLD     60
KGEPVNEADA AALEHDKAYD RQLDSGDNPY LKYNHADAEF QERLKEDTSF GGNLGRAVFQ    120
AKKRVLEPLG LVEEPVKTAP GKKRPVEHSP VEPDSSSGTG KAGQQPARKR LNFGQTGDAD    180
SVPDPQPLGQ PPAAPSGLGT NTMATGSGAP MADNNEGADG VGNSSGNWHC DSTWMGDRVI    240
TTSTRTWALP TYNNHLYKQI SSQSGASNDN HYFGYSTPWG YFDFNRFHCH FSPRDWQRLI    300
NNNWGFRPKR LNFKLFNIQV KEVTQNDGTT TIANNLTSTV QVFTDSEYQL PYVLGSAHQG    360
CLPPFPADVF MVPQYGYLTL NNGSQAVGRS SFYCLEYFPS QMLRTGNNFT FSYTFEDVPF    420
HSSYAHSQSL DRLMNPLIDQ YLYYLSRTNT PSGTTTQSRL QFSQAGASDI RDQSRNWLPG    480
PCYRQQRVSK TSADNNNSEY SWTGATKYHL NGRDSLVNPG PAMASHKDDE EKFFPQSGVL    540
IFGKQGSEKT NVDIEKVMIT DEEEIRTTNP VATEQYGSVS TNLQRGNRQA ATADVNTQGV    600
LPGMVWQDRD VYLQGPIWAK IPHTDGHFHP SPLMGGFGLK HPPPQILIKN TPVPANPSTT    660
FSAAKFASFI TQYSTGQVSV EIEWELQKEN SKRWNPEIQY TSNYNKSVNV DFTVDTNGVY    720
SEPRPIGTRY LTRNL                                                     735

SEQ ID NO: 66          moltype = AA  length = 597
FEATURE                Location/Qualifiers
source                 1..597
                       mol_type = protein
                       organism = Adeno-associated virus 2
SEQUENCE: 66
APGKKRPVEH SPVEPDSSSG TGKAGQQPAR KRLNFGQTGD ADSVPDPQPL GQPPAAPSGL     60
GTNTMATGSG APMADNNEGA DGVGNSSGNW HCDSTWMGDR VITTSTRTWA LPTYNNHLYK    120
QISSQSGASN DNHYFGYSTP WGYFDFNRFH CHFSPRDWQR LINNNWGFRP KRLNFKLFNI    180
QVKEVTQNDG TTTIANNLTS TVQVFTDSEY QLPYVLGSAH QGCLPPFPAD VFMVPQYGYL    240
TLNNGSQAVG RSSFYCLEYF PSQMLRTGNN FTFSYTFEDV PFHSSYAHSQ SLDRLMNPLI    300
DQYLYYLSRT NTPSGTTTQS RLQFSQAGAS DIRDQSRNWL PGPCYRQQRV SKTSADNNNS    360
EYSWTGATKY HLNGRDSLVN PGPAMASHKD DEEKFFPQSG VLIFGKQGSE KTNVDIEKVM    420
ITDEEEIRTT NPVATEQYGS VSTNLQRGNR QAATADVNTQ GVLPGMVWQD RDVYLQGPIW    480
AKIPHTDGHF HPSPLMGGFG LKHPPPQILI KNTPVPANPS TTFSAAKFAS FITQYSTGQV    540
SVEIEWELQK ENSKRWNPEI QYTSNYNKSV NVDFTVDTNG VYSEPRPIGT RYLTRNL       597

SEQ ID NO: 67          moltype = AA  length = 533
FEATURE                Location/Qualifiers
source                 1..533
                       mol_type = protein
                       organism = Adeno-associated virus 2
SEQUENCE: 67
MATGSGAPMA DNNEGADGVG NSSGNWHCDS TWMGDRVITT STRTWALPTY NNHLYKQISS     60
QSGASNDNHY FGYSTPWGYF DFNRFHCHFS PRDWQRLINN NWGFRPKRLN FKLFNIQVKE    120
VTQNDGTTTI ANNLTSTVQV FTDSEYQLPY VLGSAHQGCL PPFPADVFMV PQYGYLTLNN    180
GSQAVGRSSF YCLEYFPSQM LRTGNNFTFS YTFEDVPFHS SYAHSQSLDR LMNPLIDQYL    240
YYLSRTNTPS GTTTQSRLQF SQAGASDIRD QSRNWLPGPC YRQQRVSKTS ADNNNSEYSW    300
TGATKYHLNG RDSLVNPGPA MASHKDDEEK FFPQSGVLIF GKQGSEKTNV DIEKVMITDE    360
EEIRTTNPVA TEQYGSVSTN LQRGNRQAAT ADVNTQGVLP GMVWQDRDVY LQGPIWAKIP    420
HTDGHFHPSP LMGGFGLKHP PPQILIKNTP VPANPSTTFS AAKFASFITQ YSTGQVSVEI    480
EWELQKENSK RWNPEIQYTS NYNKSVNVDF TVDTNGVYSE PRPIGTRYLT RNL           533

SEQ ID NO: 68          moltype = AA  length = 252
FEATURE                Location/Qualifiers
REGION                 1..252
                       note = Description of Artificial Sequence:
                       Syntheticpolypeptide
source                 1..252
                       mol_type = protein
                       organism = synthetic construct
SEQUENCE: 68
EQKLISEEDL DIQMTQTTSS LSASLGDRVT ISCRASQDIS KYLNWYQQKP DGTVKLLIYH     60
TSRLHSGVPS RFSGSGSGTD YSLTISNLEQ EDIATYFCQQ GNTLPYTFGG GTKLEITGGG    120
GSGGGGSGGG GSEVKLQESG PGLVAPSQSL SVTCTVSGVS LPDYGVSWIR QPPRKGLEWL    180
GVIWGSETTY YNSALKSRLT IIKDNSKSQV FLKMNSLQTD DTAIYYCAKH YYYGGSYAMD    240
YWGQGTSVTV SS                                                        252
```

```
SEQ ID NO: 69          moltype = AA   length = 110
FEATURE                Location/Qualifiers
REGION                 1..110
                       note = Description of Artificial Sequence:
                       Syntheticpolypeptide
source                 1..110
                       mol_type = protein
                       organism = synthetic construct
SEQUENCE: 69
FKCEHCRILF LDHVMFTIHM GCHGFRDPFK CNMCGEKCDG PVGLFVHMAR NAHGEKPFYC    60
EHCEITFRDV VMYSLHKGYH GFRDPFECNI CGYHSQDRYE FSSHIVRGEH              110

SEQ ID NO: 70          moltype = AA   length = 110
FEATURE                Location/Qualifiers
REGION                 1..110
                       note = Description of Artificial Sequence:
                       Syntheticpolypeptide
source                 1..110
                       mol_type = protein
                       organism = synthetic construct
SEQUENCE: 70
HHCQHCDMYF ADNILYTIHM GCHSCDDVFK CNMCGEKCDG PVGLFVHMAR NAHGEKPTKC    60
VHCGIVFLDE VMYALHMSCH GFRDPFECNI CGYHSQDRYE FSSHIVRGEH              110

SEQ ID NO: 71          moltype = AA   length = 110
FEATURE                Location/Qualifiers
REGION                 1..110
                       note = Description of Artificial Sequence:
                       Syntheticpolypeptide
source                 1..110
                       mol_type = protein
                       organism = synthetic construct
SEQUENCE: 71
MGRGVQVETI SPGDGRTFPK RGQTCVVHYT GMLEDGKKFD SSRDRNKPFK FMLGKQEVIR    60
GWEEGVAQMS VGQRAKLTIS PDYAYGATGH PGIIPPHATL VFDVELLKLE              110

SEQ ID NO: 72          moltype = AA   length = 111
FEATURE                Location/Qualifiers
REGION                 1..111
                       note = Description of Artificial Sequence:
                       Syntheticpolypeptide
source                 1..111
                       mol_type = protein
                       organism = synthetic construct
SEQUENCE: 72
MASRGVQVET ISPGDGRTFP KRGQTCVVHY TGMLEDGKKV DSSRDRNKPF KFMLGKQEVI    60
RGWEEGVAQM SVGQRAKLTI SPDYAYGATG HPGIIPPHAT LVFDVELLKL E            111

SEQ ID NO: 73          moltype = AA   length = 97
FEATURE                Location/Qualifiers
REGION                 1..97
                       note = Description of Artificial Sequence:
                       Syntheticpolypeptide
source                 1..97
                       mol_type = protein
                       organism = synthetic construct
SEQUENCE: 73
MGSRILWHEM WHEGLEEASR LYFGERNVKG MFEVLEPLHA MMERGPQTLK ETSFNQAYGR    60
DLMEAQEWCR KYMKSGNVKD LLQAWDLYYH VFRRISK                            97

SEQ ID NO: 74          moltype = AA   length = 108
FEATURE                Location/Qualifiers
REGION                 1..108
                       note = Description of Artificial Sequence:
                       Syntheticpolypeptide
source                 1..108
                       mol_type = protein
                       organism = synthetic construct
SEQUENCE: 74
MGVQVETISP GDGRTFPKRG QTCVVHYTGM LEDGKKFDSS RDRNKPFKFM LGKQEVIRGW    60
EEGVAQMSVG QRAKLTISPD YAYGATGHPG IIPPHATLVF DVELLKLE                108

SEQ ID NO: 75          moltype = AA   length = 93
FEATURE                Location/Qualifiers
REGION                 1..93
                       note = Description of Artificial Sequence:
                       Syntheticpolypeptide
source                 1..93
                       mol_type = protein
```

```
                        organism = synthetic construct
SEQUENCE: 75
QGMLEMWHEG LEEASRLYFG ERNVKGMFEV LEPLHAMMER GPQTLKETSF NQAYGRDLME    60
AQEWCRKYMK SGNVKDLLQA WDLYYHVFRR ISK                                 93

SEQ ID NO: 76           moltype = AA  length = 277
FEATURE                 Location/Qualifiers
REGION                  1..277
                        note = Description of Artificial Sequence:
                          Syntheticpolypeptide
source                  1..277
                        mol_type = protein
                        organism = synthetic construct
SEQUENCE: 76
MGPDIVMTQS PSSLSASVGD RVTITCRSST GAVTTSNYAS WVQEKPGKLF KGLIGGTNNR    60
APGVPSRFSG SLIGDKATLT ISSLQPEDFA TYFCALWYSN HWVFGQGTKV ELKRGGGGSG   120
GGGSGGGGSS GGGSEVKLLE SGGGLVQPGG SLKLSCAVSG FSLTDYGVNW VRQAPGRGLE   180
WIGVIWGDGI TDYNSALKDR FIISKDNGKN TVYLQMSKVR SDDTALYYCV TGLFDYWGQG   240
TLVTVSSYPY DVPDYAGGGG GSGGGGSGGG GSGGGGS                            277

SEQ ID NO: 77           moltype = AA  length = 237
FEATURE                 Location/Qualifiers
REGION                  1..237
                        note = Description of Artificial Sequence:
                          Syntheticpolypeptide
source                  1..237
                        mol_type = protein
                        organism = synthetic construct
SEQUENCE: 77
EELLSKNYHL ENEVARLKKG SGSGEELLSK NYHLENEVAR LKKGSGSGEE LLSKNYHLEN    60
EVARLKKGSG SGEELLSKNY HLENEVARLK KGSGSGEELL SKNYHLENEV ARLKKGSGSG   120
EELLSKNYHL ENEVARLKKG SGSGEELLSK NYHLENEVAR LKKGSGSGEE LLSKNYHLEN   180
EVARLKKGSG SGEELLSKNY HLENEVARLK KGSGSGEELL SKNYHLENEV ARLKKGS      237

SEQ ID NO: 78           moltype = AA  length = 573
FEATURE                 Location/Qualifiers
REGION                  1..573
                        note = Description of Artificial Sequence:
                          Syntheticpolypeptide
source                  1..573
                        mol_type = protein
                        organism = synthetic construct
SEQUENCE: 78
EELLSKNYHL ENEVARLKKG SGSGEELLSK NYHLENEVAR LKKGSGSGEE LLSKNYHLEN    60
EVARLKKGSG SGEELLSKNY HLENEVARLK KGSGSGEELL SKNYHLENEV ARLKKGSGSG   120
EELLSKNYHL ENEVARLKKG SGSGEELLSK NYHLENEVAR LKKGSGSGEE LLSKNYHLEN   180
EVARLKKGSG SGEELLSKNY HLENEVARLK KGSGSGEELL SKNYHLENEV ARLKKGSGSG   240
EELLSKNYHL ENEVARLKKG SGSGEELLSK NYHLENEVAR LKKGSGSGEE LLSKNYHLEN   300
EVARLKKGSG SGEELLSKNY HLENEVARLK KGSGSGEELL SKNYHLENEV ARLKKGSGSG   360
EELLSKNYHL ENEVARLKKG SGSGEELLSK NYHLENEVAR LKKGSGSGEE LLSKNYHLEN   420
EVARLKKGSG SGEELLSKNY HLENEVARLK KGSGSGEELL SKNYHLENEV ARLKKGSGSG   480
EELLSKNYHL ENEVARLKKG SGSGEELLSK NYHLENEVAR LKKGSGSGEE LLSKDYHLEN   540
EVARLKKGSG SGEELLSKNY HLENEVARLK KGS                                573

SEQ ID NO: 79           moltype = AA  length = 114
FEATURE                 Location/Qualifiers
REGION                  1..114
                        note = Description of Artificial Sequence:
                          Syntheticpolypeptide
source                  1..114
                        mol_type = protein
                        organism = synthetic construct
SEQUENCE: 79
VQLVESGGAL VQPGGSLRLS CAASGFPVNR YSMRWYRQAP GKEREWVAGM SSAGDRSSYE    60
DSVKGRFTIS RDDARNTVYL QMNSLKPEDT AVYYSNVNVG FEYWGQGTQV TVSS         114

SEQ ID NO: 80           moltype = AA  length = 102
FEATURE                 Location/Qualifiers
source                  1..102
                        mol_type = protein
                        organism = Nostoc commune
SEQUENCE: 80
CLSYETEILT VEYGLLPIGK IVEKRIECTV YSVDNNGNIY TQPVAQWHDR GEQEVFEYCL    60
EDGSLIRATK DHKFMTVDGQ MLPIDEIFER ELDLMRVDNL PN                      102

SEQ ID NO: 81           moltype = AA  length = 39
FEATURE                 Location/Qualifiers
source                  1..39
                        mol_type = protein
```

```
                        organism = Nostoc commune
SEQUENCE: 81
MIKIATRKYL GKQNVYDIGV ERDHNFALKN GFIASNCFN                           39

SEQ ID NO: 82           moltype = AA   length = 101
FEATURE                 Location/Qualifiers
REGION                  1..101
                        note = Description of Artificial Sequence:
                        Syntheticpolypeptide
source                  1..101
                        mol_type = protein
                        organism = synthetic construct
SEQUENCE: 82
CLSYDTEILT VEYGFLPIGK IVEERIECTV YTVDKNGFVY TQPIAQWHNR GEQEVFEYCL    60
EDGSIIRATK DHKFMTTDGQ MLPIDEIFER GLDLKQVDGL P                        101

SEQ ID NO: 83           moltype = AA   length = 36
FEATURE                 Location/Qualifiers
REGION                  1..36
                        note = Description of Artificial Sequence:
                        Syntheticpolypeptide
source                  1..36
                        mol_type = protein
                        organism = synthetic construct
SEQUENCE: 83
MVKIISRKSL GTQNVYDIGV EKDHNFLLKN GLVASN                              36

SEQ ID NO: 84           moltype = AA   length = 184
FEATURE                 Location/Qualifiers
source                  1..184
                        mol_type = protein
                        organism = Saccharomyces cerevisiae
SEQUENCE: 84
CFAKGTNVLM ADGSIECIEN IEVGNKVMGK DGRPREVIKL PRGRETMYSV VQKSQHRAHK    60
SDSSREVPEL LKFTCNATHE LVVRTPRSVR RLSRTIKGVE YFEVITFEMG QKKAPDGRIV    120
ELVKEVSKSY PISEGPERAN ELVESYRKAS NKAYFEWTIE ARDLSLLGSH VRKATYQTYA    180
PILY                                                                 184

SEQ ID NO: 85           moltype = AA   length = 65
FEATURE                 Location/Qualifiers
source                  1..65
                        mol_type = protein
                        organism = Saccharomyces cerevisiae
SEQUENCE: 85
VLLNVLSKCA GSKKFRPAPA AAFARECRGF YFELQELKED DYYGITLSDD SDHQFLLANQ    60
VVVHN                                                                65

SEQ ID NO: 86           moltype = AA   length = 123
FEATURE                 Location/Qualifiers
source                  1..123
                        mol_type = protein
                        organism = Synechocystis sp.
SEQUENCE: 86
CLSFGTEILT VEYGPLPIGK IVSEEINCSV YSVDPEGRVY TQAIAQWHDR GEQEVLEYEL    60
EDGSVIRATS DHRFLTTDYQ LLAIEEIFAR QLDLLTLENI KQTEEALDNH RLPFPLLDAG    120
TIK                                                                  123

SEQ ID NO: 87           moltype = AA   length = 36
FEATURE                 Location/Qualifiers
source                  1..36
                        mol_type = protein
                        organism = Synechocystis sp.
SEQUENCE: 87
MVKVIGRRSL GVQRIFDIGL PQDHNFLLAN GAIAAN                              36

SEQ ID NO: 88           moltype = AA   length = 14
FEATURE                 Location/Qualifiers
REGION                  1..14
                        note = Description of Artificial Sequence: Syntheticpeptide
source                  1..14
                        mol_type = protein
                        organism = synthetic construct
SEQUENCE: 88
VPTIVMVDAY KRYK                                                      14

SEQ ID NO: 89           moltype = AA   length = 119
FEATURE                 Location/Qualifiers
REGION                  1..119
                        note = Description of Artificial Sequence:
```

```
                         Syntheticpolypeptide
source                   1..119
                         mol_type = protein
                         organism = synthetic construct
SEQUENCE: 89
MVTTLSGLSG EQGPSGDMTT EEDSATHIKF SKRDEDGREL AGATMELRDS SGKTISTWIS   60
DGHVKDFYLY PGKYTFVETA APDGYEVATA ITFTVNEQGQ VTVNGEATKG DAHTGSSGS   119

SEQ ID NO: 90            moltype = AA  length = 130
FEATURE                  Location/Qualifiers
REGION                   1..130
                         note = Description of Unknown:Enterobacteria phage MS2
                           sequence
source                   1..130
                         mol_type = protein
                         organism = unidentified
SEQUENCE: 90
MASNFTQFVL VDNGGTGDVT VAPSNFANGV AEWISSNSRS QAYKVTCSVR QSSAQNRKYT   60
IKVEVPKVAT QTVGGVELPV AAWRSYLNME LTIPIFATNS DCELIVKAMQ GLLKDGNPIP  120
SAIAANSGIY                                                         130

SEQ ID NO: 91            moltype = AA  length = 130
FEATURE                  Location/Qualifiers
REGION                   1..130
                         note = Description of Unknown:Enterobacteria phage MS2
                           sequence
source                   1..130
                         mol_type = protein
                         organism = unidentified
SEQUENCE: 91
MASNFTQFVL VDNGGTGDVT VAPSNFANGV AEWISSNSRS QAYKVTCSVR QSSAQKRKYT   60
IKVEVPKVAT QTVGGVELPV AAWRSYLNME LTIPIFATNS DCELIVKAMQ GLLKDGNPIP  120
SAIAANSGIY                                                         130

SEQ ID NO: 92            moltype = AA  length = 130
FEATURE                  Location/Qualifiers
REGION                   1..130
                         note = Description of Unknown:Enterobacteria phage MS2
                           sequence
source                   1..130
                         mol_type = protein
                         organism = unidentified
SEQUENCE: 92
MASNFTQFVL VDNGGTGDVT VAPSNFANGI AEWISSNSRS QAYKVTCSVR QSSAQKRKYT   60
IKVEVPKVAT QTVGGVELPV AAWRSYLNME LTIPIFATNS DCELIVKAMQ GLLKDGNPIP  120
SAIAANSGIY                                                         130

SEQ ID NO: 93            moltype = AA  length = 121
FEATURE                  Location/Qualifiers
REGION                   1..121
                         note = Description of Unknown:Pseudomonas phage PP7 sequence
source                   1..121
                         mol_type = protein
                         organism = unidentified
SEQUENCE: 93
KTIVLSVGEA TRTLTEIQST ADRQIFEEKV GPLVGRLRLT ASLRQNGAKT AYRVNLKLDQ   60
ADVVDSGLPK VRYTQVWSHD VTIVANSTEA SRKSLYDLTK SLVATSQVED LVVNLVPLGR  120
S                                                                  121

SEQ ID NO: 94            moltype = AA  length = 62
FEATURE                  Location/Qualifiers
source                   1..62
                         mol_type = protein
                         organism = Escherichia virus Mu
SEQUENCE: 94
MKSIRCKNCN KLLFKADSFD HIEIRCPRCK RHIIMLNACE HPTEKHCGKR EKITHSDETV   60
RY                                                                  62

SEQ ID NO: 95            moltype = AA  length = 179
FEATURE                  Location/Qualifiers
REGION                   1..179
                         note = Description of Artificial Sequence:
                           Syntheticpolypeptide
source                   1..179
                         mol_type = protein
                         organism = synthetic construct
SEQUENCE: 95
STRPGERPFQ CRICMRNFSI PNHLARHTRT HTGEKPFQCR ICMRNFSQSA HLKRHLRTHT   60
GEKPFQCRIC MRNFSQDVSL VRHLKTHLRQ KDGERPFQCR ICMRNFSSAQ ALARHTRTHT  120
```

```
GEKPFQCRIC MRNFSQGGNL TRHLRTHTGE KPFQCRICMR NFSQHPNLTR HLKTHLRGS     179

SEQ ID NO: 96           moltype = AA   length = 178
FEATURE                 Location/Qualifiers
REGION                  1..178
                        note = Description of Artificial Sequence:
                        Syntheticpolypeptide
source                  1..178
                        mol_type = protein
                        organism = synthetic construct
SEQUENCE: 96
SRPGERPFQC RICMRNFSTM AVLRRHTRTH TGEKPFQCRI CMRNFSRREV LENHLRTHTG     60
EKPFQCRICM RNFSQTVNLD RHLKTHLRQK DGERPFQCRI CMRNFSKKDH LHRHRTHTG      120
EKPFQCRICM RNFSQRPHLT NHLRTHTGEK PFQCRICMRN FSVGASLKRH LKTHLRGS       178

SEQ ID NO: 97           moltype = AA   length = 90
FEATURE                 Location/Qualifiers
REGION                  1..90
                        note = Description of Artificial Sequence:
                        Syntheticpolypeptide
source                  1..90
                        mol_type = protein
                        organism = synthetic construct
SEQUENCE: 97
SRPGERPFQC RICMRNFSDK TKLRVHTRTH TGEKPFQCRI CMRNFSVRHN LTRHLRTHTG     60
EKPFQCRICM RNFSQSTSLQ RHLKTHLRGF                                      90

SEQ ID NO: 98           moltype = AA   length = 176
FEATURE                 Location/Qualifiers
REGION                  1..176
                        note = Description of Artificial Sequence:
                        Syntheticpolypeptide
source                  1..176
                        mol_type = protein
                        organism = synthetic construct
SEQUENCE: 98
SRPGERPFQC RICMRNFSRR HGLDRHTRTH TGEKPFQCRI CMRNFSDHSS LKRHLRTHTG     60
SQKPFQCRIC MRNFSVRHNL TRHLRTHTGE KPFQCRICMR NFSDHSNLSR HLKTHTGSQK     120
PFQCRICMRN FSQRSSLVRH LRTHTGEKPF QCRICMRNFS ESGHLKRHLR THLRGS         176

SEQ ID NO: 99           moltype = AA   length = 86
FEATURE                 Location/Qualifiers
REGION                  1..86
                        note = Description of Artificial Sequence:
                        Syntheticpolypeptide
source                  1..86
                        mol_type = protein
                        organism = synthetic construct
SEQUENCE: 99
YACPVESCDR RFSRSDELTR HIRIHTGQKP FQCRICMRNF SRSDHLTTHI RTHTGEKPFA     60
CDICGRKFAR SDERKRHTKI HLRQKD                                          86

SEQ ID NO: 100          moltype = AA   length = 86
FEATURE                 Location/Qualifiers
REGION                  1..86
                        note = Description of Artificial Sequence:
                        Syntheticpolypeptide
source                  1..86
                        mol_type = protein
                        organism = synthetic construct
SEQUENCE: 100
YACPVESCDR RFSQSHDLTK HIRIHTGQKP FQCRICMRNF SDSSKLSRHI RTHTGEKPFA     60
CDICGRKFAR LDNRTAHTKI HLRQKD                                          86

SEQ ID NO: 101          moltype = AA   length = 176
FEATURE                 Location/Qualifiers
REGION                  1..176
                        note = Description of Artificial Sequence:
                        Syntheticpolypeptide
source                  1..176
                        mol_type = protein
                        organism = synthetic construct
SEQUENCE: 101
YACPVESCDR RFSRSDELTR HIRIHTGQKP FQCRICMRNF SRSDHLTTHI RTHTGEKPFA     60
CDICGRKFAR SDERKRHTKI HLRQKDGERP YACPVESCDR RFSQSHDLTK HIRIHTGQKP     120
FQCRICMRNF SDSSKLSRHI RTHTGEKPFA CDICGRKFAR LDNRTAHTKI HLRQKD         176

SEQ ID NO: 102          moltype = AA   length = 179
FEATURE                 Location/Qualifiers
```

```
REGION                      1..179
                            note = Description of Artificial Sequence:
                               Syntheticpolypeptide
source                      1..179
                            mol_type = protein
                            organism = synthetic construct
SEQUENCE: 102
YACPVESCDR RFSRSDELTR HIRIHTGQKP FQCRICMRNF SRSDHLTTHI RTHTGEKPFA    60
CDICGRKFAR SDERKRHTKI HLRQKDGGGS ERPYACPVES CDRRFSQSHD LTKHIRIHTG   120
QKPFQCRICM RNFSDSSKLS RHIRTHTGEK PFACDICGRK FARLDNRTAH TKIHLRQKD    179

SEQ ID NO: 103              moltype = AA  length = 286
FEATURE                     Location/Qualifiers
REGION                      1..286
                            note = Description of Artificial Sequence:
                               Syntheticpolypeptide
source                      1..286
                            mol_type = protein
                            organism = synthetic construct
SEQUENCE: 103
SRPGERPFQC RICMRNFSTR QNLDTHTRTH TGEKPFQCRI CMRNFSRRDT LERHLRTHTG    60
EKPFQCRICM RNFSRPDALP RHLKTHLRGS QLVKSELEEK KSELRHKLKY VPHEYIELIE   120
IARNSTQDRI LEMKVMEFFM KVYGYRGKHL GGSRKPDGAI YTVGSPIDYG VIVDTKAYSG   180
GYNLPIGQAD EMQRYVEENQ TRNKHINPNE WWKVYPSSVT EFKFLFVSGH FKGNYKAQLT   240
RLNHITNCNG AVLSVEELLI GGEMIKAGTL TLEEVRRKFN NGEINF                  286

SEQ ID NO: 104              moltype = AA  length = 286
FEATURE                     Location/Qualifiers
REGION                      1..286
                            note = Description of Artificial Sequence:
                               Syntheticpolypeptide
source                      1..286
                            mol_type = protein
                            organism = synthetic construct
SEQUENCE: 104
SRPGERPFQC RICMRNFSSP SKLIRHTRTH TGEKPFQCRI CMRNFSDGSN LARHLRTHTG    60
EKPFQCRICM RNFSRVDNLP RHLKTHLRGS QLVKSELEEK KSELRHKLKY VPHEYIELIE   120
IARNSTQDRI LEMKVMEFFM KVYGYRGKHL GGSRKPDGAI YTVGSPIDYG VIVDTKAYSG   180
GYNLPIGQAD EMQRYVEENQ TRNKHINPNE WWKVYPSSVT EFKFLFVSGH FKGNYKAQLT   240
RLNHITNCNG AVLSVEELLI GGEMIKAGTL TLEEVRRKFN NGEINF                  286

SEQ ID NO: 105              moltype = AA  length = 353
FEATURE                     Location/Qualifiers
REGION                      1..353
                            note = Description of Artificial Sequence:
                               Syntheticpolypeptide
source                      1..353
                            mol_type = protein
                            organism = synthetic construct
SEQUENCE: 105
MDYKDHDGDY KDHDIDYKDD DDKMAPKKKR KVGIHGVPAA MAERPFQCRI CMRNFSDRSN    60
LSRHIRTHTG EKPFACDICG RKFAISSNLN SHTKIHTGSQ KPFQCRICMR NFSRSDNLAR   120
HIRTHTGEKP FACDICGRKF ATSGNLTRHT KIHLRGSQLV KSELEEKKSE LRHKLKYVPH   180
EYIELIEIAR NSTQDRILEM KVMEFFMKVY GYRGKHLGGS RKPDGAIYTV GSPIDYGVIV   240
DTKAYSGGYN LPIGQADEMQ RYVEENQTRN KHINPNEWWK VYPSSVTEFK FLFVSGHFKG   300
NYKAQLTRLN HITNCNGAVL SVEELLIGGE MIKAGTLTLE EVRRKFNNGE INF          353

SEQ ID NO: 106              moltype = AA  length = 352
FEATURE                     Location/Qualifiers
REGION                      1..352
                            note = Description of Artificial Sequence:
                               Syntheticpolypeptide
source                      1..352
                            mol_type = protein
                            organism = synthetic construct
SEQUENCE: 106
MDYKDHDGDY KDHDIDYKDD DDKMAPKKKR KVGIHGVPAA MAERPFQCRI CMRNFSRSDN    60
LSVHIRTHTG EKPFACDICG RKFAQKINLQ VHTKIHTGEK PFQCRICMRN FSRSDVLSEH   120
IRTHTGEKPF ACDICGRKFA QRNHRTTHTK IHLRGSQLVK SELEEKKSEL RHKLKYVPHE   180
YIELIEIARN STQDRILEMK VMEFFMKVYG YRGKHLGGSR KPDGAIYTVG SPIDYGVIVD   240
TKAYSGGYNL PIGQADEMQR YVEENQTRNK HINPNEWWKV YPSSVTEFKF LFVSGHFKGN   300
YKAQLTRLNH ITNCNGAVLS VEELLIGGEM IKAGTLTLEE VRRKFNNGEI NF           352

SEQ ID NO: 107              moltype = AA  length = 196
FEATURE                     Location/Qualifiers
REGION                      1..196
                            note = Description of Artificial Sequence:
                               Syntheticpolypeptide
source                      1..196
```

```
                        mol_type = protein
                        organism = synthetic construct
SEQUENCE: 107
QLVKSELEEK KSELRHKLKY VPHEYIELIE IARNSTQDRI LEMKVMEFFM KVYGYRGKHL    60
GGSRKPDGAI YTVGSPIDYG VIVDTKAYSG GYNLPIGQAD EMQRYVEENQ TRNKHINPNE   120
WWKVYPSSVT EFKFLFVSGH FKGNYKAQLT RLNHITNCNG AVLSVEELLI GGEMIKAGTL   180
TLEEVRRKFN NGEINF                                                  196

SEQ ID NO: 108          moltype = AA  length = 199
FEATURE                 Location/Qualifiers
REGION                  1..199
                        note = Description of Artificial Sequence:
                        Syntheticpolypeptide
source                  1..199
                        mol_type = protein
                        organism = synthetic construct
SEQUENCE: 108
VHDHKLELAK LIRNYETNRK ECLNSRYNET LLRSDYLDPF FELLGWDIKN KAGKPTNERE    60
VVLEEALKAS ASEHSKKPDY TFRLFSERKF FLEAKKPSVH IESDNETAKQ VRRYGFTAKL   120
KISVLSNFEY LVIYDTSVKV DGDDTFNKAR IKKYHYTEYE THFDEICDLL GRESVYSGNF   180
DKEWLSIENK INHFSVDTL                                               199

SEQ ID NO: 109          moltype = AA  length = 119
FEATURE                 Location/Qualifiers
REGION                  1..119
                        note = Description of Artificial Sequence:
                        Syntheticpolypeptide
source                  1..119
                        mol_type = protein
                        organism = synthetic construct
SEQUENCE: 109
YNETLLRSDY LDPFFELLGW DIKNKAGKPT NEREVVLEEA LKASASEHSK KPDYTFRLFS    60
ERKFFLEAKK PSVHIESDNE TAKQVRRYGF TAKLKISVLS NFEYLVIYDT SVKVDGDDT   119

SEQ ID NO: 110          moltype = AA  length = 165
FEATURE                 Location/Qualifiers
source                  1..165
                        mol_type = protein
                        organism = Escherichia coli
SEQUENCE: 110
MLKPEMIEKL NEQMNLELYS SLLYQQMSAW CSYHTFEGAA AFLRRHAQEE MTHMQRLFDY    60
LTDTGNLPRI NTVESPFAEY SSLDELFQET YKHEQLITQK INELAHAAMT NQDYPTFNFL   120
QWYVSEQHEE EKLFKSIIDK LSLAGKSGEG LYFIDKELST LDTQN                   165

SEQ ID NO: 111          moltype = AA  length = 165
FEATURE                 Location/Qualifiers
source                  1..165
                        mol_type = protein
                        organism = Escherichia coli
SEQUENCE: 111
MLKPEMIEKL NEQMNLELYS SLLYQQMSAW CSYLTFEGAA AFLRRHAQEE MTHMQRLFDY    60
LTDIGNLPRI NTVESPFAEY SSLDELFQET YKHEQLITQK INELAHAAMT NQDYPTFNFL   120
QWYVSEQHEE EKLFKSIIDK LSLAGKSGEG LYFIDKELST LDTQN                   165

SEQ ID NO: 112          moltype = AA  length = 389
FEATURE                 Location/Qualifiers
REGION                  1..389
                        note = Description of Artificial Sequence:
                        Syntheticpolypeptide
source                  1..389
                        mol_type = protein
                        organism = synthetic construct
SEQUENCE: 112
MTSQIRQNYS TEVEAAVNRL VNLHLRASYT YLSLGFFFDR DDVALEGVGH FFRELAEEKR    60
EGAERLLEFQ NDRGGRALFQ DVQKPSQDEW GKTQEAMEAA LAMEKNLNQA LLDLHALGSA   120
RADPHLCDFL ESHYLDKEVK LIKKMGNHLT NLRRVAGPQP AQTGAPQGSL GEYLFERLTL   180
KHDARGGGGS DYKDDDDKGG GGSRVMTTAS PSQVRQNYHQ DAEAAINRQI NLELYASYVY   240
LSMSCYFDRD DVALKNFAKY FLHQSHEERE HAEKLMKLQN QRGGRIFLQD IKKPDRDDWE   300
SGLNAMECAL HLEKSVNQSL LELHKLATDK NDPHLCDFIE TYYLSEQVKS IKELGDHVTN   360
LRKMGAPEAG MAEYLFDKHT LGHGDESTR                                    389

SEQ ID NO: 113          moltype = AA  length = 378
FEATURE                 Location/Qualifiers
REGION                  1..378
                        note = Description of Artificial Sequence:
                        Syntheticpolypeptide
source                  1..378
                        mol_type = protein
                        organism = synthetic construct
```

```
SEQUENCE: 113
SQIRQNYSTD VEAAVNSLVN LYLQASYTYL SLGFYFDRDD VALEGVSHFF RELAEEKREG    60
YERLLKMQNQ RGGRALFQDI KKPAEDEWGK TPDAMKAAMA LEKKLNQALL DLHALGSART   120
DPHLCDFLET HFLDEEVKLI KKMGDHLTNL HRLGGPEAGL GEYLFERLTL KHDARGGGGS   180
DYKDDDDKGG GGSRVMTTAS TSQVRQNYHQ DSEAAINRQI NLELYASYVY LSMSYYFDRD   240
DVALKNFAKY FLHQSHEERE HAEKLMKLQN QRGGRIFLQD IKKPDCDDWE SGLNAMECAL   300
HLEKNVNQSL LELHKLATDK NDPHLCDFIE THYLNEQVKA IKELGDHVTN LRKMGAPESG   360
LAEYLFDKHT LGDSDNES                                                378

SEQ ID NO: 114          moltype = AA  length = 612
FEATURE                 Location/Qualifiers
source                  1..612
                        mol_type = protein
                        organism = Arabidopsis thaliana
SEQUENCE: 114
MKMDKKTIVW FRRDLRIEDN PALAAAAHEG SVFPVFIWCP EEEGQFYPGR ASRWWMKQSL    60
AHLSQSLKAL GSDLTLIKTH NTISAILDCI RVTGATKVVF NHLYDPVSLV RDHTVKEKLV   120
ERGISVQSYN GDLLYEPWEI YCEKGKPFTS FNSYWKKCLD MSIESVMLPP PWRLMPITAA   180
AEAIWACSIE ELGLENEAEK PSNALLTRAW SPGWSNADKL LNEFIEKQLI DYAKNSKKVV   240
GNSTSLLSPY LHFGEISVRH VFQCARMKQI IWARDKNSEG EESADLFLRG IGLREYSRYI   300
CFNFPFTHEQ SLLSHLRFFP WDADVDKFKA WRQGRTGYPL VDAGMRELWA TGWMHNRIRV   360
IVSSFAVKFL LLPWKWGMKY FWDTLLDADL ECDILGWQYI SGSIPDGHEL DRLDNPALQG   420
AKYDPEGEYI RQWLPELARL PTEWIHHPWD APLTVLKASG VELGTNYAKP IVIDIDTAREL  480
LAKAISRTRE AQIMIGAAPD EIVADSFEAL GANTIKEPGL CPSVSSNDQQ VPSAVRYNGS   540
AAVKPEEEEE RDMKKSRGFD ERELFSTAES SSSSSVFFVS QSCSLASEGK NLEGIQDSSD   600
QITTSLGKNG CK                                                      612

SEQ ID NO: 115          moltype = AA  length = 170
FEATURE                 Location/Qualifiers
source                  1..170
                        mol_type = protein
                        organism = Arabidopsis thaliana
SEQUENCE: 115
MNGAIGGDLL LNFPDMSVLE RQRAHLKYLN PTFDSPLAGF FADSSMITGG EMDSYLSTAG    60
LNLPMMYGET TVEGDSRLSI SPETTLGTGN FKAAKFDTET KDCNEAAKKM TMNRDDLVEE   120
GEEEKSKITE QNNGSTKSIK KMKHKAKKEE NNFSNDSSKV TKELEKTDYI              170

SEQ ID NO: 116          moltype = AA  length = 144
FEATURE                 Location/Qualifiers
REGION                  1..144
                        note = Description of Artificial Sequence:
                          Syntheticpolypeptide
source                  1..144
                        mol_type = protein
                        organism = synthetic construct
SEQUENCE: 116
SLATTLERIE KNFVITDPRL PDNPIIFASD SFLQLTEYSR EEILGRNCRF LQGPETDRAT    60
VRKIRDAIDN QTEVTVQLIN YTKSGKKFWN LFHLQPMRDQ KGDVQYFIGV QLDGTEHVRD   120
AAEREGVMLI KKTAENIDEA AKEL                                         144

SEQ ID NO: 117          moltype = AA  length = 740
FEATURE                 Location/Qualifiers
source                  1..740
                        mol_type = protein
                        organism = Homo sapiens
SEQUENCE: 117
DIEDEENMSS SSTDVKENRN LDNVSPKDGS TPGPGEGSQL SNGGGGGPGR KRPLEEGSNG    60
HSKYRLKKRR KTPGPVLPKN ALMQLNEIKP GLQYTLLSQT GPVHAPLFVM SVEVNGQVFE   120
GSGPTKKKAK LHAAEKALRS FVQFPNASEA HLAMGRTLSV NTDFTSDQAD FPDTLFNGFE   180
TPDKAEPPFY VGSNGDDSFS SSGDLSLSAS PVPASLAQPP LPVLPPFPPP SGKNPVMILN   240
ELRPGLKYDF LSESGESHAK SFVMSVVVDG QFFEGSGRNK KLAKARAAQS ALAAIFNLHL   300
DQTPSRQPIP SEGLQLHLPQ VLADAVSRLV LGKFGDLTDN FSSPHARRKV LAGVVMTTGT   360
DVKDAKVISV STGTKCINGE YMSDRGLALN DCHAEIISRR SLLRFLYTQL ELYLNNKDDQ   420
KRSIFQKSER GGFRLKENVQ FHLYISTSPC GDARIFSPHE PILEGSRSYT QAGVQWCNHG   480
SLQPRPPGLL SDPSTSTFQG AGTTEPADRH PNRKARGQLR TKIESGEGTI PVRSNASIQT   540
WDGVLQGERL LTMSCSDKIA RWNVVGIQGS LLSIFVEPIY FSSIILGSLY HGDHLSRAMY   600
QRISNIEDLP PLYTLNKPLL SGISNAEARQ PGKAPNFSVN WTVGDSAIEV INATTGKDEL   660
GRASRLCKHA LYCRWMRVHG KVPSHLLRSK ITKPNVYHES KLAAKEYQAA KARLFTAFIK   720
AGLGAWVEKP TEQDQFSLTP                                              740

SEQ ID NO: 118          moltype = AA  length = 740
FEATURE                 Location/Qualifiers
source                  1..740
                        mol_type = protein
                        organism = Homo sapiens
SEQUENCE: 118
DIEDEENMSS SSTDVKENRN LDNVSPKDGS TPGPGEGSQL SNGGGGGPGR KRPLEEGSNG    60
HSKYRLKKRR KTPGPVLPKN ALMQLNEIKP GLQYTLLSQT GPVHAPLFVM SVEVNGQVFE   120
GSGPTKKKAK LHAAEKALRS FVQFPNASEA HLAMGRTLSV NTDFTSDQAD FPDTLFNGFE   180
```

```
TPDKAEPPFY VGSNGDDSFS SSGDLSLSAS PVPASLAQPP LPVLPPFPPP SGKNPVMILN    240
ELRPGLKYDF LSESGESHAK SFVMSVVVDG QFFEGSGRNK KLAKARAAQS ALAAIFNLHL    300
DQTPSRQPIP SEGLQLHLPQ VLADAVSRLV LGKFGDLTDN FSSPHARRKV LAGVVMTTGT    360
DVKDAKVISV STGTKCINGE YMSDRGLALN DCHAEIISRR SLLRFLYTQL ELYLNNKDDQ    420
KRSIFQKSER GGFRLKENVQ FHLYISTSPC GDARIFSPHE PILEGSRSYT QAGVQWCNHG    480
SLQPRPPGLL SDPSTSTFQG AGTTEPADRH PNRKARGQLR TKIESGQGTI PVRSNASIQT    540
WDGVLQGERL LTMSCSDKIA RWNVVGIQGS LLSIFVEPIY FSSIILGSLY HGDHLSRAMY    600
QRISNIEDLP PLYTLNKPLL SGISNAEARQ PGKAPNFSVN WTVGDSAIEV INATTGKDEL    660
GRASRLCKHA LYCRWMRVHG KVPSHLLRSK ITKPNVYHES KLAAKEYQAA KARLFTAFIK    720
AGLGAWVEKP TEQDQFSLTP                                               740

SEQ ID NO: 119           moltype = AA  length = 420
FEATURE                  Location/Qualifiers
source                   1..420
                         mol_type = protein
                         organism = Homo sapiens
SEQUENCE: 119
VLADAVSRLV LGKFGDLTDN FSSPHARRKV LAGVVMTTGT DVKDAKVISV STGTKCINGE     60
YMSDRGLALN DCHAEIISRR SLLRFLYTQL ELYLNNKDDQ KRSIFQKSER GGFRLKENVQ    120
FHLYISTSPC GDARIFSPHE PILEGSRSYT QAGVQWCNHG SLQPRPPGLL SDPSTSTFQG    180
AGTTEPADRH PNRKARGQLR TKIESGEGTI PVRSNASIQT WDGVLQGERL LTMSCSDKIA    240
RWNVVGIQGS LLSIFVEPIY FSSIILGSLY HGDHLSRAMY QRISNIEDLP PLYTLNKPLL    300
SGISNAEARQ PGKAPNFSVN WTVGDSAIEV INATTGKDEL GRASRLCKHA LYCRWMRVHG    360
KVPSHLLRSK ITKPNVYHES KLAAKEYQAA KARLFTAFIK AGLGAWVEKP TEQDQFSLTP    420

SEQ ID NO: 120           moltype = AA  length = 420
FEATURE                  Location/Qualifiers
REGION                   1..420
                         note = Description of Artificial Sequence:
                           Syntheticpolypeptide
source                   1..420
                         mol_type = protein
                         organism = synthetic construct
SEQUENCE: 120
VLADAVSRLV LGKFGDLTDN FSSPHARRKV LAGVVMTTGT DVKDAKVISV STGTKCINGE     60
YMSDRGLALN DCHAEIISRR SLLRFLYTQL ELYLNNKDDQ KRSIFQKSER GGFRLKENVQ    120
FHLYISTSPC GDARIFSPHE PILEGSRSYT QAGVQWCNHG SLQPRPPGLL SDPSTSTFQG    180
AGTTEPADRH PNRKARGQLR TKIESGQGTI PVRSNASIQT WDGVLQGERL LTMSCSDKIA    240
RWNVVGIQGS LLSIFVEPIY FSSIILGSLY HGDHLSRAMY QRISNIEDLP PLYTLNKPLL    300
SGISNAEARQ PGKAPNFSVN WTVGDSAIEV INATTGKDEL GRASRLCKHA LYCRWMRVHG    360
KVPSHLLRSK ITKPNVYHES KLAAKEYQAA KARLFTAFIK AGLGAWVEKP TEQDQFSLTP    420

SEQ ID NO: 121           moltype = AA  length = 584
FEATURE                  Location/Qualifiers
REGION                   1..584
                         note = Description of Artificial Sequence:
                           Syntheticpolypeptide
source                   1..584
                         mol_type = protein
                         organism = synthetic construct
SEQUENCE: 121
MASNFTQFVL VDNGGTGDVT VAPSNFANGI AEWISSNSRS QAYKVTCSVR QSSAQNRKYT     60
IKVEVPKGAW RSYLNMELTI PIFATNSDCE LIVKAMQGLL KDGNPIPSAI AANSGIYGGS    120
GSGAGSGSPA GGGAPGSGGG SKAERMGFTE VTPVTGASLR RTMLLLSRSP EAQPKTLPLT    180
GSTFHDQIAM LSHRCFNTLT NSFQPSLLGR KILAAIIMKK DSEDMGVVVS LGTGNRCVKG    240
DSLSLKGETV NDCHAEIISR RGFIRFLYSE LMKYNSQTAK DSIFEPAKGG EKLQIKKTVS    300
FHLYISTAPC GDGALFDKSC SDRAMESTES RHYPVFENPK QGKLRTKVEN GEGTIPVESS    360
DIVPTWDGIR LGERLRTMSC SDKILRWNVL GLQGALLTHF LQPIYLKSVT LGYLFSQGHL    420
TRAICCRVTR DGSAFEDGLR HPFIVNHPKV GRVSIYDSKR VSGKTKETSV NWCLADGYDL    480
EILDGTRGTV DGPRNELSRV SKKNIFLLFK KLCSFRYRRD LLRLSYGEAK KAARDYETAK    540
NYFKKGLKDM GYGNWISKPQ EEKNFYLCPV GSGSGSLPPL ERLT                    584

SEQ ID NO: 122           moltype = AA  length = 585
FEATURE                  Location/Qualifiers
REGION                   1..585
                         note = Description of Artificial Sequence:
                           Syntheticpolypeptide
source                   1..585
                         mol_type = protein
                         organism = synthetic construct
SEQUENCE: 122
MASNFTQFVL VDNGGTGDVT VAPSNFANGI AEWISSNSRS QAYKVTCSVR QSSAQNRKYT     60
IKVEVPKGAW RSYLNMELTI PIFATNSDCE LIVKAMQGLL KDGNPIPSAI AANSGIYGGS    120
GSGAGSGSPA GGGAPGSGGG SKAERMGFTE VTPVTGASLR RTMLLLSRSP EAQPKTLPLT    180
GSTFHDQIAM LSHRCFNTLT NSFQPSLLGR KILAAIIMKK DSEDMGVVVS LGTGNRCVKG    240
DSLSLKGETV NDCHAEIISR RGFIRFLYSE LMKYNSQTAK DSIFEPAKGG EKLQIKKTVS    300
FHLYISTAPC GDGALFDKSC SDRAMESTES RHYPVFENPK QGKLRTKVEN GQGTIPVESS    360
DIVPTWDGIR LGERLRTMSC SDKILRWNVL GLQGALLTHF LQPIYLKSVT LGYLFSQGHL    420
TRAICCRVTR DGSAFEDGLR HPFIVNHPKV GRVSIYDSKR QSGKTKETSV NWCLADGYDL    480
```

```
EILDGTRGTV DGPRNELSRV SKKNIFLLFK KLCSFRYRRD LLRLSYGEAK KAARDYETAK   540
NYFKKGLKDM GYGNWISKPQ EEKNFYLCPV GSGSGSLPPL ERLTL                  585

SEQ ID NO: 123         moltype = AA  length = 972
FEATURE                Location/Qualifiers
source                 1..972
                       mol_type = protein
                       organism = Ruminococcus flavefaciens
SEQUENCE: 123
EASIEKKKSF AKGMGVKSTL VSGSKVYMTT FAEGSDARLE KIVEGDSIRS VNEGEAFSAE   60
MADKNAGYKI GNAKFSHPKG YAVVANNPLY TGPVQQDMLG LKETLEKRYF GESADGNDNI  120
CIQVIHNILD IEKILAEYIT NAAYAVNNIS GLDKDIIGFG KFSTVYTYDE FKDPEHHRAA  180
FNNNDKLINA IKAQYDEFDN FLDNPRLGYF GQAFFSKEGR NYIINYGNEC YDILALLSGL  240
RHWVVHNNEE ESRISRTWLY NLDKNLDNEY ISTLNYLYDR ITNELTNSFS KNSAANVNYI  300
AETLGINPAE FAEQYFRFSI MKEQKNLGFN ITKLREVMLD RKDMSEIRKN HKVFDSIRTK  360
VYTMMDFVIY RYYIEEDAKV AAANKSLPDN EKSLSEKDIF VINLRGSFND DQKDALYYDE  420
ANRIWRKLEN IMHNIKEFRG NKTREYKKKD APRLPRILPA GRDVSAFSKL MYALTMFLDG  480
KEINDLLTTL INKFDNIQSF LKVMPLIGVN AKFVEEYAFF KDSAKIADEL RLIKSFARMG  540
EPIADARRAM YIDAIRILGT NLSYDELKAL ADTFSLDENG NKLKKGKHGM RNFIINNVIS  600
NKRFHYLIRY GDPAHLHEIA KNEAVVKFVL GRIADIQKKQ GQNGKNQIDR YYETCIGKDK  660
GKSVSEKVDA LTKIITGMNY DQFDKKRSVI EDTGRENAER EKFKKIISLY LTVIYHILKN  720
IVNINARYVI GFHCVERDAQ LYKEKGYDIN LKKLEEKGFS SVTKLCAGID ETAPDKRKDV  780
EKEMAERAKE SIDSLESANP KLYANYIKYS DEKKAEEFTR QINREKAKTA LNAYLRNTKW  840
NVIIREDLLR IDNKTCTLFR NKAVHLEVAR YVHAYINDIA EVNSYFQLYH YIMQRIIMNE  900
RYEKSSGKVS EYFDAVNDEK KYNDRLLKLL CVPFGYCIPR FKNLSIEALF DRNEAAKFDK  960
EKKKVSGNSG SG                                                     972

SEQ ID NO: 124         moltype = AA  length = 991
FEATURE                Location/Qualifiers
REGION                 1..991
                       note = Description of Artificial Sequence:
                       Syntheticpolypeptide
source                 1..991
                       mol_type = protein
                       organism = synthetic construct
SEQUENCE: 124
EASIEKKKSF AKGMGVKSTL VSGSKVYMTT FAEGSDARLE KIVEGDSIRS VNEGEAFSAE   60
MADKNAGYKI GNAKFSHPKG YAVVANNPLY TGPVQQDMLG LKETLEKRYF GESADGNDNI  120
CIQVIHNILD IEKILAEYIT NAAYAVNNIS GLDKDIIGFG KFSTVYTYDE FKDPEHHRAA  180
FNNNDKLINA IKAQYDEFDN FLDNPRLGYF GQAFFSKEGR NYIINYGNEC YDILALLSGL  240
AHWVVANNEE ESRISRTWLY NLDKNLDNEY ISTLNYLYDR ITNELTNSFS KNSAANVNYI  300
AETLGINPAE FAEQYFRFSI MKEQKNLGFN ITKLREVMLD RKDMSEIRKN HKVFDSIRTK  360
VYTMMDFVIY RYYIEEDAKV AAANKSLPDN EKSLSEKDIF VINLRGSFND DQKDALYYDE  420
ANRIWRKLEN IMHNIKEFRG NKTREYKKKD APRLPRILPA GRDVSAFSKL MYALTMFLDG  480
KEINDLLTTL INKFDNIQSF LKVMPLIGVN AKFVEEYAFF KDSAKIADEL RLIKSFARMG  540
EPIADARRAM YIDAIRILGT NLSYDELKAL ADTFSLDENG NKLKKGKHGM RNFIINNVIS  600
NKRFHYLIRY GDPAHLHEIA KNEAVVKFVL GRIADIQKKQ GQNGKNQIDR YYETCIGKDK  660
GKSVSEKVDA LTKIITGMNY DQFDKKRSVI EDTGRENAER EKFKKIISLY LTVIYHILKN  720
IVNINARYVI GFHCVERDAQ LYKEKGYDIN LKKLEEKGFS SVTKLCAGID ETAPDKRKDV  780
EKEMAERAKE SIDSLESANP KLYANYIKYS DEKKAEEFTR QINREKAKTA LNAYLRNTKW  840
NVIIREDLLR IDNKTCTLFA NKAVALEVAR YVHAYINDIA EVNSYFQLYH YIMQRIIMNE  900
RYEKSSGKVS EYFDAVNDEK KYNDRLLKLL CVPFGYCIPR FKNLSIEALF DRNEAAKFDK  960
EKKKVSGNSG SGPKKKRKVA AAYPYDVPDY A                                 991

SEQ ID NO: 125         moltype = AA  length = 1094
FEATURE                Location/Qualifiers
source                 1..1094
                       mol_type = protein
                       organism = Prevotella sp.
SEQUENCE: 125
MNIPALVENQ KKYFGTYSVM AMLNAQTVLD HIQKVADIEG EQNENNENLW FHPVMSHLYN   60
AKNGYDKQPE KTMFIIERLQ SYFPFLKIMA ENQREYSNGK YKQNRVEVNS NDIFEVLKRA  120
FGVLKMYRDL TNHYKTYEEK LNDGCEFLTS TEQPLSGMIN NYYTVALRNM NERYGYKTED  180
LAFIQDKRFK FVKDAYGKKK SQVNTGFFLS LQDYNGDTQK KLHLSGVGIA LLICLFLDKQ  240
YINIFLSRLP IFSSYNAQSE ERRIIIRSFG INSIKLPKDR IHSEKSNKSV AMDMLNEVKR  300
CPDELFTTLS AEKQSRFRII SDDHNEVLMK RSSDRFVPLL LQYIDYGKLF DHIRFHVNMG  360
KLRYLLKADK TCIDGQTRVR VIEQPLNGFG RLEEAETMRK QENGTFGNSG IRIRDFENMK  420
RDDANPANYP YIVDTYTHYI LENNKVEMFI NDKEDSAPLL PVIEDDRYVV KTIPSCRMST  480
LEIPAMAFHM FLFGSKKTEK LIVDVHNRYK RLFQAMQKEE VTAENIASFG IAESDLPQKI  540
LDLISGNAHG KDVDAFIRLT VDDMLTDTER RIKRFKDDRK SIRSADNKMG KRGFKQISTG  600
KLADFLAKDI VLFQPSVNDG ENKITGLNYR IMQSAIAVYD SGDDYEAKQQ FKLMFEKARL  660
IGKGTTEPHP FLYKVFARSI PANAVEFYER YLIERKFYLT GLSNEIKKGN RVDVPFIRRD  720
QNKWKFTPAM K TLGRIYSEDL PVELPRQMFD NEIKSHLKSL PQMEGIDFNN ANVTYLIAEY  780
MKRVLDDDFQ TFYQWNRNYR YMDMLKGEYD RKGSLQHCFT SVEEREGLWK ERASRTERYR  840
KQASNKIRSN RQMRNASSEE IETILDKRLS NSRNEYQKSE KVIRRYRVQD ALLFLLAKKT  900
LTELADFDGE RFKLKEIMPD AEKGILSEIM PMSFTFEKGG KKYTITSEGM KLKNYGDFFV  960
LASDKRIGNL LELVGSDIVS KEDIMEEFNK YDQCRPEISS IVFNLEKWAF DTYPELSARV 1020
DREEKVDFKS ILKILLNNKN INKEQSDILR KIRNAFDHNN YPDKGVVEIK ALPEIAMSIK 1080
KAFGEYAIMK GSLQ                                                  1094
```

-continued

```
SEQ ID NO: 126          moltype = AA   length = 25
FEATURE                 Location/Qualifiers
REGION                  1..25
                        note = Description of Artificial Sequence: Syntheticpeptide
source                  1..25
                        mol_type = protein
                        organism = synthetic construct
SEQUENCE: 126
IWLTALKFLG KHAAKHEAKQ QLSKL                                              25

SEQ ID NO: 127          moltype = AA   length = 75
FEATURE                 Location/Qualifiers
REGION                  1..75
                        note = Description of Artificial Sequence:
                         Syntheticpolypeptide
source                  1..75
                        mol_type = protein
                        organism = synthetic construct
SEQUENCE: 127
IWLTALKFLG KHAAKHEAKQ QLSKLNAVGQ DTQEVIVVPH SLPFKVVVIS AILALVVLTI        60
ISLIILIMLW QKKPR                                                         75

SEQ ID NO: 128          moltype = AA   length = 30
FEATURE                 Location/Qualifiers
REGION                  1..30
                        note = Description of Artificial Sequence:
                         Syntheticpolypeptide
source                  1..30
                        mol_type = protein
                        organism = synthetic construct
SEQUENCE: 128
WEAKLAKALA KALAKHLAKA LAKALKACEA                                         30

SEQ ID NO: 129          moltype = AA   length = 80
FEATURE                 Location/Qualifiers
REGION                  1..80
                        note = Description of Artificial Sequence:
                         Syntheticpolypeptide
source                  1..80
                        mol_type = protein
                        organism = synthetic construct
SEQUENCE: 129
WEAKLAKALA KALAKHLAKA LAKALKACEA NAVGQDTQEV IVVPHSLPFK VVVISAILAL        60
VVLTIISLII LIMLWQKKPR                                                    80

SEQ ID NO: 130          moltype = AA   length = 26
FEATURE                 Location/Qualifiers
REGION                  1..26
                        note = Description of Artificial Sequence: Syntheticpeptide
source                  1..26
                        mol_type = protein
                        organism = synthetic construct
SEQUENCE: 130
KKALLHAALA HLLALAHHLL ALLKKA                                             26

SEQ ID NO: 131          moltype = AA   length = 76
FEATURE                 Location/Qualifiers
REGION                  1..76
                        note = Description of Artificial Sequence:
                         Syntheticpolypeptide
source                  1..76
                        mol_type = protein
                        organism = synthetic construct
SEQUENCE: 131
KKALLHAALA HLLALAHHLL ALLKKANAVG QDTQEVIVVP HSLPFKVVVI SAILALVVLT        60
IISLIILIML WQKKPR                                                        76

SEQ ID NO: 132          moltype = AA   length = 50
FEATURE                 Location/Qualifiers
REGION                  1..50
                        note = Description of Artificial Sequence:
                         Syntheticpolypeptide
source                  1..50
                        mol_type = protein
                        organism = synthetic construct
SEQUENCE: 132
NAVGQDTQEV IVVPHSLPFK VVVISAILAL VVLTIISLII LIMLWQKKPR                   50
```

```
SEQ ID NO: 133         moltype = AA   length = 34
FEATURE                Location/Qualifiers
source                 1..34
                       mol_type = protein
                       organism = Lactococcus lactis
SEQUENCE: 133
ITSISLCTPG CKTGALMGCN MKTATCHCSI HVSK                                  34

SEQ ID NO: 134         moltype = AA   length = 34
FEATURE                Location/Qualifiers
source                 1..34
                       mol_type = protein
                       organism = Lactococcus lactis
SEQUENCE: 134
ITSISLCTPG CKTGALMGCN MKTATCNCSI HVSK                                  34

SEQ ID NO: 135         moltype = AA   length = 34
FEATURE                Location/Qualifiers
source                 1..34
                       mol_type = protein
                       organism = Lactococcus lactis
SEQUENCE: 135
ITSISLCTPG CKTGALMGCN MKTATCNCSV HVSK                                  34

SEQ ID NO: 136         moltype = AA   length = 34
FEATURE                Location/Qualifiers
source                 1..34
                       mol_type = protein
                       organism = Lactococcus lactis
SEQUENCE: 136
ITSISLCTPG CKTGVLMGCN LKTATCNCSV HVSK                                  34

SEQ ID NO: 137         moltype = AA   length = 34
FEATURE                Location/Qualifiers
source                 1..34
                       mol_type = protein
                       organism = Streptococcus hyointestinalis
SEQUENCE: 137
FTSISMCTPG CKTGALMTCN YKTATCHCSI KVSK                                  34

SEQ ID NO: 138         moltype = AA   length = 31
FEATURE                Location/Qualifiers
source                 1..31
                       mol_type = protein
                       organism = Streptococcus uberis
SEQUENCE: 138
ITSKSLCTPG CKTGILMTCP LKTATCGCHF G                                     31

SEQ ID NO: 139         moltype = AA   length = 31
FEATURE                Location/Qualifiers
source                 1..31
                       mol_type = protein
                       organism = Streptococcus uberis
SEQUENCE: 139
VTSKSLCTPG CKTGILMTCP LKTATCGCHF G                                     31

SEQ ID NO: 140         moltype = AA   length = 31
FEATURE                Location/Qualifiers
source                 1..31
                       mol_type = protein
                       organism = Streptococcus gallolyticus
SEQUENCE: 140
VTSKSLCTPG CKTGILMTCA IKTATCGCHF G                                     31

SEQ ID NO: 141         moltype = AA   length = 34
FEATURE                Location/Qualifiers
source                 1..34
                       mol_type = protein
                       organism = Lactococcus lactis
SEQUENCE: 141
ITSISLCTPG CKTGALMGCN MKTATCHCAI HVSK                                  34

SEQ ID NO: 142         moltype = AA   length = 34
FEATURE                Location/Qualifiers
source                 1..34
                       mol_type = protein
                       organism = Lactococcus lactis
SEQUENCE: 142
ITSISLCTPG CKTGALMGCN MKTATCHCDI HVSK                                  34
```

```
SEQ ID NO: 143          moltype = AA  length = 34
FEATURE                 Location/Qualifiers
source                  1..34
                        mol_type = protein
                        organism = Lactococcus lactis
SEQUENCE: 143
ITSISLCTPG CKTGALMGCN MKTATCHCEI HVSK                              34

SEQ ID NO: 144          moltype = AA  length = 34
FEATURE                 Location/Qualifiers
source                  1..34
                        mol_type = protein
                        organism = Lactococcus lactis
SEQUENCE: 144
ITSISLCTPG CKTGALMGCN MKTATCHCGI HVSK                              34

SEQ ID NO: 145          moltype = AA  length = 34
FEATURE                 Location/Qualifiers
source                  1..34
                        mol_type = protein
                        organism = Lactococcus lactis
SEQUENCE: 145
ITSISLCTPG CKTGALMGCN MTTATCHCSI HVSK                              34

SEQ ID NO: 146          moltype = AA  length = 34
FEATURE                 Location/Qualifiers
source                  1..34
                        mol_type = protein
                        organism = Lactococcus lactis
SEQUENCE: 146
ITSISLCTPG CKTGALMGCP MKTATCHCSI HVSK                              34

SEQ ID NO: 147          moltype = AA  length = 34
FEATURE                 Location/Qualifiers
source                  1..34
                        mol_type = protein
                        organism = Lactococcus lactis
SEQUENCE: 147
ITSISLCTPG CKTGALMGCN VKTATCHCSI HVSK                              34

SEQ ID NO: 148          moltype = AA  length = 34
FEATURE                 Location/Qualifiers
source                  1..34
                        mol_type = protein
                        organism = Lactococcus lactis
SEQUENCE: 148
ITSISLCTPG CKTGALMGCN MSTATCHCSI HVSK                              34

SEQ ID NO: 149          moltype = AA  length = 34
FEATURE                 Location/Qualifiers
source                  1..34
                        mol_type = protein
                        organism = Lactococcus lactis
SEQUENCE: 149
ITSISLCTPG CKTGALMGCK MKTATCNCSI HVSK                              34

SEQ ID NO: 150          moltype = AA  length = 34
FEATURE                 Location/Qualifiers
source                  1..34
                        mol_type = protein
                        organism = Lactococcus lactis
SEQUENCE: 150
ITSISLCTPG CKTGALMGCN KKTATCNCSI HVSK                              34

SEQ ID NO: 151          moltype = RNA  length = 143
FEATURE                 Location/Qualifiers
misc_feature            1..143
                        note = Description of Artificial Sequence:
                        Syntheticpolynucleotide
source                  1..143
                        mol_type = other RNA
                        organism = synthetic construct
SEQUENCE: 151
gttttagagc taggccaaca tgaggatcac ccatgtctgc agggcctagc aagttaaaat    60
aaggctagtc cgttatcaac ttggccaaca tgaggatcac ccatgtctgc agggccaagt   120
ggcaccgagt cggtgctttt ttt                                           143

SEQ ID NO: 152          moltype = RNA  length = 199
```

```
FEATURE                Location/Qualifiers
misc_feature           1..199
                       note = Description of Artificial Sequence:
                       Syntheticpolynucleotide
source                 1..199
                       mol_type = other RNA
                       organism = synthetic construct
SEQUENCE: 152
gttttagagc taggccaaca tgaggatcac ccatgtctgc agggcctagc aagttaaaat    60
aaggctagtc cgttatcaac ttggccaaca tgaggatcac ccatgtctgc agggccaagt   120
ggcaccgagt cggtgcggga gcacatgagg atcacccatg tgcgactccc acagtcactg   180
gggagtcttc ccttttttt                                                199

SEQ ID NO: 153         moltype = RNA  length = 149
FEATURE                Location/Qualifiers
misc_feature           1..149
                       note = Description of Artificial Sequence:
                       Syntheticpolynucleotide
source                 1..149
                       mol_type = other RNA
                       organism = synthetic construct
SEQUENCE: 153
gtttaagagc tatgctggaa acagcatagc aagtttaaat aaggctagtc cgttatcaac    60
ttgaaaaagt ggcaccgagt cggtgcggga gcacatgagg atcacccatg tgcgactccc   120
acagtcactg gggagtcttc ccttttttt                                     149

SEQ ID NO: 154         moltype = RNA  length = 186
FEATURE                Location/Qualifiers
misc_feature           1..186
                       note = Description of Artificial Sequence:
                       Syntheticpolynucleotide
source                 1..186
                       mol_type = other RNA
                       organism = synthetic construct
SEQUENCE: 154
ttctagatca tcgaaacatg aggatcaccc atatctgcag tcgacatcga aacatgagga    60
tcacccatgt ctgcagtcga catcgaaaca tgaggatcac ccatgtctgc agtcgacatc   120
gaaacatgag gatcacccat gtctgcagtc gacatcgaaa tcgataagct tcagatcaga   180
tcctag                                                              186

SEQ ID NO: 155         moltype = RNA  length = 19
FEATURE                Location/Qualifiers
misc_feature           1..19
                       note = Description of Artificial Sequence:
                       Syntheticoligonucleotide
source                 1..19
                       mol_type = other RNA
                       organism = synthetic construct
SEQUENCE: 155
acatgaggat cacccatgt                                                 19

SEQ ID NO: 156         moltype = RNA  length = 19
FEATURE                Location/Qualifiers
misc_feature           1..19
                       note = Description of Artificial Sequence:
                       Syntheticoligonucleotide
source                 1..19
                       mol_type = other RNA
                       organism = synthetic construct
SEQUENCE: 156
acatgaggat cacccatat                                                 19

SEQ ID NO: 157         moltype = RNA  length = 14
FEATURE                Location/Qualifiers
misc_feature           1..14
                       note = Description of Artificial Sequence:
                       Syntheticoligonucleotide
source                 1..14
                       mol_type = other RNA
                       organism = synthetic construct
SEQUENCE: 157
ccacagtcac tggg                                                      14

SEQ ID NO: 158         moltype = RNA  length = 89
FEATURE                Location/Qualifiers
misc_feature           1..89
                       note = Description of Artificial Sequence:
                       Syntheticoligonucleotide
source                 1..89
```

```
                            mol_type = other RNA
                            organism = synthetic construct
SEQUENCE: 158
acatgaggat cacccatgtc tgcagggcct agcaagttaa aataaggcta gtccgttatc   60
aacttggcca acatgaggat cacccatgt                                     89

SEQ ID NO: 159              moltype = RNA   length = 141
FEATURE                     Location/Qualifiers
misc_feature                1..141
                            note = Description of Artificial Sequence:
                              Syntheticpolynucleotide
source                      1..141
                            mol_type = other RNA
                            organism = synthetic construct
SEQUENCE: 159
gttttagagc taggccggag cagacgatat ggcgtcgctc cggcctagca agttaaaata   60
aggctagtcc gttatcaact tggccggagc agacgatatg gcgtcgctcc ggccaagtgg  120
caccgagtcg gtgcttttt t                                             141

SEQ ID NO: 160              moltype = RNA   length = 32
FEATURE                     Location/Qualifiers
misc_feature                1..32
                            note = Description of Artificial Sequence:
                              Syntheticoligonucleotide
source                      1..32
                            mol_type = other RNA
                            organism = synthetic construct
SEQUENCE: 160
gccggagcag acgatatggc gtcgctccgg cc                                 32

SEQ ID NO: 161              moltype = RNA   length = 112
FEATURE                     Location/Qualifiers
misc_feature                1..112
                            note = Description of Artificial Sequence:
                              Syntheticpolynucleotide
source                      1..112
                            mol_type = other RNA
                            organism = synthetic construct
SEQUENCE: 161
gtttaagagc tatgctggaa acagcatagc aagtttaaat aaggctagtc cgttatcaac   60
ttgaaaaagt ggcaccgagt cggtgcctga atgcctgcga gcatcttttt tt          112

SEQ ID NO: 162              moltype = RNA   length = 19
FEATURE                     Location/Qualifiers
misc_feature                1..19
                            note = Description of Artificial Sequence:
                              Syntheticoligonucleotide
source                      1..19
                            mol_type = other RNA
                            organism = synthetic construct
SEQUENCE: 162
ctgaatgcct gcgagcatc                                                19

SEQ ID NO: 163              moltype = RNA   length = 448
FEATURE                     Location/Qualifiers
misc_feature                1..448
                            note = Description of Artificial Sequence:
                              Syntheticpolynucleotide
source                      1..448
                            mol_type = other RNA
                            organism = synthetic construct
SEQUENCE: 163
agtgacagtg gagattgtac agttttttcc tcgatttgtc aggatttttt tttttttgacg   60
gagtttaact tcttgtctcc caggtaggaa gtgcagtggc gtaatctcgg ctcactacaa  120
cctccacctc ctgggttcaa gcgtttctct tgcctcagct ttccgagtag ctgggattac  180
aggcgcctgc caccatgccc tgctgacttt tgtattttta gtagacggg ggtttcacca   240
tgttggccag gctggtcttg aactcctgac cgcaggcgat tggcctgcct cggcctccca  300
aagtgctgag attacaggcg tgagccacca ccccggcct caggagcgtt ctgatagtgc   360
ctcgatgtgc tgcctcctat aaagtgttag cagcacagat cacttttgt aaaggtacgt   420
actaatgact tttttttat acttcagg                                      448

SEQ ID NO: 164              moltype = RNA   length = 796
FEATURE                     Location/Qualifiers
misc_feature                1..796
                            note = Description of Artificial Sequence:
                              Syntheticpolynucleotide
source                      1..796
                            mol_type = other RNA
                            organism = synthetic construct
```

-continued

```
SEQUENCE: 164
taagaagcaa ggtttcattt aggggaaggg aaatgattca ggacgagagt ctttgtgctg   60
ctgagtgcct gtgatgaaga agcatgttag tcctgggcaa cgtagcgaga ccccatctct  120
acaaaaaata gaaaaattag ccaggtatag tggcgcacac ctgtgattcc agctacgcag  180
gaggctgagg tgggaggatt gcttgagccc aggaggttga ggctgcagtg agctgtaatc  240
atgccactac tccaacctgg gcaacacagc aaggaccctg tctcaaaagc tacttacaga  300
aaagaattag gctcggcacg gtagctcaca cctgtaatcc cagcactttg ggaggctgag  360
gcgggcagat cacttgaggt caggagtttg agaccagcct ggccaacatg gtgaaacctt  420
gtctctacta aaaatatgaa aattagccag gcatggtggc acattcctgt aatcccagct  480
actcgggagg ctgaggcagg agaatcactt gaacccagga ggtggaggtt gcagtaagcc  540
gagatcgtac cactgtgctc tagccttggt gacagagcga gactgtctta aaaaaaaaaa  600
aaaaaaaaaa agaattaatt aaaaatttaa aaaaaatga aaaaagctg catgcttgtt  660
ttttgttttt agtattcta cattgttgtc attattacca aatattgggg aaaatacaac  720
ttacagacca atctcaggag ttaaatgtta ctacgaaggc aaatgaacta tgcgtaatga  780
acctggtagg cattag                                                 796

SEQ ID NO: 165         moltype = RNA  length = 133
FEATURE                Location/Qualifiers
misc_feature           1..133
                       note = Description of Artificial Sequence:
                       Syntheticpolynucleotide
source                 1..133
                       mol_type = other RNA
                       organism = synthetic construct
SEQUENCE: 165
gtaagtatca aggttacaag acaggtttaa ggagaccaat agaaactggg cttgtcgaga   60
cagagaagac tcttgcgttt ctgataggca cctattggtc ttactgacat ccactttgcc  120
tttctctcca cag                                                    133

SEQ ID NO: 166         moltype = DNA  length = 18
FEATURE                Location/Qualifiers
misc_feature           1..18
                       note = Description of Artificial Sequence:
                       Syntheticoligonucleotide
source                 1..18
                       mol_type = other DNA
                       organism = synthetic construct
SEQUENCE: 166
gaagaagctg caggaggt                                                18

SEQ ID NO: 167         moltype = DNA  length = 18
FEATURE                Location/Qualifiers
misc_feature           1..18
                       note = Description of Artificial Sequence:
                       Syntheticoligonucleotide
source                 1..18
                       mol_type = other DNA
                       organism = synthetic construct
SEQUENCE: 167
gctggagggg aagtggtc                                                18

SEQ ID NO: 168         moltype = DNA  length = 36
FEATURE                Location/Qualifiers
misc_feature           1..36
                       note = Description of Artificial Sequence:
                       Syntheticoligonucleotide
source                 1..36
                       mol_type = other DNA
                       organism = synthetic construct
SEQUENCE: 168
gaagaagctg caggaggtgc tggaggggaa gtggtc                            36

SEQ ID NO: 169         moltype = DNA  length = 346
FEATURE                Location/Qualifiers
misc_feature           1..346
                       note = Description of Artificial Sequence:
                       Syntheticpolynucleotide
source                 1..346
                       mol_type = other DNA
                       organism = synthetic construct
SEQUENCE: 169
tgaagaagct gcaggaggtg ctggagggga agtggtccgg atcttgaaga agctgcagga   60
ggtgctggag gggaagtggt ccggatcttg aagaagctgc aggaggtgct ggaggggaag  120
tggtccggat cttgaagaag ctgcaggagg tgctggaggg gaagtggtc ggatcttgaa  180
gaagctgcag gaggtgctgg aggggaagtg gtccggatct tgaagaagct gcaggaggtg  240
ctggagggga agtggtccgg atcttgaaga agctgcagga ggtgctggag gggaagtggt  300
ccggatcttg aagaagctgc aggaggtgct ggaggggaag tggtcc                 346

SEQ ID NO: 170         moltype =     length =
```

```
SEQUENCE: 170
000

SEQ ID NO: 171          moltype = DNA  length = 20
FEATURE                 Location/Qualifiers
misc_feature            1..20
                        note = Description of Artificial Sequence:
                        Syntheticoligonucleotide
source                  1..20
                        mol_type = other DNA
                        organism = synthetic construct
SEQUENCE: 171
cggcgtagcc gatgtcgcgc                                                    20

SEQ ID NO: 172          moltype =      length =
SEQUENCE: 172
000

SEQ ID NO: 173          moltype =      length =
SEQUENCE: 173
000

SEQ ID NO: 174          moltype = DNA  length = 18
FEATURE                 Location/Qualifiers
misc_feature            1..18
                        note = Description of Artificial Sequence:
                        Syntheticoligonucleotide
source                  1..18
                        mol_type = other DNA
                        organism = synthetic construct
SEQUENCE: 174
aagggttcag cgtgggcg                                                      18

SEQ ID NO: 175          moltype = DNA  length = 19
FEATURE                 Location/Qualifiers
misc_feature            1..19
                        note = Description of Artificial Sequence:
                        Syntheticoligonucleotide
source                  1..19
                        mol_type = other DNA
                        organism = synthetic construct
SEQUENCE: 175
aagggttcag gcgtgggcg                                                     19

SEQ ID NO: 176          moltype = DNA  length = 20
FEATURE                 Location/Qualifiers
misc_feature            1..20
                        note = Description of Artificial Sequence:
                        Syntheticoligonucleotide
source                  1..20
                        mol_type = other DNA
                        organism = synthetic construct
SEQUENCE: 176
aagggttcag tgcgtgggcg                                                    20

SEQ ID NO: 177          moltype = DNA  length = 26
FEATURE                 Location/Qualifiers
misc_feature            1..26
                        note = Description of Artificial Sequence:
                        Syntheticoligonucleotide
source                  1..26
                        mol_type = other DNA
                        organism = synthetic construct
SEQUENCE: 177
gatccgccac aacatcgagg acggca                                             26

SEQ ID NO: 178          moltype = DNA  length = 4215
FEATURE                 Location/Qualifiers
misc_feature            1..4215
                        note = Description of Artificial Sequence:
                        Syntheticpolynucleotide
source                  1..4215
                        mol_type = other DNA
                        organism = synthetic construct
SEQUENCE: 178
atggacaaga agtacagcat cggcctggac atcggcacca actctgtggg ctgggccgtg        60
atcaccgacg agtacaaggt gcccagcaag aaattcaagg tgctgggcaa caccgaccgg       120
cacagcatca agaagaacct gatcggagcc ctgctgttcg acagcggcga aacagccgag       180
gccacccggc tgaagagaac cgccagaaga agatacacca gacggaagaa ccggatctgc       240
```

```
tatctgcaag agatcttcag caacgagatg gccaaggtgg acgacagctt cttccacaga    300
ctggaagagt ccttcctggt ggaagaggat aagaagcacg agcggcaccc catcttcggc    360
aacatcgtgg acgaggtggc ctaccacgag aagtacccca ccatctacca cctgagaaag    420
aaactggtgt acagcaccga caaggccgac ctgcggctga tctatctggc cctggcccac    480
atgatcaagt tccggggcca cttcctgatc gagggcgacc tgaaccccga caacagcgac    540
gtggacaagc tgttcatcca gctggtgcag acctacaacc agctgttcga ggaaaacccc    600
atcaacgcca gcggcgtgga cgccaaggcc atcctgtctg ccagactgag caagagcaga    660
cggctggaaa tctgatcgc ccagctgccc ggcgagaaga gaatggcct gttcggaaac    720
ctgattgccc tgagcctggg cctgaccccc aacttcaaga gcaacttcga cctggccgag    780
gatgccaaac tgcagctgag caaggacacc tacgacgacg acctggacaa cctgctggcc    840
cagatcggcg accagtacgc cgacctgttt ctggccgcca agaacctgtc cgacgccatc    900
ctgctgagcg acatcctgag agtgaacacc gagatcacca aggcccccct gagcgcctct    960
atgatcaaga gatacgacga gcaccaccag gacctgaccc tgctgaaagc tctcgtgcgg   1020
cagcagctgc ctgagaagta caaagagatt ttcttcgacc agagcaagaa ggctacgcc   1080
ggctacattg acggcggagc cagccaggaa gagttctaca agttcatcaa gcccatcctg   1140
gaaaagatgg acggcaccga ggaactgctc gtgaagctga acagagagga cctgctgcgg   1200
aagcagcgga ccttcgacaa cggcagcatc ccccaccaga tccacctggg agagctgcac   1260
gccattctgc ggcggcagga agatttttac ccattcctga aggacaaccg ggaaaagatc   1320
gagaagatcc tgaccttccg catccccctac tacgtgggcc ctctggccag gggaaacagc   1380
agattcgcct ggatgaccag aaagagcgag gaaaccatca cccccctggaa cttcgaggaa   1440
gtggtggaca agggcgcttc cgcccagagc ttcatcgagc ggatgaccaa cttcgataag   1500
aacctgccca acgagaaggt gctgcccaag cacagcctgc tgtacgagta cttcaccgtg   1560
tataacgagc tgaccaaagt gaaatacgtg accgagggga tgagaaagcc cgccttcctg   1620
agcggcgagc agaaaaaggc catcgtggac ctgctgttca agaccaaccg gaaagtgacc   1680
gtgaagcagc tgaaagagga ctacttcaag aaaatcgagt gcttcgactc cgtggaaatc   1740
tccggcgtgg aagatcggtt caacgcctcc ctgggcacat accacgatct gctgaaaatt   1800
atcaaggaca aggacttcct ggacaatgag gaaaacgagg acattctgga agatatcgtg   1860
ctgaccctga cactgtttga ggacagagag atgatcgagg aacggctgaa aacctatgcc   1920
cacctgttcg acgacaaagt gatgaagcag ctgaagcggc ggagatacac cggctggggc   1980
aggctgagcc ggaagctgat caacggcatc cgggacaagc agtccggaca gcaatcctg   2040
gatttcctga gtccgacgg cttcgccaac agaaacttca tgcagctgat ccacgacgac   2100
agcctgacct ttaaagagga catccagaaa gcccaggtgt ccggccaggg cgatagcctg   2160
cacgagcaca ttgccaatct ggccggcagc cccgccatta gaagggcat cctgcagaca   2220
gtgaaggtgg tggacgagct cgtgaaagtg atgggccggc acaagcccga gaacatcgtg   2280
atcgaaatgg ccagagagaa ccagaccacc cagaaggcac agaagaacag ccgcgagaga   2340
atgaagcgga tcgaagaggg catcaaagag ctgggcagcc agatcctgaa agaacacccc   2400
gtggaaaaca cccagctgca gaacgagaag ctgtacctgt actacctgca gaatgggcgg   2460
gatatgtacg tggaccagga actggacatc aaccggctgt ccgactacga tgtggaccat   2520
atcgtgcctc agagctttct gaaggacgac tccatcgaca aacaggtgct gaccagaagc   2580
gacaagaacc ggggcaagag cgacaacgtg ccctccgaag aggtcgtgaa aagaatgaag   2640
aactactggc ggcagctgct gaacgccaag ctgattaccc agagaaagtt cgacaatctg   2700
accaaggccg agagaggcgg cctgagcgaa ctggataagg ccggcttcat caagagacag   2760
ctggtggaaa cccggcagat cacaaagcac gtggcacaga tcctggactc ccggatgaac   2820
actaagtacg acgagaatga caagctgatc cggaagtga agtgatcac cctgaagtcc   2880
aagctggtgt ccgatttccg gaaggatttc cagttttaca agtgcgcga tcaacaac   2940
taccaccacg cccacgacgc ctacctgaac gccgtcgtgg gaaccgccct gatcaaaaag   3000
taccctaagc tggaaagcga gttcgtgtac ggcgactaca aggtgtacga cgtgcggaag   3060
atgatcgcca gagcgagca ggaaatcggc aaggctaccg ccaagtactt cttctacagc   3120
aacatcatga acttttcaa gaccgagatt accctggcca acggcgagat ccggaagcgg   3180
cctctgatcg agacaaacgg cgaaaccggg gagatcgtgt gggataaggg ccgggatttt   3240
gccaccgtgc ggaaagtgct gagcatgccc caagtgaata tcgtgaaaaa gaccgaggtg   3300
cagacaggcg gcttcagcaa agagtctatc ctgcccaaga ggaacagcga taagctgatc   3360
gccagaaaga aggactggga ccctaagaag tacggcggct tcgacagccc caccgtggcc   3420
tattctgtgc tggtggtggc caaagtgaa aagggcaagt ccaagaaact gaagagtgtg   3480
aaagagctgc tggggatcac catcatgaga gaagcgctt cgagaagaa tcccatcgac   3540
tttctgaag ccaagggcta caaagaagtg aaaaaggacc tgatcatcaa gctgcctaag   3600
tactccctgt tcgagctgga aaacggccgg aagagaatgc tggcctctgc cggcgaactg   3660
cagaagggaa acgaactggc cctgcccccc aaatatgtga acttcctgta cctggccagc   3720
cactatgaga gctgaaggg ctcccccgag gataatgagc agaaacagct gtttgtggaa   3780
cagcacaagc actacctgga cgagatcatc gagcagatca gcgagttctc caagagagtg   3840
atcctggccg acgctaatct ggacaaagtg ctgtccgcct acaacaagca ccgggataag   3900
cccatcagag agcaggccga gaatatcatc cacctgttta ccctgaccaa tctgggagcc   3960
cctgccgcct tcaagtactt tgacaccacc atcgaccgga gaggtacac cagcaccaaa   4020
gaggtgctgg acgccaccct gatccaccag agcatcaccg gcctgtacga gacacggatc   4080
gacctgtctc agctggggag cgacggatcc cccaagaaga gaggaaagt ctcgagcgac   4140
tacaaagacc atgacggtga ttataaagat catgacatcg attacaagga tgacgatgac   4200
aaggctgcag gatga                                                    4215
```

```
SEQ ID NO: 179        moltype = DNA  length = 4260
FEATURE               Location/Qualifiers
misc_feature          1..4260
                      note = Description of Artificial Sequence:
                      Syntheticpolynucleotide
source                1..4260
                      mol_type = other DNA
                      organism = synthetic construct
SEQUENCE: 179
atggacaaga agtacagcat cggcctggac atcggcacca actctgtggg ctgggccgtg     60
atcaccgacg agtacaaggt gcccagcaag aaattcaagg tgctgggcaa caccgaccgg    120
```

```
cacagcatca agaagaacct gatcggagcc ctgctgttcg acagcggcga acagccgag    180
gccaccggc tgaagagaac cgccagaaga agatacacca gacggaagaa ccggatctgc    240
tatctgcaag agatcttcag caacgagatg gccaaggtgg acgacagctt cttccacaga   300
ctggaagagt ccttcctggt ggaagaggat aagaagcacg agcggcaccc catcttcggc   360
aacatcgtgg acgaggtggc ctaccacgag aagtacccca ccatctacca cctgagaaag   420
aaactggtgg acagcaccga caaggccgac ctgcggctga tctatctggc cctggcccac   480
atgatcaagt tccggggcca cttcctgatc gagggcgacc tgaaccccga caacagcgac   540
gtggacaagc tgttcatcca gctggtgcag acctacaacc agctgttcga ggaaaacccc   600
atcaacgcca gcggcgtgga cgccaaggcc atcctgctg cagactgag caagagcaga    660
cggctggaaa atctgatcgc ccagctgccc ggcgagaaga agaatggcct gttcggaaac   720
ctgattgccc tgagcctggg cctgaccccc aacttcaaga gcaacttcga cctggccgag   780
gatgccaaac tgcagctgag caaggacacc tacgacgacg acctgacaa cctgctggcc    840
cagatcggcc accagtacgc cgacctgttt ctggccgcca agaacctgtc cgacgccatc   900
ctgctgagcg acatcctgag agtgaacacc gagatcacca aggcccccct gagcgcctct   960
atgatcaaga gatacgacga gcaccaccag gacctgaccc tgctgaaagc tctcgtgcgg  1020
cagcagctgc tgagaagta caaagagatt tccttcgacc agagcaagaa cggctacgcc  1080
ggctacattg acggcggagc cagccaggaa gagttctaca agttcatcaa gcccatcctg  1140
gaaaagatgg acggcaccga ggaactgctc gtgaagctga acagagagga cctgctgcgg  1200
aagcagcgga cctccgacaa cggcagcatc cccaccagag tccacctggg agagctgcac  1260
gccattctgc ggcggcagga agattttttac ccattcctga aggacaaccg ggaaaagatc  1320
gagaagatcc tgaccttccg catccctac tacgtgggc ctctggccag gggaaacagc    1380
agattcgcct ggatgaccag aaagagcgag gaaaccatca cccctggaa cttcgaggaa    1440
gtggtggaca agggcgcttc cgcccagagc ttcatcgagc ggatgaccaa cttcgataag  1500
aacctgccca cgagaaggt gctgcccaag cacagcctgc tgtacgagta cttcaccgtg    1560
tataacgagc tgaccaaagt gaaatacgtg accgaggaa tgaaaagcc cgccttcctg     1620
agcggcgagc agaaaaagcc catcgtggac ctgctgttca agaccaaccg gaaagtgacc  1680
gtgaagcagc tgaaagagga ctacttcaag aaaatcgagt gcttcgactc cgtggaaatc  1740
tccggcgtgg aagatcggtt caacgcctcc ctgggcacat accacgatct gctgaaaatt  1800
atcaaggaca aggacttcct ggacaatgag gaaaacgagg acattctgga agatatcgtg  1860
ctgaccctga cactgtttga ggacagagag atgatcgagg aacggctgaa aacctatgcc  1920
cacctgttcg acgacaaagt gatgaagcag ctgaagcggc ggagatacac cggctgggc   1980
aggctgagcc ggaagctgat caacggcatc cgggacaagc agtccggcaa gacaatcctg   2040
gatttcctga agtccgacgg cttcgccaac agaaacttca tgcagctgat ccacgacgac   2100
agcctgacct ttaaagagga catccagaaa gcccaggtgt ccggccaggg cgatagcctg   2160
cacgagcaca ttgccaatct ggccggcagc cccgccatta agaagggct cctgcagaca   2220
gtgaaggtgg tggacgagct cgtgaaagtg atgggccggc acaagcccga gaacatcgtg   2280
atcgaaatgg ccagagagaa ccagaccacc cagaagggac agaagaacag ccgcgagaga   2340
atgaagcgga tcgaagaggg catcaaagag ctgggcagcc agatcctgaa agaacacccc   2400
gtgaaaaca cccagctgca gaacgagaag ctgtacctgt actacctgca gaatgggcgg    2460
gatatgtacg tggaccagga actgacatc aaccggctgt ccgactacga tgtggaccat    2520
atcgtgcctc agagctttct gaaggacgac tccatcgaca caaggtgct gaccagaagc   2580
gacaagaacc ggggcaagag cgacaacgtg ccctccgaag aggtcgtgaa gaagatgaag   2640
aactactggc ggcagctgct gaacgccaag ctgattaccc agagaaagtt cgacaatctg   2700
accaaggccg agagaggcgg cctgagcgaa ctggataagg ccggcttcat caagagacag   2760
ctggtggaaa cccggcagat cacaaagcac gtggcacaga tcctggactc ccggatgaac   2820
actaagtacg acgagaatga caagctgatc cgggaagtga agtgatcac cctgaagtcc   2880
aagctgtgt ccgatttccg gaaggatttc cagtttaca aagtcgcga gatcaacaac     2940
taccaccacg cccacgacgc ctacctgaac gccgtcgtgg aaccgccct gatcaaaaag   3000
tacctaagc tggaaagcga gttcgtgtac ggcgactaca agtgtacga cgtgcggaag    3060
atgatcgcca gagcgagca ggaaatcggc aaggctaccg ccaagtactt cttctacagc   3120
aacatcatga cttttcaa gaccgagatt accctggcca acggcgagat ccggaagcgg    3180
cctctgatcg agacaaacgg cgaaaccggg gagatcgtgt gggataaggg ccggattt    3240
gccaccgtgc ggaaagtgct gagcatgccc caagtgaata tcgtgaaaaa gaccgaggtg   3300
cagacaggcg gcttcagcaa agagtctatc ctgcccaaga ggaacagcga taagctgatc   3360
gccagaaaga aggactggga ccctaagaag tacggcggtt tcgacagccc caccgtggcc   3420
tattctgtgc tggtggtggc caagtggaa aagggcaagt ccaagaaact gaagagtgtg    3480
aaagagctgc tggggatcac catcatgaa agagcagct tcgagaagaa tcccatcgac    3540
tttctgaag ccaagggcta caaagaagtg aaaaaggacc tgatcatcaa gctgcctaag  3600
tactccctgt tcgagctgga aacggccgg aagagaatgc tggcctctgc cggcgaactg   3660
cagaagggaa acgaactggc cctgccctcc aatatgtga acttcctgta cctggccagc  3720
cactatgaga agctgaaggg ctcccccgag gataatgagc agaaacagct gtttgtggaa   3780
cagcacaagc actacctgga cgagatcatc gagcagatca gcgagttctc caagagagtg   3840
atcctggccg acgctaatct ggacaaagtg ctgtccgcct acaacaagca ccgggataag   3900
cccatcagag agcaggccga aatatcatc cacctgttta cctgaccaa tctgggagcc    3960
cctgccgcct tcaagtactt tgacaccacc atcgaccgga agaggtacac cagcaccaaa  4020
gaggtgctgg acgccaccct gatccaccag agcatcaccg gcctgtacga cacacggatc  4080
gacctgtctc agctgggagg cgacggatcc ggcgaggcg gaagcgggaa aagaaccgcc  4140
gacggcgcg aattcgagcc caagaagaag aggaaagtct cgagcggagg cgactacaaa   4200
gaccatgacg gtgattataa agatcatgac atcgattaca aggatgacga tgacaagtga   4260
```

SEQ ID NO: 180      moltype = DNA   length = 5562
FEATURE             Location/Qualifiers
misc_feature        1..5562
                    note = Description of Artificial Sequence:
                    Syntheticpolynucleotide
source              1..5562
                    mol_type = other DNA
                    organism = synthetic construct
SEQUENCE: 180

```
atgaaacgga cagccgacgg aagcgagttc gagtcaccaa agaagaagcg gaaagtctcc    60
tcagagactg ggcctgtcgc cgtcgatcca accctgcgcc gccggattga acctcacgag   120
tttgaagtgt tctttgaccc ccgggagctg agaaaggaga catgcctgct gtacgagatc   180
aactggggag gcaggcactc catctggagg cacacctctc agaacacaaa taagcacgtg   240
gaggtgaact tcatcgagaa gtttaccaca gagcggtact tctgccccaa taccagatgt   300
agcatcacat ggtttctgag ctggtcccct tgcggagagt gtagcagggc catcaccgag   360
ttcctgtcca gatatccaca cgtgacactg tttatctaca tcgccaggct gtatcaccac   420
gcagacccaa ggaataggca gggcctgcgc gatctgatca gctccggcgt gaccatccag   480
atcatgacag agcaggagtc cggctactgc tggcggaact tcgtgaatta ttctcctagc   540
aacgaggccc actggcctag gtacccacac ctgtgggtgc gcctgtacgt gctggagctg   600
tattgcatca tcctgggcct gcccccttgt ctgaatatcc tgcggagaaa gcagcccag   660
ctgaccttct ttacaatcgc cctgcagtct tgtcactatc agaggctgcc accccacatc   720
ctgtgggcca caggcctgaa gtctggagga tctagcggag gatcctctgg cagcgagaca   780
ccaggaacaa gcgagtcagc aacaccagag agcagtgggc gcagcaggcc cggcagcgac   840
aagaagtaca gcatcggcct ggacatcggc accaactctg tgggctgggc cgtgatcacc   900
gacgagtaca aggtgcccag caagaaattc aaggtgctgg gcaacaccga ccggcacagc   960
atcaagaaga acctgatcgg agccctgctg ttcgacagcg gcgaaacagc cgaggccacc  1020
cggctgaaga gaaccgccaa gaagagatac accagacgga agaaccggat ctgctatctg  1080
caagagatct tcagcaacga gatggccaag gtggacgaca gcttcttcca cagactggaa  1140
gagtccttcc tggtggaaga ggataagaag cacgagcggc accccatctt cggcaacatc  1200
gtggacgagg tggcctacca cgagaagtac cccaccatct accacctgag aaagaaactg  1260
gtggacagca ccgacaaggc cgacctgcgg ctgatctatc tggccctggc ccacatgatc  1320
aagttccggg gccacttcct gatcgagggc gacctgaacc ccgacaacag cgacgtggac  1380
aagctgttca tccagctggt gcagacctac aaccagctgt tcgaggaaaa ccccatcaac  1440
gccagcggcg tggacgccaa ggccatcctg tctgccagac tgagcaagag cagacggctg  1500
gaaaatctga tcgcccagct gcccggcgag aagaagaatg gcctgttcgg aaacctgatt  1560
gccctgagcc tgggcctgac ccccaacttc aagagcaact tcgacctggc cgaggatgcc  1620
aaaactgcagc tgagcaagga cacctacgac gacgacctgg acaacctgct ggcccagatc  1680
ggcgaccagt acgccgacct gttctctggcc gccaagaacc tgtccgacgc catcctgctg  1740
agcgacatcc tgagagtgaa caccgagatc accaaggccc ccctgagcgc ctctatgatc  1800
aagagatacg acgagcacca ccaggacctg accctgctga agctctcgt gcggcagcag  1860
ctgcctgaga gtacaaaga gattttcttc gaccagagca agaacggcta cgccggctac  1920
attgacggcg gagccagcca ggaagagttc tacaagttca tcaagcccat cctggaaaag  1980
atggacggca ccgaggaact gctcgtgaag ctgaacagag aggacctgct gcggaagcag  2040
cggaccttcg acaacggcag catccccac cagatccacc tgggagagct gcacgccatt  2100
ctgcggcggc aggaagattt ttaccccattc ctgaaggaca accggaaaaa gatcgagaag  2160
atcctgacct tccgcatccc ctactacgtg ggccctctgg ccaggggaaa cagcagattc  2220
gcctggatga ccagaaagag cgaggaaacc atcaccccct ggaacttcga ggaagtggtg  2280
gacaagggcg cttccgccca gagcttcatc gagcggatga ccaacttcga caagaacctg  2340
cccaacgaga aggtgctgcc caagcacagc ctgctgtacg agtacttcac cgtgtataac  2400
gagctgacca aagtgaaata cgtgaccgag ggaatgagaa agcccgcctt cctgagcggc  2460
gagcagaaaa aggccatcgt ggacctgctg ttcaagacca ccggaaagt gaccgtgaag  2520
cagctgaaag aggactactt caagaaaatc gagtgcttcg actccggtgaa aatctccgac  2580
gtggaagatc ggttcaacgc ctccctgggc acataccacg atctgctgaa aattatcaag  2640
gacaaggact tcctggacaa tgaggaaaac gaggacattc tggaagatat cgtgctgacc  2700
ctgacactgt ttgaggacag agagatgatc gaggaacggc tgaaaaccta tgcccacctg  2760
ttcgacgaca aagtgatgaa gcagctgaag cggcggatga caccggctg gggcaggctg  2820
agccggaagc tgatcaacgg catccggac aagcagtccg gcaagacaat cctggatttc  2880
ctgaagtccg acggcttcgc caacagaaac ttcatgcagc tgatccacga cgacagcctg  2940
accttTaaag aggacatcca gaaagcccag gtgtccggcc agggcgatag cctgcacgag  3000
cacattgcca atctggccgg cagccccgcc attaagaagg gcatcctgca gacagtgaag  3060
gtggtggacg agctcgtgaa agtgatgggc cggcacaagc ccgagaacat cgtgatcgaa  3120
atggccagag agaaccagac cacccagaag ggacagaaga caagccgcga gaatgaag   3180
cggatcgaag agggcatcaa agagctgggc agccagatcc tgaaagaaca ccccgtggaa  3240
aacacccagc tgcagaacga gaagctgtac ctgtactacc tgcaaatgg gcgggatatg  3300
tacgtggacc aggaactgga catcaaccgg ctgtccgact acgatgtgga ccatatcgtg  3360
cctcagagct ttctgaagga cgactccatc gacaacaagg tgctgaccag aagcgacaag  3420
aaccggggca gagcgacaa cgtgcccctc caagaggtcg tgaagaagat gaagaactac  3480
tggcggcagc tgctgaacgc caagctgatt acccagagaa agttcgacaa tctgaccaag  3540
gccgagagag cggcctgag cgaactggat aaggcgatga tcatcaagaa cagctggtg  3600
gaaacccggc agatcacaaa gcacgtggca cagatcctgg actcccggat gaacactaag  3660
tacgacgaga atgacaagct gatccggga gtgaaagtga tcacctgaa gtccaagctg  3720
gtgtccgatt tccggaagga tttccagttt tacaaagtgc gcgagatcaa caactaccac  3780
cacgccacg acgcctacct gaaccgcgtc gtgggaaccg ccctgatcaa aaagtaccct  3840
aagctgaaaa gcgagttcgt gtacggcgac tacaaggtgt acgacgtgcg gaagatgatc  3900
gccaagagcg agcaggaaat cggcaaggct accgccaagt acttcttcta cagcaacatc  3960
atgaactttt tcaagaccga gattaccctg gccaacggcg agatccggaa gcggcctctg  4020
atcgagacaa acggcgaaac cggggagatc gtgtgggata agggccggga ttttgccacc  4080
gtgcgaaaag tgctgagcat gccccaagtg aatatcgtga aaaagaccga ggtgcagaca  4140
ggcggcttca gcaaagagtc tatcctgccc aagaggaaca gcgataagct gatcgccaga  4200
aagaaggact gggacctaa gaagtacggc ggcttcgaca cccccaccgt ggctattct  4260
gtgctggtgg tggccaaagt ggaaaaggc aagtccaaga aactgaagag tgtgaaagag  4320
ctgctgggga tcaccatcat ggaaaagagc agcttcgaga gaatcccat cgactttctg  4380
gaagccaagg gctacaaaga agtgaaaaag gacctgatca tcaagctgcc taagtactcc  4440
ctgttcgagc tggaaaacgg ccggaagaga atgctggcct ctgccggcga actgcagaag  4500
ggaaacgaac tggccctgcc ctccaaatat gtgaacttcc tgtacctggc cagccactat  4560
gagaagctga gggctccccc cgaggataat gagcagaaac agctgtttgt ggaacagcac  4620
aagcactacc tggacgagat catcgagcag atcagcgagt ctccaagag agtgatcctg  4680
gccgacgcta atctggacaa agtgctgtcc gcctacaaca agcaccggga taagcccatc  4740
```

-continued

```
agagagcagg ccgagaatat catccacctg tttaccctga ccaatctggg agccCctgcc    4800
gccttcaagt actttgacac caccatcgac cggaagaggt acaccagcac caaagaggtg    4860
ctggacgcca ccctgatcca ccagagcatc accggcctgt acgagacacg gatcgacctg    4920
tctcagctgg gaggtgacag cggcgggagc ggcgggagcg gggggagcac taatctgagc    4980
gacatcattg agaaggagac tgggaaacag ctggtcattc aggagtccat cctgatgctg    5040
cctgaggagg tggaggaagt gatcggcaac aagccagagt ctgacatcct ggtgcacacc    5100
gcctacgacg agtccacaga tgagaatgtg atgctgctga cctctgacgc ccccgagtat    5160
aagccttggg ccctggtcat ccaggattct aacggcgaga taagatcaa gatgctgagc     5220
ggaggatccg gaggatctgg aggcagcacc aacctgtctg acatcatcga gaaggagaca    5280
ggcaagcagc tggtcatcca ggagagcatc ctgatgctgc ccgaagaagt cgaagaagtg    5340
atcggaaaca agcctgagag cgatatcctg gtccataccg cctacgacga gagtaccgac    5400
gaaaatgtga tgctgctgac atccgacgcc ccagagtata agccctgggc tctggtcatc    5460
caggattcca acggagagaa caaaatcaaa atgctgtctg cggctcaaa aagaaccgcc    5520
gacggcagcg aattcgagcc caagaagaag aggaaagtct aa                     5562
```

SEQ ID NO: 181  moltype = DNA  length = 5412
FEATURE   Location/Qualifiers
misc_feature  1..5412
  note = Description of Artificial Sequence:
  Syntheticpolynucleotide
source   1..5412
  mol_type = other DNA
  organism = synthetic construct
SEQUENCE: 181

```
atgaaacgga cagccgacgg aagcgagttc gagtcaccaa agaagaagcg gaaagtctct    60
gaagtcgagt ttagccacga gtattggatg aggcacgcac tgaccctgcc aaagcgagca    120
tgggatgaaa gagaagtccc cgtgggcgcc gtgctggtgc acaacaatag agtgatcgga    180
gagggatgga acaggccaat cggccgccac gaccctaccg cacacgcaga gatcatggca    240
ctgaggcagg gaggcctggt catgcagaat taccgcctga tcgatgccac cctgtatgtg    300
acactggagc catgcgtgat gtgcgcagga gcaatgatca acagcaggat cggaagagtg    360
gtgttcggag cacggacgc caagaccgga gcagcaggct ccctgatgga tgtgctgcac    420
caccccggca tgaaccaccg ggtggagatc acagagggaa tcctggcaga cgagtgcgcc    480
gccctgctga gcgattcttt tagaatgcgg agacaggaga tcaaggccca agaagaggca    540
cagagctcca ccgactctgg aggatctagc ggaggatcct ctggaagcga gacaccaggc    600
acaagcgagt ccgccacacc agagagctcc ggcggctcct ccggaggatc ctctgaggtg    660
gagttttccc acgagtactg gatgagacat gccctgaccc tggccaagag ggcacgcgat    720
gagagggagg tgcctgtggg agccgtgctg gtgctgaaca atagagtgat cggcgagggc    780
tggaacagag ccatcggcct gcacgaccca acagcccatg ccgaaattat ggccctgaga    840
cagggcgcc tggtcatgca gaactacaga ccacccctgta cgtgacattc                900
gagccttgcg tgatgtgcgc cggcgccatg atccactcta ggatcggccg cgtggtgttt    960
ggcgtgagga acgcaaaaac cggcgccgca ggctccctga tggacgtgct gcactacccc    1020
ggcatgaatc accgcgtcga aattaccgag ggaatcctgg cagatgaatg tgccgccctg    1080
ctgtgctatt tcttttcggat gcctagacag gtgttcaatg ctcagaagaa ggccagagc    1140
tccaccgact ccggaggatc tagcggaggc tcctctggct ctgagacacc tggcacaagc    1200
gagagcgcaa caccgaaaag cagcggggc agcagcgggg gtcagacaa gaagtacagc    1260
atcggcctgg ccatcggcac caactctgtg ggctgggccg tgatcaccga cgagtacaag    1320
gtgcccagca gaaaattcaa ggtgctgggc aacaccgacc gacacagcat caagaagaac    1380
ctgatcggag ccctgctgtt cgacagcggc gaaacagccg aggccaccgc gctgaagaga    1440
accgccagaa gaagatacac cagacggaag aaccggatct gctatctgca agagatcttc    1500
agcaacgaga tggccaaggt ggacgacagc ttcttccaca gactggaaga gtccttcctg    1560
gtggaagagg ataagaagca cgagcggcac cccatcttcg gcaacatcgt ggacgaggtg    1620
gcctaccacg agaagtaccc caccatctac cacctgagaa agaaactggt ggacagcacc    1680
gacaaggccg acctgcggct gatctatctg gccctggccc acatgatcaa gttccggggc    1740
cacttcctga tcgagggcga cctgaacccc gacaacagcg acgtggacaa gctgttcatc    1800
cagctggtgc agacctacaa ccagcttgttc gaggaaaacc ccatcaacgc cagcggcgtg    1860
gacgccaagg ccatcctgtc tgccagactg agcaagagca cggctgga aaatctgatc    1920
gcccagctgc ccggcgagaa gaagaatggc ctgttcggaa acctgattgc cctgagcctg    1980
ggcctgaccc ccaacttcaa gagcaacttc gacctggccg aggatgccaa actgcagctg    2040
agcaaggaca cctacgacga cgacctggac aacctgctgg cccagatcgg cgaccagtac    2100
gccgacctgt ttctggccgc caagaacctg tccgacgcca tcctgctgag cgacatcctg    2160
agagtgaaca ccgagatcac caaggccccc ctgagcgcct ctatgatcaa gagatacgac    2220
gagcaccacc aggacctgac cctgctgaaa gctctcgtgc ggcagcagct gcctgagaag    2280
tacaaagaga ttttcttcga ccagagcaag aacggctacg ccggctacat tgacggcgga    2340
gccagccagg aagagttcta caagttcatc aagcccatcc tggaaaagat ggacggcacc    2400
gaggaactgc tcgtgaagct gaacagagag gacctgctgc ggaagcagcg gaccttcgac    2460
aacggcagca tcccccacca gatccacctg ggagagctgc acgccattct gcggcggcag    2520
gaagatttt acccattcct gaaggacaac cgggaaagaa tcgagaagat cctgaccttc    2580
cgcatcccct actacgtggg ccctctggcc aggggaaaca gcagattcgc ctggatgacc    2640
agaaagagcg aggaaaccat cacccctgg aacttcgagg aagtggtgga caagggcgct    2700
tccgcccaga gcttcatcga gcggatgacc aacttcgata agaacctgcc caacgagaag    2760
gtgctgccca gcacagcct gctgtacgag tacttcaccg tgtataacga gctgaccaaa    2820
gtgaaatacg tgaccgaggg aatgagaaag cccgccttcc tgagcggcga gcagaaaaag    2880
gccatcgtgg acctgctgtt caagaccaac cggaaagtga ccgtgaagca gctgaaagag    2940
gactacttca agaaaatcga gtgcttcgac tccgtggaga tctccggagt ggaagatcgg    3000
ttcaacgcct cccctgggcac ataccacgat ctgctgaaaa ttatcaagga caaggacttc    3060
ctggacaatg aggaaaacga ggacattctg gaagatatcg tgctgaccct gacactgttt    3120
gaggacagag agatgatcga ggaacggctg aaaacctatg cccaccctgtt cgacgacaaa    3180
gtgatgaagc agctgaagcg gcggagatac accggctggg caggctgag ccggaagctg    3240
atcaacggca tccgggacaa gcagtccggc aagacaatcc tggatttcct gaagtccgac    3300
```

-continued

```
ggcttcgcca acagaaactt catgcagctg atccacgacg acagcctgac ctttaaagag   3360
gacatccaga aagcccaggt gtccggccag ggcgatagcc tgcacgagca cattgccaat   3420
ctggccggca gccccgccat taagaagggc atcctgcaga cagtgaaggt ggtggacgag   3480
ctcgtgaaaa tgatgggccg gcacaagccc gagaacatcg tgatcgaaat ggccagagag   3540
aaccagacca cccagaaggg acagaagaac agccgcgaga gaatgaagcg gatcgaagag   3600
ggcatcaaag agctgggcag ccagatcctg aaagaacacc ccgtggaaaa cacccagctg   3660
cagaacgaga agctgtacct gtactacctg cagaatgggc gggatatgta cgtggaccag   3720
gaactggaca tcaaccggct gtccgactac gatgtggacc atatcgtgcc tcagagcttt   3780
ctgaaggacg actccatcga caacaaggtg ctgaccagaa gcgacaagaa ccggggcaag   3840
agcgacaacg tgccctccga agaggtcgtg aagaagatga agaactactg gcggcagctg   3900
ctgaacgcca agctgattac ccagagaaag ttcgacaatc tgaccaaggc cgagagaggc   3960
ggcctgagcg aactggataa ggccggcttc atcaagagac agctggtgga aacccggcag   4020
atcacaaagc acgtggcaca gatcctggac tcccggatga acactaagta cgacgagaat   4080
gacaagctga tccgggaagt gaaagtgatc accctgaagt ccaagctggt gtccgatttc   4140
cggaaggatt tccagtttta caaagtgcgc gagatcaaca actaccacca cgcccacgac   4200
gcctacctga acgccgtcgt gggaaccgcc ctgatcaaaa agtacccaaa gctggaaagc   4260
gagttcgtgt acgcgacta caaggtgtac gacgtgcgga agatgatcgc caagagcgag   4320
caggaaatcg gcaaggctac cgccaagtac ttcttctaca caacatcat gaacttttc    4380
aagaccgaga ttaccctggc caacggcgag atccggaagc ggcctctgat cgagacaaac   4440
ggcgaaaccg gggagatcgt gtgggataag gccgggatt ttgccaccgt gcggaaagtg    4500
ctgagcatgc cccaagtgaa tatcgtgaaa aagaccgagt gcagacagg cggcttcagc    4560
aaagagtcta tcctgcccaa gaggaacagc gataagctga tcgccagaaa gaaggactgg   4620
gaccctaaga agtacggcgg cttcgacagc cccaccgtgg cctattctgt gctggtggtg   4680
gccaaagtgg aaaagggcaa gtccaagaaa ctgaagagtg tgaaagagct gctggggatc   4740
accatcatgg aaagaagcag cttcgagaag aatcccatcg actttctgga agccaagggc   4800
tacaaagaag tgaaaaagga cctgatcatc aagctgccta agtactccct gttcgagctg   4860
gaaaacggcc ggaagagaat gctggcctct gccggcgaac tgcagaaggg aaacgaactg   4920
gccctgccct ccaaatatgt gaacttcctg tacctggcca gccactatga aagctgaag    4980
ggctccccg aggataatga gcagaaacag ctgtttgtgg aacagcacaa gcactacctg    5040
gacgagatca tcgagcagat cagcgagttc tccaagagag tgatcctggc cgacgctaat   5100
ctggacaaag tgctgtccgc ctacaacaag caccggata agcccatcag agagcaggcc     5160
gagaatatca tccacctgtt taccctgacc aatctgggag ccctgccgc cttcaagtac    5220
tttgacacca ccatcgaccg gaagaggtac accagcacca agaggtgct ggacgccacc    5280
ctgatccacc agagcatcac cggcctgtac gagacacgga tcgacctgtc tcagctggga   5340
ggtgactctg gcggctcaaa aagaaccgcc gacggcagca attcgagcc caagaagaag   5400
aggaaagtct aa                                                        5412

SEQ ID NO: 182        moltype = DNA  length = 1536
FEATURE               Location/Qualifiers
misc_feature          1..1536
                      note = Description of Artificial Sequence:
                      Syntheticpolynucleotide
source                1..1536
                      mol_type = other DNA
                      organism = synthetic construct
SEQUENCE: 182
atgaaatgtc tgctgtacct ggctttcctg ttcatcggcg tgaactgcaa gttcaccatc   60
gtgttccctc acaaccagaa gggcaactgg aaaaatgtgc ctagcaacta ccactactgt   120
cctagctcta gcgaccttaa ttggcataac gacctgatcg gcacagccct gcaggtgaag   180
atgcctaaga gccacaaggc catccaggcc gacggatgga tgtgccacgc cagcaagtgg   240
gtcacaacct gtgacttcag atggtacggc cctaaataca ttacccactc tatcagaagc   300
ttcaccccctt ctgtggaaca atgtaaagag tccattgagc agacaaagca gggcacctgg   360
ctgaaccccg gcttcccccc ccagagctgc ggctacgcca ccgttaccga tgccgaggcc   420
gtgatcgtgc aggtgacacc tcaccacgtg ctggtcgatg agtacaccgg cgaatgggta   480
gacagccaat ttatcaacgg caaatgcagc aattacatct gccccaccgt gcacaacagc   540
accacctggc acagcgatta caaggtgaaa ggcctgtgcg acagcaacct gatctctatg   600
gacatccacct tcttcagcga ggacggcgag ctgtctagtc tgggcaagga aggcacaggt   660
tttcggagca actacttcgc ctacgagact ggcggcaagg cctgcaagat gcagtactgc   720
aagcactggg gcgttagact gccttcaggc gtgtggttcg agatggccga taaggacctg   780
ttcgccgctg ccagattccc agagtgccct gagggcagct ccatcagcgc cccttcccag   840
acctccgtgg atgtgtcct gatccaggac gtggaaagaa tcctggacta cagcctctgt   900
caggagacat ggtccaaaat cagagccgga ctcccccatta gccctgtgga cctgagctac   960
ctggccccca agaatcctgg aaccggcccc gccttcacaa tcattaacgg caccctgaaa   1020
tacttcgaga ccagatacat ccgggtggac atcgccgctc ctatcctgtc aagaatggtg   1080
ggcatgattt ctggcacaac aacagagagg gaactgtggg acgactgggc cccttacgag   1140
gatgtggaaa tcgcccaaaa cggcgtgctg cggaccagct caggctataa gttccccctg   1200
tacatgatcg gccacggcat gctggattct gacctgcacc tgagcagcaa ggcccaggtc   1260
tttgagcacc ctcatatcca agacgccgcc agccagctgc ctgatgacga gagcctgttt   1320
tttggagata caggactgag caagaacca atcgagctgg tggaaggctg gtttagcagc   1380
tggaagtcca gcatagctag cttcttcttc atcatcggcc tgatcatcgg actgttcctg   1440
gtgctgagag tggggatcca cctgtgcatc aagctgaagc acaccaaaaa gagacagatc   1500
tacaccgaca tcgagatgaa ccggctgggg aagtga                               1536

SEQ ID NO: 183        moltype = DNA  length = 23
FEATURE               Location/Qualifiers
misc_feature          1..23
                      note = Description of Artificial Sequence:
                      Syntheticoligonucleotide
source                1..23
```

```
                        mol_type = other DNA
                        organism = synthetic construct
SEQUENCE: 183
tggggcccag actgagcacg tga                                              23

SEQ ID NO: 184         moltype = DNA  length = 30
FEATURE                Location/Qualifiers
misc_feature           1..30
                       note = Description of Artificial Sequence:
                         Syntheticoligonucleotide
source                 1..30
                       mol_type = other DNA
                       organism = synthetic construct
SEQUENCE: 184
tgtctgtgtg ggtgagtgag tgtgtgcgtg                                       30

SEQ ID NO: 185         moltype = DNA  length = 30
FEATURE                Location/Qualifiers
misc_feature           1..30
                       note = Description of Artificial Sequence:
                         Syntheticoligonucleotide
source                 1..30
                       mol_type = other DNA
                       organism = synthetic construct
SEQUENCE: 185
caatccttgg ggcccagact gagcacgtga                                       30

SEQ ID NO: 186         moltype = DNA  length = 20
FEATURE                Location/Qualifiers
misc_feature           1..20
                       note = Description of Artificial Sequence:
                         Syntheticoligonucleotide
source                 1..20
                       mol_type = other DNA
                       organism = synthetic construct
SEQUENCE: 186
gaccccctcc accccgcctc                                                  20
```